United States Patent
Van Den Boom et al.

(10) Patent No.: US 11,525,134 B2
(45) Date of Patent: Dec. 13, 2022

(54) DEVICES, SYSTEMS AND METHODS FOR ULTRA-LOW VOLUME LIQUID BIOPSY

(71) Applicant: Juno Diagnostics, Inc., San Diego, CA (US)

(72) Inventors: Dirk Van Den Boom, Encinitas, CA (US); Mathias Ehrich, San Diego, CA (US); Paul Oeth, San Diego, CA (US); Jim Chauvapun, San Diego, CA (US)

(73) Assignee: JUNO DIAGNOSTICS, INC., San Diego, CA (US)

( * ) Notice: Subject to any disclaimer, the term of this patent is extended or adjusted under 35 U.S.C. 154(b) by 0 days.

(21) Appl. No.: 17/547,950

(22) Filed: Dec. 10, 2021

(65) Prior Publication Data

US 2022/0098575 A1    Mar. 31, 2022

Related U.S. Application Data

(63) Continuation of application No. 16/759,303, filed as application No. PCT/US2018/057844 on Oct. 26, 2018.

(60) Provisional application No. 62/578,179, filed on Oct. 27, 2017.

(51) Int. Cl.
| | |
|---|---|
| *C12N 15/10* | (2006.01) |
| *G01N 1/10* | (2006.01) |
| *C12Q 1/6806* | (2018.01) |
| *C12Q 1/6869* | (2018.01) |
| *A61B 5/145* | (2006.01) |
| *A61B 5/15* | (2006.01) |
| *A61B 5/157* | (2006.01) |

(52) U.S. Cl.
CPC .......... *C12N 15/1065* (2013.01); *A61B 5/157* (2013.01); *A61B 5/150099* (2013.01); *A61B 5/150389* (2013.01); *A61B 5/150412* (2013.01); *A61B 5/150984* (2013.01); *C12N 15/1093* (2013.01); *C12Q 1/6806* (2013.01); *C12Q 1/6869* (2013.01); *G01N 1/10* (2013.01); *A61B 5/14546* (2013.01)

(58) Field of Classification Search
None
See application file for complete search history.

(56) References Cited

U.S. PATENT DOCUMENTS

| | | | |
|---|---|---|---|
| 6,156,879 A | 12/2000 | Rome et al. | |
| 6,258,540 B1 | 7/2001 | Lo et al. | |
| 6,410,278 B1 | 6/2002 | Notomi et al. | |
| 6,555,347 B1 | 4/2003 | Rome et al. | |
| 6,558,928 B1 | 5/2003 | Landegren | |
| 6,855,688 B2 | 2/2005 | Mckerracher | |
| 6,977,162 B2 | 12/2005 | Dhallan | |
| 7,332,277 B2 | 2/2008 | Dhallan | |
| 7,404,931 B2 | 7/2008 | Frey et al. | |
| 7,442,506 B2 | 10/2008 | Dhallan | |
| 7,479,393 B2 | 1/2009 | Noetzel et al. | |
| 7,482,319 B2 | 1/2009 | Rome et al. | |
| 7,582,420 B2 | 9/2009 | Oliphant et al. | |
| 7,592,134 B2 | 9/2009 | Sato et al. | |
| 7,598,060 B2 | 10/2009 | Dhallan | |
| 7,718,370 B2 | 5/2010 | Dhallan | |
| 7,727,720 B2 | 6/2010 | Dhallan | |
| 7,736,907 B2 | 6/2010 | Blankenstein et al. | |
| 7,807,450 B2 | 10/2010 | Samsoondar | |
| 7,888,017 B2 | 2/2011 | Quake et al. | |
| 7,955,794 B2 | 6/2011 | Shen et al. | |
| 8,008,018 B2 | 8/2011 | Quake et al. | |
| 8,101,404 B2 | 1/2012 | Samsoondar | |
| 8,124,109 B2 | 2/2012 | Kickhoefer et al. | |
| 8,195,415 B2 | 6/2012 | Fan et al. | |
| 8,293,470 B2 | 10/2012 | Quake et al. | |
| 8,296,076 B2 | 10/2012 | Fan et al. | |
| 8,318,430 B2 | 11/2012 | Chuu et al. | |
| 8,442,774 B2 | 5/2013 | Lo et al. | |
| 8,532,936 B2 | 9/2013 | Rava | |
| 8,632,740 B2 | 1/2014 | Dastane et al. | |
| 8,682,592 B2 | 3/2014 | Rabinowitz et al. | |
| 8,682,594 B2 | 3/2014 | Fan et al. | |
| 8,703,652 B2 | 4/2014 | Quake et al. | |
| 8,706,422 B2 | 4/2014 | Lo et al. | |
| 8,709,726 B2 | 4/2014 | Oeth et al. | |
| 8,920,807 B2 | 12/2014 | Rome et al. | |
| 8,949,036 B2 | 2/2015 | Rabinowitz et al. | |
| 8,956,530 B2 | 2/2015 | Dorrer et al. | |
| 8,972,202 B2 | 3/2015 | Lo et al. | |

(Continued)

FOREIGN PATENT DOCUMENTS

| | | | |
|---|---|---|---|
| EP | 0097952 A2 | 1/1984 | |
| EP | 0994936 A1 | 4/2000 | |

(Continued)

OTHER PUBLICATIONS

SneakPeek Gender Early DNA Test Instruction Pamphlet disclosed on Aug. 19, 2021.
Afsahi et al. Novel Graphene-Based Biosensor for Early Detection of Zika Virus Infection. Biosens Bioelectron 100:85-88 (2018).
Altschul et al. Basic local alignment search tool. J Mol Biol 215(3):403-410 (1990).
Clarigo Patient Brochure. (2018). 12 pages.
Clinical Education Center. Quest Diagnostics. (2018). 3 pages.
Dahl et al., Imaging single DNA molecules for high precision NIPT. Scientific Reports 8,: 4549 (2018).
European Application No. 18860060 Search Report dated May 14, 2021.

(Continued)

*Primary Examiner* — Kaijiang Zhang
(74) *Attorney, Agent, or Firm* — Wilson Sonsini Goodrich & Rosati

(57) ABSTRACT

Provided herein are devices, systems, kits and methods for obtaining genetic information from cell-free fetal nucleic acids in ultra-low amounts of biological samples. Due to the convenience of obtaining ultra-low amounts of samples, devices, systems, kits and methods can be at least partially employed at a point of need.

21 Claims, 15 Drawing Sheets

(56) References Cited

U.S. PATENT DOCUMENTS

| | | |
|---|---|---|
| 9,051,616 B2 | 6/2015 | Lo et al. |
| 9,114,173 B2 | 8/2015 | Rome et al. |
| 9,121,069 B2 | 9/2015 | Lo et al. |
| 9,121,849 B2 | 9/2015 | Babu et al. |
| 9,163,282 B2 | 10/2015 | Rabinowitz et al. |
| 9,218,449 B2 | 12/2015 | Lo et al. |
| 9,353,414 B2 | 5/2016 | Fan et al. |
| 9,404,157 B2 | 8/2016 | Fan et al. |
| 9,423,399 B2 | 8/2016 | Espinosa et al. |
| 9,424,392 B2 | 8/2016 | Rabinowitz et al. |
| 9,441,273 B2 | 9/2016 | Quake et al. |
| 9,493,831 B2 | 11/2016 | Chuu et al. |
| 9,580,751 B2 | 2/2017 | Hahn et al. |
| 9,738,931 B2 | 8/2017 | Hahn et al. |
| 9,777,328 B2 | 10/2017 | Quake et al. |
| 9,777,329 B2 | 10/2017 | Quake et al. |
| 9,845,497 B2 | 12/2017 | Quake et al. |
| 9,892,230 B2 | 2/2018 | Lo et al. |
| 9,993,816 B2 | 6/2018 | Biesbrouck |
| 10,081,839 B2 | 9/2018 | Rabinowitz et al. |
| 10,131,947 B2 | 11/2018 | Oliphant et al. |
| 10,152,568 B2 | 12/2018 | Lo et al. |
| 10,154,808 B2 | 12/2018 | Fletcher et al. |
| 10,266,893 B2 | 4/2019 | Rabinowitz et al. |
| 10,329,607 B2 | 6/2019 | Quake et al. |
| 10,335,078 B2 | 7/2019 | Kvam et al. |
| 10,526,658 B2 | 1/2020 | Babiarz et al. |
| 10,538,814 B2 | 1/2020 | Babiarz et al. |
| 10,557,172 B2 | 2/2020 | Babiarz et al. |
| 10,590,482 B2 | 3/2020 | Ryan et al. |
| 10,597,708 B2 | 3/2020 | Zimmermann et al. |
| 10,597,724 B2 | 3/2020 | Rabinowitz et al. |
| 10,888,259 B2 | 1/2021 | Jordan et al. |
| 10,989,706 B2 | 4/2021 | Wilson et al. |
| 11,358,138 B2 | 6/2022 | Johnson |
| 11,358,139 B2 | 6/2022 | Johnson |
| 11,360,076 B2 | 6/2022 | Johnson et al. |
| 2001/0051341 A1 | 12/2001 | Lo et al. |
| 2003/0036710 A1 | 2/2003 | Matriano et al. |
| 2006/0252054 A1 | 11/2006 | Lin et al. |
| 2006/0254962 A1 | 11/2006 | Samsoondar |
| 2006/0276724 A1 | 12/2006 | Freeman et al. |
| 2008/0113357 A1 | 5/2008 | Baggio et al. |
| 2009/0029377 A1 | 1/2009 | Lo et al. |
| 2009/0170114 A1 | 7/2009 | Quake et al. |
| 2009/0317817 A1 | 12/2009 | Oeth et al. |
| 2010/0112575 A1 | 5/2010 | Fan et al. |
| 2010/0112590 A1 | 5/2010 | Lo et al. |
| 2010/0124751 A1 | 5/2010 | Quake et al. |
| 2010/0124752 A1 | 5/2010 | Quake et al. |
| 2010/0138165 A1 | 6/2010 | Fan et al. |
| 2010/0255492 A1 | 10/2010 | Quake et al. |
| 2010/0255493 A1 | 10/2010 | Quake et al. |
| 2010/0256013 A1 | 10/2010 | Quake et al. |
| 2010/0324449 A1 | 12/2010 | Rostaing et al. |
| 2011/0246083 A1 | 10/2011 | Fan et al. |
| 2011/0318734 A1 | 12/2011 | Lo et al. |
| 2011/0319272 A1 | 12/2011 | Fan et al. |
| 2012/0003201 A1 | 1/2012 | Nicholas et al. |
| 2012/0003635 A1 | 1/2012 | Lo et al. |
| 2012/0003636 A1 | 1/2012 | Lo et al. |
| 2012/0003637 A1 | 1/2012 | Lo et al. |
| 2012/0055798 A1 | 3/2012 | Selden et al. |
| 2012/0123297 A1 | 5/2012 | Brancazio |
| 2012/0190559 A1 | 7/2012 | Lo et al. |
| 2012/0208708 A1 | 8/2012 | Lo et al. |
| 2012/0208710 A1 | 8/2012 | Fan et al. |
| 2012/0219950 A1 | 8/2012 | Oliphant et al. |
| 2012/0315633 A1 | 12/2012 | Mantzaris et al. |
| 2013/0022974 A1 | 1/2013 | Chinnaiyan et al. |
| 2013/0245961 A1 | 9/2013 | Lo et al. |
| 2013/0275103 A1 | 10/2013 | Struble et al. |
| 2013/0310263 A1 | 11/2013 | Lo et al. |
| 2014/0045181 A1 | 2/2014 | Lo et al. |
| 2014/0051583 A1 | 2/2014 | Fan et al. |
| 2014/0256559 A1 | 9/2014 | Lo et al. |
| 2014/0256560 A1 | 9/2014 | Lo et al. |
| 2014/0263059 A1 | 9/2014 | Burg et al. |
| 2014/0329691 A1 | 11/2014 | Fan et al. |
| 2014/0329695 A1 | 11/2014 | Lo et al. |
| 2014/0329696 A1 | 11/2014 | Lo et al. |
| 2014/0342371 A1 | 11/2014 | Holmes |
| 2015/0031035 A1 | 1/2015 | Kvam et al. |
| 2015/0104793 A1 | 4/2015 | Quake et al. |
| 2015/0136602 A1 | 5/2015 | Jovanovich et al. |
| 2015/0147815 A1 | 5/2015 | Babiarz et al. |
| 2016/0002621 A1 | 1/2016 | Nelson et al. |
| 2016/0029936 A1 | 2/2016 | Kvam et al. |
| 2016/0333416 A1 | 11/2016 | Babiarz et al. |
| 2016/0367653 A1 | 12/2016 | Rome et al. |
| 2016/0371428 A1 | 12/2016 | Ryan et al. |
| 2016/0374330 A1 | 12/2016 | Grolz |
| 2017/0014450 A1 | 1/2017 | Joyce et al. |
| 2017/0029890 A1 | 2/2017 | Fan et al. |
| 2017/0067803 A1* | 3/2017 | Jackson et al. .. A61B 5/150358 |
| 2017/0073757 A1 | 3/2017 | Chuu et al. |
| 2017/0095187 A1 | 4/2017 | Svoboda et al. |
| 2017/0145507 A1 | 5/2017 | Koh et al. |
| 2017/0173585 A1 | 6/2017 | Mahony et al. |
| 2017/0218450 A1 | 8/2017 | Lo et al. |
| 2017/0233829 A1 | 8/2017 | Lo et al. |
| 2017/0321279 A1 | 11/2017 | Hahn et al. |
| 2017/0327881 A1 | 11/2017 | Rava et al. |
| 2017/0342500 A1 | 11/2017 | Marquard et al. |
| 2018/0030528 A1 | 2/2018 | Van Den Boom et al. |
| 2018/0089364 A1 | 3/2018 | Muzzey et al. |
| 2018/0148144 A1 | 5/2018 | Turner |
| 2018/0214878 A1 | 8/2018 | Chang et al. |
| 2018/0245072 A1 | 8/2018 | Raymond et al. |
| 2018/0300450 A1 | 10/2018 | Hogan et al. |
| 2018/0346984 A1 | 12/2018 | Quake et al. |
| 2018/0374582 A1 | 12/2018 | Holmes et al. |
| 2019/0015790 A1 | 1/2019 | Weber et al. |
| 2019/0017109 A1 | 1/2019 | Song et al. |
| 2019/0024127 A1 | 1/2019 | Yeh |
| 2019/0111423 A1 | 4/2019 | Ismagilov et al. |
| 2019/0136323 A1 | 5/2019 | Lo et al. |
| 2019/0144919 A1 | 5/2019 | Jackson et al. |
| 2019/0216380 A1 | 7/2019 | Ivosevic et al. |
| 2019/0338362 A1 | 11/2019 | Tam et al. |
| 2020/0015725 A1 | 1/2020 | Johnson et al. |
| 2020/0056242 A1 | 2/2020 | Lo et al. |
| 2020/0087710 A1 | 3/2020 | McCullough et al. |
| 2020/0121234 A1 | 4/2020 | Johnson |
| 2020/0163603 A1 | 5/2020 | Jordan et al. |
| 2020/0263167 A1 | 8/2020 | Van Den Boom et al. |
| 2020/0299677 A1 | 9/2020 | Van Den Boom et al. |
| 2021/0020314 A1 | 1/2021 | Ehrich et al. |
| 2021/0068730 A1 | 3/2021 | Johnson et al. |
| 2022/0119801 A1 | 4/2022 | Van Den Boom et al. |
| 2022/0162591 A1 | 5/2022 | Van Den Boom et al. |

FOREIGN PATENT DOCUMENTS

| | | |
|---|---|---|
| EP | 0994963 A1 | 4/2000 |
| EP | 1524321 A1 | 4/2005 |
| EP | 1981995 A2 | 10/2008 |
| EP | 2183693 A1 | 5/2010 |
| EP | 2239583 A2 | 10/2010 |
| EP | 2264453 A1 | 12/2010 |
| EP | 2385143 A2 | 11/2011 |
| EP | 2514842 A2 | 10/2012 |
| EP | 2557517 A2 | 2/2013 |
| EP | 2557519 A2 | 2/2013 |
| EP | 2557520 A2 | 2/2013 |
| EP | 3378951 A1 | 9/2018 |
| EP | 3540739 A1 | 9/2019 |
| EP | 3591068 A1 | 1/2020 |
| EP | 3656870 A1 | 5/2020 |
| GB | 2428093 A | 1/2007 |
| JP | 2011518568 A | 6/2011 |
| JP | 2014501555 A | 1/2014 |
| JP | 2015523894 A | 8/2015 |
| WO | WO2009132860 A1 | 11/2009 |

(56) References Cited

FOREIGN PATENT DOCUMENTS

| | | | |
|---|---|---|---|
| WO | WO-2011053790 A2 | 5/2011 | |
| WO | WO-2011063324 A2 | 5/2011 | |
| WO | WO2012064802 A1 | 5/2012 | |
| WO | WO2013191552 A1 | 12/2013 | |
| WO | WO-2014145078 A1 * | 9/2014 | ........... C12Q 1/6806 |
| WO | WO-2015014935 A1 | 2/2015 | |
| WO | WO-2015183872 A1 | 12/2015 | |
| WO | WO-2016019042 A1 | 2/2016 | |
| WO | WO-2016019113 A1 | 2/2016 | |
| WO | WO-2017017314 A1 | 2/2017 | |
| WO | WO-2017062867 A1 | 4/2017 | |
| WO | WO-2017136059 A1 | 8/2017 | |
| WO | WO-2017136430 A1 | 8/2017 | |
| WO | WO-2017176985 A1 | 10/2017 | |
| WO | WO-2018057888 A1 | 3/2018 | |
| WO | WO-2018212496 A2 | 11/2018 | |
| WO | WO-2019067567 A1 | 4/2019 | |
| WO | WO-2019084489 A1 | 5/2019 | |
| WO | WO-2019191319 A1 | 10/2019 | |
| WO | WO-2019219841 A1 | 11/2019 | |
| WO | WO-2020018522 A1 | 1/2020 | |
| WO | WO-2020049558 A1 | 3/2020 | |
| WO | WO-2020198312 A1 | 10/2020 | |
| WO | WO-2021061751 A1 | 4/2021 | |
| WO | WO-2021108266 A1 | 6/2021 | |
| WO | WO-2021188594 A1 | 9/2021 | |

OTHER PUBLICATIONS

European Application No. 18871059 Search Report dated Jul. 16, 2021.
Fakruddin et al., Nucleic Acid Amplification: Alternative Methods of Polymerase Chain Reaction. J Pharm Bioallied Sci 5(4) :245-252 (2013).
Fakruddin et al., Nucleic acid sequence based amplification (NASBA)—prospects and applications. Int. J. of Life Science and Pharma Res. 2(1): L106-L121 (2012).
Fan, et al. Analysis of the size distributions of fetal and maternal cell-free DNA by paired-end sequencing. Clin Chem. Aug. 2010;56(8):1279-86. Epub Jun. 17, 2010.
Garrido-Cardenas et al. DNA Sequencing Sensors: an Overview. Sensors (Basel) 17(3): 588 (2017).
Harmony-Test Information. Test Submission Instructions. Bioscientia Human Genetics (2014).
Hovelson et al., Rapid, ultra low coverage copy number profiling of cell-free DNA as a precision oncology screening strategy. Oncotarget. 8(52):89848-89866 (2017).
Hovelson et al., Rapid, ultra low coverage copy number profiling of cell-free DNA as a precision oncology screening strategy. Oncotarget. 8(52):89848-89866 (2017) (Supplementary Materials).
Howarka et al., Building Membrane Nanopores. Nat Nanotechnol 12(7): 619-630 (2017).
Karlin, et al. Applications and statistics for multiple high-scoring segments in molecular sequences. PNAS USA 90:5873-5877 (1993).
Karlin et al. Methods for assessing the statistical significance of molecular sequence features by using general scoring schemes. PNAS USA 87:2264-2268 (1990).
Koussa et al., DNA Nanoswitches: a quantitative platform for gel-based biomolecular interaction analysis. Nat Methods 12(2): 123-126 (2015).
Legler et al., Specific Magnetic Bead-Based Capture of Free Fetal DNA From Maternal Plasma. Transfus Apher Sci 40(3): 153-157 (2009).
Liao, G.J.W. et al., "Targeted massively parallel sequencing of maternal plasma DNA permits efficient and unbiased detection of fetal alleles," Clin. Chem. 2011, 57(1), 92-101.
Liu et al.: A High-Efficiency Superhydrophobic Plasma Separator. Lab Chip. 16(3):553-560 (2016).
MaterniT21 PLUS Core + ESS. Test Details. Laboratory Corporation of America (2018). 3 pages.
Mori et al., Real-time Turbidimetry of LAMP Reaction for Quantifying Template DNA. J Biochem Biophys Methods 59(2): 145-157 (2004).
Nakabayashi et al., Massively parallel sequencing of cell-free DNA in plasma for detecting gynecological tumour-associated copy number alteration. Scientific Report 8: 11205 (2018). 12 pages.
Needleman et al. A general method applicable to the search for similarities in the amino acid sequence of two proteins. Journal of molecular biology 48(3):443-453 (1970).
Noninvasive prenatal screening Q&A. Quest Diagnostics. (2018). 3 pages.
Notomi, et al. Loop-mediated isothermal amplification of DNA. Nucleic Acids Res. Jun. 15, 2000;28(12):E63.
PCT/US2018/052891 International Preliminary Reporton Patentability dated Mar. 31, 2020.
PCT/US2018/057844 International Patent Application Invitation to Pay Additional Fees dated Dec. 17, 2018.
PCT/US2018/057844 International Preliminary Report on Patentability dated Apr. 28, 2020.
Pearson et al. Improved Tools for Biological Sequence Comparison. PNAS USA 85:2444-48 (1988).
Prenatal Screen, Cell-free DNA. The Regents of the University of California (2018). 2 pages.
Raymond et al., Collection of Cell-Free DNA for Genomic Analysis of Solid Tumors in a Clinical Laboratory Setting. PLoS One 12(4):e0176241 (2017).
Remmerie et al., Validation of a targeted, multiplex PCR-based NIPT test in an international multi-centre study. Multiplicom (2016).
Shao et al., Chip-based analysis of exosomal mRNA mediating drug resistance in glioblastoma. Nature Communications 6(1): 9 pages (2015).
Shao et al., Protein typing of circulating microvesicles allows real-time monitoring of glioblastoma therapy. Nature Medicine 18(12): 1835-1840 (2012).
Shao et al., Supplementary Information—Protein typing of circulating microvesicles allows realtime monitoring of glioblastoma therapy. Nature Medicine 18(12): 1835-1840 (2012).
Sharma et al.: Point-of-Care Diagnostics in Low Resource Settings: Present Status and Future Role of microfluidics. Biosensors. 5:577-601 (2015).
Smith et al. Comparison of Biosequences. Advances in Applied Mathematics. 2:482-489 (1981).
Toley et al., Isothermal Strand Displacement Amplification (iSDA): a Rapid and Sensitive Method of Nucleic Acid Amplification for Point-of-Care Diagnosis. Analyst 140(22): 7540-7549 (2015).
Wang et al.: Translating epigenetics into clinic: focus on lupus; Clinical Epigentics; 9:78 (1-15) (2009).
Wu et al., Aligner-mediated cleavage of nucleic acids and its application to isothermal exponential amplification. Chem Sci. 9(11): 3050-3055 (2018).
Zanoli et al. Isothermal Amplification Methods for the Detection of Nucleic Acids in Microfluidic Devices. Biosensors 3:18-43 (2013).
Zimmerman et al., Non-invasive prenatal aneuploidy testing at chromosomes 13, 18, 21, X, and Y, using targeted sequencing of polymorphic loci. Prenat Diagn 32(13): 1233-1241 (2012).
Mar. 3, 2022 Non-Final Office Action U.S. Appl. No. 17/547,920.
PCT/US2018/052891 International Search Report and Written Opinion dated Feb. 27, 2019.
PCT/US2018/057844 International Search Report and Written Opinion dated Feb. 8, 2019.
Banfi et al., The role of ethylenediamine tetraacetic acid (EDTA) as in vitro anticoagulant for diagnostic purposes. Clin Chem Lab Med. 2007;45(5):565-76. doi: 10.1515/CCLM.2007.110. PMID: 17484616.
Benjamini, et al. Summarizing and correcting the GC content bias in high-throughput sequencing. Nucleic Acids Res. May 2012;40(10):e72. doi: 10.1093/nar/gks001. Epub Feb. 9, 2012.
Breitbach et al., Direct measurement of cell-free DNA from serially collected capillary plasma during incremental exercise. J Appl Physiol (1985). Jul. 15, 2014;117(2):119-30. doi: 10.1152/japplphysiol. 00002.2014. Epub May 29, 2014. PMID: 24876361.
Canick et al., DNA sequencing of maternal plasma to identify Down syndrome and other trisomies in multiple gestations. Prenat Diagn 32(8):730-734 (2012).

(56) References Cited

OTHER PUBLICATIONS

Chatterton et al.: Brain-derived circulating cell-free DNA defines the brain region and cell specific origins associated with neuronal atrophy; bioRxiv preprint pp. 1-19 (2019).

Chung et al., Magnetically-actuated blood filter unit attachable to biochips. Proceedings of the 16th International Conference on Miniaturized Systems for Chemistry and Life Sciences, MicroTAS 2012. 1180-1182.

Cleveland, Lowess: a program for smoothing scatterplots by robust locally weighted regression, The American Statistician, 35:54 (1981).

Ellison et al., Using Targeted Sequencing of Paralogous Sequences for Noninvasive Detection of Selected Fetal Aneuploidies. Clin Chem 62(12):1621-1629 (2016).

European Patent Application No. 19777591.9 Search Report dated Nov. 26, 2021.

Final Office Action issued in U.S. Appl. No. 17/547,920 dated Jun. 30, 2022.

Gateway Genomics Previews Advanced Technology for the Future of Genetic Testing at the International Society for Prenatal Diagnosis, Aug. 4, 2015.

Haeberle et al., Centrifugal extraction of plasma from whole blood on a rotating disk. Lab Chip. Jun. 2006;6(6):776-81. doi: 10.1039/b604145k. Epub Apr. 13, 2006. PMID: 16738730.

International Search Report and Written Opinion issued in International Application No. PCT.US2022/0300903 dated Jul. 8, 2022.

International Search Report and Written Opinion issued in PCT/US2019/024416 dated Sep. 4, 2019.

International Search Report and Written Opinion issued in PCT/US2020/024638 dated Aug. 6, 2020.

International Search Report issued in PCT/US2020061599 dated Feb. 25, 2021.

Kersaudy-Kerhoas et al., "Micro-scale blood plasma separation: from acoustophoresis to egg-beaters." Lab on a chip 13 17 (2013): 3323-46.

Kingma, et al. Adam: a Method for Stochastic Optimization. Published as a conference paper at the 3rd International Conference for Learning Representations, San Diego, 2015.

Langmead et al. Ultrafast and memory-efficient alignment of short DNA sequences to the human genome. Genome biology 10:R25 (10 pgs) (2009).

Lefkowitz et al., Clinical validation of a noninvasive prenatal test for genomewide detection of fetal copy number variants. Am J Obstet Gynecol 215(2):227.e1-227.e16 (2016).

Li et al. Fast and accurate short read alignment with Burrows-Wheeler ransform. Bioinformatics 25:1754-60 (2009).

Li, et al. Mapping short DNA sequencing reads and calling variants using mapping quality scores. Genome Res. Nov. 2008;18(11):1851-8. Epub Aug. 19, 2008.

Lipton et al., Learning to Diagnose with LSTM Recurrent Neural Networks, retreived Aug. 14, 2019.

Lipton et al., Learning to Diagnose with LSTM Recurrent Neural Networks, eprint arXiv:1511.03677 (2016) [online]. Retrieved from Internet URL:https://arxiv.org/pdf/1511.03677.pdf.

Marshall et al., Utility of amplification enhancers in low copy number DNA analysis. Int J Legal Med. Jan. 2015;129(1):43-52.

Milot and Jacob, Finger Stick Self-Collection of Maternal Blood for Non-Invasive Prenatal Testing, Prenatal Diagnosis 2917, 37(Suppl. 1) p. 70.

Min et al., Chromatin accessibility prediction via convolutional long short-term memory networks with k-mer embedding. Bioinformatics. Jul. 15, 2017;33(14):i92-i101. doi: 10.1093/bioinformatics/btx234. PMID: 28881969; PMCID: PMC5870572.

Min et al., Chromatin accessibility prediction via convolutional long short-term memory networks with k-mer embedding. Bioinformatics. 33(14):i92-i101 (2017).

Nakano et al., Single-molecule PCR using water-in-oil emulsion. J Biotechnol. Apr. 24, 2003;102(2):117-24. doi: 10.1016/s0168-1656(03)00023-3. PMID: 12697388.

NEBNext Ultra II DNA Library Prep Kit for Illumina, Mar. 14, 2016.

Nguyen, N. et al., "Ultra-large alignments using phylogeny-aware profiles", Genome Biology, 2015, vol. 16, No. 1, 15 pages.

Non-Final Office Action issued in U.S. Appl. No. 16/759,303, dated May 20, 2022.

Non-Final Office Action issued in U.S. Appl. No. 17/547,920 dated Mar. 3, 2022.

Non-Final Office Action issued in U.S. Appl. No. 17/547,950 dated Jun. 2, 2022.

PCT/US2019/024416 International Patent Application Invitation to Pay Additional Fees dated Jul. 1, 2019.

PCT/US2019/024416 International Preliminary Report on Patentability dated Oct. 6, 2020.

PCT/US2019/024416 International Search Report and Written Opinion dated Sep. 4, 2019.

PCT/US2020/024638 International Search Report and Written Opinion dated Aug. 6, 2020.

PCT/US2020/025022 International Search Report and Written Opinion dated Jun. 29, 2020.

PCT/US2020/061599 International Search Report and Written Opinion dated Feb. 25, 2021.

Peng, Y. et al., "Robust Ensemble Learning for Cancer Diagnosis Based on Microarray Data Classification", In: Li X., Wang S., Dong Z.Y. (eds) Advanced Data Mining and Applications. ADMA, 2005, Lecture Notes in Computer Science, vol. 3584. pp. 564-574, Springer, Berlin, Heidelberg, https://doi.0rg/10.1007/11527503_67.

Picelli et al. Tn5 transposase and tagmentation procedures for massively scaled sequencing projectsGenome Res. 24:2033-2040 (2014).

Pickar-Oliver et al. The next generation of CRISPR-Cas technologies and applications. Nat Rev Mol Cell Biol 20:490-507 (2019).

Porreco, Richard P. et al. Noninvasive prenatal screening for fetal trisomies 21, 18, 13 and the common sex chromosome aneuploidies from maternal blood using massively parallel genomic sequencing of DNA. 211(4):365.e1-365.e12 (Oct. 2014).

Primacio et al., American Society of Human Genetics 65th Annual Meeting, Oct. 6-10, 2015, Baltimore, MD.

Restriction Requirement issued in U.S. Appl. No. 16/648,819 dated May 24, 2022.

Rothberg, et al. An integrated semiconductor device enabling non-optical genome sequencing. Nature. 475 (2011): 348-352.

Sanger et al., The nucleotide sequence of bacteriophage phiX174. J Mol Biol 125(2):225-246 (1978).

Shin et al. CRISPR-Cas9-targeted fragmentation and selective sequencing enable massively parallel microsatellite analysis. Nature Communications 8: Article No. 14291 (2017).

Stevens et al. A novel CRISPR/Cas9 associatedtechnology for sequence-specific nucleic acidenrichment. PLoS ONE 14(4):e0215441 (2019).

Third Party Submisison for U.S. Appl. No. 17/547,920 on Jul. 12, 2022.

U.S. Appl. No. 17/597,619, filed Jan. 14, 2022.
U.S. Appl. No. 17/617,881, filed Dec. 9, 2021.
U.S. Appl. No. 17/632,966, filed Feb. 4, 2022.
U.S. Appl. No. 17/780,227, filed May 26, 2022.
U.S. Appl. No. 17/824,617, filed May 25, 2022.

Wang et al. An RNA-Guided Cas9 Nickase-Based Method for Universal Isothermal DNA Amplification. Angew Chem Int Ed Engl. 58(16):5382-5386 (2019).

Weise et al., Microdeletion and Microduplication Syndromes. J Histochem Cytochem 60(5): 346-358.

Yuan, Y. et al., "DeepGene: an advanced cancer type classifier based on deep learning and somatic point mutations", BMC Bioinformatics, 2016, vol. 17, No. 17, pp. 243-256.

* cited by examiner

DEVICES, SYSTEMS AND METHODS FOR ULTRA-LOW VOLUME LIQUID BIOPSY

RELATED APPLICATIONS

This application is a continuation of U.S. patent application Ser. No. 16/759,303, filed on Apr. 24, 2020, which is a U.S. National Phase Application of International Application No. PCT/US2018/057844, filed on Oct. 26, 2018, which application claims the benefit of U.S. Provisional Patent Application No. 62/578,179, filed on Oct. 27, 2017. Priority is claimed pursuant to 35 U.S.C. § 119. The above noted patent applications are incorporated by reference as if set forth fully herein.

BACKGROUND OF THE INVENTION

Genetic testing is a means for obtaining information about a subject's DNA and/or expression of that DNA. Genetic tests are continually being developed to obtain biological information about a subject. This biological information has many uses, including determining a health status of an individual, diagnosing an individual with an infection or disease, determining a suitable treatment for the individual, solving a crime and identifying paternity. Currently, genetic testing is mainly performed in clinics and laboratories by trained personnel with expensive and bulky equipment that requires technical training and expertise to use. It typically takes days to weeks, from the time a biological sample is obtained from a patient, to provide the patient with results of a genetic test.

Cell-free nucleic acids originate from various tissue types and are released into the circulation of an individual. The pool of cell-free nucleic acids in circulation often represents the genetic makeup of contributing tissue types. In the case of a healthy individual, it can be a very homogenous pool without much variation. However, when a tissue contains a noticeably different genome, a more heterogeneous cell-free nucleic acid pool can be observed. Common examples of subjects having tissues with noticeably different genomes include, but are not limited to: (a) cancer patients, where the tumor DNA contains mutated sites (b) transplant patients, where the transplanted organ releases donor DNA into the pool of cell-free DNA and (c) pregnant women, where the placenta contributes cell-free DNA that is largely representative of the fetal DNA. In some instances, a genome may be noticeably different due to epigenetic modifications. DNA from different tissues, organs and cell types has been shown to have distinct epigenetic patterns. Thus, it may be possible to detect cell-free nucleic acids from tissues, organs, and cells including, but not limited to, brain, liver, adipose, pancreas, endothelium, and immune cells. In addition, when a tissue or cell type of an individual is affected by a disease or infection, there may be more cell-free DNA from that tissue or cell-type circulating in that individual.

SUMMARY OF THE INVENTION

Disclosed herein are devices, systems, kits and methods for analyzing components (e.g., nucleic acids, proteins) of a biological sample, including a sample from an animal (human or non-human). In general, devices, systems, kits and methods disclosed herein are capable of providing genetic information from an ultra-low volume of a sample by taking advantage of cell-free DNA fragmentation. For brevity, this may be referred to as "ultra-low volume liquid biopsy." Prior to the instant disclosure, it was not expected that one could obtain reliable and useful genetic information from ultra-low volumes of samples because it was not believed that ultra-low volumes would provide a sufficient amount of cell-free nucleic acids from a particular tissue of interest (e.g., brain, liver, placenta, tumor) to be detectable or informative. Moreover, with an abundance of background signal from other cell-free nucleic acids, particularly those from blood cells, and the variation of that background from subject to subject, reproducibility and reliable comparisons between test subjects and control subject seemed nearly impossible.

In contrast to cellular DNA, cell-free DNA is fragmented. In order to analyze cell-free DNA from ultra-low volumes of sample, methods, devices, systems and kits disclosed herein utilize cell-free DNA fragments from repetitive regions (e.g., regions with a common sequence) and/or multiple regions as statistically independent markers. Methods, devices, systems and kits disclosed herein are possible because cell-free DNA fragments from repetitive regions (e.g., regions of the genome containing multiple copies of the same or similar sequence), or many regions collectively, are present at a higher effective concentration in a sample than non-fragmented DNA sequences would be. Thus, sample volumes that contain a number of analytes sufficient to obtain useful genetic information are lower than previously thought.

Advantageously, fragments from repetitive regions may be amplified with a single pair of primers or detected with a single probe. Alternatively or additionally, multiple detection regions that do not share similar sequences may be detected in small volumes, e.g., by tagging and amplifying them with a universal primer or amplifying with multiple primer pairs (e.g. in a multiplexed format).

Due to their ability to obtain useful genetic information from ultra-low volumes of biological samples, the devices, systems, kits and methods offer the advantages of being (1) minimally invasive, (2) applicable in home with little or no technical training (e.g., do not require complex equipment); and (3) informative at early stages of a condition (e.g., pregnancy, infection). These advantages reduce or negate the requirement for a laboratory or technician, thereby improving patient accessibility, compliance, and monitoring. This ultimately leads to improved health outcomes at lower cost to the healthcare system.

Analysis of cell-free circulating nucleic acids is met with a number of technical challenges. For instance, amplification of circulating nucleic acids in blood may be inhibited by some of the components in whole blood (e.g., hemoglobin). One of the ways the instant methods, systems and devices solve this technical challenge, is by obtaining plasma (containing cell-free nucleic acids) from capillary blood in a manner that avoids contamination from components in whole blood.

Analysis of cell-free circulating nucleic acids in small sample volumes is particularly challenging. Despite past attempts to accomplish this goal, and for the reasons described herein, the field has remained skeptical that useful and accurate genetic information can be obtained from cell-free DNA in small sample volumes that can be collected at a point of need (e.g., capillary blood from a finger prick). The methods, systems and devices disclosed herein not only overcome these technical challenges, but can be used at a point of need, something that was practically inconceivable given the state of the art.

For example, past attempts to analyze circulating cell-free tumor DNA in five or more milliliters of blood were only informative when the sample had a relatively high tumor burden (e.g., 15-20%) and a fraction of the genome altered (FGA) of 15%, or more, which make the alterations easier to detect. However, in a majority of patients, the tumor burden is much lower. Thus, past attempts exclude a significant portion of the patient population. In further attempts, analyzing smaller amounts of biological sample were unsuccessful due to white blood cell contamination. In addition, obtaining five or more milliliters of blood from an individual requires a laboratory technician, which increases the cost of the genetic analysis and inconvenience to the patient (e.g., inconvenience caused by the time, discomfort, and expense of the genetic analysis). The present methods, devices, and systems are configured to provide useful and accurate genetic information by analyzing a biological sample, such as capillary blood, in amounts much lower than five milliliters that can be collected at a point of need (e.g., capillary blood from a finger prick).

Even if past attempts analyzed smaller sample volumes, they produced artificial results. For example, some past attempts of analyzing smaller amounts of sample dilute genomic DNA from cell lines and shear the genomic DNA to produce and detect cell free (cfDNA) surrogates. Downsampling or dilutions of cell line DNA/sheared DNA and in silico methods produce artificial results because they are not reflective of size and length distributions and bin information in individual samples with low input number of molecules. In another example, past attempts to analyze smaller amounts of a biological sample produce artificial results because they rely on detecting predetermined mutations, which can also be referred to as "known events." The instant disclosure presents methods, systems and devices for obtaining plasma (containing cell-free nucleic acids) from a small amount of capillary blood (e.g., finger prick) in a manner that provides accurate and non-predetermined genetic information from non-surrogate cfDNA.

The past attempts described herein would have to use a combination of low pass/low coverage whole genome sequencing in an initial detection step, and thereafter perform additional analysis in further detail to perform a genetic analysis accurately. Low pass/low coverage whole genome sequences is not optimal for detecting unknown events with high sensitivity, and likely will require more detailed follow up assays. Use of multiple assays to provide a genetic analysis is costly, inefficient, and is not a fungible solution at the point of need. By contrast, the present methods, devices, and systems solve the above problems by providing a way to obtain an accurate genetic analysis from ultra-low sample volumes by using multiple fragments of cell-free DNA that collectively are present at a high concentration that is detectable even in small samples.

Devices, systems, kits and methods disclosed herein are summarized as follows.

Disclosed herein, in some aspects are methods that comprise obtaining capillary blood from a subject, wherein the capillary blood comprises cell-free nucleic acids; sequencing at least a portion of the cell-free nucleic acids to produce sequencing reads; measuring at least a portion of sequencing reads corresponding to at least one target sequence of interest; and detecting a normal representation, an overrepresentation or an underrepresentation of the at least one target sequence. Further disclosed herein are methods that comprise obtaining capillary blood from a subject, wherein the capillary blood comprises cell-free nucleic acids; optionally amplifying the cell-free nucleic acids; tagging at least a portion of the cell-free nucleic acids to produce a library of tagged cell-free nucleic acids; optionally amplifying the tagged cell-free nucleic acids; sequencing at least a portion of the tagged cell-free nucleic acids; and detecting a normal representation, an overrepresentation or an underrepresentation of at least one target sequence in the at least a portion of the tagged cell-free nucleic acids. Methods may comprise producing a library having an efficiency of at least 0.5. Methods may comprise amplifying the cell-free nucleic acids or tagged cell-free nucleic acids in the presence of a crowding agent. Methods may comprise repairing ends of the cell-free nucleic acids. In some aspects, methods comprise obtaining a biological sample from a subject, wherein the biological sample comprises target cell-free nucleic acids and non-target cell-free nucleic acids that together make up total cell-free nucleic acids, and wherein the target cell-free nucleic acids are less than 5% of the total cell-free nucleic acids; sequencing at least a portion of the target cell-free nucleic acids to produce sequencing reads; measuring at least a portion of sequencing reads corresponding to at least one target sequence of interest; and detecting a normal representation, an overrepresentation or an underrepresentation of the at least one target sequence. The biological sample may comprise capillary blood. The biological sample may consist essentially of capillary blood. Obtaining the biological sample may comprise obtaining capillary blood. Obtaining the biological sample may consist essentially of obtaining capillary blood. Obtaining the biological sample may not comprise obtaining venous blood. Obtaining the biological sample may not comprise performing a phlebotomy. Obtaining the biological sample may comprise obtaining not more than 1 milliliter of blood. Obtaining the biological sample may comprise obtaining not more than 100 microliters of blood. Obtaining the biological sample may comprise obtaining not more than 40 microliters of blood. Methods may comprise detecting the normal representation, overrepresentation or underrepresentation of the at least one target sequence with at least 98% accuracy. Methods may comprise whole genome amplification. Methods may not comprise whole genome amplification. In some instances, the target cell-free nucleic acids are cell-free nucleic acids from a tumor. In some instances, the target cell-free nucleic acids are cell-free nucleic acids from a fetus. In some instances, the target cell-free nucleic acids are cell-free nucleic acids from a transplanted tissue or organ.

Disclosed herein are method that comprise obtaining a biological sample from a subject, wherein the biological sample contains up to about $10^9$ cell-free nucleic acid molecules; sequencing at least a portion of the cell-free nucleic acid molecules to produce sequencing reads; measuring at least a portion of sequencing reads corresponding to at least one chromosomal region; and detecting a normal representation, an overrepresentation or an underrepresentation of the at least one chromosomal region. In some instances, the biological sample is a biological fluid having a volume of less than about 500 µl. In some instances, the biological sample is a biological fluid having a volume of about 1 µL to about 100 µl. In some instances, the biological sample is a biological fluid having a volume of about 5 µL to about 80 µl. In some instances, the biological sample has a volume of about 5 µL to about 60 µl. Methods may comprise amplifying the cell-free nucleic acid molecules before sequencing. Methods may comprise tagging the cell-free nucleic acid molecules before sequencing and after amplifying. Methods may comprise tagging the cell-free nucleic acid molecules before sequencing. Methods may comprise amplifying the cell-free nucleic acid molecules after tagging the cell-free nucleic acid molecules. Methods may comprise amplifying the cell-free nucleic acid molecules before tagging the cell-free nucleic acid molecules. Methods may comprise amplifying comprises contacting the cell-free nucleic acid molecules with random oligonucleotide primers. Amplifying may comprise isothermal amplification. Methods may comprise detecting an overrepresentation of sequencing reads corresponding to at least one target chromosome. Methods may comprise detecting an underrepresentation of sequencing reads corresponding to at least one target chromosome. Methods may comprise comparing the number of sequencing reads corresponding to the at least one target chromosome to a reference number of sequencing reads corresponding to the at least one target chromosome. Methods may comprise measuring at least 1000 sequencing reads corresponding to the at least one chromosomal region. Methods may comprise measuring at least 1000 sequencing reads corresponding to at least one non-target chromosomal region. In general, the biological sample is biological fluid. The biological sample may comprise blood, plasma, serum, urine, interstitial fluid, vaginal cells, vaginal fluid, buccal cells, or saliva. The biological sample may consist essentially of blood, plasma, serum, urine, interstitial fluid, vaginal fluid, or saliva. In some instances, the biological sample is serum. In some instances, the biological sample is plasma. Methods may further comprise separating the plasma or serum from a blood sample. Separating may comprise filtering the blood sample to remove cells, cell fragments, microvesicles, or a combination thereof, from the blood sample to produce the plasma sample. The biological sample may be a blood sample having a volume of about 5 µl to about 1 ml. The biological sample may be a blood sample having a volume of about 5 µl to about 150 µl. Obtaining the blood sample may comprise pricking a finger. Obtaining the blood sample may further comprise milking or squeezing blood from the pricked finger. In some instances, the method does not comprising milking or squeezing blood from the pricked finger. In some instances, obtaining the blood sample does not comprise a phlebotomy. Biological samples may contain about $10^4$ to about $10^9$ cell-free nucleic acid molecules. Biological samples may contain about $10^4$ to about $10^8$ cell-free nucleic acid molecules. Biological samples may contain about $10^4$ to about $10^7$ cell-free nucleic acid molecules. Biological samples may contain less than 300 pg of cell-free nucleic acid molecules. Biological samples may contain less than 3 ng of cell-free nucleic acid molecules. Methods may comprise detecting the normal representation, overrepresentation or underrepresentation with greater than 98% accuracy. Methods may comprise detecting the normal representation, overrepresentation or underrepresentation with greater than 99% accuracy. In some instances, the subject is a pregnant subject and the cell-free nucleic acid molecules comprise cell-free fetal nucleic acid molecules. Methods may comprise comparing the number of sequencing reads corresponding to the at least one chromosomal region to a reference number of sequencing reads corresponding to the at least one chromosomal region. In some instances, the reference number is based on at least one sample from at least one euploid pregnant subject with a euploid fetus. In some instances, the reference number is based on at least one sample from at least one euploid pregnant subject with an aneuploid fetus. In some instances, the at least one sample is the same sample type and same sample volume as the biological sample. In some instances, the biological sample comprises about $10^6$ to about $10^{12}$ total cell-free nucleic acid molecules, wherein the total cell-free nucleic acid molecules consist essentially of the cell-free fetal nucleic acid molecules and maternal cell-free nucleic acid molecules. Methods may comprise detecting that there is a fetal aneuploidy of the at least one chromosomal region when a ratio of sequencing reads corresponding to the at least one chromosomal region to sequencing reads corresponding to at least one non-target chromosomal region is different from a respective ratio in a control biological sample from a control pregnant euploid subject with a euploid fetus. Methods may comprise detecting, that there is not a fetal aneuploidy of the at least one chromosomal region when a ratio of sequencing reads corresponding to the at least one chromosomal region to sequencing reads corresponding to at least one non-target chromosomal region is the same as a respective ratio in a control biological sample from a control pregnant euploid subject with a euploid fetus. In some instances, the at least one chromosomal region is located on at least one of chromosome 13, chromosome 16, chromosome 18, chromosome 21, chromosome 22, chromosome X, or chromosome Y. In some instances, the at least one non-target chromosomal region is at least one of a chromosome other than chromosome 13, chromosome 16, chromosome 18, chromosome 21, chromosome 22, chromosome X, or chromosome Y. In some instances, the pregnant subject is as few as 5 weeks pregnant. In some instances, the pregnant subject is euploid. In some instances, the biological sample contains about $10^4$ to about $10^9$ cell-free fetal nucleic acids. In some instances, the biological sample contains about $10^4$ to about $10^8$ cell-free fetal nucleic acids. Methods may comprise sequencing at least 2000 cell-free fetal nucleic acids. Methods may comprise measuring at least 1000 of the sequencing reads corresponding to the at least chromosomal region. In some instances, representation of the at least one chromosomal region is relative to control representation in at least one control pregnant subject carrying a control fetus. In some instances, the at least one control pregnant subject and control fetus does not have an aneuploidy. In some instances, the at least one control pregnant subject and control fetus does not have a genetic abnormality. In some instances, the at least one control pregnant subject and control fetus has an aneuploidy corresponding to the chromosomal region. In some instances, the at least one control pregnant subject and control fetus has a genetic abnormality corresponding to the target chromosomal region. In some instances, the cell-free nucleic acids comprise nucleic acids from a tumor in a tissue. Methods may comprise comparing the number of sequencing reads corresponding to the at least one chromosomal region to a reference number of sequencing reads corresponding to the at least one chromosomal region. In some instances, the reference number is based on at least one sample from a subject without the tumor in the tissue. In some instances, the reference number is based on at least one sample from a subject with the tumor in the tissue. In some instances, the cell-free nucleic acids comprise nucleic acids from an organ or a tissue that has been transplanted into the subject. In some instances, the cell-free nucleic acids are specific to the organ or the tissue. In some instances, sequencing comprises whole genome sequencing. In some instances, sequencing comprises random massively parallel sequencing. In some instances, sequencing comprises targeted sequencing. In some instances, sequencing comprises nanopore sequencing.

Further disclosed herein are methods that comprise obtaining a biological sample from a subject, wherein the biological sample contains up to about $10^{10}$ cell-free nucleic acid molecules; analyzing epigenetic modifications on at least one chromosomal region of at least a portion of the cell-free nucleic acid molecules; and detecting a normal representation, an overrepresentation or an underrepresentation of the at least one chromosomal region. In some instances, the biological sample contains up to about $10^9$ cell-free nucleic acid molecules. Also disclosed herein are methods that comprise obtaining capillary blood from a subject; analyzing epigenetic modifications on at least one chromosomal region of at least a portion of the cell-free nucleic acid molecules; and detecting a normal representation, an overrepresentation or an underrepresentation of the at least one chromosomal region. Methods may comprise obtaining not more than 200 µl of capillary blood. Methods may comprise obtaining not more than 100 µl of capillary blood.

Disclosed herein are systems that comprise a sample collector configured to collect a fluid sample of a subject; a sample processor that is configured to isolate a sample component from the fluid sample; a nucleic acid detector that is configured to detect nucleic acids in the fluid sample or the sample component; and a nucleic acid information output. Systems disclosed herein may also be presented as kits. In some instances, the sample collector comprises a transdermal puncture device. In some instances, the transdermal puncture device comprises at least one of a needle, a lancet, a microneedle, a vacuum, and a microneedle array. In some instances, the sample component is selected from a cell, a carbohydrate, a phospholipid, a protein, a nucleic acid, and a microvesicle. In some instances, the sample component is a blood cell. In some instances, the sample component does not comprise a cell-free nucleic acid. In some instances, the sample component comprises a cell-free nucleic acid. In some instances, the sample component is plasma or serum. The sample purifier may be configured to isolate plasma from less than 1 milliliter of blood. The sample purifier may be configured to isolate plasma from less than 250 µl of blood. The sample purifier may be configured to isolate plasma from less than 150 µl of blood. The sample purifier may be configured to isolate plasma from less than 100 µl of blood. The nucleic acid detector may comprise a nucleic acid sequencer. Systems may be configured to label nucleic acids of interest in the fluid sample, and the nucleic acid detector comprises a counting system that counts the labels to detect a representation of the nucleic acids of interest in the sample. Systems may comprise labels, wherein the labels comprise an oligonucleotide that hybridizes to the nucleic acids of interest. The oligonucleotide may be specific to a chromosomal region of interest. The chromosomal region of interest may be located on a chromosome selected from chromosome 13, chromosome 16, chromosome 18, chromosome 21, chromosome 22, chromosome X, and chromosome Y. The chromosomal region of interest may comprise, or may be capable of comprising, a sequence that is indicative of a disease or condition. The chromosomal region of interest may comprise, or may be capable of comprising, at least one epigenetic modification that is indicative of a disease or condition. The condition may be a genetic abnormality. The condition may be a cancer. The condition may be a transplanted tissue or organ. Systems may comprise at least one nucleic acid amplification reagent selected from a primer, a polymerase, and a combination thereof. The at least one nucleic acid amplification reagent may comprise at least one isothermal amplification reagent. The at least one isothermal amplification reagent may comprise a recombinase polymerase, a single-strand DNA-binding protein, a strand-displacing polymerase, or a combination thereof. Systems may comprise at least one nucleic acid amplification reagent and at least one crowding agent. Systems may comprise at least a first label for producing a library of cell-free nucleic acids from the fluid sample, and at least one amplification reagent. Systems may be configured to amplify the cell-free nucleic acids with the at least one amplification reagent to produce at least one amplicon and contacting the at least one amplicon with at least the first label to produce the library. Systems may be configured to contact the at least one amplicon with a second label, wherein the second label is detectable. Systems may be configured to produce the library and amplify at least one member of the library with the at least one amplification reagent. The nucleic acid sequence output may be selected from a wireless communication device, a wired communication device, a cable port, and an electronic display. In some instances, all components of the system are present in a single location. In some instances, all components of the system are housed in a single device. In some instances, the sample collector is located at a first location and at least one of the sample purifier and nucleic acid detector are second location. In some instances, the sample collector and at least one of the sample purifier and nucleic acid detector are at the same location. In some instances, the sample purifier comprises a filter. In some instances, the sample purifier comprises a wicking material or capillary device for pushing or pulling the biological fluid through the filter. In some instances, the filter has a pore size of about 0.05 microns to about 2 microns. In some instances, the sample purifier comprises a binding moiety that binds a nucleic acid, protein, cell surface marker, or microvesicle surface marker in the biological fluid sample. In some instances, the binding moiety comprises an antibody, antigen binding antibody fragment, a ligand, a receptor, a peptide, a small molecule, or a combination thereof. In some instances, the binding moiety is capable of binding an extracellular vesicle, wherein the extracellular vesicle is released from a fetal cell or a placental cell of the female subject. In some instances, the binding moiety is attached to a solid support, wherein the solid support can be separated from the rest of the biological sample or the biological sample can be separated from the solid support, after the binding moiety has made contact with the biological sample. Systems may comprise a transport or storage compartment for transporting or storing at least a portion of the fluid sample. In some instances, the transport or storage compartment comprises an absorption pad, a fluid container, a sample preservative, or a combination thereof. In some instances, the transport or storage compartment contains a reagent or material that stabilizes a cell of the fluid sample for transport or storage. Systems may comprise at least one of a container, pouch, wire and cable, for heating or cooling the device of a component thereof. Systems may comprise at least one buffer for at least one of repairing, purifying, amplifying, and sequencing cell-free nucleic acids.

Disclosed herein are devices that comprise a sample collector configured to collect a fluid sample of a subject; a sample processor that is configured to isolate a sample component from the fluid sample; a nucleic acid detector that is configured to detect nucleic acids in the fluid sample or the sample component; and a nucleic acid information output. In some instances, the sample collector comprises a transdermal puncture device. In some instances, the transdermal puncture device comprises at least one of a needle, a lancet, a microneedle, a vacuum, and a microneedle array. In some instances, the sample component is selected from a cell, a carbohydrate, a phospholipid, a protein, a nucleic acid, and a microvesicle. In some instances, the sample component is a blood cell. In some instances, the sample component does not comprise a cell-free nucleic acid. In some instances, the sample component comprises a cell-free nucleic acid. In some instances, the sample component is plasma or serum. The sample purifier may be configured to isolate plasma from less than 1 milliliter of blood. The sample purifier may be configured to isolate plasma from less than 250 µl of blood. The sample purifier may be configured to isolate plasma from less than 150 µl of blood. The sample purifier may be configured to isolate plasma from less than 100 µl of blood. The nucleic acid detector may comprise a nucleic acid sequencer. Devices may be configured to label nucleic acids of interest in the fluid sample, and the nucleic acid detector comprises a counting system that counts the labels to detect a representation of the nucleic acids of interest in the sample. Devices may comprise labels, wherein the labels comprise an oligonucleotide that hybridizes to the nucleic acids of interest. The oligonucleotide may be specific to a chromosomal region of interest. The chromosomal region of interest may be located on a chromosome selected from chromosome 13, chromosome 16, chromosome 18, chromosome 21, chromosome 22, chromosome X, and chromosome Y. The chromosomal region of interest may comprise, or may be capable of comprising, a sequence that is indicative of a disease or condition. The chromosomal region of interest may comprise, or may be capable of comprising, at least one epigenetic modification that is indicative of a disease or condition. The condition may be a genetic abnormality. The condition may be a cancer. The condition may be a transplanted tissue or organ. Devices may comprise at least one nucleic acid amplification reagent selected from a primer, a polymerase, and a combination thereof. The at least one nucleic acid amplification reagent may comprise at least one isothermal amplification reagent. The at least one isothermal amplification reagent may comprise a recombinase polymerase, a single-strand DNA-binding protein, a strand-displacing polymerase, or a combination thereof. Devices may comprise at least one nucleic acid amplification reagent and at least one crowding agent. Devices may comprise at least a first label for producing a library of cell-free nucleic acids from the fluid sample, and at least one amplification reagent. Devices may be configured to amplify the cell-free nucleic acids with the at least one amplification reagent to produce at least one amplicon and contacting the at least one amplicon with at least the first label to produce the library. Devices may be configured to contact the at least one amplicon with a second label, wherein the second label is detectable. Devices may be configured to produce the library and amplify at least one member of the library with the at least one amplification reagent. The nucleic acid sequence output may be selected from a wireless communication device, a wired communication device, a cable port, and an electronic display. In some instances, all components of the device are present in a single location. In some instances, all components of the device are housed in a single device. In some instances, the sample collector is located at a first location and at least one of the sample purifier and nucleic acid detector are second location. In some instances, the sample collector and at least one of the sample purifier and nucleic acid detector are at the same location. In some instances, the sample purifier comprises a filter. In some instances, the sample purifier comprises a wicking material or capillary device for pushing or pulling the biological fluid through the filter. In some instances, the filter has a pore size of about 0.05 microns to about 2 microns. In some instances, the sample purifier comprises a binding moiety that binds a nucleic acid, protein, cell surface marker, or microvesicle surface marker in the biological fluid sample. In some instances, the binding moiety comprises an antibody, antigen binding antibody fragment, a ligand, a receptor, a peptide, a small molecule, or a combination thereof. In some instances, the binding moiety is capable of binding an extracellular vesicle, wherein the extracellular vesicle is released from a fetal cell or a placental cell of the female subject. In some instances, the binding moiety is attached to a solid support, wherein the solid support can be separated from the rest of the biological sample or the biological sample can be separated from the solid support, after the binding moiety has made contact with the biological sample. Devices may comprise a transport or storage compartment for transporting or storing at least a portion of the fluid sample. In some instances, the transport or storage compartment comprises an absorption pad, a fluid container, a sample preservative, or a combination thereof. In some instances, the transport or storage compartment contains a reagent or material that stabilizes a cell of the fluid sample for transport or storage. Devices may comprise at least one of a container, pouch, wire and cable, for heating or cooling the device of a component thereof. Devices may comprise at least one buffer for at least one of repairing, purifying, amplifying, and sequencing cell-free nucleic acids.

Further disclosed herein is the use of a system for detecting the presence of a tumor in the subject. Disclosed herein is the use of a system for detecting an aneuploidy of a fetus in the subject. Further disclosed herein is the use of a system for detecting the status of a transplanted organ in the subject. Disclosed herein is the use of a device for detecting the presence of a tumor in the subject. Further disclosed herein is the use of a device for detecting an aneuploidy of a fetus in the subject. Disclosed herein is the use of a device for detecting the status of a transplanted organ in the subject.

In some aspects, disclosed herein are methods comprising: obtaining a biological sample from a pregnant subject, wherein the biological sample contains up to about $10^9$ cell-free fetal nucleic acid molecules; sequencing at least a portion of the cell-free fetal nucleic acid molecules to produce sequencing reads; measuring at least a portion of sequencing reads corresponding to at least one chromosomal region; and detecting a normal representation, an overrepresentation or an underrepresentation of the at least one chromosomal region. In some instances, the biological sample has a volume of less than about 500 µl. In some instances, the biological sample has a volume of about 1 µl to about 100 µl. In some instances, the biological sample has a volume of about 5 µl to about 80 µl. In some instances, the biological sample has a volume of about 5 µl to about 60 µl. In some instances, methods comprise amplifying the cell-free fetal nucleic acid molecules before sequencing. In some instances, methods comprise tagging the cell-free fetal nucleic acid molecules before sequencing and after amplifying. In some instances, methods comprise tagging the cell-free fetal nucleic acid molecules before sequencing. In some instances, methods comprise amplifying the cell-free fetal nucleic acid molecules after tagging the cell-free fetal nucleic acid molecules. In some instances, methods comprise detecting an overrepresentation of sequencing reads corresponding to at least one target chromosome. In some instances, methods comprise detecting an underrepresentation of sequencing reads corresponding to at least one target chromosome. In some instances, methods comprise comparing the number of sequencing reads corresponding to the at least one target chromosome to a reference number of sequencing reads corresponding to the at least one target chromosome. In some instances, the reference number is based on at least one sample from at least one euploid pregnant subject with a euploid fetus. In some instances, the reference number is based on at least one sample from at least one euploid pregnant subject with an aneuploid fetus. In some instances, the at least one sample is the same sample type and same sample volume as the biological sample. In some instances, methods comprise measuring at least 1000 sequencing reads corresponding to the at least one chromosomal region. In some instances, methods comprise measuring at least 1000 sequencing reads corresponding to at least one non-target chromosomal region. In some instances, methods comprise detecting that there is a fetal aneuploidy of the at least one target chromosomal region when a ratio of sequencing reads corresponding to the at least one target chromosome to sequencing reads corresponding to the at least one non-target chromosome is different from a respective ratio in a control biological sample from a control pregnant euploid subject with a euploid fetus. In some instances, methods comprise detecting, that there is not a fetal aneuploidy of the at least one target chromosome when a ratio of sequencing reads corresponding to the at least one target chromosome to sequencing reads corresponding to the at least one non-target chromosome is the same as a respective ratio in a control biological sample from a control pregnant euploid subject with a euploid fetus. In some instances, the biological sample is biological fluid. In some instances, the biological sample comprises blood, plasma, serum, urine, interstitial fluid, vaginal cells, vaginal fluid, buccal cells, or saliva. In some instances, the biological sample is serum or plasma. In some instances, methods comprise separating the plasma or serum from a blood sample. In some instances, separating comprises filtering the blood sample to remove cells, cell fragments, microvesicles, or a combination thereof, from the blood sample to produce the plasma sample. In some instances, methods comprise obtaining a blood sample from the pregnant subject, the blood sample having a volume of about 5 µl to about 1 ml. In some instances, methods comprise obtaining a blood sample from the pregnant subject, the blood sample having a volume of about 5 µl to about 150 µl. In some instances, obtaining the blood sample comprises contacting the subject with a transdermal puncture device. In some instances, obtaining the blood sample comprises a pricking a finger. In some instances, methods comprise milking blood from the pricked finger. In some instances, obtaining the blood sample does not comprise a phlebotomy. In some instances, the biological sample contains about $10^4$ to about $10^9$ cell-free fetal nucleic acid molecules. In some instances, the biological sample contains about $10^4$ to about $10^8$ cell-free fetal nucleic acid molecules. In some instances, the biological sample contains about $10^4$ to about $10^7$ cell-free fetal nucleic acid molecules. In some instances, the biological sample comprises about $10^6$ to about $10^{12}$ total cell-free nucleic acid molecules, wherein the total cell-free nucleic acid molecules consist essentially of the cell-free fetal nucleic acid molecules and maternal cell-free nucleic acid molecules. In some instances, the biological sample contains less than 3 ng of total cell-free nucleic acid molecules. In some instances, the biological sample contains less than 300 pg of cell-free fetal nucleic acid molecules. In some instances, the pregnant subject is as few as 5 weeks pregnant. In some instances, amplifying comprises contacting the cell-free fetal nucleic acid molecules with random oligonucleotide primers. In some instances, amplifying comprises isothermal amplification. In some instances, amplifying occurs at room temperature. In some instances, the status is detected with greater than 98% accuracy. In some instances, the status is detected with greater than 99% accuracy. In some instances, the at least one chromosome region is located on at least one of chromosome 13, chromosome 16, chromosome 18, chromosome 21, chromosome 22, chromosome X, or chromosome Y. In some instances, the at least one non-target chromosomal region is at least one of a chromosome other than chromosome 13, chromosome 16, chromosome 18, chromosome 21, chromosome 22, chromosome X, or chromosome Y. In some instances, the pregnant subject is euploid. In some instances, sequencing comprises whole genome sequencing. In some instances, sequencing comprises random massively parallel sequencing. In some instances, sequencing comprises targeted sequencing. In some instances, the biological sample contains about $10^4$ to about $10^9$ cell-free fetal nucleic acids. In some instances, the biological sample contains about $10^4$ to about $10^8$ cell-free fetal nucleic acids. In some instances, methods comprise sequencing at least 2000 of the cell-free fetal nucleic acids. In some instances, methods comprise measuring at least 1000 of the sequencing reads corresponding to at least one target chromosome. In some instances, representation of the chromosomal region is relative to control representation in at least one control pregnant subject carrying a control fetus. In some instances, at least one of the control pregnant subject and control fetus does not have an aneuploidy. In some instances, at least one of the control pregnant subject and control fetus does not have a genetic abnormality. In some instances, at least one of the control pregnant subject and control fetus has an aneuploidy corresponding to the chromosomal region. In some instances, at least one of the control pregnant subject and control fetus has a genetic abnormality corresponding to the target chromosomal region.

In some aspects, disclosed herein are methods comprising obtaining a biological sample from a pregnant subject, wherein the biological sample contains up to about $10^9$ cell-free fetal nucleic acid molecules; tagging at least a portion of the cell-free fetal nucleic acid molecules to produce tagged cell-free fetal nucleic acid molecules; measuring the number of tagged cell-free fetal nucleic acid molecules; and detecting a normal representation, an overrepresentation or an underrepresentation of the at least one chromosomal region. In some instances, tagging at least a portion of the cell-free fetal nucleic acid molecules comprises tagging cell-free fetal nucleic acid molecules from a target chromosomal region. In some instances, the method does not comprise sequencing. In some instances, methods comprise obtaining a plurality of biological sample from at least one pregnant subject, wherein the biological samples each contain up to about $10^9$ cell-free fetal nucleic acid molecules; and indexing the cell-free fetal nucleic acid molecules from each biological sample with a different index, thereby providing a sample identifier to the cell-free fetal nucleic acid molecules. In some instances, methods comprise tagging the cell-free fetal nucleic acid molecules from a target chromosomal region.

In some aspects, disclosed herein are systems that comprise a sample collector for collection of a fluid sample of a pregnant subject; a sample purifier that captures or removes a sample component from the fluid sample; a nucleic acid detector; and a nucleic acid information output. In some instances, the sample collector comprises a transdermal puncture device. In some instances, the transdermal puncture device is selected from a needle, a lancet, a microneedle, and a microneedle array. In some instances, the sample component is selected from a cell, a protein, a nucleic acid, and a microvesicle. In some instances, the nucleic acid detector comprises a nucleic acid sequencer. In some instances, the nucleic acid detector comprises a counting system that labels nucleic acids of interest in the fluid sample and counts the labels to detect a representation of the nucleic acids of interest in the sample. In some instances, the counting system comprises labels, wherein the labels comprise an oligonucleotide that hybridizes to the nucleic acids of interest. In some instances, the nucleic acid sequence output is selected from a wireless communication device, a wired communication device, a cable port, and an electronic display. In some instances, all components of the system are present in a single location. In some instances, all components of the system are housed in a single device. In some instances, the sample collector is located at a first location and at least one of the sample purifier and nucleic acid detector are second location. In some instances, the sample purifier comprises a filter. In some instances, the sample purifier comprises a wicking material or capillary device for pushing the biological fluid through the filter. In some instances, the filter has a pore size of about 0.05 microns to about 2 microns. In some instances, the sample purifier comprises a binding moiety that binds a nucleic acid, protein, cell surface marker, or microvesicle surface marker in the biological fluid sample. In some instances, the binding moiety comprises an antibody, antigen binding antibody fragment, a ligand, a receptor, a peptide, a small molecule, or a combination thereof. In some instances, the binding moiety is capable of binding an extracellular vesicle, wherein the extracellular vesicle is released from a fetal cell or a placental cell of the female subject. In some instances, the binding moiety is attached to a solid support, wherein the solid support can be separated from the rest of the biological sample or the biological sample can be separated from the solid support, after the binding moiety has made contact with the biological sample. In some instances, the system comprises at least one nucleic acid amplification reagent selected from a primer, a polymerase, and a combination thereof. In some instances, the at least one nucleic acid amplification reagent comprises at least one isothermal amplification reagent. In some instances, the at least one isothermal amplification reagent comprises a recombinase polymerase, a single-strand DNA-binding protein, a strand-displacing polymerase, or a combination thereof. In some instances, systems comprise a transport or storage compartment for transporting at least a portion of the biological sample. In some instances, the transport or storage compartment comprises an absorption pad, a fluid container, a sample preservative, or a combination thereof. In some instances, systems comprise at least one of a container, pouch, wire and cable, for heating or cooling the device of a component thereof. In some instances, systems comprise at least one buffer for at least one of repairing, purifying, amplifying, and sequencing cell-free nucleic acids.

Other objects, features and advantages of the present disclosure will become apparent to those skilled in the art from the following detailed description. It is to be understood, however, that the detailed description and specific examples, while indicating some embodiments of the present disclosure are given by way of illustration and not limitation. Many changes and modifications within the scope of the present disclosure may be made without departing from the spirit thereof, and the disclosure includes all such modifications. Moreover aspects of one embodiment may be utilized in other, different embodiments.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the methods, devices, systems and kits disclosed herein are set forth with particularity in the appended claims. A better understanding of the features and advantages of the present devices, systems and kits disclosed herein will be obtained by reference to the following detailed description that sets forth illustrative embodiments, in which the principles of the devices, systems and kits disclosed herein are utilized, and the accompanying drawings of which:

FIG. 5 shows a mobile device and how a mobile application is configured to connect with, communicate with, and receive genetic information and other information from the devices, systems and kits disclosed herein.

Certain Terminologies

Figure 1:
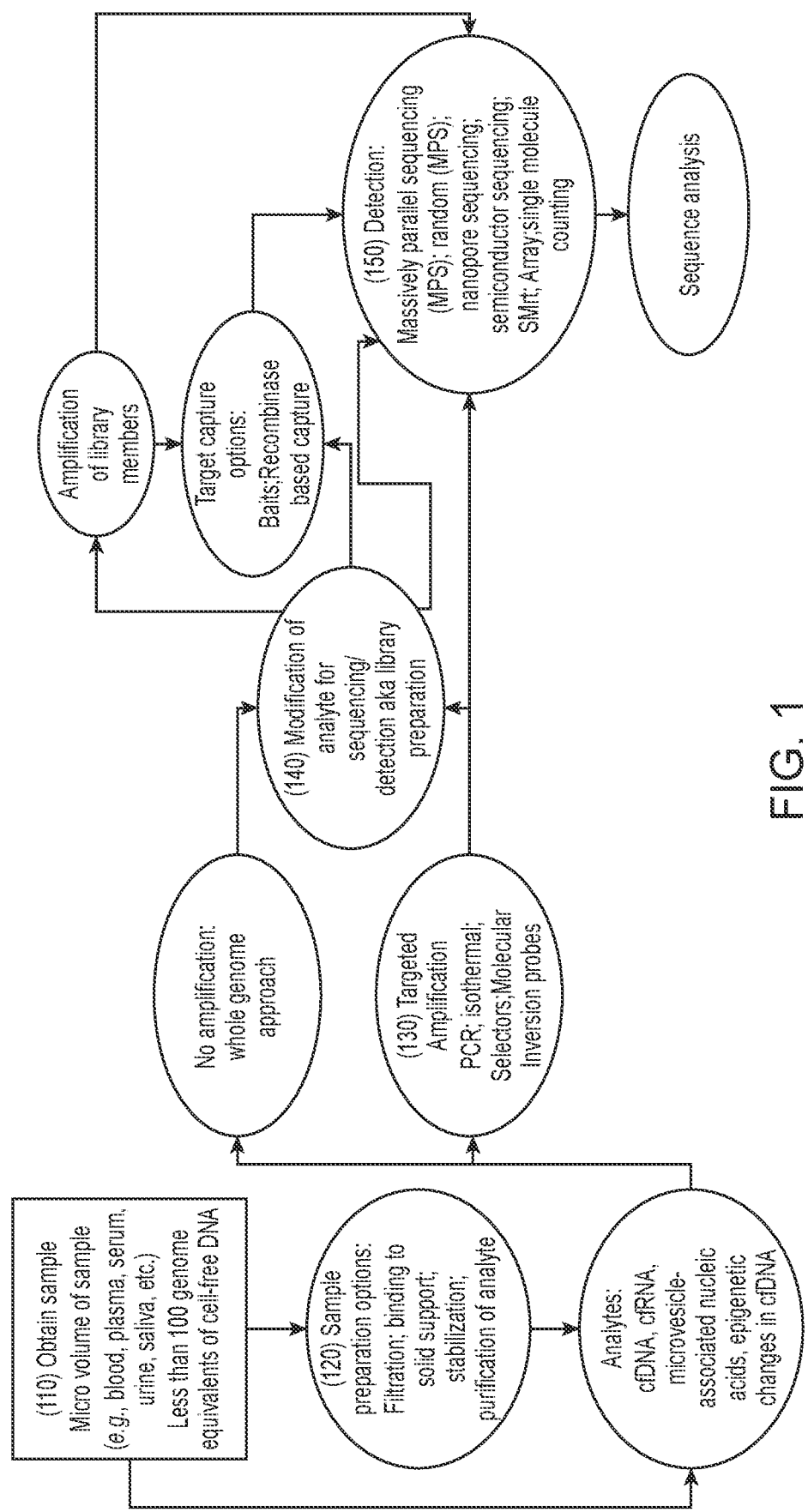
FIG. 1 shows optional workflows for methods disclosed herein.

The following descriptions are provided to aid the understanding of the methods, systems and kits disclosed herein. The following descriptions of terms used herein are not intended to be limiting definitions of these terms. These terms are further described and exemplified throughout the present application.

In general, the terms "cell-free polynucleotide," "cell-free nucleic acid," used interchangeably herein, refer to polynucleotides and nucleic acids that can be isolated from a sample without extracting the polynucleotide or nucleic acid from a cell. A cell-free nucleic acid may comprise DNA. A cell-free nucleic acid may comprise RNA. A cell-free nucleic acid is a nucleic acid that is not contained within a cell membrane, i.e., it is not encapsulated in a cellular compartment. In some embodiments, a cell-free nucleic acid is a nucleic acid that is not bounded by a cell membrane and is circulating or present in blood or other fluid. In some embodiments, the cell-free nucleic acid is cell-free before and/or upon collection of the biological sample containing it, and is not released from the cell as a result of sample manipulation by man, intentional or otherwise, including manipulation upon or after collection of the sample. In some instances, cell-free nucleic acids are produced in a cell and released from the cell by physiological means, including, e.g., apoptosis, and non-apoptotic cell death, necrosis, autophagy, spontaneous release (e.g., of a DNA/RNA-lipoprotein complex), secretion, and/or mitotic catastrophe. In some embodiments, a cell-free nucleic acid comprises a nucleic acid that is released from a cell by a biological mechanism, (e.g., apoptosis, cell secretion, vesicular release). In further or additional embodiments, a cell-free nucleic acid is not a nucleic acid that has been extracted from a cell by human manipulation of the cell or sample processing (e.g., cell membrane disruption, lysis, vortex, shearing, etc.).

In some instances, the cell-free nucleic acid is a cell-free fetal nucleic acid. In general, the term, "cell-free fetal nucleic acid," as used herein, refers to a cell-free nucleic acid, as described herein, wherein the cell-free nucleic acid is from a cell that comprises fetal DNA. In pregnant women, the cell-free DNA originating from the placenta can contribute a noticeable portion of the total amount of cell-free DNA. Placental DNA is often a good surrogate for the fetal DNA, because in most cases it is highly similar to the DNA of the fetus. Applications like chorionic villus sampling have exploited this fact to establish diagnostic application. Often, a large portion of cell-free fetal nucleic acids are found in maternal biological samples as a result of placental tissue being regularly shed during the pregnant subject's pregnancy. Often, many of the cells in the placental tissue shed are cells that contain fetal DNA. Cells shed from the placenta release fetal nucleic acids. Thus, in some instances, cell-free fetal nucleic acids disclosed herein are nucleic acids release from a placental cell.

As used herein, the term "cellular nucleic acid" refers to a polynucleotide that is contained in a cell or released from a cell due to manipulation of the biological sample. Non-limiting examples of manipulation of the biological sample include centrifuging, vortexing, shearing, mixing, lysing, and adding a reagent (e.g., detergent, buffer, salt, enzyme) to the biological sample that is not present in the biological sample when it is obtained. In some instances, the cellular nucleic acid is a nucleic acid that has been released from a cell due to disruption or lysis of the cell by a machine, human or robot. In some instances, cellular nucleic acids (nucleic acids contained by cells) are intentionally or unintentionally released from cells by devices and methods disclosed herein. However, these are not considered "cell-free nucleic acids," as the term is used herein. In some instances, devices, systems, kits and methods disclosed herein provide for analyzing cell-free nucleic acids in biological samples, and in the process analyze cellular nucleic acids as well.

As used herein, the term "biomarker" generally refers to any marker of a subject's biology or condition. A biomarker may be an indicator or result of a disease or condition. A biomarker may be an indicator of health. A biomarker may be an indicator of a genetic abnormality or inherited condition. A biomarker may be a circulating biomarker (e.g., found in a biological fluid such as blood). A biomarker may be a tissue biomarker (e.g., found in a solid organ such as liver or bone marrow). Non-limiting examples of biomarkers include nucleic acids, epigenetic modifications, proteins, peptides, antibodies, antibody fragments, lipids, fatty acids, sterols, polysaccharides, carbohydrates, viral particles, microbial particles. In some cases, biomarkers may even include whole cells or cell fragments.

As used herein, the term, "tag" generally refers to a molecule that can be used to identify, detect or isolate a nucleic acid of interest. The term, "tag," may be used interchangeably with other terms, such as "label," "adapter," "oligo," and "barcode," unless specified otherwise. Note, however, that the term, "adapter," can be used to ligate two ends of a nucleic acid or multiple nucleic acids without acting as a tag.

As used herein, the term "genetic information" generally refers to one or more nucleic acid sequences. In some instances, genetic information may be a single nucleotide or amino acid. For example, genetic information could be the presence (or absence) of a single nucleotide polymorphism. Unless specified otherwise, the term "genetic information" may also refer to epigenetic modification patterns, gene expression data, and protein expression data. In some instances, the presence, absence or quantity of a biomarker provides genetic information. For instance, cholesterol levels may be indicative of a genetic form of hypercholesterolemia. Thus, genetic information should not be limited to nucleic acid sequences.

As used herein, the term, "genetic mutation," generally refers to an alteration of a nucleotide sequence of a genome. A genetic mutation is different from natural variation or allelic differences. The genetic mutation may be found in less than 10% of the subject's species. The genetic mutation may be found in less than 5% of the subject's species. The genetic mutation may be found in less than 1% of the subject's species. A genetic mutation in a subject may cause a disease or a condition in the subject. The genetic mutation may result in a frameshift of a protein-coding sequence. The genetic mutation may result in a deletion of at least a portion of a protein-coding sequence. The genetic mutation may result in a loss of a stop codon in a protein-coding sequence. The genetic mutation may result in a premature stop codon in a protein-coding sequence. The genetic mutation may result in a sequence that encodes a misfolded protein. The genetic mutation may result in a sequence that encodes a dysfunctional protein or non-functional protein (e.g., loss of binding or enzymatic activity). The genetic mutation may result in a sequence that encodes an overactive protein (e.g., increased binding or enzymatic activity). The genetic mutation my affect a single nucleotide (e.g., a single nucleotide variation or single nucleotide polymorphism). The genetic mutation my affect multiple nucleotides (e.g., frameshift, translocation).

As used herein, the terms, "healthy individual" and "healthy subject" refer to a subject that does not have a condition or disease of interest. For example, if the method or device being described is being used to detect a type of cancer, a healthy subject does not have that type of cancer. The healthy subject may not have cancer at all. In some instances, the healthy subject is not diagnosed with any disease or condition. In some instances, the healthy subject does not have a known genetic mutation. In some instances, the healthy subject does not have a genetic mutation that results in a detectable phenotype that would distinguish the subject from a healthy subject that does not have a known genetic mutation. In some instances, the healthy subject is not infected by a pathogen. In some instances, the healthy subject is infected by a pathogen, but has no known genetic mutation.

As used herein, the term "genomic equivalent" generally refers to the amount of DNA necessary to be present in a purified sample to guarantee that all genes will be present.

As used herein, the term "tissue-specific," or the phrase, "specific to a tissue," generally refers to a polynucleotide that is predominantly expressed in a specific tissue. Often, methods, systems and kits disclosed herein utilize cell-free, tissue-specific polynucleotides. Cell-free, tissue-specific polynucleotides described herein are polynucleotides expressed at levels that can be quantified in a biological fluid upon damage or disease of the tissue or organ in which they are expressed. In some cases, the presence of cell-free tissue-specific polynucleotides disclosed herein in a biological fluid is due to release of cell-free tissue-specific polynucleotides upon damage or disease of the tissue or organ, and not due to a change in expression of the cell-free tissue-specific polynucleotides. Elevated levels of cell-free tissue-specific polynucleotides disclosed herein may be indicative of damage to the corresponding tissue or organ. In some instances, cell-free polynucleotides disclosed herein are expressed/produced in several tissues, but at tissue-specific levels in at least one of those tissues. In these cases, the absolute or relative quantity of the cell-free tissue-specific polynucleotide is indicative of damage to, or disease of, a specific tissue or organ, or collection of tissues or organs. Alternatively or additionally, tissue-specific polynucleotides are nucleic acids with tissue-specific modifications. Tissue-specific polynucleotides may comprise RNA. Tissue-specific polynucleotides may comprise DNA. By way of non-limiting example, tissue-specific polynucleotides or markers disclosed herein include DNA molecules (e.g., a portion of a gene or non-coding region) with tissue-specific methylation patterns. In other words, the polynucleotides and markers may be expressed similarly in many tissues, or even ubiquitously throughout a subject, but the modifications are tissue-specific. Generally, tissue-specific polynucleotides or levels thereof disclosed herein are not specific to a disease. Generally, tissue-specific polynucleotides disclosed herein do not encode a protein implicated in a disease mechanism.

In some instances, a tissue-specific polynucleotide is present in a greater amount in a tissue of interest than it is present in blood of the subject. In some instances, the RNA is present in a greater amount in a tissue of interest than it is present in a blood cell. In some instances, the tissue-specific polynucleotide is not expressed by a blood cell. In some instances, the presence of the tissue-specific polynucleotide is at least two fold greater in the tissue than in the blood. In some instances, the presence of the tissue-specific polynucleotide is at least five fold greater in the tissue than in the blood. In some instances, the presence of the tissue-specific polynucleotide is at least ten fold greater in the tissue than in the blood.

In some instances, the presence of the tissue-specific polynucleotide is at least three fold higher in the tissue than any other tissue of the subject. In some instances, the presence of the tissue-specific polynucleotide is at least five fold higher in the tissue than any other tissue. In some instances, the presence of the tissue-specific polynucleotide is at least ten fold higher in the tissue than any other tissue. In some instances, the presence of the tissue-specific polynucleotide is at least three fold higher in no more than two tissues than any other tissue. In some instances, the presence of the tissue-specific polynucleotide is at least five fold higher in no more than two tissues than any other tissue. In some instances, the presence of the tissue-specific polynucleotide is at least ten fold higher in no more than two tissues than any other tissue. In some instances, the presence of the tissue-specific polynucleotide is at least three fold higher in no more than three tissues than any other tissue. In some instances, the presence of the tissue-specific polynucleotide is at least five fold higher in no more than three tissues than any other tissue. In some instances, the presence of the tissue-specific polynucleotide is at least ten fold higher in no more than three tissues than any other tissue.

In some instances, the tissue-specific polynucleotide is specific to a target cell type. In some instances, the presence of the tissue-specific polynucleotide is at least three fold higher in the target cell type than a non-target cell type. In some instances, the presence of the tissue-specific polynucleotide is at least five fold higher in the target cell type than the non-target other cell type. In some instances, the presence of the tissue-specific polynucleotide is at least ten fold higher in the target cell type than the non-target cell type. In some instances, the presence of the tissue-specific polynucleotide is at least three fold higher in no more than two target cell types than non-target cell types. In some instances, the presence of the tissue-specific polynucleotide is at least five fold higher in no more than two target cell types than non-target cell types. In some instances, the RNA is expressed at least ten fold higher in no more than two target cell types than non-target cell types. In some instances, the presence of the tissue-specific polynucleotide is at least three fold higher in no more than three target cell types than non-target cell types. In some instances, the presence of the tissue-specific polynucleotide is at least five fold higher in no more than three target cell types than non-target cell types. In some instances, the presence of the tissue-specific polynucleotide is at least ten fold higher in no more than three target cell types than non-target cell types.

As used herein, the terms, "isolate," "purify," "remove," "capture," and "separate," may all be used interchangeably unless specified otherwise.

As used herein, the terms, "clinic," "clinical setting," "laboratory" or "laboratory setting" refer to a hospital, a clinic, a pharmacy, a research institution, a pathology laboratory, a or other commercial business setting where trained personnel are employed to process and/or analyze biological and/or environmental samples. These terms are contrasted with point of care, a remote location, a home, a school, and otherwise non-business, non-institutional setting.

As used herein, the term 'about' a number refers to that number plus or minus 10% of that number. The term 'about' when used in the context of a range refers to that range minus 10% of its lowest value and plus 10% of its greatest value.

As used herein, the singular forms "a", "an" and "the" include plural references unless the context clearly dictates otherwise. For example, the term "a sample" includes a plurality of samples, including mixtures thereof.

The term, "accuracy," should be given its broadest definition in light of the specification. However, the term "accuracy" may be used to refer to a statistical measure of how well a binary classification test correctly identifies or excludes a condition. As used herein, the term "accuracy" may also refer to the proportion of true results (both true positives and true negatives) among all samples examined. As used herein, the term "accuracy" may encompass "Rand accuracy" or accuracy as determined by the "Rand index."

As used herein, the terms "homologous," "homology," or "percent homology" describe sequence similarity of a first amino acid sequence or a nucleic acid sequence relative to a second amino acid sequence or a nucleic acid sequence. In some instances, homology can be determined using the formula described by Karlin and Altschul (Proc. Natl. Acad. Sci. USA 87: 2264-2268, 1990, modified as in Proc. Natl. Acad. Sci. USA 90:5873-5877, 1993). Such a formula is incorporated into the basic local alignment search tool (BLAST) programs of Altschul et al. (J. Mol. Biol. 215: 403-410, 1990). Percent homology of sequences can be determined using the most recent version of BLAST, as of the filing date of this application. In some cases, 2 or more sequences may be homologous if they share at least 20%, 25%, 30%. 35%, 40%, 45% 50%, 55%, 60% identity, 65%, 70%, 75%, 80%, 85%, 90%, 91%, 92%, 93%, 94%, 95%, 96%, 97%, 98%, 99% or higher identity when compared and aligned for maximum correspondence over a comparison window, or designated region as measured using one of the following sequence comparison algorithms or by manual alignment and visual inspection. In some cases, 2 or more sequences may be homologous if they share at most 20%, 25%, 30%. 35%, 40%, 45% 50%, 55%, 60% identity, 65%, 70%, 75%, 80%, 85%, 90%, 91%, 92%, 93%, 94%, 95%, 96%, 97%, 98%, 99% or higher identity. Preferably, the % identity or homology exists over a region that is at least 16 amino acids or nucleotides in length or in some cases over a region that is about 50 to about 100 amino acids or nucleotides in length. In some cases, the % identity or homology exists over a region that is about 100 to about 1000 amino acids or nucleotides in length. In some cases, 2 or more sequences may be homologous and share at least 20% identity over at least 100 amino acids in a sequence. For sequence comparison, generally one sequence acts as a reference sequence, to which test sequences may be compared. When using a sequence comparison algorithm, test and reference sequences may be entered into a computer, subsequent coordinates may be designated, if necessary, and sequence algorithm program parameters may be designated. Any suitable algorithm may be used, including but not limited to Smith-Waterman alignment algorithm, Viterbi, Bayesians, Hidden Markov and the like. Default program parameters can be used, or alternative parameters can be designated. The sequence comparison algorithm may then be used to calculate the percent sequence identities for the test sequences relative to the reference sequence, based on the program parameters. Any suitable algorithm may be used, whereby a percent identity is calculated. Some programs for example, calculate percent identity as the number of aligned positions that identical residues, divided by the total number of aligned positions. A "comparison window", as used herein, includes reference to a segment of any one of the number of contiguous or non-contiguous positions which may range from 10 to 600 positions. In some cases the comparison window may comprise at least 10, 20, 50, 100, 200, 300, 400, 500, or 600 positions. In some cases the comparison window may comprise at most 10, 20, 50, 100, 200, 300, 400, 500, or 600 positions. In some cases the comparison window may comprise at least 50 to 200 positions, or at least 100 to at least 150 positions in which a sequence may be compared to a reference sequence of the same number of contiguous or non-contiguous positions after the two sequences are optimally aligned. Methods of alignment of sequences for comparison are well-known in the art. Optimal alignment of sequences for comparison can be conducted, e.g., by the local homology algorithm of Smith and Waterman, Adv. Appl. Math. 2:482 (1981), by the homology alignment algorithm of Needleman and Wunsch, J. Mol. Biol. 48:443 (1970), by the search for similarity method of Pearson and Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al, eds. 1995 supplement)). In some cases, a comparison window may comprise any subset of the total alignment, either contiguous positions in primary sequence, adjacent positions in tertiary space but discontinuous in the primary sequence, or any other subset of 1 up to all residues in the alignment.

As used herein, the terms overrepresentation and underrepresentation generally refer to the difference between a sample and a control representation of target nucleic acids. A representation may be significantly less than a control representation and therefore underrepresented. A representation may be significantly more than a control representation and therefore underrepresented. The significance may be statistical. Methods of determining statistical significance are well known in the art. By way of non-limiting example, statistical significance performed using standard two-tailed t-test (*: $p<0.05$; **$p<0.01$).

As used herein, the term "cloud" refers to shared or sharable storage of electronic data. The cloud may be used for archiving electronic data, sharing electronic data, and analyzing electronic data.

Throughout the application, there is recitation of the phrases "nucleic acid corresponding to a chromosome," and "sequence corresponding to a chromosome." As used herein, these phrases are intended to convey that the "nucleic acid corresponding to the chromosome" is represented by a nucleic acid sequence that is identical or homologous to a sequence found in that chromosome. The term "homologous" is described in the foregoing description.

DETAILED DESCRIPTION OF THE INVENTION

Genetic testing is traditionally performed in a laboratory or clinical setting. However, in many instances where genetic testing would be useful, access to a laboratory or clinic is unavailable or impractical. High complexity testing such as analysis of circulating tumor DNA or fetal DNA testing is still rare because of limited access to such tests (e.g., requirement for a phlebotomy, timing, appointments required, distance to a clinic/laboratory) and cost of such tests (e.g., costs of performing a phlebotomy, processing milliliters of samples, sample tubes and reagents, shipping, particularly cold shipping). Thus, genetic tests that are operable at a point of need (e.g., locations remote from laboratories and clinics) are desirable. Genetic tests for operation at a point of need (e.g., home, school, farm) are preferably cost effective and simple for an untrained individual to perform. Genetic tests at point of need preferably require only small amounts of a biological sample. Traditionally, genetic testing requires a venous blood draw (phlebotomy) to obtain milliliters of blood containing enough DNA to be analyzed. However, a phlebotomy is not practical at a point of need. Ideally, a genetic test would only require amounts of blood achieved through the retrieval of capillary blood, e.g., via a transdermal puncture device. This means point of need devices and methods for genetic testing need to be designed to function with ultra-low inputs of sample and a lower abundance of target molecules that are intended to be detected.

In addition to accommodating ultra-low inputs of sample, it is desirable to have a genetic test that is capable of analyzing circulating cell-free nucleic acids (DNA and RNA), e.g., circulating cell-free fetal DNA, circulating tumor DNA, circulating DNA from a transplanted donor organ, and circulating DNA released from a specific tissue as part of a health related issue, disease progression or treatment response. However, analysis of circulating cell-free nucleic acids is challenging due to their short half-life and therefore low abundance. In addition, circulating cell-free nucleic acids in blood can be diluted by DNA released from white blood cells if care is not taken with the sample to avoid white blood cell lysis. White blood cell DNA creates background noise during detection of circulating cell-free nucleic acids, decreasing assay sensitivity and specificity.

Devices, systems, kits and methods disclosed herein overcome these challenges by combining gentle and efficient processing of small sample volumes (e.g., less than 1 ml) with a unique target region selection and assay design that takes advantage of the highly fragmented nature of circulating cell-free DNA (cfDNA). For example, devices, systems, kits and methods disclosed herein may provide reliable genetic information from a single finger prick. Devices, systems, kits and methods disclosed herein provide for analysis of multiple target regions along a target gene that are spaced far enough apart that the target regions are likely going to be physically separate when the target gene is fragmented in circulation. Thus, while the above described limits of statistical sampling exist for individual long DNA fragments that are traditionally analyzed in genetic testing, the sampling statistics change favorably for cfDNA fragments. While there may be an aggregate of only 1 genome equivalent present in a capillary blood sample, there are many individual cfDNA fragments. Consequently, sensitive amplification can be achieved from ultra-low input amounts.

As an example, if twenty target regions are present along a genomic region and they are spaced far enough apart that they can be independently analyzed and detected when the region is fragmented, the input volume required to have at least 1 target region in 99% of all samples changes from 140 µl to 25 µl, significantly increasing sensitivity. In some instances, the target regions contain identical sequences or similar sequences. These target regions may be referred to as copies.

In other instances, target regions may not share similar sequences, but share another characteristic such as a similar epigenetic status. For example, the target regions may have different sequences but they are all hyper-methylated. Regardless of the basis for the similarity between the regions, they are spaced appropriately to leverage the fragmentation pattern of circulating cell-free DNA which produces many circulating cfDNA fragments of which at least one can be detected in a small volume. By way of non-limiting example, selected target regions that are distant enough from each other to be on separate cfDNA fragments and are all hyper-methylated when a subject has cancer can be detected with bisulfite sequencing. In a small sample volume (e.g., a finger prick of blood), the likelihood that all of these fragments are present (which is equivalent to non-fragmented DNA) is low, but the likelihood that at least one fragment is present is high, and the cancer can be detected.

In yet other instances, the target regions may not contain similar sequences and may not contain similar epigenetic status. In this case, detection may require multiple primer sets or library preparation followed by amplification with universal primers to detect several distinct target regions. By way of non-limiting example, the detection of a fetal RHD gene in an RHD negative pregnant mother could be achieved from a finger prick amount of blood by using multiple sets of primers to detect multiple different exons of the RHD gene in cell-free fetal DNA fragments. Sensitivity can be increased by choosing primers that amplify regions that are physically distant in the RHD gene and therefore likely to be present on different cell-free DNA fragments. Detecting a fetal RHD gene in an RHD negative pregnant mother is important to prevent hemolytic disease of a newborn by the mother having antibodies against the child's blood. RHD testing is currently performed today from full blood draws (eight milliliters of blood) to achieve the appropriate reliable results. This volume is believed to be necessary to achieve reliable results because it is based on the likelihood that the entire RHD gene will be present in the sample. Based on this assumption, the likelihood of getting the whole RHD gene in a finger prick amount of blood is low and would easily lead to false negative results.

Regardless of how target regions are chosen, these regions are present in the sample as individual biomarkers when amplification or detection is performed on cell-free fragmented DNA. The concentration of the fragments containing the target region is greater than the corresponding non-fragmented DNA or a fragment that cannot be assayed as a group. Thus, there will be more signal from the target region than one would get from non-fragmented DNA or from assaying for one copy of the target region. One will be much more likely to detect a target region present in an ultra-low volume of sample than a non-target region that is not repeated or does not share some commonality with another region. By assaying multiple target regions in multiple DNA fragments, assay sensitivity is increased relative to traditional testing.

Blood is a reliable source of cell-free nucleic acids. The methods disclosed herein for analyzing cell-free nucleic acids from blood involve isolating the plasma or serum fraction containing the cell-free nucleic acids. Devices, systems, kits and methods disclosed herein allow for gentle processing of a blood sample at a point of need. This may avoid, prevent or reduce white blood cell lysis. Devices, systems, kits and methods disclosed herein allow for rapid processing of a blood sample at a point of need. This avoids elongated storage and shipment of samples that can lead to blood cell lysis. In some instances, devices disclosed herein perform integrated separation, e.g. immediate isolation of plasma through filtration, to avoid, reduce or prevent cell lysis. Immediate separation of cells from cfDNA may be desirable when a reagent (e.g., probe, primer, antibody) or detection method does not provide much specificity. In some instances, methods are performed with whole blood in an effort to avoid any white blood cell lysis. When relatively higher specificity can be achieved, analysis from whole blood may be more desirable.

In addition to requiring only small volumes of samples, devices, systems, kits and methods disclosed herein are highly desirable for at least the following reasons. Devices, systems, kits and methods disclosed herein generally require little to no technical training. Thus, the costs of performing genetic testing is reduced relative to the cost of testing performed by trained personnel, and the test is available to subjects who do not have access to trained personnel. Furthermore, results may be obtained within minutes (e.g., less than an hour). This may be especially important when testing for an infection. An individual or animal testing positive for an infection may be isolated and treated quickly, preventing the spread of infection. Moreover, results may be obtained privately. In some cases, only the patient that is being tested is privy to the genetic information obtained. Devices, systems and kits disclosed herein are generally lightweight and handheld, making them suitable and accessible to remote locations. Thus, they may be employed at home, in a school, in a workplace, on a battlefield, on a farm, or any other site where it would be impractical or inconvenient to visit a laboratory or clinical setting. Furthermore, since the sample may be analyzed at the point of care, the sample does not need to be stored or shipped, reducing the risk of sample degradation and misidentification (e.g., sample swapping).

FIG. 1 shows a general flow chart with various routes that methods, devices and systems disclosed herein can follow. Initially a sample is obtained in step 110. A minimal amount of sample must be obtained in order to gather useful information from the sample. The sample may be a biological sample disclosed herein. The sample may be a crude, unprocessed sample (e.g., whole blood). The sample may be a processed sample (e.g., plasma). The amount of sample is likely based on the sample type. Typically, the sample is processed or an analyte (e.g., a nucleic acid or other biomarker) is purified from the sample in step 120 to produce an analyte that can be amplified and/or detected. Processing may comprise filtering a sample, binding a component of the sample that contains an analyte, binding the analyte, stabilizing the analyte, purifying the analyte, or a combination thereof. Non-limiting examples of sample components are cells, viral particles, bacterial particles, exosome, and nucleosomes. In some instances, the analyte is a nucleic acid and it is amplified to produce an amplicon for analysis in step 130. In other instances, the analyte may or may not be a nucleic acid, but regardless is not amplified. The analyte or amplicon is optionally modified (140) before detection and analysis. In some instances, modification occurs during amplification (not shown). For example, the analyte or amplicon may be tagged or labeled. Detection may involve sequencing, target-specific probes, isothermal amplification and detection methods, quantitative PCR, or single molecule detection. FIG. 1 is provided as a broad overview of devices and methods disclosed herein, but devices and methods disclosed herein are not limited by FIG. 1. Devices and methods may comprise additional components and steps, respectively that are not shown in FIG. 1.

In some instances, devices, systems, kits and methods disclosed herein are desirable because the genetic information can be kept private to the user. In fact, even the use of the device can be kept private. Alternatively, devices, systems, kits and methods are configured to share information with others or can be easily adapted by the user to share information (e.g., turning on a Bluetooth signal). For example, information may be easily shared with a nurse or doctor. In some instances, the device or system can send/share test results through a secure portal or application programming interface (API) to a medical practitioner or staff at an office or hospital. In some instances, the user may choose to share information with the medical practitioner in person after receiving the result. In some instances, the information may even be shared in real-time. This kind of communication would be desirable for couples or families that are split up, for example, by military commitments, employment obligations, migration policies, or health issues.

There are myriad applications for the devices, systems, kits, and methods disclosed herein. Devices, systems, kits and methods disclosed herein allow for diagnosing and monitoring medical conditions. Non-limiting examples of medical conditions include autoimmune conditions, metabolic conditions, cancer, and neurological conditions. Devices, systems, kits and methods disclosed herein allow for personalized medicine, including microbiome testing, determining an appropriate personal medical dosage and/or detecting a response to a drug or dose thereof. Devices, systems, kits and methods disclosed herein provide for detecting an infection by a pathogen and/or a subject's resistance to drugs that could be used to treat the infection. In almost all cases, there is little to no need for technical training or large, expensive laboratory equipment.

FIG. 1 shows that one using the devices, systems, kits or methods disclosed herein may start with a microvolume (e.g., less than a milliliter) of a biological sample from a subject. The biological sample generally contains less than 5000 genome equivalents of cell-free DNA. The sample may be processed by filtration, stabilization, purification, or a combination thereof, to allow for analysis. In some instances the sample does not require processing, such as filtration, stabilization or purification. Several different analytes in the sample can be informative, e.g., cell-free DNA, cell-free RNA, microvesicle-associated nucleic acids, and epigenetic markers on the cell-free DNA. One or more of these analytes may be analyzed. In some instances, the analyte is not amplified. In some instances, the analyte is sequenced without amplification or modification of the analyte. In some instances, the analyte is amplified (e.g., polymerase-mediated nucleic acid amplification) to generate amplicons of the analyte. In some instances, the amplicons are sequenced. In some instances, the amplicons are sequenced without further preparation or modification. In some instances, a feature such as a polymorphism, mutation, epigenetic mark or aberration within an amplicon or target region is used for further analysis.

In some instances, the analyte, the amplicons, or a combination thereof are converted to a library by labeling the analyte with a label, bar-code or tag. The terms label, bar-code and tag are used interchangeably herein, unless otherwise specified. In some instances, library members are amplified to produce amplified library members. In some instances, library members are subjected to whole genome amplification. In some instances, library members are products of whole genome amplification. In some instances, library members are not amplified to produce amplified library members. In some instances, library members are not subjected to whole genome amplification. In some instances, library members are not the products of whole genome amplification. In some instances, library members are captured to produce captured library members. In some instances, library members are captured and amplified to produce captured, amplified library members. In some instances, library members are sequenced. In some instances, amplified library members are sequenced. In some instances, captured library members are sequenced. In some instances, captured, amplified library members are sequenced. In some instances, library members are not sequenced. For instance, library members may be detected or quantified by an array of probes or by single molecule counting. In some instances, the amplified library members are detected or quantified by an array of probes or by single molecule counting. In some instances, the captured library members are detected or quantified by an array of probes or by single molecule counting. In some instances, the captured, amplified library members are detected or quantified by an array of probes or by single molecule counting.

Figure 2:
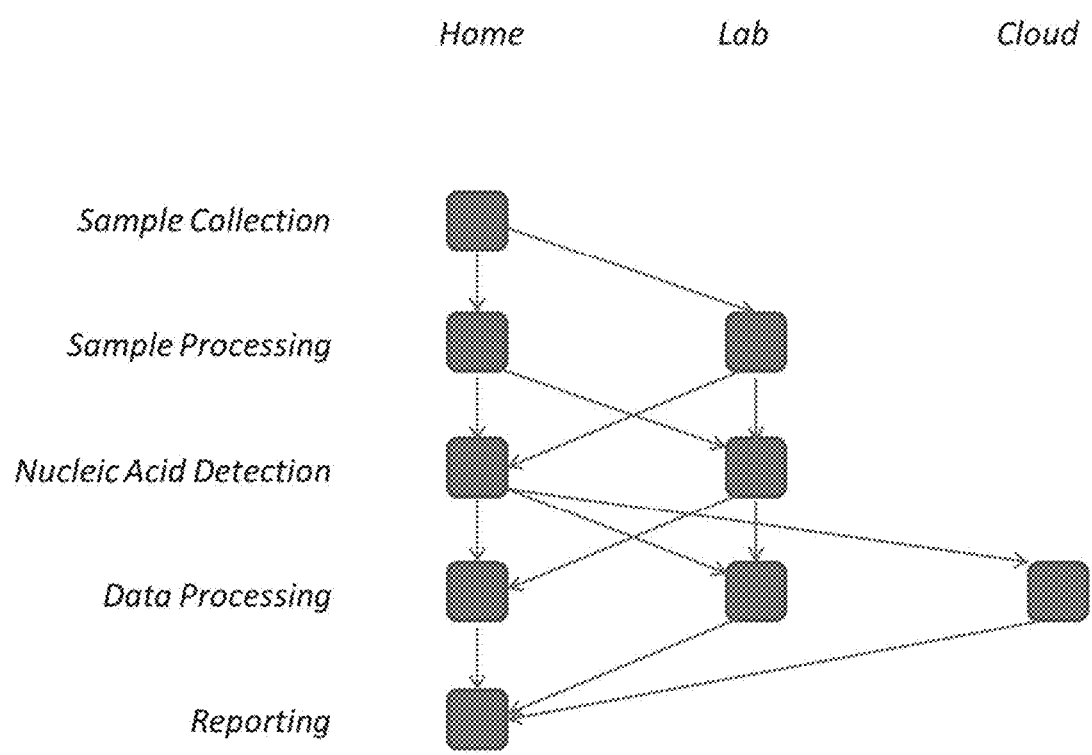
FIG. 2 shows a diagram of how components of the methods and systems disclosed herein can be distributed amongst various locations (physical and/or electronic), or focused primarily in one physical location.

FIG. 2 shows that methods, systems, devices and kits disclosed herein can be distributed amongst several locations. For instances, methods disclosed herein may be fully performed in a home setting, or other point of need. This is particularly important for subjects that do not have access (e.g., physically, financially) to a laboratory, nucleic acid processing and analyzing equipment, or a technician or doctor. In some instances, samples may be processed in a laboratory (e.g., laboratory equipment required). However, methods, systems, devices and kits disclosed herein may still allow for sample collection and reporting in the home. By way of example, the sample may be collected at home, shipped to a laboratory where processing occurs, and the results are delivered to the subject in the home via electronic communication. Therefore, even when processing in a laboratory is required, methods, systems, devices and kits disclosed herein are still convenient to the user, requiring only that they have a means to ship/transport their sample. In some instances, it is convenient for data processing to occur in a cloud or on a server that can communicate test results to the subject. In some instances, it is convenient for data processing to occur in a laboratory and the results reported to the subject in their home without relying on a cloud or internet server.

Non-Invasive Prenatal Testing

One application for methods, devices and systems disclosed herein is non-invasive prenatal testing (NIPT). The health of the fetus is one of the key concerns of expecting parents after the initial awareness and confirmation of a pregnancy. In addition to other general pregnancy-related health tests, assessment of the risk of fetal chromosomal or genetic aberrations has become a standard of care in the management of pregnancies in many countries. Currently, there are several ways to determine genetic information from the fetus. During the first trimester (week 1 through 12), an ultrasound test for nuchal translucency can reveal if there is a likelihood of a chromosomal abnormality, like trisomy 18 or trisomy 21. In addition, a maternal phlebotomy can be performed to test for levels of pregnancy-associated plasma protein and human chorionic gonadotropin. Elevated levels of these proteins may be indicative of a chromosomal abnormality as well. However, these tests are not conclusive and generally require additional, more invasive testing (e.g., chorionic villus sampling (sampling of placental tissue), or amniocentesis (needle penetrates the amniotic sac)) to determine if there is indeed an abnormality. Additional tests can be performed during the second trimester, but typically more testing, additional ultrasounds and an amniocentesis, are required for a more definitive determination.

The foregoing described screening requires medical providers with technical training in clinical settings. Many of these tests are invasive (e.g., amniocentesis), thereby carrying a health risk to the fetus, as well as the mother. Typically, the foregoing described screening is necessary at both trimesters to detect a chromosomal abnormality. Thus, detection of a chromosomal abnormality typically cannot be achieved until the fetus is halfway through gestation using the current methods in the field.

Since the discovery of the presence of circulating cell-free fetal DNA in the blood of pregnant women, prenatal care has seen significant improvements. The presence of fetal DNA circulating in maternal blood has afforded a means to study the genetic make-up of the fetus and identify potential health risks or pregnancy complications without the risk associated with procedures such as chorionic villus sampling and amniocentesis. A number of medically relevant tests that utilize circulating cell-free fetal DNA have been developed, but the most prominent ones are NIPT for fetal chromosomal abnormalities.

Existing NIPT can be categorized into two main categories. They are either targeted assays that only amplify and analyze certain chromosomes or chromosomal regions or they are whole genome assays. Unfortunately, existing NIPT requires venipuncture (e.g., a phlebotomy) to obtain amounts of maternal blood/plasma sufficient to achieve appropriate screening performance. For example, existing NIPT often require collection of as much as 16 ml of blood. Because of the large amounts of blood required in existing NIPT, there are significant restrictions in convenience and access to testing. In addition, sample-handling logistics, as well as testing costs and reagent costs are burdensome.

NIPT has previously been thought of as only being feasible with large amounts of cfDNA copy numbers (genome equivalents) such as those obtained with a phlebotomy (e.g., milliliters of blood). Several statistical reasons (resolving very small differences require large sample numbers) as well as traditional reasons (limited marker availability for FISH) have cemented this practice. The instant application shows how NIPT by cfDNA analysis is possible from ultra-low input amounts. See Examples 1-5. Methods, devices, systems and kits disclosed herein combine existing methods for high efficiency library creation, with low level DNA amplification (e.g., 8-10 cycles) in a novel way to enable NIPT from minimal sample volumes.

In contrast to existing NIPT, the methods, systems and devices disclosed herein minimize the amount of cell-free fetal DNA required for accurate screening of fetal chromosomal aberrations, thereby avoiding the need for large sample volumes. In the case when the sample is blood, a sufficient amount of blood may be obtained with a finger prick. See, e.g., Example 3. Thus, methods and systems disclosed herein eliminate the need for a venipuncture, thereby providing for NIPT at point of care with a significant reduction in cost of testing. Since the fetal fraction in maternal blood can be low and maternal cell-free nucleic acids can vary, it was unexpected that the methods, systems and devices disclosed herein would successfully reveal reliable and useful genetic information about a fetus. Maternal biology is always changing and there is a lot of variability in maternal cell-free nucleic acids of maternal subjects. There are cell-free nucleic acids from various organs of the mother (e.g., liver, skin) that contribute to circulating cell-free nucleic acids and the biology of those organs can change with age, disease, infection, and even time of day. It was unpredictable that maternal representation is reproducible enough to compare cell-free fetal nucleic acids from a test subject to cell-free fetal nucleic acids from a reference/control subject. One has to experimentally prove that the host background DNA is actually giving a stable enough distribution so that a trisomy or other genomic variations can be accurately detected.

Disclosed herein are devices, systems, kits and methods for obtaining genetic information of a fetus. Devices, systems, kits and methods disclosed herein may be advantageously capable of obtaining genetic information at very early stages of gestation. Devices, systems, kits and methods disclosed herein may obtain genetic information of a fetus in the privacy of a home, without the need for laboratory equipment and without the risk of sample swapping. Genetic information can be detected in minutes or seconds with devices, systems, kits and methods disclosed herein.

Disclosed herein are devices, systems, kits and methods for analyzing cell-free fetal nucleic acids from a biological fluid sample of a pregnant subject. Analysis of cell-free circulating nucleic acids is met with a number of technical challenges. For instance, amplification of circulating nucleic acids in blood may be inhibited by some of the components in whole blood. Non-limiting examples of components in whole blood are hemoglobin and associated iron. The devices, systems, kits and methods disclosed herein aim to overcome many of these technical challenges. In addition, the devices, systems, kits and methods offer the advantage of being (1) minimally invasive, (2) applicable in home with little or no technical training; (3) informative at early stages of a condition (e.g., pregnancy). Furthermore, devices, systems, kits and methods generally do not require complex or expensive equipment.

In some aspects, the devices, systems, kits and methods disclosed herein are useful for analyzing cell-free nucleic acids from a fetus, referred to herein as "cell-free fetal nucleic acids." In some instances, cell-free fetal nucleic acids are from at least one cell of the fetus, at least one cell of the placenta, or a combination thereof. Prenatal applications of cell-free fetal nucleic acids in maternal blood are presented with the additional challenge of analyzing cell-free fetal nucleic acids in the presence of cell-free maternal nucleic acids, the latter of which create a large background signal to the former. For example, a sample of maternal blood may contain about 500 to 2000 genome equivalents of total cell-free DNA (maternal and fetal) per milliliter of whole blood. The fetal fraction in blood sampled from pregnant women may be around 10%, about 50 to 200 fetal genome equivalents per ml. Furthermore, the process of obtaining cell-free nucleic acids may involve obtaining plasma or serum from the blood. If not performed carefully, blood cells may be destroyed, releasing additional cellular nucleic acids into the sample, creating additional background signal to the fetal cell-free nucleic acids. The typical white cell count is around $4*10^6$ to $10*10^6$ cells per ml of blood and therefore the available nuclear DNA is around 10,000 times higher than the overall cell-free DNA (cfDNA). Consequently, even if only a small fraction of maternal white blood cells is destroyed, releasing nuclear DNA into the plasma or serum, the fetal fraction is reduced dramatically. For example, a white cell degradation of 0.01% may reduce the fetal fraction from 10% to about 5%. Devices, systems, kits and methods disclosed herein aim to reduce these background signals.

I. Methods

In general, methods disclosed herein comprise obtaining a biological sample and detecting a component thereof. In some instances, methods disclosed herein are performed with a device, system or kit described herein. Obtaining the biological sample may occur in a clinical or laboratory setting, such as, by way of non-limiting example, a medical clinic, a hospital, a scientific research laboratory, a pathology laboratory, or a clinical test laboratory. Alternatively, obtaining may occur at a location remote from a clinical or laboratory setting, such as, by way of non-limiting example, a home, a family planning center, a workplace, a school, a farm, or a battlefield. In general, methods disclosed herein comprise collecting and analyzing a relatively small volume of a biological sample, regardless of whether collection occurs in a clinical setting or a remote location. In some instances, detecting occurs in a clinical or laboratory setting. In other instances, detecting occurs at a location remote from a clinical or laboratory setting. Other steps of the methods disclosed herein, e.g., amplifying a nucleic acid, may occur in the clinical/laboratory setting or at a remote location. In some instances, the methods may be performed by the subject. In some instances, methods disclosed herein are performed by a user that has not received any technical training necessary to perform the method.

In some aspects, disclosed herein are methods comprising: obtaining a biological sample from a subject, wherein the biological sample contains cell-free nucleic acid molecules; sequencing at least a portion of the cell-free nucleic acid molecules to produce sequencing reads; measuring at least a portion of sequencing reads corresponding to at least one region of interest; and detecting a normal representation, an overrepresentation or an underrepresentation of the at least one region of interest. The biological sample may comprise less than about $10^{10}$ cell-free nucleic acids. The biological sample may comprise about $10^5$ to about $10^{10}$ cell-free nucleic acids. The biological sample may comprise about $10^4$ to about $10^{10}$ cell-free nucleic acids. The biological sample may comprise about $10^3$ to about $10^{10}$ cell-free nucleic acids. The biological sample may comprise about $10^2$ to about $10^{10}$ cell-free nucleic acids. The biological sample may comprise about $10^5$ to about $10^9$ cell-free nucleic acids. The biological sample may comprise about $10^5$ to about $10^8$ cell-free nucleic acids. The biological sample may comprise about $10^5$ to about $10^7$ cell-free nucleic acids. The biological sample may comprise about $10^6$ to about $10^{11}$ cell-free nucleic acids. The biological sample may comprise about $10^6$ to about $10^9$ cell-free DNA. The biological sample may comprise about $10^7$ to about $10^9$ cell-free nucleic acids.

In some instances, overrepresentation or an underrepresentation is a representation of the region of interest in a test sample from a test subject relative to representation of the region of interest in at least one control subject. In some instances, the control subject is a healthy subject. In some instances, the control subject does not comprise a mutation in the region of interest. In some instances, the control subject has a wildtype copy number of the region of interest. In some instances, there is an overrepresentation or an underrepresentation of an epigenetically modified version of the region of interest. In some instances, overrepresentation or an underrepresentation is a representation of the region of interest in a test sample relative to representation of the region of interest in at least one reference sample. The reference sample may be analyzed at the same time as the test sample. The reference sample may be analyzed prior to analyzing the test sample. The at least one reference sample may comprise a plurality of reference samples. In some instances, overrepresentation or an underrepresentation is a representation of the region of interest in a test sample relative to a mean representation of the region of interest in a plurality of reference samples.

In some instances, methods comprise analyzing and detecting genetic information in a control sample. In some instances, methods comprise analyzing and detecting genetic information in a control sample, and instead use a predetermined control reference value obtained from control reference data. This would be particularly useful when the subject performs analysis of his/her sample at home and does not have access to a control sample. However, often, the subject could also easily obtain a control sample (e.g., from a relative, spouse, friend). Furthermore, systems and methods, as described herein, provide for analyzing multiple samples simultaneously by indexing each sample.

In some aspects, described herein are methods comprising: obtaining a biological sample from a subject; sequencing at least a portion of the cell-free nucleic acids to produce sequencing reads; measuring sequencing reads corresponding to a target sequence; measuring sequencing reads corresponding to at least one non-target sequence; and detecting, with greater than 98% accuracy, that there is an abnormality in the target sequence. The abnormality may be a feature or characteristic not present in a healthy subject. The abnormality may be a feature or characteristic not present in a wildtype subject. The abnormality may be a feature or characteristic not present in a control subject. The abnormality may be a genetic mutation. The abnormality may be a plurality of genetic mutations. Genetic mutations are described herein and throughout. The abnormality may be an epigenetic modification. The abnormality may be a plurality of epigenetic modifications.

In some aspects, described herein are methods comprising: obtaining a biological sample from a subject; sequencing at least a portion of the cell-free nucleic acids to produce sequencing reads; measuring sequencing reads corresponding to at least one target sequence; measuring sequencing reads corresponding to at least one non-target sequence; and measuring, with greater than 98% accuracy, that there is an abnormal number of copies of the target sequence relative to a wildtype number of copies.

In some aspects, described herein are methods comprising: obtaining a biological sample from a subject, wherein the biological sample contains cell-free nucleic acids; amplifying at least a portion of the cell-free nucleic acids to produce amplified nucleic acids; sequencing the amplified nucleic acids to produce sequencing reads; measuring a first portion of the sequencing reads corresponding to at least one target sequence; measuring a second portion of sequencing reads corresponding to at least one sequence of non-target sequence; and measuring, with greater than 98% accuracy, that there is an abnormality in the target sequence when a ratio of the first portion of sequencing reads to the second portion of sequencing reads is different from a respective ratio in a control biological sample from a control subject. In some instances, the methods comprise barcoding or tagging the cell-free nucleic acids prior to, during or after amplification and before sequencing.

In some aspects, described herein are methods comprising: obtaining a biological sample from a subject, wherein the biological sample contains cell-free nucleic acid molecules; barcoding and/or tagging at least a portion of the cell-free nucleic acids present in the biological sample to produce tagged nucleic acids; sequencing the tagged nucleic acids to produce sequencing reads; measuring a first portion of the sequencing reads corresponding to a target sequence; measuring a second portion of sequencing reads corresponding to a non-target sequence; and measuring, with greater than 98% accuracy, that there is an abnormality in the target sequence when a ratio of the first portion of sequencing reads to the second portion of sequencing reads is different from a respective ratio in a control biological sample from a control subject.

In some aspects, described herein are methods comprising: obtaining a biological sample from a subject, wherein the biological sample contains cell-free nucleic acids; sequencing the cell-free nucleic acids to produce sequencing reads; measuring a first portion of the sequencing reads corresponding to at least one target sequence; measuring a second portion of sequencing reads corresponding to at least one non-target sequence; and measuring, with greater than 98% accuracy, that there is an abnormality in the at least one target sequence when a ratio of the first portion of sequencing reads to the second portion of sequencing reads is different from a respective ratio in a control biological sample from a control subject.

In some aspects, described herein are methods comprising: obtaining capillary blood from a subject, wherein the capillary blood comprises cell-free nucleic acids; sequencing at least a portion of the cell-free nucleic acids to produce sequencing reads; measuring at least a portion of sequencing reads corresponding to at least one target sequence of interest; and detecting a normal representation, an overrepresentation or an underrepresentation of the at least one target sequence.

In some aspects, described herein are methods that comprise obtaining a biological sample from a subject, wherein the biological sample comprises target cell-free nucleic acids and non-target cell-free nucleic acids that together make up total cell-free nucleic acids, and wherein the target cell-free nucleic acids are less than 5% of the total cell-free nucleic acids; sequencing at least a portion of the target cell-free nucleic acids to produce sequencing reads; measuring at least a portion of sequencing reads corresponding to at least one target sequence of interest; and detecting a normal representation, an overrepresentation or an underrepresentation of the at least one target sequence. In general, obtaining does not comprise performing a phlebotomy or receiving a sample from a phlebotomy. In some instances, the biological sample does not comprise venous blood. The biological sample may comprise capillary blood. The biological sample may consist essentially of capillary blood.

In some aspects, described herein are methods that comprise obtaining a biological sample from a subject, wherein the biological sample contains up to about $10^9$ cell-free nucleic acid molecules; sequencing at least a portion of the cell-free nucleic acid molecules to produce sequencing reads; measuring at least a portion of sequencing reads corresponding to at least one chromosomal region; and detecting a normal representation, an overrepresentation or an underrepresentation of the at least one chromosomal region. The methods may comprise amplifying the cell-free nucleic acid molecules before sequencing. The methods may comprise tagging the cell-free nucleic acid molecules before sequencing and after amplifying. The methods may comprise tagging the cell-free nucleic acid molecules before sequencing. The methods may comprise amplifying the cell-free nucleic acid molecules after tagging the cell-free nucleic acid molecules. The methods may comprise amplifying the cell-free nucleic acid molecules before tagging the cell-free nucleic acid molecules.

Non-Invasive Prenatal Testing (NIPT)

In some aspects, disclosed herein are methods comprising: obtaining a biological sample from a pregnant subject, wherein the biological sample contains up to about $10^9$ cell-free fetal nucleic acid molecules; sequencing at least a portion of the cell-free fetal nucleic acid molecules to produce sequencing reads; measuring at least a portion of sequencing reads corresponding to at least one chromosomal region; and detecting a normal representation, an overrepresentation or an underrepresentation of the at least one chromosomal region.

In some instances, overrepresentation or an underrepresentation is relative to representation of a chromosome or chromosomal region in at least one control pregnant subject. In some instances, the at least one control pregnant subject is a pregnant euploid subject. In some instances, the at least one control pregnant subject is a pregnant aneuploid subject. In some instances, the at least one control pregnant subject is a pregnant subject with no chromosomal abnormalities. In some instances, the at least one control pregnant subject is a pregnant subject with at least one chromosomal abnormality. In some instances, the control pregnant subject has a euploid fetus. In some instances, the control pregnant subject has an aneuploid fetus. In some instances, the control pregnant subject has a fetus with no genetic abnormalities. In some instances, the control pregnant subject has a fetus with at least one genetic abnormality. In some instances, the at least one control pregnant subject comprises a plurality of pregnant subjects having the same presence or lack of chromosomal abnormalities.

In some instances, methods, devices, systems and kits disclosed herein utilize additional controls. In some instances, the control is a representation of a chromosome that is expected if a fetus is euploid. In some instances, the control is a representation of a chromosome that is expected if a fetus is aneuploid. In some instances, the control is a quantity of a chromosome that is expected if a fetus is euploid. In some instances, the control is a quantity of a chromosome that is expected if a fetus is aneuploid. In some instances, the control is a quantity of sequencing reads corresponding to a chromosome that is expected if a fetus is euploid. In some instances, the control is a quantity of sequencing reads corresponding to a chromosome that is expected if a fetus is aneuploid. In some instances, methods comprise analyzing and detecting genetic information in a control sample. In some instances, methods comprise analyzing and detecting genetic information in a control sample, and instead use a predetermined control reference value obtained from control reference data. This would be particularly useful when the pregnant subject performs analysis of her sample at home and does not have access to a control sample. However, often, the pregnant subject could also easily obtain a control sample (e.g., from a relative, spouse, friend). Furthermore, systems and methods, as described herein, provide for analyzing multiple samples simultaneously by indexing each sample.

In some aspects, described herein are methods comprising: obtaining a biological sample from a pregnant subject, wherein the biological sample contains up to about $10^9$ cell-free fetal nucleic acid molecules; sequencing at least a portion of the cell-free fetal nucleic acids to produce sequencing reads; measuring sequencing reads corresponding to at least one target chromosome; measuring at sequencing reads corresponding to at least one non-target chromosome; and measuring, with greater than 98% accuracy, that there is a fetal aneuploidy of the at least one target chromosome.

In some aspects, described herein are methods comprising: obtaining a biological sample from a pregnant subject, wherein the biological sample contains up to about $10^9$ cell-free fetal nucleic acid molecules; sequencing at least 2000 of the cell-free fetal nucleic acids to produce sequencing reads; measuring at least 1000 sequencing reads corresponding to at least one target chromosome; measuring at least 1000 sequencing reads corresponding to at least one non-target chromosome; and measuring, with greater than 98% accuracy, that there is a fetal aneuploidy of the at least one target chromosome. These numbers of sequencing reads are sufficient even when the fraction of cell-free fetal nucleic acid molecules in the total cell-free nucleic acid molecules of the biological sample is low.

In some aspects, described herein are methods comprising: obtaining a biological sample from a pregnant subject, wherein the biological sample contains up to about $10^9$ cell-free fetal nucleic acid molecules; amplifying at least a portion of the cell-free fetal nucleic acid molecules to produce amplified nucleic acids; sequencing at least 2000 amplified fetal nucleic acids to produce sequencing reads; measuring at least 1000 sequencing reads corresponding to at least one target chromosome; measuring at least 1000 sequencing reads corresponding to at least one non-target chromosome; and measuring, with greater than 98% accuracy, that there is a fetal aneuploidy of the at least one target chromosome when a ratio of sequencing reads corresponding to the at least one target chromosome to sequencing reads corresponding to the at least one non-target chromosome is different from a respective ratio in a control biological sample from a control pregnant euploid subject with a euploid fetus. In some instances, the methods comprise barcoding or tagging the nucleic acids prior to, during or after amplification and before sequencing the at least 2000 amplified fetal nucleic acids. In some instances, the nucleic acids are cell-free nucleic acids.

In some aspects, described herein are methods comprising: obtaining a biological sample from a pregnant subject, wherein the biological sample contains about up to about $10^9$ cell-free fetal nucleic acid molecules; barcoding and/or tagging at least a portion of the cell-free fetal nucleic acid molecules present in the biological sample to produce tagged nucleic acids; sequencing at least 2000 tagged nucleic acids to produce sequencing reads; measuring at least 1000 sequencing reads corresponding to at least one target chromosome; measuring at least 1000 sequencing reads corresponding to at least one non-target chromosome; and measuring, with greater than 98% accuracy, there is a fetal aneuploidy of the at least one target chromosome when a ratio of sequencing reads corresponding to the at least one target chromosome to sequencing reads corresponding to the at least one non-target chromosome is different from a respective ratio in a control biological sample from a control pregnant euploid subject with a euploid fetus. In some instances, the methods comprise amplifying the barcoded and/or tagged nucleic acids before sequencing the at least 8000 tagged nucleic acids.

In some aspects, described herein are methods comprising: obtaining a biological sample from a pregnant subject, wherein the biological sample contains up to about $10^{10}$ cell-free nucleic acid molecules; sequencing at least 8000 cell-free nucleic acid molecules to produce sequencing reads; measuring at least 4000 sequencing reads corresponding to at least one target chromosome; measuring at least 4000 sequencing reads corresponding to at least one non-target chromosome; and measuring, with greater than 98% accuracy, that there is a fetal aneuploidy of the at least one target chromosome when a ratio of sequencing reads corresponding to the at least one target chromosome to sequencing reads corresponding to the at least one non-target chromosome is different from a respective ratio in a control biological sample from a control pregnant euploid subject with a euploid fetus. In some instances, the cell-free nucleic acids are not from a blood cell. In some instances, the cell-free nucleic acids do not comprise nucleic acids that are from a blood cell. In some instances, the cell-free nucleic acids comprise nucleic acids that are from a blood cell.

In some aspects, described herein are methods comprising: obtaining a biological sample from a pregnant subject, wherein the biological sample contains up to about $10^{10}$ cell-free nucleic acid molecules; amplifying the cell-free nucleic acid molecules to produce amplified cell-free nucleic acid molecules; sequencing at least 8000 amplified cell-free nucleic acid molecules to produce sequencing reads; measuring at least 4000 sequencing reads corresponding to at least one target chromosome; measuring at least 4000 sequencing reads corresponding to at least one non-target chromosome; and measuring, with greater than 98% accuracy, that there is a fetal aneuploidy of the at least one target chromosome when a ratio of sequencing reads corresponding to the at least one target chromosome to sequencing reads corresponding to the at least one non-target chromosome is different from a respective ratio in a control biological sample from a control pregnant euploid subject with a euploid fetus. In some instances, the methods comprise tagging the amplified cell-free nucleic acid molecules before sequencing the at least 8000 amplified cell-free nucleic acid molecules.

In some aspects, described herein are methods comprising: obtaining a biological sample from a pregnant subject, wherein the biological sample contains up to about $10^{10}$ cell-free nucleic acid molecules; tagging the cell-free nucleic acid molecules to produce tagged cell-free nucleic acid molecules; sequencing at least 8000 tagged cell-free nucleic acid molecules present to produce sequencing reads; measuring at least 4000 sequencing reads corresponding to at least one target chromosome; measuring at least 4000 of sequencing reads corresponding to at least one non-target chromosome; and measuring, with greater than 98% accuracy, there is a fetal aneuploidy of the at least one target chromosome when a ratio of sequencing reads corresponding to the at least one target chromosome to sequencing reads corresponding to the at least one non-target chromosome is different from a respective ratio in a control biological sample from a control pregnant euploid subject with a euploid fetus. In some instances, the methods comprise amplifying the tagged cell-free DNA fragments before sequencing the at least 8000 tagged cell-free nucleic acid molecules.

Obtaining Samples

In some instances, methods disclosed herein comprise obtaining a biological sample described herein. A sample may be obtained directly (e.g., a doctor takes a blood sample from a subject). A sample may be obtained indirectly (e.g., through shipping, by a technician from a doctor or a subject). In some instances, the biological sample is a biological fluid. In some instances, the biological sample is a swab sample (e.g., buccal swab, vaginal swab). In some instances, methods disclosed herein comprise obtaining whole blood, plasma, serum, urine, saliva, interstitial fluid, or vaginal fluid. In some instances, methods disclosed herein comprise obtaining a blood sample via a finger prick. In some instances, methods disclosed herein comprise obtaining a blood sample via a single finger prick. In some instances, methods disclosed herein comprise obtaining a blood sample with not more than a single finger prick. In some instances, methods disclosed herein comprise obtaining capillary blood (e.g., blood obtained from a finger or a prick of the skin). In some instances, methods comprise squeezing or milking blood from a prick to obtain a desired volume of blood. In other instances, methods do not comprise squeezing or milking blood from a prick to obtain a desired volume of blood. While a finger prick is a common method for obtaining capillary blood, other locations on the body would also be suitable, e.g., toe, heel, arm, palm, shoulder, earlobe. In some instances, methods disclosed herein comprise obtaining a blood sample without a phlebotomy. In some instances, methods disclosed herein comprise obtaining capillary blood. In some instances, methods disclosed herein comprise obtaining venous blood. In some instances, methods disclosed herein do not comprise obtaining venous blood (e.g., blood obtained from a vein). In some instances, methods comprise obtaining a biological sample via a biopsy. In some instances, methods comprise obtaining a biological fluid via a liquid biopsy.

In some instances, methods comprise obtaining samples with fragmented nucleic acids. The sample may have been subjected to conditions that are not conducive to preserving the integrity of nucleic acids. By way of non-limiting example, the sample may be a forensic sample. Forensic samples are often contaminated, exposed to air, heat, light, etc. The sample may have been frozen and thawed. The sample may have been exposed to chemicals or enzymes that degrade nucleic acids. In some instances, methods comprise obtaining a tissue sample wherein the tissue sample comprises fragmented nucleic acids. In some instances, methods comprise obtaining a tissue sample wherein the tissue sample comprises nucleic acids and fragmenting the nucleic acids to produced fragmented nucleic acids. In some instances, the tissue sample is a frozen sample. In some instances, the sample is a preserved sample. In some instances the tissue sample is a fixed sample (e.g. formaldehyde-fixed). Methods may comprise isolating the (fragmented) nucleic acids from the sample. Methods may comprise providing the fragmented nucleic acids in a solution for genetic analysis.

In some instances, methods disclosed herein are performed with not more than 50 µl of the biological fluid sample. In some instances, methods disclosed herein are performed with not more than 75 µl of the biological fluid sample. In some instances, methods disclosed herein are performed with not more than 100 µl of the biological fluid sample. In some instances, methods disclosed herein are performed with not more than 125 µl of the biological fluid sample. In some instances, methods disclosed herein are performed with not more than 150 µl of the biological fluid sample. In some instances, methods disclosed herein are performed with not more than 200 µl of the biological fluid sample. In some instances, methods disclosed herein are performed with not more than 300 µl of the biological fluid sample. In some instances, methods disclosed herein are performed with not more than 400 µl of the biological fluid sample. In some instances, methods disclosed herein are performed with not more than 500 µl of the biological fluid sample.

In some instances, methods disclosed herein comprise obtaining an ultra-low volume of a biological fluid sample, wherein the ultra-low volume falls within a range of sample volumes. In some instances, the range of sample volumes is about 5 µl to about one milliliter. In some instances, the range of sample volumes is about 5 µl to about 900 µl. In some instances, the range of sample volumes is about 5 µl to about 800 µl. In some instances, the range of sample volumes is about 5 µl to about 700 µl. In some instances, the range of sample volumes is about 5 µl to about 600 µl. In some instances, the range of sample volumes is about 5 µl to about 500 µl. In some instances, the range of sample volumes is about 5 µl to about 400 µl. In some instances, the range of sample volumes is about 5 µl to about 300 µl. In some instances, the range of sample volumes is about 5 µl to about 200 µl. In some instances, the range of sample volumes is about 5 µl to about 150 µl. In some instances, the range of sample volumes is 5 µl to about 100 µl. In some instances, the range of sample volumes is about 5 µl to about 90 µl. In some instances, the range of sample volumes is about 5 µl to about 85 µl. In some instances, the range of sample volumes is about 5 µl to about 80 µl. In some instances, the range of sample volumes is about 5 µl to about 75 µl. In some instances, the range of sample volumes is about 5 µl to about 70 µl. In some instances, the range of sample volumes is about 5 µl to about 65 µl. In some instances, the range of sample volumes is about 5 µl to about 60 µl. In some instances, the range of sample volumes is about 5 µl to about 55 µl. In some instances, the range of sample volumes is about 5 µl to about 50 µl. In some instances, the range of sample volumes is about 15 µl to about 150 µl. In some instances, the range of sample volumes is about 15 µl to about 120 µl. In some instances, the range of sample volumes is 15 µl to about 100 µl. In some instances, the range of sample volumes is about 15 µl to about 90 µl. In some instances, the range of sample volumes is about 15 µl to about 85 µl. In some instances, the range of sample volumes is about 15 µl to about 80 µl. In some instances, the range of sample volumes is about 15 µl to about 75 µl. In some instances, the range of sample volumes is about 15 µl to about 70 µl. In some instances, the range of sample volumes is about 15 µl to about 65 µl. In some instances, the range of sample volumes is about 15 µl to about 60 µl. In some instances, the range of sample volumes is about 15 µl to about 55 µl. In some instances, the range of sample volumes is about 15 µl to about 50 µl.

In some instances, methods disclosed herein comprise obtaining an ultra-low volume of a biological fluid sample, wherein the ultra-low volume is about 100 µl to about 500 µl. In some instances, methods disclosed herein comprise obtaining an ultra-low volume of the biological fluid sample, wherein the ultra-low volume about 100 µl to about 1000 µl. In some instances, the ultra-low volume is about 500 µl to about 1 ml. In some instances, the ultra-low volume is about 500 µl to about 2 ml. In some instances, the ultra-low volume is about 500 µl to about 3 ml. In some instances, the ultra-low volume is about 500 µl to about 5 ml.

In some instances, methods disclosed herein comprise obtaining an ultra-low volume of a biological sample, wherein the biological sample is whole blood. The ultra-low volume may be about 1 µl to about 250 µl. The ultra-low volume may be about 5 µl to about 250 µl. The ultra-low volume may be about 10 µl to about 25 µl. The ultra-low volume may be about 10 µl to about 35 µl. The ultra-low volume may be about 10 µl to about 45 µl. The ultra-low volume may be about 10 µl to about 50 µl. The ultra-low volume may be about 10 µl to about 60 µl. The ultra-low volume may be about 10 µl to about 80 µl. The ultra-low volume may be about 10 µl to about 100 µl. The ultra-low volume may be about 10 µl to about 120 µl. The ultra-low volume may be about 10 µl to about 140 µl. The ultra-low volume may be about 10 µl to about 150 µl. The ultra-low volume may be about 10 µl to about 160 µl. The ultra-low volume may be about 10 µl to about 180 µl. The ultra-low volume may be about 10 µl to about 200 µl.

In some instances, methods disclosed herein comprise obtaining a ultra-low volume of a biological sample wherein the biological sample is plasma or serum. The ultra-low volume may be about 1 µl to about 200 µl. The ultra-low volume may be about 1 µl to about 190 µl. The ultra-low volume may be about 1 µl to about 180 µl. The ultra-low volume may be about 1 µl to about 160 µl. The ultra-low volume may be about 1 µl to about 150 µl. The ultra-low volume may be about 1 µl to about 140 µl. The ultra-low volume may be about 5 µl to about 15 µl. The ultra-low volume may be about 5 µl to about 25 µl. The ultra-low volume may be about 5 µl to about 35 µl. The ultra-low volume may be about 5 µl to about 45 µl. The ultra-low volume may be about 5 µl to about 50 µl. The ultra-low volume may be about 5 µl to about 60 µl. The ultra-low volume may be about 5 µl to about 70 µl. The ultra-low volume may be about 5 µl to about 80 µl. The ultra-low volume may be about 5 µl to about 90 The ultra-low volume may be about 5 µl to about 100 µl. The ultra-low volume may be about 5 µl to about 125 µl. The ultra-low volume may be about 5 µl to about 150 µl. The ultra-low volume may be about 5 µl to about 175 µl. The ultra-low volume may be about 5 µl to about 200 µl.

In some instances, methods disclosed herein comprise obtaining an ultra-low volume of a biological sample, wherein the biological sample is urine. Generally, the concentration of DNA in urine is about 40 ng/ml to about 200 ng/ml. In some instances, the ultra-low volume of urine is about 0.25 µl to 1 milliliter. In some instances, the ultra-low volume of urine is about 0.25 µl to about 1 milliliter. In some instances, the ultra-low volume of urine is at least about 0.25 µl. In some instances, the ultra-low volume of urine is at most about 1 milliliter. In some instances, the ultra-low volume of urine is about 0.25 µl to about 0.5 µl about 0.25 µl to about 0.75 µl about 0.25 µl to about 1 µl about 0.25 µl to about 5 µl about 0.25 µl to about 10 µl, about 0.25 µl to about 50 µl about 0.25 µl to about 100 µl about 0.25 µl to about 150 µl, about 0.25 µl to about 200 µl, about 0.25 µl to about 500 µl about 0.25 µl to about 1 milliliter, about 0.5 µl to about 0.75 µl about 0.5 µl to about 1 µl about 0.5 µl to about 5 µl about 0.5 µl to about 10 µl about 0.5 µl to about 50 µl about 0.5 µl to about 100 µl about 0.5 µl to about 150 µl about 0.5 µl to about 200 µl about 0.5 µl to about 500 µl about 0.5 µl to about 1 milliliter, about 0.75 µl to about 1 µl about 0.75 µl to about 5 µl, about 0.75 µl to about 10 µl about 0.75 µl to about 50 µl about 0.75 µl to about 100 µl about 0.75 µl to about 150 µl about 0.75 µl to about 200 µl about 0.75 µl to about 500 µl about 0.75 µl to about 1 milliliter, about 1 µl to about 5 µl about 1 µl to about 10 µl, about 1 µl to about 50 µl about 1 µl to about 100 µl about 1 µl to about 150 µl about 1 µl to about 200 µl about 1 µl to about 500 µl about 1 µl to about 1 milliliter, about 5 µl to about 10 about 5 µl to about 50 µl about 5 µl to about 100 µl, about 5 µl to about 150 µl about 5 µl to about 200 µl, about 5 µl to about 500 µl about 5 µl to about 1 milliliter, about 10 µl to about 50 µl about 10 µl to about 100 µl about 10 µl to about 150 µl about 10 µl to about 200 µl about 10 µl to about 500 µl about 10 µl to about 1 milliliter, about 50 µl to about 100 µl about 50 µl to about 150 µl about 50 µl to about 200 µl about 50 µl to about 500 µl about 50 µl to about 1 milliliter, about 100 µl to about 150 µl about 100 µl to about 200 µl, about 100 µl to about 500 µl about 100 µl to about 1 milliliter, about 150 µl to about 200 µl about 150 µl to about 500 µl, about 150 µl to about 1 milliliter, about 200 µl to about 500 µl about 200 µl to about 1 milliliter, or about 500 µl to about 1 milliliter. In some instances, the volume of urine used is about 0.25 µl about 0.5 µl about 0.75 µl about 1 µl about 5 µl about 10 µl about 50 µl about 100 µl about 150 µl about 200 µl, about 500 µl or about 1 milliliter.

In some instances, methods disclosed herein comprise obtaining at least about 5 µL of blood to provide a test result with at least about 90% confidence or accuracy. In some instances, methods disclosed herein comprise obtaining at least about 10 µl of blood to provide a test result with at least about 90% confidence or accuracy. In some instances, methods disclosed herein comprise obtaining at least about 15 µL of blood to provide a test result with at least about 90% confidence or accuracy. In some instances, methods disclosed herein comprise obtaining at least about 20 µL of blood to provide a test result with at least about 90% confidence or accuracy. In some instances, methods disclosed herein comprise obtaining at least about 20 µL of blood to provide a test result with at least about 90% confidence or accuracy. In some instances, methods disclosed herein comprise obtaining at least about 20 µL of blood to provide a test result with at least about 95% confidence or accuracy. In some instances, methods disclosed herein comprise obtaining at least about 20 µL of blood to provide a test result with at least about 98% confidence or accuracy. In some instances, methods disclosed herein comprise obtaining at least about 20 µL of blood to provide a test result with at least about 99% confidence or accuracy. In some instances, methods disclosed herein comprise obtaining only about 20 µL to about 120 µL of blood to provide a test result with at least about 90% confidence or accuracy. In some instances, methods disclosed herein comprise obtaining only about 20 µL to about 120 µL of blood to provide a test result with at least about 95% confidence or accuracy. In some instances, the methods disclosed herein comprise obtaining only about 20 µL to about 120 µL of blood to provide a test result with at least about 97% confidence or accuracy. In some instances, methods disclosed herein comprise obtaining only about 20 µL to about 120 µL, of blood to provide a test result with at least about 98% confidence or accuracy. In some instances, the methods disclosed herein comprise obtaining only about 20 µL to about 120 µL of blood to provide a test result with at least about 99% confidence or accuracy. In some instances, methods disclosed herein comprise obtaining only about 20 µl to about 120 µL of blood to provide a test result with at least about 99.5% confidence or accuracy.

In some instances, the biological fluid sample is plasma or serum. Plasma or serum makes up roughly 55% of whole blood. In some instances, methods disclosed herein comprise obtaining at least about 10 µL of plasma or serum to provide a test result with at least about 90% confidence or accuracy. In some instances, methods disclosed herein comprise obtaining at least about 10 µL of plasma or serum to provide a test result with at least about 98% confidence or accuracy. In some instances, methods disclosed herein comprise obtaining at least about 12 of plasma or serum to provide a test result with at least about 90% confidence or accuracy. In some instances, methods disclosed herein comprise obtaining at least about 12 µL of plasma or serum to provide a test result with at least about 95% confidence or accuracy. In some instances, methods disclosed herein comprise obtaining at least about 12 µL of plasma or serum to provide a test result with at least about 98% confidence or accuracy. In some instances, methods disclosed herein comprise obtaining at least about 12 µL of plasma or serum to provide a test result with at least about 99% confidence or accuracy. In some instances, methods disclosed herein comprise obtaining only about 10 µL to about 60 µL of plasma or serum to provide a test result with at least about 90% confidence or accuracy. In some instances, methods disclosed herein comprise obtaining only about 10 µL to about 60 P. of plasma or serum to provide a test result with at least about 95% confidence or accuracy. In some instances, methods disclosed herein comprise obtaining only about 10 µL about 60 µL of plasma or serum to provide a test result with at least about 97% confidence or accuracy. In some instances, methods disclosed herein comprise obtaining only about 10 µL to about 60 µL of plasma or serum to provide a test result with at least about 98% confidence or accuracy. In some instances, v only about 10 µL to about 60 µL of plasma or serum to provide a test result with at least about 99% confidence or accuracy. In some instances, methods disclosed herein comprise obtaining only about 10 µL to about 60 µL of plasma or serum to provide a test result with at least about 99.5% confidence or accuracy.

In some instances, methods disclosed herein comprise obtaining a biological sample from a subject, wherein the biological sample contains an amount of cell-free nucleic acid molecules. In some instances, obtaining the biological sample results in disrupting or lysing cells in the biological sample. Thus, in some instances, the biological sample comprises cellular nucleic acid molecules. In some instances, cellular nucleic acid molecules make up less than about 1% of the total cellular nucleic acid molecules in the biological sample. In some instances, cellular nucleic acid molecules make up less than about 5% of the total cellular nucleic acid molecules in the biological sample. In some instances, cellular nucleic acid molecules make up less than about 10% of the total cellular nucleic acid molecules in the biological sample. In some instances, cellular nucleic acid molecules make up less than about 20% of the total cellular nucleic acid molecules in the biological sample. In some instances, cellular nucleic acid molecules make up more than about 50% of the total cellular nucleic acid molecules in the biological sample. In some instances, cellular nucleic acid molecules make up less than about 90% of the total cellular nucleic acid molecules in the biological sample.

In some instances, methods disclosed herein comprise obtaining an ultra-low volume of a biological fluid sample from a subject, wherein the biological fluid sample contains an ultra-low amount of cell-free nucleic acids. In some instances, the ultra-low amount is between about 4 pg to about 100 pg. In some instances, the ultra-low amount is between about 4 pg to about 150 pg. In some instances, the ultra-low amount is between about 4 pg to about 200 pg. In some instances, the ultra-low amount is between about 4 pg to about 300 pg. In some instances, the ultra-low amount is between about 4 pg to about 400 pg. In some instances, the ultra-low amount is between about 4 pg to about 500 pg. In some instances, the ultra-low amount is between about 4 pg to about 1 ng. In some instances, the ultra-low amount is between about 10 pg to about 100 pg. In some instances, the ultra-low amount is between about 10 pg to about 150 pg. In some instances, the ultra-low amount is between about 10 pg to about 200 pg. In some instances, the ultra-low amount is between about 10 pg to about 300 pg. In some instances, the ultra-low amount is between about 10 pg to about 400 pg. In some instances, the ultra-low amount is between about 10 pg to about 500 pg. In some instances, the ultra-low amount is between about 10 pg to about 1 ng. In some instances, the ultra-low amount is between about 20 pg to about 100 pg. In some instances, the ultra-low amount is between about 20 pg to about 200 pg. In some instances, the ultra-low amount is between about 20 pg to about 500 pg. In some instances, the ultra-low amount is between about 20 pg to about 1 ng. In some instances, the ultra-low amount is between about 30 pg to about 150 pg. In some instances, the ultra-low amount is between about 30 pg to about 180 pg. In some instances, the ultra-low amount is between about 30 pg to about 200 pg. In some instances, the ultra-low amount is between is about 30 pg to about 300 pg. In some instances, the ultra-low amount is between about 30 pg to about 400 pg. In some instances, the ultra-low amount is between about 30 pg to about 500 pg. In some instances, the ultra-low amount is between is about 30 pg to about 1 ng. In some instance, the subject is a pregnant subject and the cell-free nucleic acids comprise cell-free fetal DNA. In some instances, the subject has a tumor and the cell-free nucleic acids comprise cell-free tumor DNA. In some instances, the subject is an organ transplant recipient and the cell-free nucleic acids comprise organ donor DNA.

In some instances, methods comprise obtaining less than about 1 ng of cell-free fetal nucleic acids. In some instances, methods comprise obtaining less than about 500 pg of cell-free fetal nucleic acids. In some instances, methods comprise obtaining less than about 100 pg of cell-free fetal nucleic acids. In some instances, methods comprise obtaining at least 3.5 pg of cell-free fetal nucleic acids. In some instances, methods comprise obtaining at least 10 pg of cell-free fetal nucleic acids. In some instances, methods comprise obtaining not more than about 100 pg of cell-free fetal nucleic acids. In some instances, methods comprise obtaining not more than about 500 pg of cell-free fetal nucleic acids. In some instances, methods comprise obtaining not more than about 1 ng of cell-free fetal nucleic acids.

In some instances, methods disclosed herein comprise obtaining a biological fluid sample from a subject, wherein the biological fluid sample contains at least 1 genome equivalent of cell-free DNA. One skilled in the art understands that a genome equivalent is the amount of DNA necessary to be present in a sample to guarantee that all genes will be present. Ultra-low volumes of biological fluid samples disclosed herein may contain an ultra-low number of genome equivalents. In some instances, the biological fluid sample contains less than 1 genome equivalent of cell-free nucleic acids. In some instances, the biological fluid sample contains at least 5 genome equivalents of cell-free nucleic acids. In some instances, the biological fluid sample contains at least 10 genome equivalents of cell-free nucleic acids. In some instances, the biological fluid sample contains at least 15 genome equivalents of cell-free nucleic acids. In some instances, the biological fluid sample contains at least 20 genome equivalents of cell-free nucleic acids. In some instances, the biological fluid sample contains about 5 to about 50 genome equivalents. In some instances, the biological fluid sample contains about 10 to about 50 genome equivalents. In some instances, the biological fluid sample contains about 10 to about 100 genome equivalents. In some instances, the biological fluid sample contains not more than 50 genome equivalents of cell-free nucleic acids. In some instances, the biological fluid sample contains not more than 60 genome equivalents of cell-free nucleic acids. In some instances, the biological fluid sample contains not more than 80 genome equivalents of cell-free nucleic acids. In some instances, the biological fluid sample contains not more than 100 genome equivalents of cell-free nucleic acids.

Ultra-low volumes of biological fluid samples disclosed herein may contain an ultra-low number of cell equivalents. In some instances, methods disclosed herein comprise obtaining a biological fluid sample from a subject, wherein the biological fluid sample contains at least 1 cell equivalent of cell-free DNA. In some instances, the biological fluid sample contains at least 2 cell equivalents of cell-free nucleic acids. In some instances, the biological fluid sample contains at least 5 cell equivalents of cell-free nucleic acids. In some instances, the biological fluid sample contains about 5 cell equivalents of cell-free nucleic acids to about 40 cell equivalents. In some instances, the biological fluid sample contains at least 5 cell equivalents to about 100 cell equivalents of cell-free nucleic acids. In some instances, the biological fluid sample contains not more than 30 cell equivalents of cell-free nucleic acids. In some instances, the biological fluid sample contains not more than 50 cell equivalents of cell-free nucleic acids. In some instances, the biological fluid sample contains not more than 80 cell equivalents of cell-free nucleic acids. In some instances, the biological fluid sample contains not more than 100 cell equivalents of cell-free nucleic acids.

In some instances, methods disclosed herein comprise obtaining a biological sample from a subject, wherein the biological sample contains at least one cell-free nucleic acid of interest. By way of non-limiting example, the cell-free nucleic acid of interest may be a cell-free fetal nucleic acid, cell-free tumor DNA, or DNA from a transplanted organ. In some instances, methods disclosed herein comprise obtaining a biological sample from the subject, wherein the biological sample contains about 1 to about 5 cell-free nucleic acids. In some instances, methods disclosed herein comprise obtaining a biological sample from the subject, wherein the biological sample contains about 1 to about 15 cell-free nucleic acids. In some instances, methods disclosed herein comprise obtaining a biological sample from the subject, wherein the biological sample contains about 1 to about 25 cell-free nucleic acids. In some instances, methods disclosed herein comprise obtaining a biological sample from the subject, wherein the biological sample contains about 1 to about 100 cell-free nucleic acids. In some instances, methods disclosed herein comprise obtaining a biological sample from the subject, wherein the biological sample contains about 5 to about 100 cell-free nucleic acids. In some instances, the at least one cell-free nucleic acid is represented by a sequence that is unique to a target chromosome disclosed herein.

In some instances, methods disclosed herein comprise obtaining a biological sample from a subject, wherein the biological sample contains about $10^2$ cell-free nucleic acids to about $10^{10}$ cell-free nucleic acids. In some instances, the biological sample contains about $10^2$ cell-free nucleic acids to about $10^9$ cell-free nucleic acids. In some instances, the biological sample contains about $10^2$ cell-free nucleic acids to about $10^8$ cell-free nucleic acids. In some instances, the biological sample contains about $10^2$ cell-free nucleic acids to about $10^7$ cell-free nucleic acids. In some instances, the biological sample contains about $10^2$ cell-free nucleic acids to about $10^6$ cell-free nucleic acids. In some instances, the biological sample contains about $10^2$ cell-free nucleic acids to about $10^5$ cell-free nucleic acids.

In some instances, methods disclosed herein comprise obtaining a biological sample from a subject, wherein the biological sample contains about $10^3$ cell-free nucleic acids to about $10^{10}$ cell-free nucleic acids. In some instances, the biological sample contains about $10^3$ cell-free nucleic acids to about $10^9$ cell-free nucleic acids. In some instances, the biological sample contains about $10^3$ cell-free nucleic acids to about $10^8$ cell-free nucleic acids. In some instances, the biological sample contains about $10^3$ cell-free nucleic acids to about $10^7$ cell-free nucleic acids. In some instances, the biological sample contains about $10^3$ cell-free nucleic acids to about $10^6$ cell-free nucleic acids. In some instances, the biological sample contains about $10^3$ cell-free nucleic acids to about $10^5$ cell-free nucleic acids.

In some instances, methods disclosed herein comprise obtaining a biological sample from a subject, wherein the biological sample has a number of cell-free nucleic acids that correspond to a typical sample type volume. By way of non-limiting example, 4 ml of human blood from a pregnant subject typically contains about $10^{10}$ cell-free fetal nucleic acids. However, the concentration of cell-free fetal nucleic acids in a sample, and thus, the sample volume required to be informative about fetal genetics, will depend on the sample type. Example 7, provided herein, also demonstrates how one of skill in the art can determine the minimum volume necessary to obtain a sufficient number of cell-free fetal nucleic acids.

Sample Processing

In some instances, methods disclosed herein comprise isolating or purifying cell-free nucleic acid molecules from a biological sample. In some instances, methods disclosed herein comprise isolating or purifying nucleic cell-free fetal nucleic acid molecules from a biological sample. In some instances, methods disclosed herein comprise removing non-nucleic acid components from a biological sample described herein. In some instances, isolating or purifying comprises reducing unwanted non-nucleic acid components from a biological sample. In some instances, isolating or purifying comprises removing unwanted non-nucleic acid components from a biological sample. In some instances, isolating or purifying comprises removing at least 5%, at least 10%, at least 20%, at least 30%, at least 40%, at least 50%, at least 60%, at least 70%, at least 80%, or at least 90% of unwanted non-nucleic acid components from a biological sample. In some instances, isolating or purifying comprises removing at least 95% of unwanted non-nucleic acid components from a biological sample. In some instances, isolating or purifying comprises removing at least 97% of unwanted non-nucleic acid components from a biological sample. In some instances, isolating or purifying comprises removing at least 98% of unwanted non-nucleic acid components from a biological sample. In some instances, isolating or purifying comprises removing at least 99% of unwanted non-nucleic acid components from a biological sample. In some instances, isolating or purifying comprises removing at least 95% of unwanted non-nucleic acid components from a biological sample. In some instances, isolating or purifying comprises removing at least 97% of unwanted non-nucleic acid components from a biological sample. In some instances, isolating or purifying comprises removing at least 98% of unwanted non-nucleic acid components from a biological sample. In some instances, isolating or purifying comprises removing at least 99% of unwanted non-nucleic acid components from a biological sample.

In some instances, methods disclosed herein comprise isolating or purifying nucleic acids from one or more non-nucleic acid components of a biological sample. Non-nucleic acid components may also be considered unwanted substances. Non-limiting examples of non-nucleic acid components include cells (e.g., blood cells), cell fragments, extracellular vesicles, lipids, proteins or a combination thereof. Additional non-nucleic acid components are described herein and throughout. It should be noted that while methods may comprise isolating/purifying nucleic acids, they may also comprise analyzing a non-nucleic acid component of a sample that is considered an unwanted substance in a nucleic acid purifying step. Isolating or purifying may comprise removing components of a biological sample that would inhibit, interfere with or otherwise be detrimental to the later process steps such as nucleic acid amplification or detection.

Isolating or purifying may be performed with a device or system disclosed herein. Isolating or purifying may be performed within a device or system disclosed herein. Isolating and/or purifying may occur with the use of a sample purifier disclosed herein. In some instances, isolating or purifying nucleic acids comprises removing non-nucleic acid components from a biological sample described herein. In some instances, isolating or purifying nucleic acids comprises discarding non-nucleic acid components from a biological sample. In some instances, isolating or purifying comprises collecting, processing and analyzing the non-nucleic acid components. In some instances, the non-nucleic acid components may be considered biomarkers because they provide additional information about the subject.

In some instances, isolating or purifying nucleic acids comprise lysing a cell. In some instances, isolating or purifying nucleic acids avoids lysing a cell. In some instances, isolating or purifying nucleic acids does not comprise lysing a cell. In some instances, isolating or purifying nucleic acids does not comprise an active step intended to lyse a cell. In some instances, isolating or purifying nucleic acids does not comprise intentionally lysing a cell. Intentionally lysing a cell may include mechanically disrupting a cell membrane (e.g., shearing). Intentionally lysing a cell may include contacting the cell with a lysis reagent. Exemplary lysis reagents are described herein.

In some instances, isolating or purifying nucleic acids comprises lysing and performing sequence specific capture of a target nucleic acid with "bait" in a solution followed by binding of the "bait" to solid supports such as magnetic beads, e.g. Legler et al., Specific magnetic bead-based capture of free fetal DNA from maternal plasma, Transfusion and Apheresis Science 40 (2009), 153-157. In some instances, methods comprise performing sequence specific capture in the presence of a recombinase or helicase. Use of a recombinase or helicase may avoid the need for heat denaturation of a nucleic acid and speed up the detection step.

In some instances, isolating or purifying comprises separating components of a biological sample disclosed herein. By way of non-limiting example, isolating or purifying may comprise separating plasma from blood. In some instances, isolating or purifying comprises centrifuging the biological sample. In some instances, isolating or purifying comprises filtering the biological sample in order to separate components of a biological sample. In some instances, isolating or purifying comprises filtering the biological sample in order to remove non-nucleic acid components from the biological sample. In some instances, isolating or purifying comprises filtering the biological sample in order to capture nucleic acids from the biological sample.

In some instances, the biological sample is blood and isolating or purifying a nucleic acid comprises obtaining or isolating plasma from blood. Obtaining plasma may comprise separating plasma from cellular components of a blood sample. Obtaining plasma may comprise centrifuging the blood, filtering the blood, or a combination thereof. Obtaining plasma may comprise allowing blood to be subjected to gravity (e.g., sedimentation). Obtaining plasma may comprise subjecting blood to a material that wicks a portion of the blood away from non-nucleic acid components of the blood. In some instances, methods comprise subjecting the blood to vertical filtration. In some instances, methods comprise subjecting the blood to a sample purifier comprising a filter matrix for receiving whole blood, the filter matrix having a pore size that is prohibitive for cells to pass through, while plasma can pass through the filter matrix uninhibited. Such vertical filtration and filter matrices are described for devices disclosed herein.

In some instances, isolating or purifying comprises subjecting a biological sample, or a fraction thereof, or a modified version thereof, to a binding moiety. The binding moiety may be capable of binding to a component of a biological sample and removing it to produce a modified sample depleted of cells, cell fragments, nucleic acids or proteins that are unwanted or of no interest. In some instances, isolating or purifying comprises subjecting a biological sample to a binding moiety to reduce unwanted substances or non-nucleic acid components in a biological sample. In some instances, isolating or purifying comprises subjecting a biological sample to a binding moiety to produce a modified sample enriched with target cell, target cell fragments, target nucleic acids or target proteins. By way of non-limiting example, isolating or purifying may comprise subjecting a biological sample to a binding moiety for capturing placenta educated platelets, which may contain fetal DNA or RNA fragments. The resulting cell-bound binding moieties can be captured/enriched for with antibodies or other methods, e.g., low speed centrifugation.

Isolating or purifying may comprise capturing an extracellular vesicle or extracellular microparticle in the biological sample with a binding moiety. In some instances, the extracellular vesicle contains at least one of DNA and RNA. In some instances, the extracellular vesicle is fetal/placental in origin. Methods may comprise capturing an extracellular vesicle or extracellular microparticle in the biological sample that comes from a maternal cell. In some instances, methods disclosed herein comprise capturing and discarding an extracellular vesicle or extracellular microparticle from a maternal cell to enrich the sample for fetal/placental nucleic acids.

In some instances, methods comprise capturing a nucleosome in a biological sample and analyzing nucleic acids attached to the nucleosome. In some instances, methods comprise capturing an exosome in a biological sample and analyzing nucleic acids attached to the exosome. Capturing nucleosomes and/or exosomes may preclude the need for a lysis step or reagent, thereby simplifying the method and reducing time from sample collection to detection.

In some instances, methods comprise subjecting a biological sample to a cell-binding moiety for capturing placenta educated platelets, which may contain fetal DNA or RNA fragments. Capturing may comprise contacting the placenta educated platelets with a binding moiety (e.g., an antibody for a cell surface marker), subjecting the biological sample to low speed centrifugation, or a combination thereof. In some instances, the binding moiety is attached to a solid support disclosed herein, and methods comprise separating the solid support from the rest of the biological sample after the binding moiety has made contact with the biological sample.

In some instances, methods disclosed herein comprise removing unwanted non-nucleic acid components from a biological sample. In some instances, methods disclosed herein comprise removing and discarding non-nucleic acid components from a biological sample. Non-limiting examples of non-nucleic acid components include cells (e.g., blood cells), cell fragments, extracellular vesicles, lipids, proteins or a combination thereof. In some instances, removing non-nucleic acid components may comprise centrifuging the biological sample. In some instances, removing non-nucleic acid components may comprise filtering the biological fluid sample. In some instances, removing non-nucleic acid components may comprise contacting the biological sample with a binding moiety described herein.

In some embodiments, methods disclosed herein comprise purifying nucleic acids in a sample. In some instances, purifying does not comprise washing the nucleic acids with a wash buffer. In some instances, the nucleic acids are cell-free fetal nucleic acids. In some embodiments, purifying comprises capturing the nucleic acids with a nucleic acid capturing moiety to produce captured nucleic acids. Non-limiting examples of nucleic acid capturing moieties are silica particles and paramagnetic particles. In some embodiments, purifying comprises passing the sample containing the captured nucleic acids through a hydrophobic phase (e.g., a liquid or wax). The hydrophobic phase retains impurities in the sample that would otherwise inhibit further manipulation (e.g., amplification, sequencing) of the nucleic acids.

In some instances, methods disclosed herein comprise removing nucleic acid components from a biological sample described herein. In some instances, the removed nucleic acid components are discarded. By way of non-limiting example, methods may comprise analyzing only DNA. Thus, RNA is unwanted and creates undesirable background noise or contamination to the DNA. In some instances, methods disclosed herein comprise removing RNA from a biological sample. In some instances, methods disclosed herein comprise removing mRNA from a biological sample. In some instances, methods disclosed herein comprise removing microRNA from a biological sample. In some instances, methods disclosed herein comprise removing maternal RNA from a biological sample. In some instances, methods disclosed herein comprise removing DNA from a biological sample. In some instances, methods disclosed herein comprise removing maternal DNA from a biological sample of a pregnant subject. In some instances, removing nucleic acid components comprises contacting the nucleic acid components with an oligonucleotide capable of hybridizing to the nucleic acid, wherein the oligonucleotide is conjugated, attached or bound to a capturing device (e.g., bead, column, matrix, nanoparticle, magnetic particle, etc.). In some instances, the removed nucleic acid components are discarded.

In some instances, removing nucleic acid components comprises separating the nucleic acid components on a gel by size. For example, circulating cell-free fetal DNA fragments are generally less than 200 base pairs in length. In some instances, methods disclosed herein comprise removing cell-free DNA from the biological sample. In some instances, methods disclosed herein comprise capturing cell-free DNA from the biological sample. In some instances, methods disclosed herein comprise selecting cell-free DNA from the biological sample. In some instances, the cell-free DNA has a minimum length. In some instances, the minimum length is about 50 base pairs. In some instances, the minimum length is about 100 base pairs. In some instances, the minimum length is about 110 base pairs. In some instances, the minimum length is about 120 base pairs. In some instances, the minimum length is about 140 base pairs. In some instances, the cell-free DNA has a maximum length. In some instances, the maximum length is about 180 base pairs. In some instances, the maximum length is about 200 base pairs. In some instances, the maximum length is about 220 base pairs. In some instances, the maximum length is about 240 base pairs. In some instances, the maximum length is about 300 base pairs. Size based separation would be useful for other categories of nucleic acids having limited size ranges, which are well known in the art (e.g., microRNAs).

Amplifying Nucleic Acids

In some instances, methods disclosed herein comprise amplifying at least one nucleic acid in a sample to produce at least one amplification product. The at least one nucleic acid may be a cell-free nucleic acid. The sample may be a biological sample disclosed herein or a fraction or portion thereof. In some instances, methods comprise producing a copy of the nucleic acid in the sample and amplifying the copy to produce the at least one amplification product. In some instances, methods comprise producing a reverse transcript of the nucleic acid in the sample and amplifying the reverse transcript to produce the at least one amplification product.

In some instances, methods comprise performing whole genome amplification. In some instances, methods do not comprise performing whole genome amplification. The term, "whole genome amplification" may refer to amplifying all of the cell-free nucleic acids in a biological sample. The term, "whole genome amplification" may refer to amplifying at least 90% of the cell-free nucleic acids in a biological sample. Whole genome may refer to multiple genomes. Whole genome amplification may comprise amplifying cell-free nucleic acids from a biological sample of a subject, wherein the biological sample comprises cell-free nucleic acids from the subject and a foreign tissue. For example, whole genome amplification may comprise amplifying cell-free nucleic acids from both a subject (a host genome) and an organ or tissue that has been transplanted into the subject (a donor genome). Also by way of non-limiting example, whole genome amplification may comprise amplifying cell-free nucleic acids from a biological sample of a pregnant subject, wherein the biological sample comprises cell-free nucleic acids from the pregnant subject and her fetus. Whole genome amplification may comprise amplifying cell-free nucleic acids from a biological sample of a subject having cancer, wherein the biological sample comprises cell-free nucleic acids from benign tissue of the subject and a tumor in the subject. Whole genome amplification may comprise amplifying cell-free nucleic acids from a biological sample of a subject having an infection, wherein the biological sample comprises cell-free nucleic acids from the subject and a pathogen.

In some instances, methods disclosed herein comprise amplifying a nucleic acid, wherein amplifying comprises performing an isothermal amplification of the nucleic acid. Non-limiting examples of isothermal amplification are as follows: loop-mediated isothermal amplification (LAMP), strand displacement amplification (SDA), helicase dependent amplification (HDA), nicking enzyme amplification reaction (NEAR), and recombinase polymerase amplification (RPA).

Any appropriate nucleic acid amplification method known in the art is contemplated for use in the devices and methods described herein. In some instances, isothermal amplification is used. In some instances, amplification is isothermal with the exception of an initial heating step before isothermal amplification begins. A number of isothermal amplification methods, each having different considerations and providing different advantages, are known in the art and have been discussed in the literature, e.g., by Zanoli and Spoto, 2013, "Isothermal Amplification Methods for the Detection of Nucleic Acids in Microfluidic Devices," Biosensors 3: 18-43, and Fakruddin, et al., 2013, "Alternative Methods of Polymerase Chain Reaction (PCR)," Journal of Pharmacy and Bioallied Sciences 5(4): 245-252, each incorporated herein by reference in its entirety. In some instances, any appropriate isothermic amplification method is used. In some instances, the isothermic amplification method used is selected from: Loop Mediated Isothermal Amplification (LAMP); Nucleic Acid Sequence Based Amplification (NASBA); Multiple Displacement Amplification (MDA); Rolling Circle Amplification (RCA); Helicase Dependent Amplification (HDA); Strand Displacement Amplification (SDA); Nicking Enzyme Amplification Reaction (NEAR); Ramification Amplification Method (RAM); and Recombinase Polymerase Amplification (RPA).

In some instances, the amplification method used is LAMP (see, e.g., Notomi, et al., 2000, "Loop Mediated Isothermal Amplification" NAR 28(12): e63 i-vii, and U.S. Pat. No. 6,410,278, "Process for synthesizing nucleic acid" each incorporated by reference herein in its entirety). LAMP is a one-step amplification system using auto-cycling strand displacement deoxyribonucleic acid (DNA) synthesis. In some instances, LAMP is carried out at 60-65° C. for 45-60 min in the presence of a thermostable polymerase, e.g., *Bacillus stearothermophilus* (Bst) DNA polymerase I, deoxyribonucleotide triphosphate (dNTPs), specific primers and the target DNA template. In some instances, the template is RNA and a polymerase having both reverse transcriptase activity and strand displacement-type DNA polymerase activity, e.g., Bca DNA polymerase, is used, or a polymerase having reverse transcriptase activity is used for the reverse transcriptase step and a polymerase not having reverse transcriptase activity is used for the strand displacement-DNA synthesis step.

In some instances, the amplification method is Nucleic Acid Sequence Based Amplification (NASBA). NASBA (also known as 3SR, and transcription-mediated amplification) is an isothermal transcription-based RNA amplification system. Three enzymes (avian myeloblastosis virus reverse transcriptase, RNase H and T7 DNA dependent RNA polymerase) are used to generate single-stranded RNA. In certain cases NASBA can be used to amplify DNA. The amplification reaction is performed at 41° C., maintaining constant temperature, typically for about 60 to about 90 minutes (see, e.g., Fakruddin, et al., 2012, "Nucleic Acid Sequence Based Amplification (NASBA) Prospects and Applications," Int. J. of Life Science and Pharma Res. 2(1):L106-L121, incorporated by reference herein).

In some instances, the NASBA reaction is carried out at about 40° C. to about 42° C. In some instances, the NASBA reaction is carried out at 41° C. In some instances, the NASBA reaction is carried out at at most about 42° C. In some instances, the NASBA reaction is carried out at about 40° C. to about 41° C., about 40° C. to about 42° C., or about 41° C. to about 42° C. In some instances, the NASBA reaction is carried out at about 40° C., about 41° C., or about 42° C.

In some instances, the amplification method is Strand Displacement Amplification (SDA). SDA is an isothermal amplification method that uses four different primers. A primer containing a restriction site (a recognition sequence for HincII exonuclease) is annealed to the DNA template. An exonuclease-deficient fragment of *Eschericia coli* DNA polymerase 1 (exo-Klenow) elongates the primers. Each SDA cycle consists of (1) primer binding to a displaced target fragment, (2) extension of the primer/target complex by exo-Klenow, (3) nicking of the resultant hemiphosphothioate HincII site, (4) dissociation of HincII from the nicked site and (5) extension of the nick and displacement of the downstream strand by exo-Klenow.

In some instances, methods comprise contacting DNA in a sample with a helicase. In some instances, the amplification method is Helicase Dependent Amplification (HDA). HDA is an isothermal reaction because a helicase, instead of heat, is used to denature DNA.

In some instances, the amplification method is Multiple Displacement Amplification (MDA). The MDA is an isothermal, strand-displacing method based on the use of the highly processive and strand-displacing DNA polymerase from bacteriophage Ø29, in conjunction with modified random primers to amplify the entire genome with high fidelity. It has been developed to amplify all DNA in a sample from a very small amount of starting material. In MDA Ø29 DNA polymerase is incubated with dNTPs, random hexamers and denatured template DNA at 30° C. for 16 to 18 hours and the enzyme must be inactivated at high temperature (65° C.) for 10 min. No repeated recycling is required, but a short initial denaturation step, the amplification step, and a final inactivation of the enzyme are needed.

In some instances, the amplification method is Rolling Circle Amplification (RCA). RCA is an isothermal nucleic acid amplification method which allows amplification of the probe DNA sequences by more than $10^9$ fold at a single temperature, typically about 30° C. Numerous rounds of isothermal enzymatic synthesis are carried out by Ø29 DNA polymerase, which extends a circle-hybridized primer by continuously progressing around the circular DNA probe. In some instances, the amplification reaction is carried out using RCA, at about 28° C. to about 32° C.

Additional amplification methods can be found in the art that could be incorporated into devices and methods disclosed herein. Ideally, the amplification method is isothermal and fast relative to traditional PCR. In some instances, amplifying comprises performing an exponential amplification reaction (EXPAR), which is an isothermal molecular chain reaction in that the products of one reaction catalyze further reactions that create the same products. In some instances, amplifying occurs in the presence of an endonuclease. The endonuclease may be a nicking endonuclease. See, e.g., Wu et al., "Aligner-Mediated Cleavage of Nucleic Acids," Chemical Science (2018). In some instances, amplifying does not require initial heat denaturation of target DNA. See, e.g., Toley et al., "Isothermal strand displacement amplification (iSDA): a rapid and sensitive method of nucleic acid amplification for point-of-care diagnosis," The Analyst (2015). Pulse controlled amplification in an ultrafast amplification method developed by GNA Biosolutions GmbH.

In some instances, methods comprise performing multiple cycles of nucleic acid amplification with a pair of primers. The number of amplification cycles is important because amplification may introduce a bias into the representation of regions. With ultra low input amounts, amplification is even more prone to create biases and hence increasing efficiency prior to amplification is important for high accuracy. Not all regions amplify with the same efficiency and therefore the overall representation may not be uniform which will impact the accuracy of the analysis. Usually fewer cycles are ideal if amplification is necessary at all. In some instances, methods comprise performing fewer than 30 cycles of amplification. In some instances, methods comprise performing fewer than 25 cycles of amplification. In some instances, methods comprise performing fewer than 20 cycles of amplification. In some instances, methods comprise performing fewer than 15 cycles of amplification. In some instances, methods comprise performing fewer than 12 cycles of amplification. In some instances, methods comprise performing fewer than 11 cycles of amplification. In some instances, methods comprise performing fewer than 10 cycles of amplification. In some instances, methods comprise performing at least 3 cycles of amplification. In some instances, methods comprise performing at least 5 cycles of amplification. In some instances, methods comprise performing at least 8 cycles of amplification. In some instances, methods comprise performing at least 10 cycles of amplification.

In some instances, the amplification reaction is carried for about 30 to about 90 minutes. In some instances, the amplification reaction is carried out for at least about 30 minutes. In some instances, the amplification reaction is carried out for at most about 90 minutes. In some instances, the amplification reaction is carried out for about 30 minutes to about 35 minutes, about 30 minutes to about 40 minutes, about 30 minutes to about 45 minutes, about 30 minutes to about 50 minutes, about 30 minutes to about 55 minutes, about 30 minutes to about 60 minutes, about 30 minutes to about 65 minutes, about 30 minutes to about 70 minutes, about 30 minutes to about 75 minutes, about 30 minutes to about 80 minutes, about 30 minutes to about 90 minutes, about 35 minutes to about 40 minutes, about 35 minutes to about 45 minutes, about 35 minutes to about 50 minutes, about 35 minutes to about 55 minutes, about 35 minutes to about 60 minutes, about 35 minutes to about 65 minutes, about 35 minutes to about 70 minutes, about 35 minutes to about 75 minutes, about 35 minutes to about 80 minutes, about 35 minutes to about 90 minutes, about 40 minutes to about 45 minutes, about 40 minutes to about 50 minutes, about 40 minutes to about 55 minutes, about 40 minutes to about 60 minutes, about 40 minutes to about 65 minutes, about 40 minutes to about 70 minutes, about 40 minutes to about 75 minutes, about 40 minutes to about 80 minutes, about 40 minutes to about 90 minutes, about 45 minutes to about 50 minutes, about 45 minutes to about 55 minutes, about 45 minutes to about 60 minutes, about 45 minutes to about 65 minutes, about 45 minutes to about 70 minutes, about 45 minutes to about 75 minutes, about 45 minutes to about 80 minutes, about 45 minutes to about 90 minutes, about 50 minutes to about 55 minutes, about 50 minutes to about 60 minutes, about 50 minutes to about 65 minutes, about 50 minutes to about 70 minutes, about 50 minutes to about 75 minutes, about 50 minutes to about 80 minutes, about 50 minutes to about 90 minutes, about 55 minutes to about 60 minutes, about 55 minutes to about 65 minutes, about 55 minutes to about 70 minutes, about 55 minutes to about 75 minutes, about 55 minutes to about 80 minutes, about 55 minutes to about 90 minutes, about 60 minutes to about 65 minutes, about 60 minutes to about 70 minutes, about 60 minutes to about 75 minutes, about 60 minutes to about 80 minutes, about 60 minutes to about 90 minutes, about 65 minutes to about 70 minutes, about 65 minutes to about 75 minutes, about 65 minutes to about 80 minutes, about 65 minutes to about 90 minutes, about 70 minutes to about 75 minutes, about 70 minutes to about 80 minutes, about 70 minutes to about 90 minutes, about 75 minutes to about 80 minutes, about 75 minutes to about 90 minutes, or about 80 minutes to about 90 minutes. In some instances, the amplification reaction is carried out for about 30 minutes, about 35 minutes, about 40 minutes, about 45 minutes, about 50 minutes, about 55 minutes, about 60 minutes, about 65 minutes, about 70 minutes, about 75 minutes, about 80 minutes, or about 90 minutes.

In some instances, methods disclosed herein comprise amplifying a nucleic acid at least at one temperature. In some instances, methods disclosed herein comprise amplifying a nucleic acid at a single temperature (e.g., isothermal amplification). In some instances, methods disclosed herein comprise amplifying a nucleic acid, wherein the amplifying occurs at not more than two temperatures. Amplifying may occur in one step or multiple steps. Non-limiting examples of amplifying steps include double strand denaturing, primer hybridization, and primer extension.

In some instances, at least one step of amplifying occurs at room temperature. In some instances, all steps of amplifying occur at room temperature. In some instances, at least one step of amplifying occurs in a temperature range. In some instances, all steps of amplifying occur in a temperature range. In some instances, the temperature range is about 0° C. to about 100° C. In some instances, the temperature range is about 15° C. to about 100° C. In some instances, the temperature range is about 25° C. to about 100° C. In some instances, the temperature range is about 35° C. to about 100° C. In some instances, the temperature range is about 55° C. to about 100° C. In some instances, the temperature range is about 65° C. to about 100° C. In some instances, the temperature range is about 15° C. to about 80° C. In some instances, the temperature range is about 25° C. to about 80° C. In some instances, the temperature range is about 35° C. to about 80° C. In some instances, the temperature range is about 55° C. to about 80° C. In some instances, the temperature range is about 65° C. to about 80° C. In some instances, the temperature range is about 15° C. to about 60° C. In some instances, the temperature range is about 25° C. to about 60° C. In some instances, the temperature range is about 35° C. to about 60° C. In some instances, the temperature range is about 15° C. to about 40° C. In some instances, the temperature range is about −20° C. to about 100° C. In some instances, the temperature range is about −20° C. to about 90° C. In some instances, the temperature range is about −20° C. to about 50° C. In some instances, the temperature range is about −20° C. to about 40° C. In some instances, the temperature range is about −20° C. to about 10° C. In some instances, the temperature range is about 0° C. to about 100° C. In some instances, the temperature range is about 0° C. to about 40° C. In some instances, the temperature range is about 0° C. to about 30° C. In some instances, the temperature range is about 0° C. to about 20° C. In some instances, the temperature range is about 0° C. to about 10° C. In some instances, the temperature range is about 15° C. to about 100° C. In some instances, the temperature range is about 15° C. to about 90° C. In some instances, the temperature range is about 15° C. to about 80° C. In some instances, the temperature range is about is about 15° C. to about 70° C. In some instances, the temperature range is about 15° C. to about 60° C. In some instances, the temperature range is about 15° C. to about 50° C. In some instances, the temperature range is about 15° C. to about 30° C. In some instances, the temperature range is about 10° C. to about 30° C. In some instances, methods disclose herein are performed at room temperature, not requiring cooling, freezing or heating. In some instances, amplifying comprises contacting the sample with random oligonucleotide primers. In some instances, amplifying comprises contacting cell-free nucleic acid molecules disclosed herein with random oligonucleotide primers. In some instances, amplifying comprises contacting cell-free fetal nucleic acid molecules disclosed herein with random oligonucleotide primers. In some instances, amplifying comprises contacting the tagged nucleic acid molecules disclosed herein with random oligonucleotide primers. Amplifying with a plurality of random primers generally results in non-targeted amplification of multiple nucleic acids of different sequences or an overall amplification of most nucleic acids in a sample.

In some instances, amplifying comprises targeted amplification (e.g., selector method (described in U.S. Pat. No. 6,558,928), molecular inversion probes). In some instances, amplifying a nucleic acid comprises contacting a nucleic acid with at least one primer having a sequence corresponding to a target chromosome sequence. Exemplary chromosome sequences are disclosed herein. In some instances, amplifying comprises contacting the nucleic acid with at least one primer having a sequence corresponding to a non-target chromosome sequence. In some instances, amplifying comprises contacting the nucleic acid with not more than one pair of primers, wherein each primer of the pair of primers comprises a sequence corresponding to a sequence on a target chromosome disclosed herein. In some instances, amplifying comprises contacting the nucleic acid with multiple sets of primers, wherein each of a first pair in a first set and each of a pair in a second set are all different.

In some instances, amplifying comprises contacting the sample with at least one primer having a sequence corresponding to a sequence on a target chromosome disclosed herein. In some instances, amplifying comprises contacting the sample with at least one primer having a sequence corresponding to a sequence on a non-target chromosome disclosed herein. In some instances, amplifying comprises contacting the sample with not more than one pair of primers, wherein each primer of the pair of primers comprises a sequence corresponding to a sequence on a target chromosome disclosed herein. In some instances, amplifying comprises contacting the sample with multiple sets of primers, wherein each of a first pair in a first set and each of a pair in a second set are all different.

In some instances, amplifying comprises multiplexing (nucleic acid amplification of a plurality of nucleic acids in one reaction). In some instances, multiplexing comprises contacting nucleic acids of the biological sample with a plurality of oligonucleotide primer pairs. In some instances, multiplexing comprising contacting a first nucleic acid and a second nucleic acid, wherein the first nucleic acid corresponds to a first sequence and the second nucleic acid corresponds to a second sequence. In some instances, the first sequence and the second sequence are the same. In some instances, the first sequence and the second sequence are different. In some instances, amplifying does not comprise multiplexing. In some instances, amplifying does not require multiplexing. In some instance, amplifying comprises nested primer amplification. Methods may comprise multiplex PCR of multiple regions, wherein each region comprises a single nucleotide polymorphism (SNP). Multiplexing may occur in a single tube. In some instances, methods comprise multiplex PCR of more than 100 regions wherein each region comprises a SNP. In some instances, methods comprise multiplex PCR of more than 500 regions wherein each region comprises a SNP. In some instances, methods comprise multiplex PCR of more than 1000 regions wherein each region comprises a SNP. In some instances, methods comprise multiplex PCR of more than 2000 regions wherein each region comprises a SNP. In some instances, methods comprise multiplex PCR of more than 300 regions wherein each region comprises a SNP.

In some instances, methods comprise amplifying a nucleic acid in the sample, wherein amplifying comprises contacting the sample with at least one oligonucleotide primer, wherein the at least one oligonucleotide primer is not active or extendable until it is in contact with the sample. In some instances, amplifying comprises contacting the sample with at least one oligonucleotide primer, wherein the at least one oligonucleotide primer is not active or extendable until it is exposed to a selected temperature. In some instances, amplifying comprises contacting the sample with at least one oligonucleotide primer, wherein the at least one oligonucleotide primer is not active or extendable until it is contacted with an activating reagent. By way of non-limiting example, the at least one oligonucleotide primer may comprise a blocking group. Using such oligonucleotide primers may minimize primer dimers, allow recognition of unused primer, and/or avoid false results caused by unused primers. In some instances, amplifying comprises contacting the sample with at least one oligonucleotide primer comprising a sequence corresponding to a sequence on a target chromosome disclosed herein.

In some instances, methods disclosed herein comprise the use of one or more tags. The use of one or more tags may increase at least one of the efficiency, speed and accuracy of methods disclosed herein. In some instances, the oligonucleotide primer comprises a tag, wherein the tag is not specific to a target sequence. Such a tag may be referred to as a universal tag. In some instances, methods comprise tagging a target sequence, or fragment thereof, in the sample with a tag that is not specific to the target sequence. In some instances, the tag that is not specific to a sequence on a human chromosome. Alternatively or additionally, methods comprise contacting the sample with a tag and at least one oligonucleotide primer comprising a sequence corresponding to a target sequence, wherein the tag is separate from the oligonucleotide primer. In some instances, the tag is incorporated in an amplification product produced by extension of the oligonucleotide primer after it hybridizes to the target sequence. The tag may be an oligonucleotide, a small molecule, or a peptide. In some instances, the tag does not comprise a nucleotide. In some instances, the tag does not comprise an oligonucleotide. In some instances, the tag does not comprise an amino acid. In some instances, the tag does not comprise a peptide. In some instances, the tag is not sequence specific. In some instances, the tag comprises a generic sequence that does not correspond to any particular target sequence. In some instances, the tag is detectable when an amplification product is produced, regardless of the sequence amplified. In some instances, at least one of the oligonucleotide primer and tag comprises a peptide nucleic acid (PNA). In some instances, at least one of the oligonucleotide primer and tag comprises a locked nucleic acid (LNA).

In some instances, methods disclosed herein comprise the use of a plurality of tags, thereby increasing at least one of the accuracy of the method, speed of the method and information obtained by the method. In some instances, methods disclosed herein comprise the use of a plurality of tags, thereby decreasing the volume of sample required to obtain a reliable result. In some instances, the plurality of tags comprises at least one capture tag. In some instances, the plurality of tags comprises at least one detection tag. In some instances, the plurality of tags comprises a combination of least one capture tag and at least one detection tag. A capture tag is generally used to isolate or separate a specific sequence or region from other regions. A typical example for a capture tag is biotin (that can be captured using streptavidin coated surfaces for example). Examples of detection tags are digoxigenin and a fluorescent tag. The detection tag may be detected directly (e.g., laser irradiation and/or measuring emitted light) or indirectly through an antibody that carries or interacts with a secondary detection system such as a luminescent assay or enzymatic assay. In some instances, the plurality of tags comprises a combination of least one capture tag (a tag used to isolate an analyte) and at least one detection tag (a tag used to detect the analyte). In some instance, a single tag acts as a detection tag and a capture tag.

In some instances, methods comprise contacting the at least one circulating cell-free nucleic acid in the sample with a first tag and a second tag, wherein the first tag comprises a first oligonucleotide that is complementary to a sense strand of the circulating cell-free nucleic acid, and the second capture tag comprises a second oligonucleotide that is complementary to an antisense strand of the circulating cell-free nucleic acid. In some instances, methods comprise contacting the at least one circulating cell-free nucleic acid in the sample with a first tag and a second tag, wherein the first tag carries the same label as the second tag. In some instances, methods comprise contacting the at least one circulating cell-free nucleic acid in the sample with a first tag and a second tag, wherein the first tag carries a different label than the second tag. In some instances, the tags are the same and there is a single qualitative or quantitative signal that is the aggregate of all probes/regions detected. In some instances, the tags are different. One tag may be used to purify and one tag may be used to detect. In some instances, a first oligonucleotide tag is specific to a region (e.g., cfDNA fragment) and carries a fluorescent label and a second oligonucleotide is specific to an adjacent region and carries the same fluorescent label because only the aggregate signal is desired. In other instances, a first oligonucleotide tag is specific to a region (e.g., cfDNA fragment) and carries a fluorescent label and a second oligonucleotide is specific to an adjacent region and carries a different fluorescent label to detect two distinct regions.

In some instances, methods comprise detecting an amplification product, wherein the amplification product is produced by amplifying at least a portion of a target chromosome disclosed herein, or fragment thereof. The portion or fragment of the target chromosome may comprise at least 5 nucleotides. The portion or fragment of the target chromosome may comprise at least about 10 nucleotides. The portion or fragment of the target chromosome may comprise at least about 15 nucleotides. In some instances, detecting amplification products disclosed herein does not comprise tagging or labeling the amplification product. In some instances, methods detect the amplification product based on its amount. For example, the methods may detect an increase in the amount of double stranded DNA in the sample. In some instances, detecting the amplification product is at least partially based on its size. In some instances, the amplification product has a length of about 50 base pairs to about 500 base pairs.

In some instances, detecting the amplification product comprises contacting the amplification product with a tag. In some instances, the tag comprises a sequence that is complementary to a sequence of the amplification product. In some instances, the tag does not comprise a sequence that is complementary to a sequence of the amplification product. Non-limiting examples of tags are described in the foregoing and following disclosure.

In some instances, detecting the amplification product, whether tagged or not tagged, comprises subjecting the amplification product to a signal detector or assay assembly of a device, system, or kit disclosed herein. In some instances, methods comprise comprises amplifying and detecting on an assay assembly of a device, system, or kit disclosed herein. In some instances, the assay assembly comprises amplification reagents. In some instances, methods comprise applying an instrument or reagent to an assay assembly (e.g., lateral flow assay) disclosed herein to control the flow of a biological sample, solution, or combination thereof, through the lateral flow assay. In some instances, the instrument is a vacuum, a pipet, a pump, or a combination thereof.

Sequencing

In some instances, methods disclosed herein comprise sequencing a nucleic acid. The nucleic acid may be a nucleic acid disclosed herein, such as a tagged nucleic acid, an amplified nucleic acid, a cell-free nucleic acid, a cell-free fetal nucleic acid, a nucleic acid having a sequence corresponding to a target chromosome, a nucleic acid having a sequence corresponding to a region of a target chromosome, a nucleic acid having a sequence corresponding to a non-target chromosome, or a combination thereof. In some instances, the nucleic acid is DNA. In some instances, the nucleic acid is RNA. In some instances, the nucleic acid comprises DNA. In some instances, the nucleic acid comprises RNA.

In some instances, sequencing comprises targeted sequencing. In some instances, sequencing comprises whole genome sequencing. In some instances, sequencing comprises targeted sequencing and whole genome sequencing. In some instances, whole genome sequencing comprises massive parallel sequencing, also referred to in the art as next generation sequencing or second generation sequencing. In some instances, whole genome sequencing comprises random massive parallel sequencing. In some instances, sequencing comprises random massive parallel sequencing of target regions captured from a whole genome library.

In some instances, methods comprise sequencing amplified nucleic acids disclosed herein. In some instances, amplified nucleic acids are produced by targeted amplification (e.g., with primers specific to target sequences of interest). In some instances, amplified nucleic acids are produced by non-targeted amplification (e.g., with random oligonucleotide primers). In some instances, methods comprise sequencing amplified nucleic acids, wherein the sequencing comprises massive parallel sequencing.

In some instances, methods comprise performing a genome sequence alignment using an algorithm. By way of non-limiting example, the algorithm may be designed to recognize a chromosome copy number. The algorithm may be designed to reveal an observed number of sequence reads associated with each relevant allele at various SNP loci. The algorithm may use parental genotypes and crossover frequency data to create monosomic, disomic and trisomic fetal genotypes at measured loci in silico, which are then used to predict sequencing data for each genotype. Using a Bayesian model, the sequencing data with the maximum likelihood is selected as the copy number and fetal fraction and the likelihood is the calculated accuracy. Different probability distributions may be expected for each of the two possible alleles for each SNP and compared the observed alleles. This is described by Zimmermann et al., in *Prenat Diagn* (2012) 32:1233-1241. However, Zimmermann et al. believed that samples containing less than a 4.0% fetal fraction could not be informative and that a volume of at least 20 ml of blood was necessary to get enough cell-free DNA to perform this type of analysis. In contrast, the methods of the instant application may employ this analysis with samples with less than a 4% fetal fraction and samples that do not require nearly as much sample.

Library Preparation

In some instances, methods disclosed herein comprise modifying cell-free nucleic acids in the biological sample to produce a library of cell-free nucleic acids for detection. In some instances, methods comprise modifying cell-free nucleic acids for nucleic acid sequencing. In some instances, methods comprise modifying cell-free nucleic acids for detection, wherein detection does not comprise nucleic acid sequencing. In some instances, methods comprise modifying cell-free nucleic acids for detection, wherein detection comprises counting tagged cell-free nucleic acids based on an occurrence of tag detection. In some instances, methods disclosed herein comprise modifying cell-free nucleic acids in the biological sample to produce a library of cell-free nucleic acids, wherein the method comprises amplifying the cell-free nucleic acids. In some instances, modifying occurs before amplifying. In some instances, modifying occurs after amplifying.

In some instances, modifying the cell-free nucleic acids comprises repairing ends of cell-free nucleic acids that are fragments of a nucleic acid. By way of non-limiting example, repairing ends may comprise restoring a 5' phosphate group, a 3' hydroxy group, or a combination thereof to the cell-free nucleic acid. In some instances, repairing comprises 5'-phosphorylation, A-tailing, gap filling, closing nick sites or a combination thereof. In some instances, repairing may comprise removing overhangs. In some instances, repairing may comprise filling in overhangs with complementary nucleotides.

In some instances, modifying the cell-free nucleic acids for preparing a library comprises use of an adapter. The adapter may also be referred to herein as a sequencing adapter. In some instances, the adapter aids in sequencing. Generally, the adapter comprises an oligonucleotide. By way of non-limiting example, the adapter may simplify other steps in the methods, such as amplifying, purification and sequencing because it is a sequence that is universal to multiple, if not all, cell-free nucleic acids in a sample after modifying. In some instances, modifying the cell-free nucleic acids comprises ligating an adapter to the cell-free nucleic acids. Ligating may comprise blunt ligation. In some instances, modifying the cell-free nucleic acids comprises hybridizing an adapter to the nucleic acids.

The efficiency of library preparation steps (e.g., end repair, tailing, and ligation of adaptors) and amplifying may benefit from the addition of crowding agents to the sample or the amplifying reaction. Enzymatic processes in their natural environments (e.g., DNA replication in a cell) often occur in a crowded environment. Some of these enzymatic processes are more efficient in a crowded environment. For example, a crowded environment may enhance the activity of DNA helicase and the sensitivity of DNA polymerase. Thus, crowding agents can be added to mimic the crowded environment. The crowding agent may be a polymer. The crowding agent may be a protein. The crowding agent may be a polysaccharide. Non-limiting examples of crowding agents are polyethylene glycol, dextran and Ficoll. Concentrations that mimic crowding in vivo are often desirable. For example, 4% (40 mg/ml) PEG 1 kDa provides an approximate crowding effect found in vivo. In some instances, the concentration of the crowding agent is about 2% to about 20% w/v in the amplification reaction. In some instances, the concentration of the crowding agent is about 2% to about 15% w/v in the amplification reaction. In some instances, the concentration of the crowding agent is about 2% to about 10% w/v in the amplification reaction. In some instances, the concentration of the crowding agent is about 2% to about 8% w/v in the amplification reaction. In some instances, the concentration of the crowding agent is about 3% to about 6% w/v in the amplification reaction.

In some instances, modifying the cell-free nucleic acids for preparing a library comprises use of a tag. The tag may also be referred to herein as a barcode. In some instances, methods disclosed herein comprise modifying cell-free nucleic acids with a tag that corresponds to a chromosomal region of interest. In some instances, methods disclosed herein comprise modifying cell-free nucleic acids with a tag that is specific to a chromosomal region that is not of interest. In some instances, methods disclosed herein comprise modifying a first portion of cell-free nucleic acids with a first tag that corresponds to at least one chromosomal region that is of interest and a second portion of cell-free nucleic acids with a second tag that corresponds to at least one chromosomal region that is not of interest. In some instances, modifying the cell-free nucleic acids comprises ligating a tag to the cell-free nucleic acids. Ligating may comprise blunt ligation. In some instances, modifying the cell-free nucleic acids comprises hybridizing a tag to the nucleic acids. In some instances, the tags comprise oligonucleotides. In some instances, the tags comprise a non-oligonucleotide marker or label that can be detected by means other than nucleic acid analysis. By way of non-limiting example, a non-oligonucleotide marker or label could comprise a fluorescent molecule, a nanoparticle, a dye, a peptide, or other detectable/quantifiable small molecule.

In some instances, modifying the cell-free nucleic acids for preparing a library comprises use of a sample index, also simply referred to herein as an index. By way of non-limiting example, the index may comprise an oligonucleotide, a small molecule, a nanoparticle, a peptide, a fluorescent molecule, a dye, or other detectable/quantifiable moiety. In some instances, a first group of cell-free nucleic acids from a first biological sample are labeled with a first index, and a first group of cell-free nucleic acids from a first biological sample are labeled with a second index, wherein the first index and the second index are different. Thus, multiple indexes allow for distinguishing cell-free nucleic acids from multiple samples when multiple samples are analyzed at once. In some instances, methods disclose amplifying cell-free nucleic acids wherein an oligonucleotide primer used to amplify the cell-free nucleic acids comprises an index.

While DNA loss can occur at every step of DNA isolation and analysis, the highest loss typically appears at the step of library preparation. Traditional methods show losses of 80% to 90% of material. Often this loss is compensated by a subsequent amplification step to bring the concentration of DNA up to the necessary level required for next generation sequencing, but the amplification cannot compensate for a loss of information that occurred during the prior steps. A library suffering a loss of 80% of initial DNA in the sample can be described as a library with a 20% efficiency or an efficiency of 0.2. In some instances, methods disclosed herein comprise achieving a library with an efficiency of at least about 0.2, at least about 0.3, at least about 0.4, at least about 0.5, at least about 0.6 or at least about 0.8. In some instances, methods disclosed herein comprise producing a library with an efficiency of at least about 0.4. In some instances, methods disclosed herein comprise producing a library with an efficiency of at least about 0.5. Methods that produce a library with such efficiencies may achieve these efficiencies by using crowding agents and repairing cell-free DNA fragment ends, ligation methods, purification methods, cycling parameters and stoichiometric ratios as described herein.

Detecting Genetic Information

In general, methods disclosed herein comprise detecting a biomarker, an analyte or a modified form thereof. In some instances, methods comprise detecting nucleic acids. In some instances, methods comprise detecting cell-free nucleic acids. In some instances, methods comprise detecting a tag of a nucleic acid. In some instances, methods comprise detecting an amplicon of a nucleic acid. Alternatively or additionally, methods comprise detecting a non-nucleic acid component. By way of non-limiting example, the non-nucleic acid component may be selected from a protein, a peptide, a lipid, a fatty acid, a sterol, a phospholipid, a carbohydrate, a viral component, a microbial component, and a combination thereof. In the instance of a viral component or a microbial component, methods may comprise releasing, purifying, and/or amplifying a nucleic acid from a virus or bacteria before detecting.

Detecting may comprise sequencing a nucleic acid of interest. Detecting may comprise detecting a tag on a nucleic acid of interest. Detecting may comprise detecting a tag on a biomarker of interest. The biomarker may be an epigenetic modification. The biomarker may be an epigenetic profile (plurality of epigenetic modifications). The biomarker may be an epigenetically modified nucleic acid. Detecting may comprise bisulfite sequencing. Detecting may comprise performing a chromatin immunoprecipitation (ChIP) assay. Detecting may comprise sequencing a tag on a biomarker of interest.

Detecting may comprise amplifying, as described herein. For example, amplifying may comprise qPCR in which a signal is generated based on the presence or absence of a target analyte. In some instances, amplifying comprises PCR. In some instances, amplifying does not comprise PCR. In some instances, amplifying comprises rolling circle amplification (RCA). In some instances, cfDNA is contacted with a DNA ligase and probes designed to hybridize to cfDNA. In some instances, cfDNA is first cleaved (e.g., subjected to a restriction enzyme) to produce cfDNA fragments and the cfDNA fragments are contacted with the ligase and probes. The ligase creates circularized cfDNA labeled with probes. Optionally a backbone oligo is used to circularize the cfDNA or cfDNA fragments. These circularized fragments are replicated by RCA to produce concatamers. The probes can be recognized with a detectable oligonucleotide (e.g., fluorescent) and imaged.

Methods may comprise detecting a genetic mutation in a nucleic acid of a biological sample. Methods may comprise detecting a plurality of genetic mutations in a nucleic acid of a biological sample. Methods may comprise detecting a genetic mutation in each of a plurality of nucleic acids of a biological sample. Methods may comprise detecting a plurality of genetic mutations in a plurality of nucleic acids of a biological sample.

Methods may comprise detecting an epigenetic modification of a nucleic acid of a biological sample. In some instances, detecting the epigenetic modification comprises performing bisulfite sequencing. In some instances, detecting the epigenetic modification comprises performing a chromatin immunoprecipitation (ChIP) assay. In some instances, the epigenetic modification is a heritable alteration. In some instances, the epigenetic modification is an alteration that allows a cell to affect transcription in response to one or more environmental stimuli. By way of non-limiting example, the epigenetic modification may be a methylation of a cytosine or adenine residue. In some instances, the epigenetic modification is an absence of a methyl group. Typically methylations promote silencing of a gene. Epigenetic modifications also include acetylation, methylation, ubiquitination and phosphorylation of histones. The epigenetic modification may promote, inhibit, prevent or reduce a biological process (e.g., an immune response, cellular proliferation). Methods may comprise detecting a plurality of epigenetic modifications of a nucleic acid of a biological sample. Methods may comprise detecting an epigenetic modification of each of a plurality of nucleic acids of a biological sample. Methods may comprise detecting an epigenetic modification of a plurality of nucleic acids of a biological sample. Methods may comprise performing a genome wide analysis of epigenetic modifications to identify differentially methylated regions between a test sample and a control/reference sample.

Methods may comprise detecting one or more epigenetic modifications that is specific to a tissue. For instances, tissues have distinct methylation profiles that can be used to track the origin of cell-free nucleic acids. This may be useful in determining where a cell-free nucleic acid originated. By way of non-limiting example, the epigenetic modification may be specific to the brain and a cell-free nucleic acid bearing that epigenetic modification may be indicative of a neurodegenerative disease or a brain tumor. Methods may further comprise testing, biopsying, imaging, or treating a tissue if such a cell-free nucleic acid is detected. Methods may comprise detecting one or more epigenetic modifications that is specific to only two tissues. Methods may comprise detecting one or more epigenetic modifications that is specific to fewer than three tissues. Methods may comprise detecting one or more epigenetic modifications that is specific to fewer than five tissues.

Methods may comprise detecting a detectable label or detectable signal of a nucleic acid or non-nucleic acid component. Methods may comprise detecting a detectable label or detectable signal of a binding moiety (e.g., small molecule, peptide, aptamer, antibody, or antigen binding fragment thereof) that binds the nucleic acid or non-nucleic acid component. By way of non-limiting example, the detectable label or signal may be a fluorescent molecule, a bioluminescent molecule, a luminescent molecule, a radioactive signal, a magnetic signal, an electric signal, or a dye. For example, methods may comprise detecting an interaction between the binding moiety and a protein of interest. By way of non-limiting example, detecting may comprise performing IPCR or PLA.

Detecting may comprise viewing an interface of a device or system disclosed herein where the result of a test is displayed. See, e.g., FIG. 4 and FIGS. 5A-E. Detecting may comprise viewing a color appearance or fluorescent signal on a lateral flow device. Detecting may comprise receiving a result of a test on a device disclosed herein. Detecting may comprise receiving a result of a test on a mobile device, computer, notepad or other electronic device in communication with a device of system disclosed herein.

Generally, the methods, kits, systems and devices disclosed herein are capable of providing genetic information in a short amount of time. In some instances, methods disclosed herein can be performed in less than about 1 minute. In some instances, methods disclosed herein can be performed in less than about 2 minutes. In some instances, methods disclosed herein can be performed in less than about 5 minutes. In some instances, methods disclosed herein can be performed in less than about 10 minutes. In some instances, methods disclosed herein can be performed in less than about 15 minutes. In some instances, methods disclosed herein can be performed in less than about 20 minutes. In some instances, methods disclosed herein can be performed in less than about 30 minutes. In some instances, methods disclosed herein can be performed in less than about 45 minutes. In some instances, methods disclosed herein can be performed in less than about 60 minutes. In some instances, methods disclosed herein can be performed in less than about 90 minutes. In some instances, methods disclosed herein can be performed in less than about 2 hours. In some instances, methods disclosed herein can be performed in less than about 3 hours. In some instances, methods disclosed herein can be performed in less than about 4 hours.

In some instances, methods disclosed herein require minimal technical training. In some instances, methods disclosed herein do not require any technical training. In some instances, methods disclosed herein require only that an individual practicing the methods disclosed herein follow a simple protocol of transferring and mixing samples and solutions. For instance, methods disclosed herein may be used by the pregnant subject in her home without the assistance of a technician or medical provider. In some instances, methods disclosed herein can be performed by a user with no medical training or technical training. In some instances, methods, kits, systems and devices disclosed herein simply require that a user add a biological sample to the system or device and view a result to obtain genetic information.

Methods may comprise detecting the presence of a disease or condition based on the detecting. Methods may comprise detecting the risk of a disease or condition based on the detecting. Methods may comprise detecting the status of a disease or condition based on the detecting. Methods may comprise monitoring the status of a disease or condition based on the detecting. Methods may comprise administering a therapy based on the detecting. Methods may comprise modifying the dose of a drug that is being administered to the subject based on the detecting. Methods may comprise monitoring the response of a subject to a therapy based on the detecting. For example, the disease may be a cancer and the therapy may be a chemotherapy. Other cancer therapies include, but are not limited to antibodies, antibody-drug conjugates, antisense molecules, engineered T cells, and radiation. Methods may comprise further testing a subject based on the detecting. For example, the disease may be cancer and further testing may include, but is not limited to imaging (e.g., CAT-SCAN, PET-SCAN), and performing a biopsy.

In some instances, methods disclosed herein comprise detecting that there is a fetal aneuploidy of at least one target chromosome. In some instances, methods disclosed herein comprise detecting that there is a fetal aneuploidy of the at least one target chromosome when a quantity of sequencing reads is detected in a sample disclosed herein. In some instances, the quantity of sequencing reads corresponds to sequences from a chromosome or chromosome region that is known to present aneuploidy in the human population, as described herein.

In some instances, methods disclosed herein comprise detecting that there is a fetal aneuploidy of the at least one target chromosome when a ratio of sequencing reads corresponding to the at least one target chromosome to sequencing reads corresponding to the at least one non-target chromosome is different from a respective ratio in a control biological sample from a control pregnant subject with a euploid fetus. In some instances, methods disclosed herein comprise detecting that there is a fetal aneuploidy of the at least one target chromosome because a ratio of sequencing reads corresponding to the at least one target chromosome to sequencing reads corresponding to the at least one non-target chromosome is different from a respective ratio in a control biological sample from a control pregnant subject with a euploid fetus. In some instances, methods disclosed herein comprise detecting that there is not a fetal aneuploidy of the at least one target chromosome because a ratio of sequencing reads corresponding to the at least one target chromosome to sequencing reads corresponding to the at least one non-target chromosome is not different from a respective ratio in a control biological sample from a control pregnant subject with a euploid fetus.

In some instances, the sequencing reads corresponding to the at least one target chromosome comprises sequencing reads corresponding to a chromosome region of the at least one target chromosome. In some instances, the sequencing reads corresponding to the at least one non-target chromosome comprises sequencing reads corresponding to a chromosome region of the non-target chromosome. In some instances, the chromosome region is at least about 10 base pairs in length. In some instances, the chromosome region is at least about 20 base pairs in length. In some instances, the chromosome region is at least about 50 base pairs in length.

In some instances, the at least one target chromosome is at least one of chromosome 13, chromosome 16, chromosome 18, chromosome 21, chromosome 22, chromosome X, or chromosome Y. In some instances, the at least one target chromosome is at least one of chromosome 13, chromosome 18, and chromosome 21. In some instances, the at least one target chromosome is at least one of chromosome 13, chromosome 18, chromosome 21, and chromosome X. In some instances, the at least one target chromosome is at least one of chromosome 13, chromosome 18, chromosome 21, and chromosome Y. In some instances, the at least one target chromosome is at least one of chromosome 13, chromosome 18, chromosome 21, chromosome X, and chromosome Y. In some instances, the at least one target chromosome is chromosome 13. In some instances, the at least one target chromosome is chromosome 16. In some instances, the at least one target chromosome is chromosome 18. In some instances, the at least one target chromosome is chromosome 21. In some instances, the target chromosome is chromosome 22. In some instances, the at least one target chromosome is a sex chromosome. In some instances, the at least one target chromosome is chromosome X. In some instances, the at least one target chromosome is chromosome Y.

In some instances, the at least one non-target chromosome is at least one of a chromosome other than chromosome 13, chromosome 16, chromosome 18, chromosome 21, chromosome 22, chromosome X, or chromosome Y. In some instances, the at least one non-target chromosome is not chromosome 13, chromosome 16, chromosome 18, chromosome 21, chromosome 22, chromosome X, or chromosome Y. In some instances, the at least one non-target chromosome is selected from chromosome 1, chromosome 2, chromosome 3, chromosome 4, chromosome 5, chromosome 6, chromosome 7, chromosome 8, chromosome 9, chromosome 10, chromosome 11, chromosome 12, chromosome 14, chromosome 15, chromosome 17, chromosome 19, and chromosome 20. In some instances, the non-target chromosome is chromosome 1. In some instances, the at least one non-target chromosome is chromosome 2. In some instances, the at least one non-target chromosome is chromosome 3. In some instances, the non-target chromosome is chromosome 4. In some instances, the at least one non-target chromosome is chromosome 5. In some instances, the at least one non-target chromosome is chromosome 6. In some instances, the at least one non-target chromosome is chromosome 7. In some instances, the at least one non-target chromosome is chromosome 8. In some instances, the at least one non-target chromosome is chromosome 9. In some instances, the at least one non-target chromosome is chromosome 10. In some instances, the at least one non-target chromosome is chromosome 11. In some instances, the at least one non-target chromosome is chromosome 12. In some instances, the at least one non-target chromosome is chromosome 14. In some instances, the at least one non-target chromosome is chromosome 15. In some instances, the at least one non-target chromosome is chromosome 17. In some instances, the at least one non-target chromosome is chromosome 19. In some instances, the at least one non-target chromosome is chromosome 20.

In some instances, the at least one target chromosome is chromosome 13, and the at least one non-target chromosome is a chromosome other than chromosome 13. In some instances, the at least one target chromosome is chromosome 16, and the at least one non-target chromosome is a chromosome other than chromosome 16. In some instances, the at least one target chromosome is chromosome 18, and the at least one non-target chromosome is a chromosome other than chromosome 18. In some instances, the at least one target chromosome is chromosome 21, and the at least one non-target chromosome is a chromosome other than chromosome 21. In some instances, the at least one target chromosome is chromosome 22, and the at least one non-target chromosome is a chromosome other than chromosome 22. In some instances, the at least one target chromosome is chromosome X, and the at least one non-target chromosome is a chromosome other than chromosome X. In some instances, the at least one target chromosome is chromosome Y, and the at least one non-target chromosome is a chromosome other than chromosome Y.

In some instances, methods disclosed herein comprise detecting that the fetus of the pregnant subject has a genetic abnormality. In some instances, the genetic abnormality is due to insertion of at least one nucleotide in a target chromosomal region. In some instances, the genetic abnormality is due to deletion of at least one nucleotide in a target chromosomal region. In some instances, the genetic abnormality is due to translocation of nucleotide between a first target chromosomal region and a second chromosomal target region. Generally, the first target chromosomal region and a second chromosomal target region are located on different chromosomes.

In some instances, the target chromosomal region is defined by a minimal length. In some instances, the target chromosomal region is at least about 50 base pairs in length. In some instances, the target chromosomal region is at least about 100 base pairs in length. In some instances, the target chromosomal region is at least about 200 base pairs in length. In some instances, the target chromosomal region is at least about 300 base pairs in length. In some instances, the target chromosomal region is at least about 500 base pairs in length. In some instances, the target chromosomal region is at least about 1000 base pairs in length.

In some instances, the target chromosomal region is defined by a maximum length. In some instances, the target chromosomal region is as long as about 100,000 base pairs. In some instances, the target chromosomal region is as long as about 500,000 base pairs. In some instances, the target chromosomal region is as long as about 1,000,000 base pairs. In some instances, the target chromosomal region is as long as about 10,000,000 base pairs. In some instances, the target chromosomal region is as long as about 100,000,000 base pairs. In some instances, the target chromosomal region is as long as about 200,000,000 base pairs.

In some instances, the genetic abnormality is a copy number variation. In some instances, the copy number variation comprises a deletion of a gene on at least one chromosome. In some instances, the copy number variation comprises a duplication of a gene on at least one chromosome. In some instances, the copy number variation comprises a triplication of a gene on at least one chromosome. In some instances, the copy number variation comprises more than three copies of the gene. In some instances, the copy number variation comprises a duplication of a non-protein coding sequence on at least one chromosome. In some instances, the copy number variation comprises a triplication of a non-coding region on at least one chromosome. In some instances, the copy number variation comprises a duplication of a non-coding region on at least one chromosome.

In some instances, the genetic abnormality results in at least about 0.001% of a chromosomal arm being duplicated. In some instances, the genetic abnormality results in at least about 0.01% of a chromosomal arm being duplicated. In some instances, the genetic abnormality results in at least about 0.1% of a chromosomal arm being duplicated. In some instances, the genetic abnormality results in at least about 1% of a chromosomal arm being duplicated. In some instances, the genetic abnormality results in at least about 10% of a chromosomal arm being duplicated. In some instances, at least about 20% of a chromosomal arm is duplicated. In some instances, at least about 30% of a chromosomal arm is duplicated. In some instances, at least about 50% of a chromosomal arm is duplicated. In some instances, at least about 70% of a chromosomal arm is duplicated. In some instances, at least about 90% of a chromosomal arm is duplicated. In some instances, an entire chromosomal arm is duplicated.

In some instances, the genetic abnormality results in at least about 0.001% of a chromosomal arm being deleted. In some instances, the genetic abnormality results in at least about 0.01% of a chromosomal arm being deleted. In some instances, the genetic abnormality results in at least about 0.1% of a chromosomal arm being deleted. In some instances, the genetic abnormality results in at least about 1% of a chromosomal arm being deleted. In some instances, the genetic abnormality results in at least about 10% of a chromosomal arm being deleted. In some instances, at least about 20% of a chromosomal arm is deleted. In some instances, at least about 30% of a chromosomal arm is deleted. In some instances, at least about 50% of a chromosomal arm is deleted. In some instances, at least about 70% of a chromosomal arm is deleted. In some instances, at least about 90% of a chromosomal arm is deleted. In some instances, an entire chromosomal arm is deleted.

In some instances, methods comprise detecting that the fetus has a genetic abnormality when a quantity of sequencing reads corresponding to the target chromosomal region are detected, wherein the quantity is indicative of the genetic abnormality.

In some instances methods disclosed herein comprise sequencing nucleic acids. In some instances, the nucleic acids are cell-free nucleic acids. In some instances, the nucleic acids comprise cell-free fetal nucleic acids. In some instances, the nucleic acids are cell-free fetal nucleic acids. In some instances methods disclosed herein comprise producing at least a minimum amount of sequencing reads. In some instances, the minimum amount of sequencing reads is about 100. In some instances, the minimum amount of sequencing reads is about 1000. In some instances, the minimum amount of sequencing reads is about 2000. In some instances, the minimum amount of sequencing reads is about 3000. In some instances, the minimum amount of sequencing reads is about 4000. In some instances, the minimum amount of sequencing reads is about 5000. In some instances, the minimum amount of sequencing reads is about 6000. In some instances, the minimum amount of sequencing reads is about 7000. In some instances, the minimum amount of sequencing reads is about 8000. In some instances, the minimum amount of sequencing reads is about 9000. In some instances, the minimum amount of sequencing reads is about 10,000.

In some instances, methods comprise detecting that the fetus has a genetic abnormality when a ratio of (1) sequencing reads corresponding to the target chromosomal region to (2) sequencing reads corresponding to the at least one non-target chromosomal region is different from a respective ratio in a control biological sample from a control pregnant subject with a fetus not having the genetic abnormality. In some instances, methods comprise detecting that the fetus has a genetic abnormality because a ratio of (1) sequencing reads corresponding to the target chromosomal region to (2) sequencing reads corresponding to the at least one non-target chromosomal region is different from a respective ratio in a control biological sample from a control pregnant subject with a fetus not having the genetic abnormality. In some instances, methods comprise detecting that the fetus does not have a genetic abnormality when a ratio of (1) sequencing reads corresponding to the target chromosomal region to (2) sequencing reads corresponding to the at least one non-target chromosomal region is not different from a respective ratio in a control biological sample from a control pregnant subject with a fetus not having the genetic abnormality. In some instances the chromosomal region and the non-target chromosomal region are on the same chromosome. In some instances the chromosomal region and the non-target chromosomal region are on different chromosomes.

In some instances, genetic information is detected with a certain degree of accuracy. Non-limiting examples of genetic information include fetal aneuploidy, genetic abnormality, presence/quantity of tumor DNA, and presence/quantity of transplanted organ/tissue DNA. In some instances, genetic information is detected with at least about 95% accuracy. In some instances, genetic information is detected with at least about 96% accuracy. In some instances, genetic information is detected with at least about 97% accuracy. In some instances, genetic information is detected with at least about 98% accuracy. In some instances, genetic information is detected with at least about 99% accuracy. In some instances, genetic information is detected with at least about 99.5% accuracy. In some instances, genetic information is detected with at least about 99.9% accuracy. In some instances, genetic information is detected with at least about 99.99% accuracy.

Reads from each chromosome are roughly represented according to the length of the chromosome. Most reads are obtained from chromosome 1, while the fewest reads from an autosome will originate from chromosome 21. A common method for detecting a trisomic sample is to measure the percentage of reads originating from a chromosome in a population of euploid samples. Next, a mean and a standard deviation for this set of chromosome percentage values are calculated. A cutoff value is determined by adding three standard deviations to the mean. If a new sample has a chromosome percentage value above the cutoff value, an overrepresentation of that chromosome can be assumed, which is often consistent with a trisomy of the chromosome. A prophetic example of detecting an over presentation of a chromosome is presented in Example 13.

In some instances, fetal aneuploidy is detected when the ratio of (1) sequencing reads corresponding to the at least one target chromosome to (2) sequencing reads corresponding to the at least one non-target chromosome differs from a respective ratio in a control biological sample from a control pregnant subject with a euploid fetus by at least about 0.1%. In some instances, the ratios differ by at least 1%.

In some instances, the control pregnant subject is a euploid pregnant subject. In some instances the control is a mean or median value from a group of pregnant subjects. In some instances the control is a mean or median value from a pool of plasma samples from pregnant subjects. In some instances, the control is a similarly obtained value from an artificial mixture of nucleic acids mimicking a pregnant subject with a euploid fetus. In some instances, the control pregnant subject is a euploid pregnant subject carrying a fetus with a euploid chromosome set. In some instances, the control pregnant subject does not have a genetic abnormality, e.g., copy number variation. In some instances, the fetus carried by the control pregnant subject does not have a genetic abnormality, e.g., copy number variation. In some instances, the control pregnant subject does not have a genetic abnormality in a target chromosome disclosed herein. In some instances, the fetus carried by the control pregnant subject does not have a genetic abnormality in a target chromosome disclosed herein. In some instances, at least one of the control pregnant subject and her fetus has an aneuploidy. In some instances, at least one of the control pregnant subject and her fetus has a genetic abnormality disclosed herein. In some instances, at least one of the control pregnant subject and her fetus has a genetic abnormality in a target chromosome disclosed herein. In some instances, methods disclosed herein comprise use of a respective ratio in a control biological sample from a control pregnant population. In some instances, the respective ratio is from a respective mean ratio in the control pregnant population. In some instances, the respective ratio is from a respective median ratio in the control pregnant population.

In some instances, methods disclosed herein employ the following devices, systems and kits.

II. Devices, Systems and Kits

In some aspects disclosed herein are devices, systems and kits for obtaining genetic information from a biological sample. As described herein, devices, systems and kits disclosed herein allow a user to collect and test a biological sample at a location of choice to detect the presence and/or quantity of a target analyte in the sample. In some instances, devices, systems and kits disclosed herein are used in the foregoing methods. In some instances, devices, systems and kits disclosed herein comprise a sample purifier that removes at least one component (e.g., cell, cell fragment, protein) from a biological sample of a subject; a nucleic acid sequencer for sequencing at least one nucleic acid in the biological sample; and a nucleic acid sequence output for relaying sequence information to a user of the device, system or kit.

In general, devices, systems, and kits of the present disclosure, integrate multiple functions, e.g., purification, amplification, and detection of the target analyte (e.g., including amplification products thereof), and combinations thereof. In some instances, the multiple functions are carried out within a single assay assembly unit or a single device. In some instances, all of the functions occur outside of the single unit or device. In some instances, at least one of the functions occurs outside of the single unit or device. In some instances, only one of the functions occurs outside of the single unit or device. In some instances, the sample purifier, nucleic acid amplification reagent, oligonucleotide, and detection reagent or component are housed in a single device. In general, devices, systems, and kits of the present disclosure comprise a display, a connection to a display, or a communication to a display for relaying information about the biological sample to one or more people.

In some instances, devices, systems and kits comprise an additional component disclosed herein. Non-limiting examples of an additional component include a sample transportation compartment, a sample storage compartment, a sample and/or reagent receptacle, a temperature indicator, an electronic port, a communication connection, a communication device, a sample collection device, and a housing unit. In some instances, the additional component is integrated with the device. In some instances, the additional component is not integrated with the device. In some instances, the additional component is housed with the sample purifier, nucleic acid amplification reagent, oligonucleotide, and detection reagent or component in a single device. In some instances, the additional component is not housed within the single device.

In some instances, devices, systems and kits disclosed herein comprise components to obtain a sample, extract cell-free nucleic acids, and purify cell-free nucleic acids. In some instances, devices, systems and kits disclosed herein comprise components to obtain a sample, extract cell-free nucleic acids, purify cell-free nucleic acids, and prepare a library of the cell-free nucleic acids. In some instances, devices, systems and kits disclosed herein comprise components to obtain a sample, extract cell-free nucleic acids, purify cell-free nucleic acids, and sequence cell-free nucleic acids. In some instances, devices, systems and kits disclosed herein comprise components to obtain a sample, extract cell-free nucleic acids, purify cell-free nucleic acids, prepare a library of the cell-free nucleic acids, and sequence the cell-free nucleic acids. By way of non-limiting example, components for obtaining a sample are a transdermal puncture device and a filter for obtaining plasma from blood. Also, by way of non-limiting example, components for extracting and purifying cell-free nucleic acids comprise buffers, beads and magnets. Buffers, beads and magnets may be supplied at volumes appropriate for receiving a general sample volume from a finger prick (e.g., 50-150 µl of blood).

In some instances, devices, systems and kits comprise a receptacle for receiving the biological sample. The receptacle may be configured to hold a volume of a biological sample between 1 µl and 1 ml. The receptacle may be configured to hold a volume of a biological sample between 1 µl and 500 µl. The receptacle may be configured to hold a volume of a biological sample between 1 µl and 200 µl. The receptacle may have a defined volume that is the same as a suitable volume of sample for processing and analysis by the rest of the device/system components. This would preclude the need for a user of the device, system or kit to measure out a specified volume of the sample. The user would only need to fill the receptacle and thereby be assured that the appropriate volume of sample had been delivered to the device/system. In some instances, devices, systems and kits do not comprise a receptacle for receiving the biological sample. In some instances, the sample purifier receives the biological sample directly. Similar to the description above for the receptacle, the sample purifier may have a defined volume that is suitable for processing and analysis by the rest of the device/system components. In general, devices, systems, and kits disclosed herein are intended to be used entirely at point of care. However, in some instances, the user may want to preserve or send the analyzed sample to another location (e.g., lab, clinic) for additional analysis or confirmation of results obtained at point of care. By way of non-limiting example, the device/system may separate plasma from blood. The plasma may be analyzed at point of care and the cells from the blood shipped to another location for analysis. In some instances, devices, systems and kits comprise a transport compartment or storage compartment for these purposes. The transport compartment or storage compartment may be capable of containing a biological sample, a component thereof, or a portion thereof. The transport compartment or storage compartment may be capable of containing the biological sample, portion thereof, or component thereof, during transit to a site remote to the immediate user. The transport compartment or storage compartment may be capable of containing cells that are removed from a biological sample, so that the cells can be sent to a site remote to the immediate user for testing. Non-limiting examples of a site remote to the immediate user may be a laboratory or a clinic when the immediate user is at home. In some instances, the home does not have a machine or additional device to perform an additional analysis of the biological sample. The transport compartment or storage compartment may be capable of containing a product of a reaction or process that result from adding the biological sample to the device. In some instances, the product of the reaction or process is a nucleic acid amplification product or a reverse transcription product. In some instances, the product of the reaction or process is a biological sample component bound to a binding moiety described herein. The biological sample component may comprise a nucleic acid, a cell fragment, an extracellular vesicle, a protein, a peptide, a sterol, a lipid, a vitamin, or glucose, any of which may be analyzed at a remote location to the user. In some instances, the transport compartment or storage compartment comprises an absorption pad, a paper, a glass container, a plastic container, a polymer matrix, a liquid solution, a gel, a preservative, or a combination thereof. An absorption pad or a paper may be useful for stabilizing and transporting a dried biological fluid with a protein or other biomarker for screening.

In some instances, devices and systems disclosed herein provide for analysis of cell-free nucleic acids (e.g., circulating RNA and/or DNA) and non-nucleic acid components of a sample. Analysis of both cell-free nucleic acids and non-nucleic acid components may both occur at a point of need. In some instances, systems and devices provide an analysis of cell-free nucleic acids at a point of need and preservation of at least a portion or component of the sample for analysis of non-nucleic acid components at a site remote from the point of need. In some instances, systems and devices provide an analysis of non-nucleic acid components at a point of need and preservation of at least a portion or component of the sample for analysis of cell-free nucleic acids at a site remote from the point of need. These devices and systems may be useful for carrier testing and detecting inherited diseases, such as those disclosed herein.

In some instances, the transport compartment or storage compartment comprises a preservative. The preservative may also be referred to herein as a stabilizer or biological stabilizer. In some instances, the device, system or kit comprises a preservative that reduces enzymatic activity during storage and/or transportation. In some instances, the preservative is a whole blood preservative. Non-limiting examples of whole blood preservatives, or components thereof, are glucose, adenine, citric acid, trisodium citrate, dextrose, sodium di-phosphate, and monobasic sodium phosphate. In some instances, the preservative comprises EDTA. EDTA may reduce enzymatic activity that would otherwise degrade nucleic acids. In some instances, the preservative comprises formaldehyde. In some instances, the preservative is a known derivative of formaldehyde. Formaldehyde, or a derivative thereof, may cross link proteins and therefore stabilize cells and prevent cell lysis.

Generally, devices and systems disclosed herein are portable for a single person. In some instances, devices and systems are handheld. In some instances, devices and systems have a maximum length, maximum width or maximum height. In some instances, devices and systems are housed in a single unit having a maximum length, maximum width or maximum height. In some instances the maximum length is not greater than 12 inches. In some instances the maximum length is not greater than 10 inches. In some instances the maximum length is not greater than 8 inches. In some instances the maximum length is not greater than 6 inches. In some instances the maximum width is not greater than 12 inches. In some instances the maximum width is not greater than 10 inches. In some instances the maximum width is not greater than 8 inches. In some instances the maximum width is not greater than 6 inches. In some instances the maximum width is not greater than 4 inches. In some instances the maximum height is not greater than 12 inches. In some instances the maximum height is not greater than 10 inches. In some instances the maximum height is not greater than 8 inches. In some instances the maximum height is not greater than 6 inches. In some instances the maximum height is not greater than 4 inches. In some instances the maximum height is not greater than 2 inches. In some instances the maximum height is not greater than 1 inch.

Sample Collection

In some instances, devices, systems and kits disclosed herein comprise a sample collector. In some instances, the sample collector is provided separately from the rest of the device, system or kit. In some instances, the sample collector is physically integrated with the device, system or kit, or a component thereof. In some instances, the sample collector is integrated with a receptacle described herein. In some instances, the sample collector may be a cup, tube, capillary, or well for applying the biological fluid. In some instances, the sample collector may be a cup for applying urine. In some instances, the sample collector may comprise a pipet for applying urine in the cup to the device, system or kit. In some instances, the sample collector may be a capillary integrated with a device disclosed herein for applying blood. In some instances, the sample collector may be tube, well, pad or paper integrated with a device disclosed herein for applying saliva. In some instances, the sample collector may be pad or paper for applying sweat.

In some instances, devices, systems and kits disclosed herein comprise a transdermal puncture device. Non-limiting examples of transdermal puncture devices are needles and lancets. In some instances, the sample collector comprises the transdermal puncture device. In some instances, devices, systems and kits disclosed herein comprise a microneedle, microneedle array or microneedle patch. In some instances, devices, systems and kits disclosed herein comprise a hollow microneedle. By way of non-limiting example, the transdermal puncture device is integrated with a well or capillary so that as the subject punctures their finger, blood is released into the well or capillary where it will be available to the system or device for analysis of its components. In some instances, the transdermal puncture device is a push button device with a needle or lancet in a concave surface. In some instances, the needle is a microneedle. In some instances, the transdermal puncture device comprises an array of microneedles. By pressing an actuator, button or location on the non-needle side of the concave surface, the needle punctures the skin of the subject in a more controlled manner than a lancet. Furthermore, the push button device may comprise a vacuum source or plunger to help draw blood from the puncture site.

Sample Processing and Purification

Disclosed herein are devices, systems and kits that comprise a sample processor, wherein the sample processor modifies a biological sample to remove a component of the sample or separate the sample into multiple fractions (e.g., blood cell fraction and plasma or serum). The sample processor may comprise a sample purifier, wherein the sample purifier is configured to remove an unwanted substance or non-target component of a biological sample, thereby modifying the sample. Depending on the source of the biological sample, unwanted substances can include, but are not limited to, proteins (e.g., antibodies, hormones, enzymes, serum albumin, lipoproteins), free amino acids and other metabolites, microvesicles, nucleic acids, lipids, electrolytes, urea, urobilin, pharmaceutical drugs, mucous, bacteria, and other microorganisms, and combinations thereof. In some instances, the sample purifier separates components of a biological sample disclosed herein. In some instances, sample purifiers disclosed herein remove components of a sample that would inhibit, interfere with or otherwise be detrimental to the later process steps such as nucleic acid amplification or detection. In some instances, the resulting modified sample is enriched for target analytes. This can be considered indirect enrichment of target analytes. Alternatively or additionally, target analytes may be captured directly, which is considered direct enrichment of target analytes.

In some instances, the sample purifier comprises a separation material for removing unwanted substances other than patient cells from the biological sample. Useful separation materials may include specific binding moieties that bind to or associate with the substance. Binding can be covalent or noncovalent. Any suitable binding moiety known in the art for removing a particular substance can be used. For example, antibodies and fragments thereof are commonly used for protein removal from samples. In some instances, a sample purifier disclosed herein comprises a binding moiety that binds a nucleic acid, protein, cell surface marker, or microvesicle surface marker in the biological sample. In some instances, the binding moiety comprises an antibody, antigen binding antibody fragment, a ligand, a receptor, a peptide, a small molecule, or a combination thereof.

In some instances, sample purifiers disclosed herein comprise a filter. In some instances, sample purifiers disclosed herein comprise a membrane. Generally the filter or membrane is capable of separating or removing cells, cell particles, cell fragments, blood components other than cell-free nucleic acids, or a combination thereof, from the biological samples disclosed herein.

In some instances, the sample purifier facilitates separation of plasma or serum from cellular components of a blood sample. In some instances, the sample purifier facilitates separation of plasma or serum from cellular components of a blood sample before starting a molecular amplification reaction or a sequencing reaction. Plasma or serum separation can be achieved by several different methods such as centrifugation, sedimentation or filtration. In some instances, the sample purifier comprises a filter matrix for receiving whole blood, the filter matrix having a pore size that is prohibitive for cells to pass through, while plasma or serum can pass through the filter matrix uninhibited. In some instances, the filter matrix combines a large pore size at the top with a small pore size at the bottom of the filter, which leads to very gentle treatment of the cells preventing cell degradation or lysis, during the filtration process. This is advantageous because cell degradation or lysis would result in release of nucleic acids from blood cells or maternal cells that would contaminate target cell-free nucleic acids. Non-limiting examples of such filters include Pall Vivid™ GR membrane, Munktell Ahlstrom filter paper (see, e.g., WO2017017314), TeraPore filters.

In some instances devices, systems, and kits disclosed herein employ vertical filtration, driven by capillary force to separate a component or fraction from a sample (e.g., plasma from blood). By way of non-limiting example, vertical filtration may comprise gravitation assisted plasma separation. A high-efficiency superhydrophobic plasma separator is described, e.g., by Liu et al., A High Efficiency Superhydrophobic Plasma Separation, Lab Chip 2015.

The sample purifier may comprise a lateral filter (e.g., sample does not move in a gravitational direction or the sample moves perpendicular to a gravitational direction). The sample purifier may comprise a vertical filter (e.g., sample moves in a gravitational direction). The sample purifier may comprise vertical filter and a lateral filter. The sample purifier may be configured to receive a sample or portion thereof with a vertical filter, followed by a lateral filter. The sample purifier may be configured to receive a sample or portion thereof with a lateral filter, followed by a vertical filter. In some instances, a vertical filter comprises a filter matrix. In some instances, the filter matrix of the vertical filter comprises a pore with a pore size that is prohibitive for cells to pass through, while plasma can pass the filter matrix uninhibited. In some instances, the filter matrix comprises a membrane that is especially suited for this application because it combines a large pore size at the top with a small pore size at the bottom of the filter, which leads to very gentle treatment of the cells preventing cell degradation during the filtration process.

In some instances, the sample purifier comprises an appropriate separation material, e.g., a filter or membrane, that removes unwanted substances from a biological sample without removing cell-free nucleic acids. In some instances, the separation material separates substances in the biological sample based on size, for example, the separation material has a pore size that excludes a cell but is permeable to cell-free nucleic acids. Therefore, when the biological sample is blood, the plasma or serum can move more rapidly than a blood cell through the separation material in the sample purifier, and the plasma or serum containing any cell-free nucleic acids permeates the holes of the separation material. In some instances, the biological sample is blood, and the cell that is slowed and/or trapped in the separation material is a red blood cell, a white blood cell, or a platelet. In some instances, the cell is from a tissue that contacted the biological sample in the body, including, but not limited to, a bladder or urinary tract epithelial cell (in urine), or a buccal cell (in saliva). In some instances, the cell is a bacterium or other microorganism.

In some instances, the sample purifier is capable of slowing and/or trapping a cell without damaging the cell, thereby avoiding the release of cell contents including cellular nucleic acids and other proteins or cell fragments that could interfere with subsequent evaluation of the cell-free nucleic acids. This can be accomplished, for example, by a gradual, progressive reduction in pore size along the path of a lateral flow strip or other suitable assay format, to allow gentle slowing of cell movement, and thereby minimize the force on the cell. In some instances, at least 95%, at least 98%, at least 99%, or up to 100% of the cells in a biological sample remain intact when trapped in the separation material. In addition to or independently of size separation, the separation material can trap or separate unwanted substances based on a cell property other than size, for example, the separation material can comprise a binding moiety that binds to a cell surface marker. In some instances, the binding moiety is an antibody or antigen binding antibody fragment. In some instances, the binding moiety is a ligand or receptor binding protein for a receptor on a blood cell or microvesicle.

In some instances, systems and devices disclosed herein comprise a separation material that moves, draws, pushes, or pulls the biological sample through the sample purifier, filter and/or membrane. In some instances, the material is a wicking material. Examples of appropriate separation materials used in the sample purifier to remove cells include, but are not limited to, polyvinylidene difluoride, polytetrafluoroethylene, acetylcellulose, nitrocellulose, polycarbonate, polyethylene terephthalate, polyethylene, polypropylene, glass fiber, borosilicate, vinyl chloride, silver. Suitable separation materials may be characterized as preventing passage of cells. In some instances, the separation material is not limited as long as it has a property that can prevent passage of the red blood cells. In some instances, the separation material is a hydrophobic filter, for example a glass fiber filter, a composite filter, for example Cytosep (e.g., Ahlstrom Filtration or Pall Specialty Materials, Port Washington, N.Y.), or a hydrophilic filter, for example cellulose (e.g., Pall Specialty Materials). In some instances, whole blood can be fractionated into red blood cells, white blood cells and serum components for further processing according to the methods of the present disclosure using a commercially available kit (e.g., Arrayit Blood Card Serum Isolation Kit, Cat. ABCS, Arrayit Corporation, Sunnyvale, Calif.).

In some instances the sample purifier comprises at least one filter or at least one membrane characterized by at least one pore size. In some instances, the sample purifier comprises multiple filters and/or membranes, wherein the pore size of at least a first filter or membrane differs from a second filter or membrane. In some instances, at least one pore size of at least one filter/membrane is about 0.05 microns to about 10 microns. In some instances, the pore size is about 0.05 microns to about 8 microns. In some instances, the pore size is about 0.05 microns to about 6 microns. In some instances, the pore size is about 0.05 microns to about 4 microns. In some instances, the pore size is about 0.05 microns to about 2 microns. In some instances, the pore size is about 0.05 microns to about 1 micron. In some instances, at least one pore size of at least one filter/membrane is about 0.1 microns to about 10 microns. In some instances, the pore size is about 0.1 microns to about 8 microns. In some instances, the pore size is about 0.1 microns to about 6 microns. In some instances, the pore size is about 0.1 microns to about 4 microns. In some instances, the pore size is about 0.1 microns to about 2 microns. In some instances, the pore size is about 0.1 microns to about 1 micron.

In some instances, the sample purifier is characterized as a gentle sample purifier. Gentle sample purifiers, such as those comprising a filter matrix, a vertical filter, a wicking material, or a membrane with pores that do not allow passage of cells, are particularly useful for analyzing cell-free nucleic acids. For example, prenatal applications of cell-free fetal nucleic acids in maternal blood are presented with the additional challenge of analyzing cell-free fetal nucleic acids in the presence of cell-free maternal nucleic acids, the latter of which create a large background signal to the former. By way of non-limiting example, a sample of maternal blood may contain about 500 to 750 genome equivalents of total cell-free DNA (maternal and fetal) per milliliter of whole blood when the sample is obtained without cell lysis or other cell disruption caused by the sample collection method. The fetal fraction in blood sampled from pregnant women may be around 10%, about 50 to 75 genome equivalents per ml. The process of obtaining cell-free nucleic acids usually involves obtaining plasma from the blood. If not performed carefully, maternal white blood cells may be destroyed, releasing additional cellular nucleic acids into the sample, creating a lot of background noise to the fetal cell-free nucleic acids. The typical white cell count is around $4*10^6$ to $10*10^6$ cells per ml of blood and therefore the available nuclear DNA is around 4,000 to 10,000 times higher than the overall cell-free DNA (cfDNA). Consequently, even if only a small fraction of maternal white blood cells is destroyed, releasing nuclear DNA into the plasma, the fetal fraction is reduced dramatically. For example, a white cell degradation of 0.01% may reduce the fetal fraction from 10% to about 5%. Devices, systems, and kits disclosed herein aim to reduce these background signals. 100230 1 1n some instances, the sample processor is configured to separate blood cells from whole blood. In some instances, the sample processor is configured to isolate plasma from whole blood. In some instances, the sample processor is configured to isolate serum from whole blood. In some instances, the sample processor is configured to isolate plasma or serum from less than 1 milliliter of whole blood. In some instances, the sample processor is configured to isolate plasma or serum from less than 1 milliliter of whole blood. In some instances, the sample processor is configured to isolate plasma or serum from less than 500 μL it of whole blood. In some instances, the sample processor is configured to isolate plasma or serum from less than 400 µL of whole blood. In some instances, the sample processor is configured to isolate plasma or serum from less than 300 µL of whole blood. In some instances, the sample processor is configured to isolate plasma or serum from less than 200 µL of whole blood. In some instances, the sample processor is configured to isolate plasma or serum from less than 150 µL of whole blood. In some instances, the sample processor is configured to isolate plasma or serum from less than 100 µL of whole blood.

In some instances, devices, systems and kits disclosed herein comprise a binding moiety for producing a modified sample depleted of cells, cell fragments, nucleic acids or proteins that are unwanted or of no interest. In some instances, devices, systems and kits disclosed herein comprise a binding moiety for reducing cells, cell fragments, nucleic acids or proteins that are unwanted or of no interest, in a biological sample. In some instances, devices, systems and kits disclosed herein comprise a binding moiety for producing a modified sample enriched with target cell, target cell fragments, target nucleic acids or target proteins.

In some instances, devices, systems and kits disclosed herein comprise a binding moiety capable of binding a nucleic acid, a protein, a peptide, a cell surface marker, or microvesicle surface marker. In some instances, devices, systems and kits disclosed herein comprise a binding moiety for capturing an extracellular vesicle or extracellular microparticle in the biological sample. In some instances, the extracellular vesicle contains at least one of DNA and RNA. In some instances, devices, systems and kits disclosed herein comprise reagents or components for analyzing DNA or RNA contained in the extracellular vesicle. In some instances, the binding moiety comprises an antibody, antigen binding antibody fragment, a ligand, a receptor, a protein, a peptide, a small molecule, or a combination thereof.

In some instances, devices, systems and kits disclosed herein comprise a binding moiety capable of interacting with or capturing an extracellular vesicle that is released from a cell. In some instances, the cell is a fetal cell. In some instances, the cell is a placental cell. The fetal cell or the placental cell may be circulating in a biological fluid (e.g., blood) of a female pregnant subject. In some instances, the extracellular vesicle is released from an organ, gland or tissue. By way of non-limiting example, the organ, gland or tissue may be diseased, aging, infected, or growing. Non-limiting examples of organs, glands and tissues are brain, liver, heart, kidney, colon, pancreas, muscle, adipose, thyroid, prostate, breast tissue, and bone marrow.

By way of non-limiting example, devices, systems and kits disclosed herein may be capable of capturing and discarding an extracellular vesicle or extracellular microparticle from a maternal sample to enrich the sample for fetal/placental nucleic acids. In some instances, the extracellular vesicle is fetal/placental in origin. In some instances, the extracellular vesicle originates from a fetal cell. In some instances, the extracellular vesicle is released by a fetal cell. In some instances, the extracellular vesicle is released by a placental cell. The placental cell may be a trophoblast cell. In some instances, devices, systems and kits disclosed herein comprise a cell-binding moiety for capturing placenta educated platelets, which may contain fetal DNA or RNA fragments. These can be captured/enriched for with antibodies or other methods (low speed centrifugation). In such instances, the fetal DNA or RNA fragments may be analyzed as described herein to detect or indicate chromosomal information (e.g., gender). Alternatively or additionally, devices, systems and kits disclosed herein comprise a binding moiety for capturing an extracellular vesicle or extracellular microparticle in the biological sample that comes from a maternal cell.

In some instances, the binding moiety is attached to a solid support, wherein the solid support can be separated from the rest of the biological sample or the biological sample can be separated from the solid support, after the binding moiety has made contact with the biological sample. Non-limiting examples of solid supports include a bead, a nanoparticle, a magnetic particle, a chip, a microchip, a fibrous strip, a polymer strip, a membrane, a matrix, a column, a plate, or a combination thereof.

Devices, systems and kits disclosed herein may comprise a cell lysis reagent. Non-limiting examples of cell lysis reagents include detergents such as NP-40, sodium dodecyl sulfate, and salt solutions comprising ammonium, chloride, or potassium. Devices, systems and kits disclosed herein may have a cell lysis component. The cell lysis component may be structural or mechanical and capable of lysing a cell. By way of non-limiting example, the cell lysis component may shear the cells to release intracellular components such as nucleic acids. In some instances, devices, systems and kits disclosed herein do not comprise a cell lysis reagent. Some devices, systems and kits disclosed herein are intended to analyze cell-free nucleic acids.

Nucleic Acid Amplification

Generally, devices, systems and kits disclosed herein are capable of amplifying a nucleic acid. Often devices, systems and kits disclosed herein comprise a DNA polymerase. In some instances, the devices, systems and kits disclosed herein comprise a reverse transcriptase enzyme to produce complementary DNA (cDNA) from RNA in biological samples disclosed herein, wherein the cDNA can be amplified and/or analyzed similarly to genomic DNA as described herein. Devices, systems and kits disclosed herein also often contain a crowding agent which can increase the efficiency enzymes like DNA polymerases and helicases. Crowding agents may increase an efficiency of a library, as described elsewhere herein. The crowding agent may comprise a polymer, a protein, a polysaccharide, or a combination thereof. Non-limiting examples of crowding agents that may be used in devices, systems and kits disclosed herein are dextran, poly(ethylene glycol) and dextran.

A traditional polymerase chain reaction requires thermocycling. This would be possible, but inconvenient for a typical at-home user without a thermocycler machine. In some instances, devices, systems and kits disclosed herein are capable of amplifying a nucleic acid without changing the temperature of the device or system or a component thereof. In some instances, devices, systems and kits disclosed herein are capable of amplifying a nucleic acid isothermally. Non-limiting examples of isothermal amplification are as follows: loop-mediated isothermal amplification (LAMP), strand displacement amplification (SDA), helicase dependent amplification (HDA), nicking enzyme amplification reaction (NEAR), and recombinase polymerase amplification (RPA). Thus, devices, systems and kits disclosed herein may comprise reagents necessary to carry out an isothermal amplification. Non-limiting examples of isothermal amplification reagents include recombinase polymerases, single-strand DNA-binding proteins, and strand-displacing polymerases. Generally, isothermal amplification using recombinase polymerase amplification (RPA) employs three core enzymes, recombinase, single-strand DNA-binding protein, and strand-displacing polymerase, to (1) pair oligonucleotide primers with homologous sequence in DNA, (2) stabilize displaced DNA strands to prevent primer displacement, and (3) extend the oligonucleotide primer using a strand displacing DNA polymerase. Using paired oligonucleotide primers, exponential DNA amplification can take place with incubation at room temperature (optimal at 37° C.).

In some instances, devices, systems and kits disclosed herein are capable of amplifying a nucleic acid at a temperature. In some instances, devices, systems and kits disclosed herein are capable of amplifying a nucleic acid at not more than two temperatures. In some instances, devices, systems and kits disclosed herein are capable of amplifying a nucleic acid at not more than three temperatures. In some instances, devices, systems and kits disclosed herein only require initially heating one reagent or component of the device, system or kit.

In some instances, devices, systems and kits disclosed herein are capable of amplifying a nucleic acid at a range of temperatures. In some instances, the range of temperatures is about −50° C. to about 100° C. In some instances, the range of temperatures is about −50° C. to about 90° C. In some instances, the range of temperatures is about −50° C. to about 80° C. In some instances, the range of temperatures is about is about −50° C. to about 70° C. In some instances, the range of temperatures is about −50° C. to about 60° C. In some instances, the range of temperatures is about −50° C. to about 50° C. In some instances, the range of temperatures is about −50° C. to about 40° C. In some instances, the range of temperatures is about −50° C. to about 30° C. In some instances, the range of temperatures is about −50° C. to about 20° C. In some instances, the range of temperatures is about −50° C. to about 10° C. In some instances, the range of temperatures is about 0° C. to about 100° C. In some instances, the range of temperatures is about 0° C. to about 90° C. In some instances, the range of temperatures is about 0° C. to about 80° C. In some instances, the range of temperatures is about is about 0° C. to about 70° C. In some instances, the range of temperatures is about 0° C. to about 60° C. In some instances, the range of temperatures is about 0° C. to about 50° C. In some instances, the range of temperatures is about 0° C. to about 40° C. In some instances, the range of temperatures is about 0° C. to about 30° C. In some instances, the range of temperatures is about 0° C. to about 20° C. In some instances, the range of temperatures is about 0° C. to about 10° C. In some instances, the range of temperatures is about 15° C. to about 100° C. In some instances, the range of temperatures is about 15° C. to about 90° C. In some instances, the range of temperatures is about 15° C. to about 80° C. In some instances, the range of temperatures is about is about 15° C. to about 70° C. In some instances, the range of temperatures is about 15° C. to about 60° C. In some instances, the range of temperatures is about 15° C. to about 50° C. In some instances, the range of temperatures is about 15° C. to about 40° C. In some instances, the range of temperatures is about 15° C. to about 30° C. In some instances, the range of temperatures is about 10° C. to about 30° C. In some instances, devices, systems, kits disclosed herein, including all components thereof, and all reagents thereof, are completely operable at room temperature, not requiring cooling, freezing or heating.

In some instances, at least a portion of the devices, systems and kits disclosed herein operate at about 20° C. to about 50° C. In some instances, at least a portion of the devices, systems, and kits disclosed herein operate at about 37° C. In some instances, at least a portion of the devices, systems and kits disclosed herein operate at about 42° C. In some instances, the devices, systems and kits disclosed herein are advantageously operated at room temperature. In some instances, at least a portion of the devices, systems and kits disclosed herein are capable of amplifying a nucleic acid isothermally at about 20° C. to about 30° C. In some instances, at least a portion of the devices, systems and kits disclosed herein are capable of amplifying a nucleic acid isothermally at about 23° C. to about 27° C.

In some instances, devices, systems, kits, and methods disclosed herein comprise a hybridization probe with an abasic site, a fluorophore and quencher to monitor amplification. Exonuclease III may be included to cleave the abasic site and release the quencher to allow fluorescent excitation. In some instances, amplification products are detected or monitored via lateral flow by attaching a capture molecule (e.g. Biotin) to one of the amplification primers and labeling a hybridization primer with a 5'-antigenic molecule (e.g. fluorescein derivative FAM) for capture to allow for detection. As such, in some instances, devices, systems, kits, and methods disclosed herein provide for detection of nucleic acids and amplification products on a lateral flow device. Lateral flow devices are described herein.

In some instances, devices, systems and kits disclosed herein comprise at least one nucleic acid amplification reagent and at least one oligonucleotide primer capable of amplifying a first sequence in a genome and a second sequence in a genome, wherein the first sequence and the second sequence are similar, and wherein the first sequence is physically distant enough from the second sequence such that the first sequence is present on a first cell-free nucleic acid of the subject and the second sequence is present on a second cell-free nucleic acid of the subject. In some instances, the at least two sequences are immediately adjacent. In some instances the at least two sequences are separated by at least one nucleotide. In some instances, the at least two sequences are separated by at least two nucleotides. In some instances, the at least two sequences are separated by at least about 5, at least about 10, at least about 15, at least about 20, at least about 30, at least about 40, at least about 50, or at least about 100 nucleotides. In some instances, the at least two sequences are at least about 50% identical. In some instances, the at least two sequences are at least about 60% identical, at least about 60% identical, at least about 60%, at least about 70%, at least about 80%, at least about 90%, at least about 95%, at least about 99%, or 100% identical. In some instances, the first sequence and the second sequence are each at least 10 nucleotides in length. In some instances, the first sequence and the second sequence are each at least about 10, at least about 15, at least about 20, at least about 30, at least about 50, or at least about 100 nucleotides in length. In some instances, the first sequence and the second sequence are on the same chromosome. In some instances, the first sequence is on a first chromosome and the second sequence is on a second chromosome. In some instances, the first sequence and the second sequence are in functional linkage. For example, all CpG sites in the promotor region of gene AOX1 show the same hypermethylation in prostate cancer, so these sites are in functional linkage because they functionally carry the same information but are located one or more nucleotides apart.

In some instances, devices, systems and kits disclosed herein comprise at least one of an oligonucleotide probe or oligonucleotide primer that is capable of annealing to a strand of a cell-free nucleic acid, wherein the cell-free nucleic acid comprises a sequence corresponding to a region of interest or a portion thereof. In some instances, the region of interest is a region of a Y chromosome. In some instances, the region of interest is a region of an X chromosome. In some instances, the region of interest is a region of an autosome. In some instances, the region of interest, or portion thereof, comprises a repeat sequence as described herein that is present in a genome more than once. In some instances, the region of interest is about 10 nucleotides to about 1,000,000 nucleotides in length. In some instances, the region of interest is at least 10 nucleotides in length. In some instances, the region of interest is at least 100 nucleotides in length. In some instances, the region is at least 1000 nucleotides in length. In some instances, the region of interest is about 10 nucleotides to about 500,000 nucleotides in length. In some instances, the region of interest is about 10 nucleotides to about 300,000 nucleotides in length. In some instances, the region of interest is about 100 nucleotides to about 1,000,000 nucleotides in length. In some instances, the region of interest is about 100 nucleotides to about 500,000 nucleotides in length. In some instances, the region of interest is about 100 nucleotides to about 300,000 base pairs in length. In some instances, the region of interest is about 1000 nucleotides to about 1,000,000 nucleotides in length. In some instances, the region of interest is about 1000 nucleotides to about 500,000 nucleotides in length. In some instances, the region of interest is about 1000 nucleotides to about 300,000 nucleotides in length. In some instances, the region of interest is about 10,000 nucleotides to about 1,000,000 nucleotides in length. In some instances, the region of interest is about 10,000 nucleotides to about 500,000 nucleotides in length. In some instances, the region of interest is about 10,000 nucleotides to about 300,000 nucleotides in length. In some instances, the region of interest is about 300,000 nucleotides in length.

In some instances, the sequence corresponding to the region of interest is at least about 5 nucleotides in length. In some instances, the sequence corresponding to the region of interest is at least about 8 nucleotides in length. In some instances, the sequence corresponding to the region of interest is at least about 10 nucleotides in length. In some instances, the sequence corresponding to the region of interest is at least about 15 nucleotides in length. In some instances, the sequence corresponding to the region of interest is at least about 20 nucleotides in length. In some instances, the sequence corresponding to the region of interest is at least about 50 nucleotides in length. In some instances, the sequence corresponding to the region of interest is at least about 100 nucleotides in length. In some instances, the sequence is about 5 nucleotides to about 1000 nucleotides in length. In some instances, the sequence is about 10 nucleotides to about 1000 nucleotides in length. In some instances, the sequence is about 10 nucleotides to about 500 nucleotides in length. In some instances, the sequence is about 10 nucleotides to about 400 nucleotides in length. In some instances, the sequence is about 10 nucleotides to about 300 nucleotides in length. In some instances, the sequence is about 50 nucleotides to about 1000 nucleotides in length. In some instances, the sequence is about 50 nucleotides to about 500 nucleotides in length.

In some instances, devices, systems and kits disclosed herein comprise at least one of an oligonucleotide probe and oligonucleotide primer that is capable of annealing to a strand of a cell-free nucleic acid, wherein the cell-free nucleic acid comprises a sequence corresponding to a sub-region of interest disclosed herein. In some instances, the sub-region is represented by a sequence that is present in the region of interest more than once. In some instances, the sub-region is about 10 to about 1000 nucleotides in length. In some instances, the sub-region is about 50 to about 500 nucleotides in length. In some instances, the sub-region is about 50 to about 250 nucleotides in length. In some instances, the sub-region is about 50 to about 150 nucleotides in length. In some instances, the sub-region is about 100 nucleotides in length.

Any appropriate nucleic acid amplification method known in the art is contemplated for use in the devices and methods described herein. In some instances, isothermal amplification is used. In some instances, amplification is isothermal with the exception of an initial heating step before isothermal amplification begins. A number of isothermal amplification methods, each having different considerations and providing different advantages, are known in the art and have been discussed in the literature, e.g., by Zanoli and Spoto, 2013, "Isothermal Amplification Methods for the Detection of Nucleic Acids in Microfluidic Devices," Biosensors 3: 18-43, and Fakruddin, et al., 2013, "Alternative Methods of Polymerase Chain Reaction (PCR)," Journal of Pharmacy and Bioallied Sciences 5(4): 245-252, each incorporated herein by reference in its entirety. In some instances, any appropriate isothermic amplification method is used. In some instances, the isothermic amplification method used is selected from: Loop Mediated Isothermal Amplification (LAMP); Nucleic Acid Sequence Based Amplification (NASBA); Multiple Displacement Amplification (MDA); Rolling Circle Amplification (RCA); Helicase Dependent Amplification (HDA); Strand Displacement Amplification (SDA); Nicking Enzyme Amplification Reaction (NEAR); Ramification Amplification Method (RAM); and Recombinase Polymerase Amplification (RPA).

In some instances, the amplification method used is LAMP (see, e.g., Notomi, et al., 2000, "Loop Mediated Isothermal Amplification" NAR 28(12): e63 i-vii, and U.S. Pat. No. 6,410,278, "Process for synthesizing nucleic acid" each incorporated by reference herein in its entirety). LAMP is a one-step amplification system using auto-cycling strand displacement deoxyribonucleic acid (DNA) synthesis. In some instances, LAMP is carried out at 60-65° C. for 45-60 min in the presence of a thermostable polymerase, e.g., *Bacillus stearothermophilus* (Bst) DNA polymerase I, deoxyribonucleotide triphosphate (dNTPs), specific primers and the target DNA template. In some instances, the template is RNA and a polymerase having both reverse transcriptase activity and strand displacement-type DNA polymerase activity, e.g., Bca DNA polymerase, is used, or a polymerase having reverse transcriptase activity is used for the reverse transcriptase step and a polymerase not having reverse transcriptase activity is used for the strand displacement-DNA synthesis step.

In some instances, the amplification reaction is carried out using LAMP, at about 55° C. to about 70° C. In some instances, the LAMP reaction is carried out at 55° C. or greater. In some instances, the LAMP reaction is carried out 70° C. or less. In some instances, the LAMP reaction is carried out at about 55° C. to about 57° C., about 55° C. to about 59° C., about 55° C. to about 60° C., about 55° C. to about 61° C., about 55° C. to about 62° C., about 55° C. to about 63° C., about 55° C. to about 64° C., about 55° C. to about 65° C., about 55° C. to about 66° C., about 55° C. to about 68° C., about 55° C. to about 70° C., about 57° C. to about 59° C., about 57° C. to about 60° C., about 57° C. to about 61° C., about 57° C. to about 62° C., about 57° C. to about 63° C., about 57° C. to about 64° C., about 57° C. to about 65° C., about 57° C. to about 66° C., about 57° C. to about 68° C., about 57° C. to about 70° C., about 59° C. to about 60° C., about 59° C. to about 61° C., about 59° C. to about 62° C., about 59° C. to about 63° C., about 59° C. to about 64° C., about 59° C. to about 65° C., about 59° C. to about 66° C., about 59° C. to about 68° C., about 59° C. to about 70° C., about 60° C. to about 61° C., about 60° C. to about 62° C., about 60° C. to about 63° C., about 60° C. to about 64° C., about 60° C. to about 65° C., about 60° C. to about 66° C., about 60° C. to about 68° C., about 60° C. to about 70° C., about 61° C. to about 62° C., about 61° C. to about 63° C., about 61° C. to about 64° C., about 61° C. to about 65° C., about 61° C. to about 66° C., about 61° C. to about 68° C., about 61° C. to about 70° C., about 62° C. to about 63° C., about 62° C. to about 64° C., about 62° C. to about 65° C., about 62° C. to about 66° C., about 62° C. to about 68° C., about 62° C. to about 70° C., about 63° C. to about 64° C., about 63° C. to about 65° C., about 63° C. to about 66° C., about 63° C. to about 68° C., about 63° C. to about 70° C., about 64° C. to about 65° C., about 64° C. to about 66° C., about 64° C. to about 68° C., about 64° C. to about 70° C., about 65° C. to about 66° C., about 65° C. to about 68° C., about 65° C. to about 70° C., about 66° C. to about 68° C., about 66° C. to about 70° C., or about 68° C. to about 70° C. In some instances, the LAMP reaction is carried out at about 55° C., about 57° C., about 59° C., about 60° C., about 61° C., about 62° C., about 63° C., about 64° C., about 65° C., about 66° C., about 68° C., or about 70° C.

In some instances, the amplification reaction is carried out using LAMP, for about 30 to about 90 minutes. In some instances, the LAMP reaction is carried out for at least about 30 minutes. In some instances, the LAMP reaction is carried out for at most about 90 minutes. In some instances, the LAMP reaction is carried out for about 30 minutes to about 35 minutes, about 30 minutes to about 40 minutes, about 30 minutes to about 45 minutes, about 30 minutes to about 50 minutes, about 30 minutes to about 55 minutes, about 30 minutes to about 60 minutes, about 30 minutes to about 65 minutes, about 30 minutes to about 70 minutes, about 30 minutes to about 75 minutes, about 30 minutes to about 80 minutes, about 30 minutes to about 90 minutes, about 35 minutes to about 40 minutes, about 35 minutes to about 45 minutes, about 35 minutes to about 50 minutes, about 35 minutes to about 55 minutes, about 35 minutes to about 60 minutes, about 35 minutes to about 65 minutes, about 35 minutes to about 70 minutes, about 35 minutes to about 75 minutes, about 35 minutes to about 80 minutes, about 35 minutes to about 90 minutes, about 40 minutes to about 45 minutes, about 40 minutes to about 50 minutes, about 40 minutes to about 55 minutes, about 40 minutes to about 60 minutes, about 40 minutes to about 65 minutes, about 40 minutes to about 70 minutes, about 40 minutes to about 75 minutes, about 40 minutes to about 80 minutes, about 40 minutes to about 90 minutes, about 45 minutes to about 50 minutes, about 45 minutes to about 55 minutes, about 45 minutes to about 60 minutes, about 45 minutes to about 65 minutes, about 45 minutes to about 70 minutes, about 45 minutes to about 75 minutes, about 45 minutes to about 80 minutes, about 45 minutes to about 90 minutes, about 50 minutes to about 55 minutes, about 50 minutes to about 60 minutes, about 50 minutes to about 65 minutes, about 50 minutes to about 70 minutes, about 50 minutes to about 75 minutes, about 50 minutes to about 80 minutes, about 50 minutes to about 90 minutes, about 55 minutes to about 60 minutes, about 55 minutes to about 65 minutes, about 55 minutes to about 70 minutes, about 55 minutes to about 75 minutes, about 55 minutes to about 80 minutes, about 55 minutes to about 90 minutes, about 60 minutes to about 65 minutes, about 60 minutes to about 70 minutes, about 60 minutes to about 75 minutes, about 60 minutes to about 80 minutes, about 60 minutes to about 90 minutes, about 65 minutes to about 70 minutes, about 65 minutes to about 75 minutes, about 65 minutes to about 80 minutes, about 65 minutes to about 90 minutes, about 70 minutes to about 75 minutes, about 70 minutes to about 80 minutes, about 70 minutes to about 90 minutes, about 75 minutes to about 80 minutes, about 75 minutes to about 90 minutes, or about 80 minutes to about 90 minutes. In some instances, the LAMP reaction is carried out for about 30 minutes, about 35 minutes, about 40 minutes, about 45 minutes, about 50 minutes, about 55 minutes, about 60 minutes, about 65 minutes, about 70 minutes, about 75 minutes, about 80 minutes, or about 90 minutes.

In some instances, the amplification method is Nucleic Acid Sequence Based Amplification (NASBA). NASBA (also known as 3SR, and transcription-mediated amplification) is an isothermal transcription-based RNA amplification system. Three enzymes (avian myeloblastosis virus reverse transcriptase, RNase H and T7 DNA dependent RNA polymerase) are used to generate single-stranded RNA. In certain cases NASBA can be used to amplify DNA. The amplification reaction is performed at 41° C., maintaining constant temperature, typically for about 60 to about 90 minutes (see, e.g., Fakruddin, et al., 2012, "Nucleic Acid Sequence Based Amplification (NASBA) Prospects and Applications," Int. J. of Life Science and Pharma Res. 2(1):L106-L121, incorporated by reference herein).

In some instances, the NASBA reaction is carried out at about 40° C. to about 42° C. In some instances, the NASBA reaction is carried out at 41° C. In some instances, the NASBA reaction is carried out at most at about 42° C. In some instances, the NASBA reaction is carried out at about 40° C. to about 41° C., about 40° C. to about 42° C., or about 41° C. to about 42° C. In some instances, the NASBA reaction is carried out at about 40° C., about 41° C., or about 42° C.

In some instances, the amplification reaction is carried out using NASBA, for about 45 to about 120 minutes. In some instances, the NASBA reaction is carried out for about 30 minutes to about 120 minutes. In some instances, the NASBA reaction is carried out for at least about 30 minutes. In some instances, the NASBA reaction is carried out for at most about 120 minutes. In some instances, the NASBA reaction is carried out for up to 180 minutes. In some instances, the NASBA reaction is carried out for about 30 minutes to about 45 minutes, about 30 minutes to about 60 minutes, about 30 minutes to about 65 minutes, about 30 minutes to about 70 minutes, about 30 minutes to about 75 minutes, about 30 minutes to about 80 minutes, about 30 minutes to about 85 minutes, about 30 minutes to about 90 minutes, about 30 minutes to about 95 minutes, about 30 minutes to about 100 minutes, about 30 minutes to about 120 minutes, about 45 minutes to about 60 minutes, about 45 minutes to about 65 minutes, about 45 minutes to about 70 minutes, about 45 minutes to about 75 minutes, about 45 minutes to about 80 minutes, about 45 minutes to about 85 minutes, about 45 minutes to about 90 minutes, about 45 minutes to about 95 minutes, about 45 minutes to about 100 minutes, about 45 minutes to about 120 minutes, about 60 minutes to about 65 minutes, about 60 minutes to about 70 minutes, about 60 minutes to about 75 minutes, about 60 minutes to about 80 minutes, about 60 minutes to about 85 minutes, about 60 minutes to about 90 minutes, about 60 minutes to about 95 minutes, about 60 minutes to about 100 minutes, about 60 minutes to about 120 minutes, about 65 minutes to about 70 minutes, about 65 minutes to about 75 minutes, about 65 minutes to about 80 minutes, about 65 minutes to about 85 minutes, about 65 minutes to about 90 minutes, about 65 minutes to about 95 minutes, about 65 minutes to about 100 minutes, about 65 minutes to about 120 minutes, about 70 minutes to about 75 minutes, about 70 minutes to about 80 minutes, about 70 minutes to about 85 minutes, about 70 minutes to about 90 minutes, about 70 minutes to about 95 minutes, about 70 minutes to about 100 minutes, about 70 minutes to about 120 minutes, about 75 minutes to about 80 minutes, about 75 minutes to about 85 minutes, about 75 minutes to about 90 minutes, about 75 minutes to about 95 minutes, about 75 minutes to about 100 minutes, about 75 minutes to about 120 minutes, about 80 minutes to about 85 minutes, about 80 minutes to about 90 minutes, about 80 minutes to about 95 minutes, about 80 minutes to about 100 minutes, about 80 minutes to about 120 minutes, about 85 minutes to about 90 minutes, about 85 minutes to about 95 minutes, about 85 minutes to about 100 minutes, about 85 minutes to about 120 minutes, about 90 minutes to about 95 minutes, about 90 minutes to about 100 minutes, about 90 minutes to about 120 minutes, about 95 minutes to about 100 minutes, about 95 minutes to about 120 minutes, or about 100 minutes to about 120 minutes. In some instances, the NASBA reaction is carried out for about 30 minutes, about 45 minutes, about 60 minutes, about 65 minutes, about 70 minutes, about 75 minutes, about 80 minutes, about 85 minutes, about 90 minutes, about 95 minutes, about 100 minutes, about 120 minutes, about 150 minutes, or about 180 minutes.

In some instances, the amplification method is Strand Displacement Amplification (SDA). SDA is an isothermal amplification method that uses four different primers. A primer containing a restriction site (a recognition sequence for HincII exonuclease) is annealed to the DNA template. An exonuclease-deficient fragment of *Eschericia coli* DNA polymerase 1 (exo-Klenow) elongates the primers. Each SDA cycle consists of (1) primer binding to a displaced target fragment, (2) extension of the primer/target complex by exo-Klenow, (3) nicking of the resultant hemiphosphothioate HincII site, (4) dissociation of HincII from the nicked site and (5) extension of the nick and displacement of the downstream strand by exo-Klenow.

In some instances, the amplification method is Multiple Displacement Amplification (MDA). The MDA is an isothermal, strand-displacing method based on the use of the highly processive and strand-displacing DNA polymerase from bacteriophage Ø29, in conjunction with modified random primers to amplify the entire genome with high fidelity. It has been developed to amplify all DNA in a sample from a very small amount of starting material. In MDA Ø29 DNA polymerase is incubated with dNTPs, random hexamers and denatured template DNA at 30° C. for 16 to 18 hours and the enzyme must be inactivated at high temperature (65° C.) for 10 min. No repeated recycling is required, but a short initial denaturation step, the amplification step, and a final inactivation of the enzyme are needed.

In some instances, the amplification method is Rolling Circle Amplification (RCA).

RCA is an isothermal nucleic acid amplification method which allows amplification of the probe DNA sequences by more than $10^9$ fold at a single temperature, typically about 30° C. Numerous rounds of isothermal enzymatic synthesis are carried out by Ø29 DNA polymerase, which extends a circle-hybridized primer by continuously progressing around the circular DNA probe. In some instances, the amplification reaction is carried out using RCA, at about 28° C. to about 32° C.

In some instances, devices, systems and kits disclosed herein comprise at least one oligonucleotide primer, wherein the oligonucleotide primer has a sequence complementary to or corresponding to a Y chromosome sequence. In some instances, devices, systems and kits disclosed herein comprise a pair of oligonucleotide primers, wherein the pair of oligonucleotide primers have sequences complementary to or corresponding to a Y chromosome sequence. In some instances, devices, systems and kits disclosed herein comprise at least one oligonucleotide primer, wherein the oligonucleotide primer comprises a sequence complementary to or corresponding to a Y chromosome sequence. In some instances, devices, systems and kits disclosed herein comprise a pair of oligonucleotide primers, wherein the pair of oligonucleotide primers comprise sequences complementary to or corresponding to a Y chromosome sequence. In some instances, devices, systems and kits disclosed herein comprise at least one oligonucleotide primer, wherein the oligonucleotide primer consists of a sequence complementary to or corresponding to a Y chromosome sequence. In some instances, devices, systems and kits disclosed herein comprise a pair of oligonucleotide primers, wherein the pair of oligonucleotide primers consists of sequences complementary to or corresponding to a Y chromosome sequence. In some instances, the sequence(s) complementary to or corresponding to a Y chromosome sequence is at least 75% homologous to a wild-type human Y chromosome sequence. In some instances, the sequence(s) complementary to or corresponding to a Y chromosome sequence is at least 80% homologous to a wild-type human Y chromosome sequence. In some instances, the sequence(s) complementary to or corresponding to a Y chromosome sequence is at least 85% homologous to a wild-type human Y chromosome sequence. In some instances, the sequence(s) complementary to or corresponding to a Y chromosome sequence is at least 80% homologous to a wild-type human Y chromosome sequence. In some instances, the sequence(s) complementary to or corresponding to a Y chromosome sequence is at least 90% homologous to a wild-type human Y chromosome sequence. In some instances, the sequence(s) complementary to or corresponding to a Y chromosome sequence is at least 95% homologous to a wild-type human Y chromosome sequence. In some instances, the sequence(s) complementary to or corresponding to a Y chromosome sequence is at least 97% homologous to a wild-type human Y chromosome sequence. In some instances, the sequence(s) complementary to or corresponding to a Y chromosome sequence is 100% homologous to a wild-type human Y chromosome sequence.

Nucleic Acid Detector

In some instances, devices, systems and kits disclosed herein comprise a nucleic acid detector. In some instances, the nucleic acid detector comprises a nucleic acid sequencer. In some instances, devices, systems and kits disclosed herein are configured to amplify nucleic acids and sequence the resulting amplified nucleic acids. In some instances, devices, systems and kits disclosed herein are configured to sequence nucleic acids without amplifying nucleic acids. In some instances, devices, systems and kits disclosed herein comprise a nucleic acid sequencer, but do not comprise a nucleic acid amplifying reagent or nucleic acid amplifying component. In some instances, the nucleic acid sequencer comprises a signal detector that detects a signal that reflects successful amplification or unsuccessful amplification. In some instances, the nucleic acid sequencer is the signal detector. In some instances, the signal detector comprises the nucleic acid sequencer.

In some instances, the nucleic acid sequencer has a communication connection with an electronic device that analyzes sequencing reads from the nucleic acid sequencer.

In some instances the communication connection is hard wired. In some instances the communication connection is wireless. For example, a mobile device app or computer software, such as those disclosed herein, may receive the sequencing reads, and based on the sequencing reads, display or report genetic information about the sample (e.g., presence of a disease/infection, response to a drug, genetic abnormality or mutation of a fetus).

In some instances, the nucleic acid sequencer comprises a nanopore sequencer. In some instances, the nanopore sequencer comprises a nanopore. In some instances, the nanopore sequencer comprises a membrane and solutions that create a current across the membrane and drive movement of charged molecules (e.g., nucleic acids) through the nanopore. In some instances, the nanopore sequencer comprises a transmembrane protein, a portion thereof, or a modification thereof. In some instances, the transmembrane protein is a bacterial protein. In some instances, the transmembrane protein is not a bacterial protein. In some instances, the nanopore is synthetic. In some instances, the nanopore performs solid state nanopore sequencing. In some instances, the nanopore sequencer is described as pocket-sized, portable, or roughly the size of a cell phone. In some instances, the nanopore sequencer is configured to sequence at least one of RNA and DNA. Non-limiting examples of nanopore sequencing devices include Oxford Nanopore Technologies MinION and SmidgION nanopore sequencing USB devices. Both of these devices are small enough to be handheld. Nanopore sequencing devices and components are further described in reviews by Howorka (Nat Nanotechnol. 2017 Jul. 6; 12(7):619-630), and Garrido-Cardenas et al. (Sensors (Basel). 2017 Mar. 14; 17(3)), both incorporated herein by reference. Other non-limiting examples of nanopore sequencing devices are offered by Electronic Biosciences, Two Pore Guys, Stratos, and Agilent (technology originally from Genia).

In some instances, the nucleic acid detector comprises reagents and components required for bisulfite sequencing to detect epigenetic modifications. For instance, a long region with many methylation markers can be fragmented. Here, each fragment carrying a methylation marker can be an independent signal. Signals from all the fragments are sufficient in combination to obtain useful genetic information.

In some instances, the nucleic acid detector does not comprise a nucleic acid sequencer. In some instances, the nucleic acid detector is configured to count tagged nucleic acids, wherein the nucleic acid detector quantifies a collective signal from one or more tags.

Capture and Detection

In some instances, devices, systems and kits disclosed herein comprise at least one of a nucleic acid detector, capture component, signal detector, a detection reagent, or a combination thereof, for detecting a nucleic acid in the biological sample. In some instances, the capture component and the signal detector are integrated. In some instances, the capture component comprises a solid support. In some instances the solid support comprises a bead, a chip, a strip, a membrane, a matrix, a column, a plate, or a combination thereof.

In some instances, devices, systems and kits disclosed herein comprise at least one probe for an epigenetically modified region of a chromosome or fragment thereof. In some instances, the epigenetic modification of the epigenetically modified region of a chromosome is indicative of gender or a marker of gender. In some instances, devices, systems and kits disclosed herein comprise at least one probe for a paternally inherited sequence that is not present in the maternal DNA. In some instances, devices, systems and kits disclosed herein comprise at least one probe for a paternally inherited single nucleotide polymorphism. In some instances, the chromosome is a Y chromosome. In some instances, the chromosome is an X chromosome. In some instances, the chromosome is a Y chromosome. In some instances, the chromosome is an autosome. In some instances, the probe comprises a peptide, an antibody, an antigen binding antibody fragment, a nucleic acid or a small molecule.

In some instances, devices, systems and kits comprise a sample purifier disclosed herein and a capture component disclosed herein. In some instances, the sample purifier comprises the capture component. In some instances, the sample purifier and the capture component are integrated. In some instances, the sample purifier and the capture component are separate.

In some instances, the capture component comprises a binding moiety described herein. In some instances, the binding moiety is present in a lateral flow assay. In some instances, the binding moiety is added to the sample before the sample is added to the lateral flow assay. In some instances, the binding moiety comprises a signaling molecule. In some instances, the binding moiety is physically associated with a signaling molecule. In some instances, the binding moiety incapable of physically associating with a signaling molecule. In some instances, the binding moiety is connected to a signaling molecule. Non-limiting examples of signaling molecules include a gold particle, a fluorescent particle, a luminescent particle, and a dye molecule. In some instances the capture component comprises a binding moiety that is capable of interacting with an amplification product described herein. In some instances the capture component comprises a binding moiety that is capable of interacting with a tag on an amplification product described herein.

In some instances, devices, systems and kits disclosed herein comprise a detection system. In some instances, the detection system comprises a signal detector. Non-limiting examples of a signal detector include a fluorescence reader, a colorimeter, a sensor, a wire, a circuit, a receiver. In some instances, the detection system comprises a detection reagent. Non-limiting examples of a detection reagent include a fluorophore, a chemical, a nanoparticle, an antibody, and a nucleic acid probe. In some instances, the detection system comprises a pH sensor and a complementary metal-oxide semiconductor, which can be used to detect changes in pH. In some instances, production of an amplification product by devices, systems, kits or methods disclosed herein changes the pH, thereby indicating genetic information.

In some instances, the detection system comprises a signal detector. In some instances, the signal detector is a photodetector that detects photons. In some instances, the signal detector detects fluorescence. In some instances, the signal detector detects a chemical or compound. In some instances, the signal detector detects a chemical that is released when the amplification product is produced. In some instances, the signal detector detects a chemical that is released when the amplification product is added to the detection system. In some instances, the signal detector detects a compound that is produced when the amplification product is produced. In some instances, the signal detector detects a compound that is produced when the amplification product is added to the detection system.

In some instances, the signal detector detects an electrical signal. In some instances, the signal detector comprises an electrode. In some instances, the signal detector comprises a circuit a current, or a current generator. In some instances, the circuit or current is provided by a gradient of two or more solutions or polymers. In some instances, the circuit or current is provided by an energy source (e.g., battery, cell phone, wire from electrical outlet). In some instances, nucleic acids, amplification products, chemicals or compounds disclosed herein provide an electrical signal by disrupting the current and the signal detector detects the electrical signal.

In some instances, the signal detector detects light. In some instances, the signal detector comprises a light sensor. In some instances, the signal detector comprises a camera. In some instances, the signal detector comprises a cell phone camera or a component thereof.

In some instances, the signal detector comprises a nanowire that detects the charge of different bases in nucleic acids. In some instances, the nanowire has a diameter of about 1 nm to about 99 nm. In some instances, the nanowire has a diameter of about 1 nm to about 999 nm. In some instances, the nanowire comprises an inorganic molecule, e.g., nickel, platinum, silicon, gold, zinc, graphene, or titanium. In some instances, the nanowire comprises an organic molecule (e.g., a nucleotide).

In some instances, the detection system comprises an assay assembly, wherein the assay assembly is capable of detecting a target analyte (e.g., nucleic acid amplification product). In some instances, the assay assembly comprises a lateral flow strip, also referred to herein and in the field, as a lateral flow assay, lateral flow test or lateral flow device. In some instances, a lateral flow assay provides a fast, inexpensive, and technically simple method to detect amplification products disclosed herein. Generally, lateral flow assays disclosed herein comprise a porous material or porous matrix that transports a fluid, and a detector that detects the amplification product when it is present. The porous material may comprise a porous paper, a polymer structure, a sintered polymer, or a combination thereof. In some instances, the lateral flow assay transports the biological fluid or portion thereof (e.g., plasma of blood sample). In some instances, the lateral flow assay transports a solution containing the biological fluid or portion thereof. For instance, methods may comprise adding a solution to the biological fluid before or during addition of the sample to the device or system. The solution may comprise a salt, a polymer, or any other component that facilitates transport of the sample and or amplification product through the lateral flow assay. In some instances, nucleic acids are amplified after they have traveled through the lateral flow strip.

In some instances, devices, the detection system comprises a lateral flow device, wherein the lateral flow device comprises multiple sectors or zones, wherein each desired function can be present in a separate sector or zone. In general, in a lateral flow device, a liquid sample, e.g., a body fluid sample as described herein, containing the target analyte moves with or without the assistance of external forces through sectors or zones of the lateral flow device. In some instances, the target analyte moves without the assistance of external forces, e.g., by capillary action. In some instances, the target analyte moves with assistance of external forces, e.g., by facilitation of capillary action by movement of the lateral flow device. Movement can comprise any motion caused by external input, e.g., shaking, turning, centrifuging, applying an electrical field or magnetic field, applying a pump, applying a vacuum, or rocking of the lateral flow device.

In some instances, the lateral flow device is a lateral flow test strip, comprising zones or sectors that are situated laterally, e.g., behind or ahead of each other. In general, a lateral flow test strip allows accessibility of the functional zones or sectors from each side of (e.g., above and below) the test strip as a result of exposure of a large surface area of each functional zone or sector. This facilitates the addition of reagents, including those used in sample purification, or target analyte amplification, and/or detection.

Any suitable lateral flow test strip detection format known to those of skill in the art is contemplated for use in an assay assembly of the present disclosure. Lateral flow test strip detection formats are well known and have been described in the literature. Lateral flow test strip assay formats are generally described by, e.g., Sharma et al., (2015) Biosensors 5:577-601, incorporated by reference herein in its entirety. Detection of nucleic acids using lateral flow test strip sandwich assay formats is described by, e.g., U.S. Pat. No. 9,121,849, "Lateral Flow Assays," incorporated by reference herein in its entirety. Detection of nucleic acids using lateral flow test strip competitive assay formats is described by, e.g., U.S. Pat. No. 9,423,399, "Lateral Flow Assays for Tagged Analytes," incorporated by reference herein in its entirety.

In some instances, a lateral flow test strip detects the target analyte in a test sample using a sandwich format, a competitive format, or a multiplex detection format. In a traditional sandwich assay format, the detected signal is directly proportional to the amount of the target analyte present in the sample, so that increasing amounts of the target analyte lead to increasing signal intensity. In traditional competitive assay formats, the detected signal has an inverse relationship with the amount of analyte present, and increasing amounts of analyte lead to decreasing signal intensity.

In a lateral flow sandwich format, also referred to as a "sandwich assay," the test sample typically is applied to a sample application pad at one end of a test strip. The applied test sample flows through the test strip, from the sample application pad to a conjugate pad located adjacent to the sample application pad, where the conjugate pad is downstream in the direction of sample flow. In some instances, the conjugate pad comprises a labeled, reversibly-immobilized probe, e.g., an antibody or aptamer labeled with, e.g., a dye, enzyme, or nanoparticle. A labeled probe-target analyte complex is formed if the target analyte is present in the test sample. This complex then flows to a first test zone or sector (e.g., a test line) comprising an immobilized second probe which is specific to the target analyte, thereby trapping any labeled probe-target analyte complex. In some instances, the intensity or magnitude of signal, e.g., color, at the first test zone or sector is used to indicate the presence or absence, quantity, or presence and quantity of target analyte in the test sample. A second test zone or sector can comprise a third probe that binds to excess labeled probe. If the applied test sample comprises the target analyte, little or no excess labeled probe will be present on the test strip following capture of the target analyte by the labeled probe on the conjugate pad. Consequently, the second test zone or sector will not bind any labeled probe, and little or no signal (e.g., color) at the second test zone or sector is expected to be observed. The absence of signal at the second test zone or sector thus can provide assurance that signal observed in the first test zone or sector is due to the presence of the target analyte.

In some instances, devices and systems disclosed herein comprise a sandwich assay. In some instances, the sandwich assay is configured to receive a biological sample disclosed herein and retain sample components (e.g., nucleic acids, cells, microparticles). In some instances, the sandwich assay is configured to receive a flow solution that flushes non-nucleic acid components of the biological sample (e.g., proteins, cells, microparticles), leaving nucleic acids of the biological sample behind. In some instances, the sandwich assay comprises a membrane that binds nucleic acids to help retain the nucleic acids when the flow solution is applied. Non-limiting examples of a membrane the binds nucleic acids includes chitosan modified nitrocellulose.

Similarly, in a lateral flow competitive format a test sample is applied to a sample application pad at one end of a test strip, and the target analyte binds to a labeled probe to form a probe-target analyte complex in a conjugate pad downstream of the sample application pad. In the competitive format, the first test zone or sector typically comprises the target analyte or an analog of the target analyte. The target analyte in the first test zone or sector binds any free labeled probe that did not bind to the test analyte in the conjugate pad. Thus, the amount of signal observed in the first test zone or sector is higher when there is no target analyte in the applied test sample than when target analyte is present. A second test zone or sector comprises a probe that specifically binds to the probe-target analyte complex. The amount of signal observed in this second test zone or sector is higher when the target analyte is present in the applied test sample.

In a lateral flow test strip multiplex detection format, more than one target analyte is detected using the test strip through the use of additional test zones or sectors comprising, e.g., probes specific for each of the target analytes.

In some instances, the lateral flow device is a layered lateral flow device, comprising zones or sectors that are present in layers situated medially, e.g., above or below each other. In some instances, one or more zones or sectors are present in a given layer. In some instances, each zone or sector is present in an individual layer. In some instances, a layer comprises multiple zones or sectors. In some instances, the layers are laminated. In a layered lateral flow device, processes controlled by diffusion and directed by the concentration gradient are possible driving forces. For example, multilayer analytical elements for fluorometric assay or fluorometric quantitative analysis of an analyte contained in a sample liquid are described in EP0097952, "Multilayer analytical element," incorporated by reference herein.

A lateral flow device can comprise one or more functional zones or sectors. In some instances, the test assembly comprises 1 to 20 functional zones or sectors. In some instances, the functional zones ore sectors comprise at least one sample purification zone or sector, at least one target analyte amplification zone or sector, at least one target analyte detection zone or sector, and at least one target analyte detection zone or sector.

In some instances, the target analyte is a nucleic acid sequence, and the lateral flow device is a nucleic acid lateral flow assay. In some instances, devices, systems and kits disclosed herein comprise a nucleic acid lateral flow assay, wherein the nucleic acid lateral flow assay comprises nucleic acid amplification function. In some instances, target nucleic acid amplification that is carried out by the nucleic acid amplification function takes place prior to, or at the same time as, detection of the amplified nucleic acid species. In some instances, detection comprises one or more of qualitative, semi-quantitative, or quantitative detection of the presence of the target analyte.

In some instances, devices, systems and kits disclosed herein comprise an assay assembly wherein a target nucleic acid analyte is amplified in a lateral flow test strip to generate a labeled amplification product, or an amplification product that can be labeled after amplification. In some instances, a label is present on one or more amplification primers, or subsequently conjugated to one or more amplification primers, following amplification. In some instances, at least one target nucleic acid amplification product is detected on the lateral flow test strip. For example, one or more zones or sectors on the lateral flow test strip may comprise a probe that is specific for a target nucleic acid amplification product.

In some instances, the devices, systems and kits disclosed herein comprise a detector, wherein the detector comprises a graphene biosensor. Graphene biosensors are described, e.g., by Afsahi et al., in the article entitled, "Novel graphene-based biosensor for early detection of Zika virus infection, Biosensor and Bioelectronics," (2018) 100:85-88.

In some instances, a detector disclosed herein comprises a nanopore, a nanosensor, or a nanoswitch. For instance, the detector may be capable of nanopore sequencing, a method of transporting a nucleic acid through a nanpore based on an electric current across a membrane, the detector measuring disruptions in the current corresponding to specific nucleotides. A nanoswitch or nanosensor undergoes a structural change upon exposure to the detectable signal. See, e.g., Koussa et al., "DNA nanoswitches: A quantitative platform for gel-based biomolecular interaction analysis," (2015) Nature Methods, 12(2): 123-126.

In some instances, the detector comprises a rapid multiplex biomarker assay where probes for an analyte of interest are produced on a chip that is used for real-time detection. Thus, there is no need for a tag, label or reporter. Binding of analytes to these probes causes a change in a refractive index that corresponds to a concentration of the analyte. All steps may be automated. Incubations may be not be necessary. Results may be available in less than an hour (e.g., 10-30 minutes). A non-limiting example of such a detector is the Genalyte Maverick Detection System.

Additional Tests

In some instances, devices, systems and kits disclosed herein comprise additional features, reagents, tests or assays for detection or analysis of biological components besides nucleic acids. By way of non-limiting example, the biological component may be selected from a peptide, a lipid, a fatty acid, a sterol, a carbohydrate, a viral component, a microbial component, and a combination thereof. The biological component may be an antibody. The biological component may be an antibody produced in response to a peptide in the subject. These additional assays may be capable of detecting or analyzing biological components in the small volumes or sample sizes disclosed herein and throughout. An additional test may comprise a reagent capable of interacting with a biological component of interest. Non-limiting examples of such reagents include antibodies, peptides, oligonucleotides, aptamers, and small molecules, and combinations thereof. The reagent may comprise a detectable label. The reagent may be capable of interacting with a detectable label. The reagent may be capable of providing a detectable signal.

Additional tests may require one or more antibodies. For instance, the additional test may comprise reagents or components that provide for performing Immuno-PCR (IPCR). IPCR is a method wherein a first antibody for a protein of interest is immobilized and exposed to a sample. If the sample contains the protein of interest, it will be captured by the first antibody. The captured protein of interest is then exposed to a second antibody that binds the protein of interest. The second antibody has been coupled to a polynucleotide that can be detected by real-time PCR. Alternatively or additionally, the additional test may comprise reagents or components that provide for performing a proximity ligation assay (PLA), wherein the sample is exposed to two antibodies specific for a protein of interest, each antibody comprising an oligonucleotide. If both antibodies bind to the protein of interest, the oligonucleotides of each antibody will be close enough to be amplified and/or detected.

In some instances, devices, systems and kits disclosed herein comprise a pregnancy test to confirm the subject is pregnant. In some instances, devices, systems and kits disclosed herein comprise a test for presence of a Y chromosome or absence of a Y chromosome (gender test). In some instances, devices, systems and kits disclosed herein comprise a test for gestational age.

In some instances, devices, systems, and kits disclosed herein comprise a test for multiple pregnancies, e.g., twins or triplets. In some instances, methods disclosed herein quantify (absolute or relative) the total amount of fetal nucleic acids in a maternal sample, and the amount of sequences represented by the various autosomes, X and Y chromosomes to detect if one, both or all fetuses are male or female, euploid or aneuploid, etc.

In some instances, devices, systems and kits disclosed herein comprise a pregnancy test for indicating, detecting or verifying the subject is pregnant. In some instances the pregnancy test comprises a reagent or component for measuring a pregnancy related factor. By way of non-limiting example, the pregnancy related factor may be human chorionic gonadotropin protein (hCG) and the reagent or component for hCG comprising an anti-hCG antibody. Also by way of non-limiting example, the pregnancy related factor may be an hCG transcript and the reagent or component for measuring the hCG transcript is an oligonucleotide probe or primer that hybridizes to the hCG transcript. In some instances, the pregnancy related factor is heat shock protein 10 kDa protein 1, also known as early-pregnancy factor (EPF).

In some instances, devices, systems and kits disclosed herein are capable of conveying the age of the fetus. For example, a signal may be generated from the device or system, wherein the level of the signal corresponds to the amount of hCG in the sample from the subject. This level or strength of the signal may be translated or equivocated with a numerical value representing the amount of hCG in the sample. The amount of hCG may indicate an approximate age of the fetus.

In some instances, devices, systems and kits disclosed herein provide an indication or verification of pregnancy, an indication or verification of gestational age, and an indication or verification of gender. In some instances, devices, systems and kits disclosed herein provide an indication of pregnancy, gestational age, and/or gender with at least about 90% confidence (e.g., 90% of the time, the indication is accurate). In some instances, devices, systems and kits disclosed herein provide an indication of pregnancy, gestational age, and/or gender with at least about 95% confidence. In some instances, devices, systems and kits disclosed herein provide an indication of pregnancy, gestational age, and/or gender with at least about 99% confidence.

Performance Parameters

In some instances, the devices, systems and kits disclosed herein are operable at one or more temperatures. In some instances, the temperature of a component or reagent of the device system, or kit needs to be altered in order for the device system, or kit to be operable. Generally, devices, systems and kits are considered "operable" when they are capable of providing information conveyed by biomarkers (e.g., RNA/DNA, peptides) in the biological sample. In some instances, temperature(s) at which the devices, systems, kits, components thereof, or reagents thereof are operable are obtained in a common household. By way of non-limiting example, temperature(s) obtained in a common household may be provided by room temperature, a refrigerator, a freezer, a microwave, a stove, an electric hot pot, hot/cold water bath, or an oven.

In some instances, devices, systems, kits, components thereof, or reagents thereof, as described herein, are operable at a single temperature. In some instances, devices, systems, kits, components thereof, or reagents thereof, as described herein, only require a single temperature to be operable. In some instances, devices, systems, kits, components thereof, or reagents thereof, as described herein, only require two temperatures to be operable. In some instances, devices, systems, kits, components thereof; or reagents thereof, as described herein, only require three temperatures to be operable.

In some instances, devices, systems, kits disclosed herein comprises a heating device or a cooling device to allow a user to obtain the at least one temperature. Non-limiting examples of heating devices and cooling devices are pouches or bag of material that can be cooled in a refrigerator or freezer, or microwaved or boiled on a stove top, or plugged into an electrical socket, and subsequently applied to devices disclosed herein or components thereof, thereby transmitting heat to the device or component thereof or cooling the device or component thereof. Another non-limiting example of a heating device is an electrical wire or coil that runs through the device or portion thereof. The electrical wire or coil may be activated by external (e.g. solar, outlet) or internal (e.g., battery, cell phone) power to convey heat to the device or portion thereof. In some instances, devices, systems, kits disclosed herein comprise a thermometer or temperature indicator to assist a user with assessing a temperature within the range of temperatures. Alternatively, or additionally, the user employs a device in a typical home setting (e.g., thermometer, cell phone, etc.) to assess the temperature.

In some instances, temperature at which the devices, systems, kits, components thereof, or reagents thereof are operable at a range of temperatures or at least one temperature that falls within a range of temperatures. In some instances, the range of temperatures is about −50° C. to about 100° C. In some instances, the range of temperatures is about −50° C. to about 90° C. In some instances, the range of temperatures is about −50° C. to about 80° C. In some instances, the range of temperatures is about is about −50° C. to about 70° C. In some instances, the range of temperatures is about −50° C. to about 60° C. In some instances, the range of temperatures is about −50° C. to about 50° C. In some instances, the range of temperatures is about −50° C. to about 40° C. In some instances, the range of temperatures is about −50° C. to about 30° C. In some instances, the range of temperatures is about −50° C. to about 20° C. In some instances, the range of temperatures is about −50° C. to about 10° C. In some instances, the range of temperatures is about 0° C. to about 100° C. In some instances, the range of temperatures is about 0° C. to about 90° C. In some instances, the range of temperatures is about 0° C. to about 80° C. In some instances, the range of temperatures is about is about 0° C. to about 70° C. In some instances, the range of temperatures is about 0° C. to about 60° C. In some instances, the range of temperatures is about 0° C. to about 50° C. In some instances, the range of temperatures is about 0° C. to about 40° C. In some instances, the range of temperatures is about 0° C. to about 30° C. In some instances, the range of temperatures is about 0° C. to about 20° C. In some instances, the range of temperatures is about 0° C. to about 10° C. In some instances, the range of temperatures is about 15° C. to about 100° C. In some instances, the range of temperatures is about 15° C. to about 90° C. In some instances, the range of temperatures is about 15° C. to about 80° C. In some instances, the range of temperatures is about is about 15° C. to about 70° C. In some instances, the range of temperatures is about 15° C. to about 60° C. In some instances, the range of temperatures is about 15° C. to about 50° C. In some instances, the range of temperatures is about 15° C. to about 40° C. In some instances, the range of temperatures is about 15° C. to about 30° C. In some instances, the range of temperatures is about 10° C. to about 30° C. In some instances, devices, systems, kits disclosed herein, including all components thereof, and all reagents thereof, are completely operable at room temperature, not requiring cooling, freezing or heating.

In some instances, devices, systems and kits disclosed herein detect components of the biological sample or products thereof (e.g., amplification products, conjugation products, binding products) within a time range of receiving the biological sample. In some instances, detecting occurs via a signaling molecule described herein. In some instances, the time range is about one second to about one minute. In some instances, the time range is about ten seconds to about one minute. In some instances, the time range is about ten seconds to about one minute. In some instances, the time range is about thirty seconds to about one minute. In some instances, the time range is about 10 seconds to about 2 minutes. In some instances, the time range is about 10 seconds to about 3 minutes. In some instances, the time range is about 10 seconds to about 5 minutes. In some instances, the time range is about 10 seconds to about 10 minutes. In some instances, the time range is about 10 seconds to about 15 minutes. In some instances, the time range is about 10 seconds to about 20 minutes. In some instances, the time range is about 30 seconds to about 2 minutes. In some instances, the time range is about 30 seconds to about 5 minutes. In some instances, the time range is about 30 seconds to about 10 minutes. In some instances, the time range is about 30 seconds to about 15 minutes. In some instances, the time range is about 30 seconds to about 20 minutes. In some instances, the time range is about 30 seconds to about 30 minutes. In some instances, the time range is about 1 minute to about 2 minutes. In some instances, the time range is about 1 minute to about 3 minutes. In some instances, the time range is about 1 minute to about 5 minutes. In some instances, the time range is about 1 minute to about 10 minutes. In some instances, the time range is about 1 minute to about 20 minutes. In some instances, the time range is about 1 minute to about 30 minutes. In some instances, the time range is about 5 minutes to about 10 minutes. In some instances, the time range is about 5 minutes to about 15 minutes. In some instances, the time range is about 5 minutes to about 20 minutes. In some instances, the time range is about 5 minutes to about 30 minutes. In some instances, the time range is about 5 minutes to about 60 minutes. In some instances, the time range is about 30 minutes to about 60 minutes. In some instances, the time range is about 30 minutes to about 2 hours. In some instances, the time range is about 1 hour to about 2 hours. In some instances, the time range is about 1 hour to about 4 hours.

In some instances, devices, systems and kits disclosed herein detect a component of the biological sample or a product thereof (e.g., amplification product, conjugation product, binding product) in less than a given amount of time. In some instances, devices, systems and kits disclosed herein provide an analysis of a component of a biological sample or product thereof in less than a given amount of time. In some instances, the amount of time is less than 1 minute. In some instances, the amount of time is less than 5 minutes. In some instances, the amount of time is less than 10 minutes. In some instances, the amount of time is 15 minutes. In some instances, the amount of time is less than 20 minutes. In some instances, the amount of time is less than 30 minutes. In some instances, the amount of time is less than 60 minutes. In some instances, the amount of time is less than 2 hours. In some instances, the amount of time is less than 8 hours.

Communication & Information Storage

In general, devices, systems and kits disclosed herein comprise a nucleic acid information output. The nucleic acid information output is configured to communicate genetic information from the sample to the user. In some instances, the nucleic acid information output comprises a communication connection or interface so that genetic information obtained can be shared with others not physically present (e.g., family member, physician, or genetic counselor). The communication connection or interface may also allow for input from other sources. In some instances, devices, systems and kits disclosed herein comprise an interface for receiving information based on the genetic information obtained. The interface or communication connection may also receive non-genetic information from the user (e.g., medical history, medical conditions, age, weight, heart rate, blood pressure, physical activity, etc.). The interface or communication connection may also receive information provided by someone or something other than the user. By way of non-limiting example, this includes web-based information, information from a medical practitioner, and information from an insurance company. In some instances, devices, systems and kits disclosed herein comprise an interface for communicating information based on the genetic information obtained. In some instances, the interface provides a description of a genetic or chromosomal abnormality. In some instances, the interface provides a list of local contacts, such as doctors, support groups, stores and service providers, which support families of children with a genetic or chromosomal abnormality. In some instances, the interface provides an online listing of products or services that would be useful to children with a genetic or chromosomal abnormality. In some instances, devices, systems and kits disclosed herein comprise an information storage unit, e.g., a computer chip. In some instances, the devices, systems and kits disclosed herein comprise means to store genetic information securely. For example, devices, systems and kits disclosed herein may comprise a data chip or a connection (wired or wireless) to a hard drive, server, database or cloud. Non-limiting examples of interfaces for devices and systems disclosed herein are shown in FIG. 4B and FIGS. 5A-E.

In some instances, the devices, systems and kits disclosed herein are capable of collecting, encrypting, and/or storing information from users in a secure manner. Non-limiting examples of such information include health information, information from their wearables, other tests they have done or will do, demographic information etc.

In some instances, the devices, systems and kits disclosed herein are capable of communicating information about biomarkers in the biological sample to a communication device. In some instances the communication device is capable of being connected to the internet (e.g., via port or wireless connection). In some instances the communication device is connected to the internet. In some instances the communication device is not connected to the internet. In some instances, devices, systems and kits disclosed herein are capable of communicating information about biomarkers in the biological sample through the communication device to the internet. Non-limiting examples of communication devices are cell phones, electronic notepads, and computers.

In some instances, devices, systems and kits disclosed herein comprise a communication connection or a communication interface. In some embodiments, the communication interface provides a wired interface. In further embodiments, the wired communications interface utilizes Universal Serial Bus (USB) (including mini-USB, micro-USB, USB Type A, USB Type B, and USB Type C), IEEE 1394 (FireWire), Thunderbolt, Ethernet, and optical interconnect.

In some embodiments, the communication interface provides a wireless interface. See, e.g., FIGS. 5A-E. In further embodiments, the wireless communications interface utilizes a wireless communications protocol such as infrared, near-field communications (NFC) (including RFID), Bluetooth, Bluetooth Low Energy (BLE), ZigBee, ANT, IEEE 802.11 (Wi-Fi), Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), or 3G/4G/LTE/5G cellular communication methods.

In some embodiments, devices, systems, kits, and methods described herein include a digital processing device, or use of the same. In further embodiments, the digital processing device includes one or more hardware central processing units (CPUs) or general purpose graphics processing units (GPGPUs) that carry out the device's functions. In still further embodiments, the digital processing device further comprises an operating system configured to perform executable instructions. In some embodiments, the digital processing device includes a communication interface (e.g., network adapter) for communicating with one or more peripheral devices, one or more distinct digital processing devices, one or more computing systems, one or more computer networks, and/or one or more communications networks.

In some embodiments, the digital processing device is communicatively coupled to a computer network ("network") with the aid of the communication interface. Suitable networks include, a personal area network (PAN), a local area networks (LAN), a wide area network (WAN), an intranet, an extranet, the Internet (providing access to the World Wide Web) and combinations thereof. The network in some cases is a telecommunication and/or data network. The network, in various cases, includes one or more computer servers, which enable distributed computing, such as cloud computing. The network, in some cases and with the aid of the device, implements a peer-to-peer network, which enables devices coupled to the device to behave as a client or a server.

In accordance with the description herein, suitable digital processing devices include, by way of non-limiting examples, server computers, desktop computers, laptop computers, notebook computers, sub-notebook computers, netbook computers, netpad computers, set-top computers, media streaming devices, handheld computers, Internet appliances, fitness trackers, smart watches, mobile smartphones, tablet computers, and personal digital assistants. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®. Those of skill in the art will also recognize that suitable media streaming device operating systems include, by way of non-limiting examples, Apple TV®, Roku®, Boxee®, Google TV®, Google Chromecast®, Amazon Fire®, and Samsung® HomeSync®. In some instances, the operating system comprises an Internet of Things (IoT) device. Non-limiting examples of an IoT device include Amazon's Alexa®, Microsoft's Cortana®, Apple Home Pod®, and Google Speaker®. In some instances, devices, systems, and kits disclosed herein comprise a virtual reality and/or augmented reality system.

In some embodiments, devices, systems, and kits disclosed herein comprise a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In yet other embodiments, the display is a head-mounted display in communication with the digital processing device, such as a VR headset.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In further embodiments, the input device is a Kinect, Leap Motion, or the like. In still further embodiments, the input device is a combination of devices such as those disclosed herein.

Mobile Application

In some embodiments, devices, systems, kits, and methods disclosed herein comprise a digital processing device, or use of the same, wherein the digital processing device is provided with executable instructions in the form of a mobile application. In some embodiments, the mobile application is provided to a mobile digital processing device at the time it is manufactured. In other embodiments, the mobile application is provided to a mobile digital processing device via the computer network described herein. Mobile applications disclosed herein may be configured to locate, encrypt, index, and/or access information. Mobile applications disclosed herein may be configured to acquire, encrypt, create, manipulate, index, and peruse data.

Figure 5A:
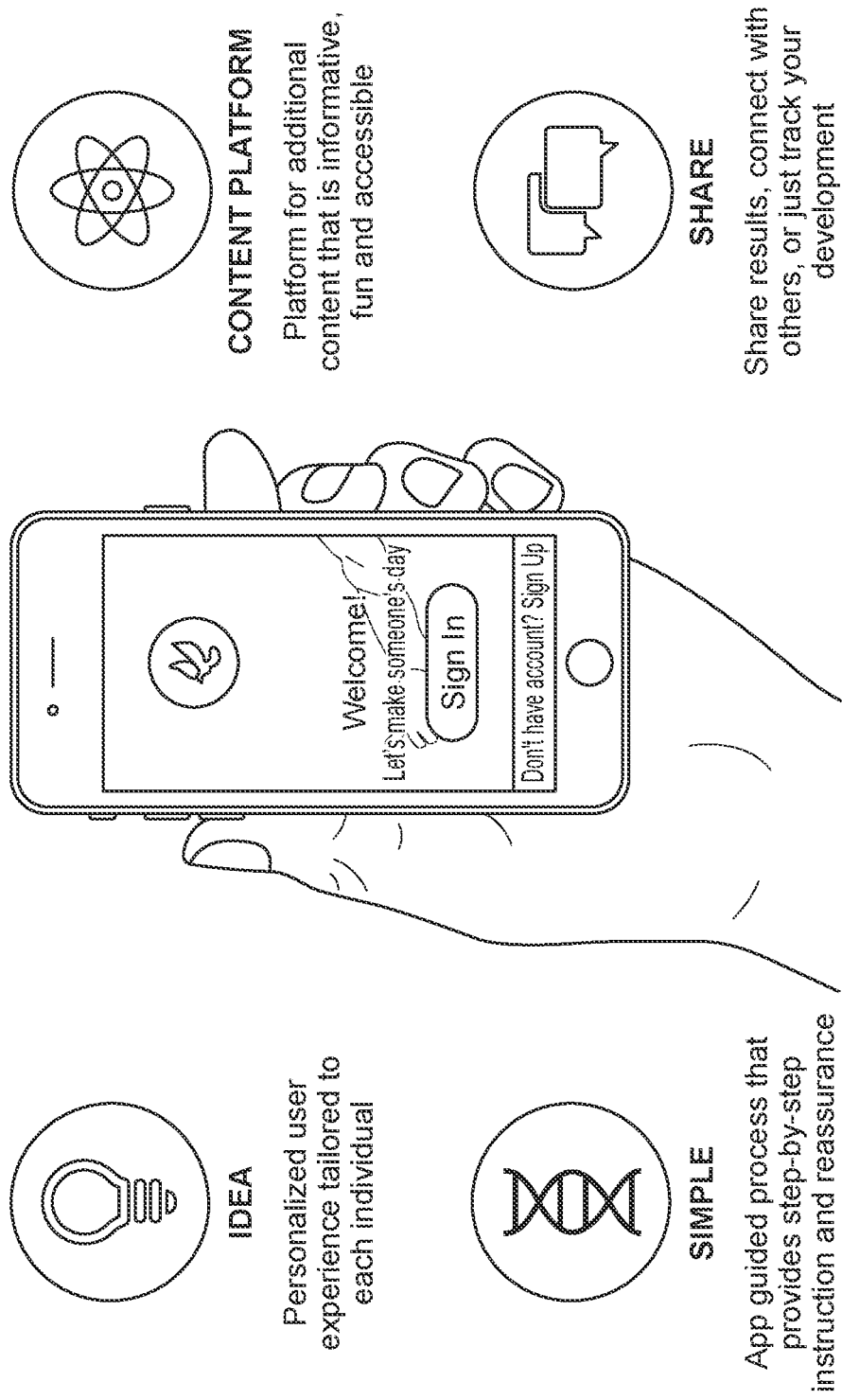
FIG. 5A shows various functions that the mobile application provides.

Referring to FIG. 5A, in a particular embodiment, a mobile application is configured to connect with, communicate with, and receive genetic information and other information from the devices, systems and kits disclosed herein. FIG. 5A is a diagram depicting various functions that the mobile application optionally provides to users. In this embodiment, the mobile application optionally provides: 1) a personalized, tailored user experience (UX) based on the personal information and preferences of the user; 2) an interactive text-, audio-, and/or video-driven instructional experience to inform the user how to utilize the devices, systems, and kits; 3) a content platform that provides the user with access to articles, news, media, games, and the like; and 4) tools for tracking and sharing information, test results, and events.

Figure 5B:
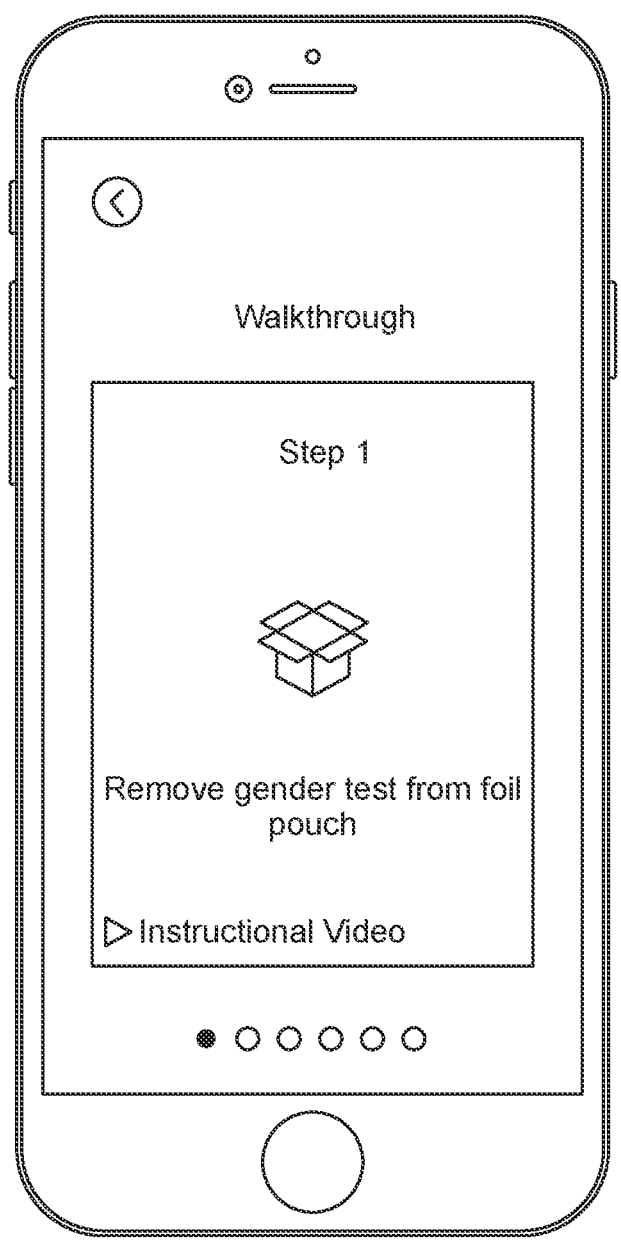
FIG. 5B shows a step-by-step walkthrough to guide a user through use of the devices, systems and kits disclosed herein.

Referring to FIG. 5B, in a particular embodiment, the mobile application optionally includes an interactive interface providing a step-by-step walkthrough to guide a user through use of the devices, systems and kits disclosed herein. In various embodiments, the interactive walkthrough includes text, images, animations, audio, video, and the like to inform and instruct the user.

Figure 5C:
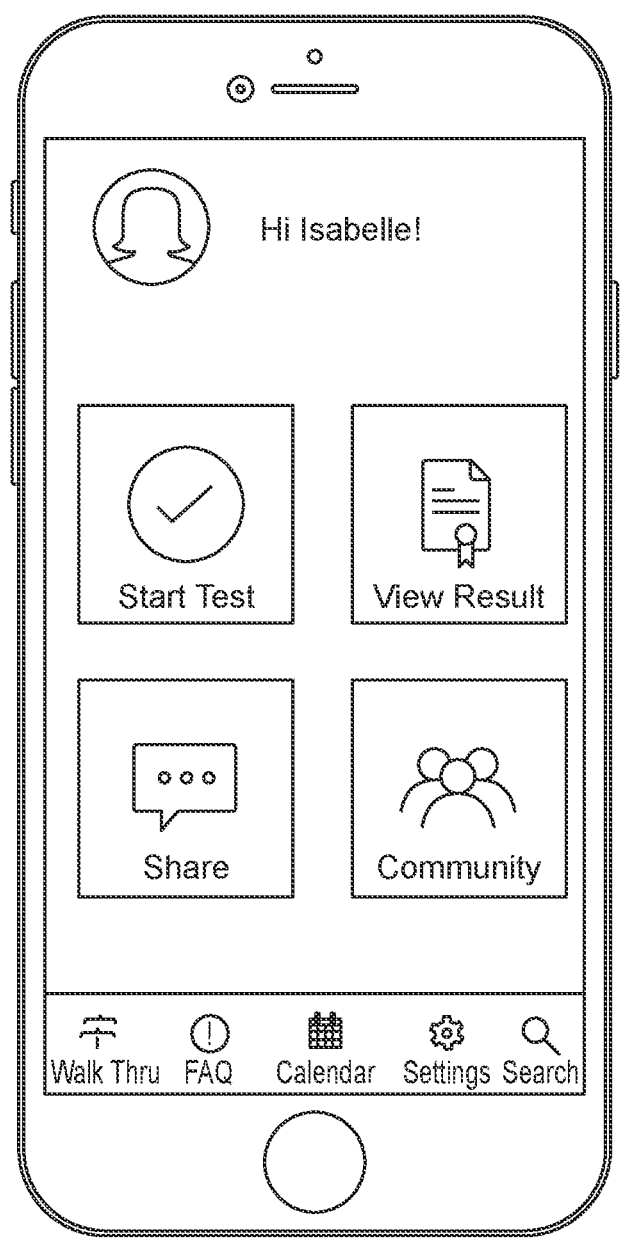
FIG. 5C shows interface elements allowing a user to start a test, view and share test results, and interact with others.

Referring to FIG. 5C, in a particular embodiment, the mobile application optionally includes a home screen allowing a user to access the mobile application functionality disclosed herein. In this embodiment, the home screen includes a personalized greeting as well as interface elements allowing the user to start a test, view current and historic test results, share test results, and interact with a larger community of users.

Figure 5D:
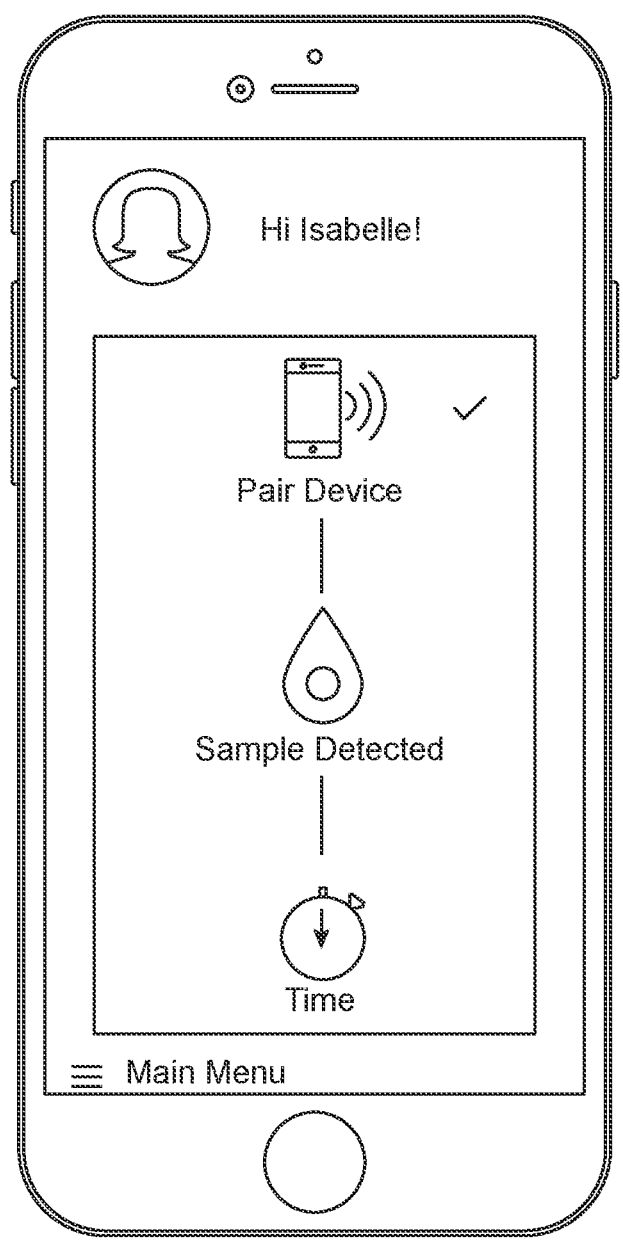
FIG. 5D shows an interface for monitoring the status of a test.

Referring to FIG. 5D, in a particular embodiment, the mobile application optionally includes a progress diagram informing a user of the status of a process for connecting to a device, system, or kit disclosed herein. In this embodiment, the diagram shows all the steps and indicates the current step. The steps are: 1) pair with the device via, for example, Bluetooth; 2) detect a sample in the device; and 3) wait for the sample to be processed. In some embodiments, the diagram is interactive, animated, or augmented with media or other content.

Figure 5E:
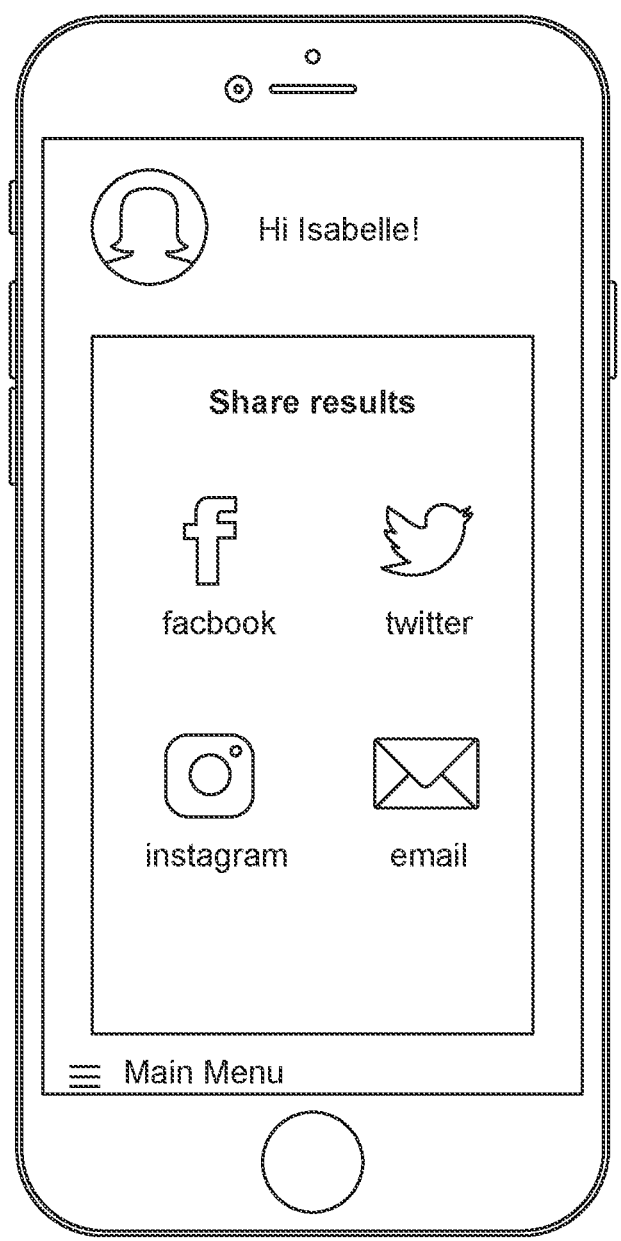
FIG. 5E shows how results can be shared.

Referring to FIG. 5E, in a particular embodiment, the mobile application optionally includes a social sharing screen allowing a user to access features to share test results. Many services, platforms, and networks are suitable for sharing test results and other information and events. Suitable social networking and sharing platforms include, by way of non-limiting examples, Facebook, YouTube, Twitter, LinkedIn, Pinterest, Google Plus+, Tumblr, Instagram, Reddit, VK, Snapchat, Flickr, Vine, Meetup, Ask.fm, Classmates, QQ, WeChat, Swarm by Foursquare, Kik, Yik Yak, Shots, Periscope, Medium, Soundcloud, Tinder, WhatsApp, Snap Chat, Slack, Musical.ly, Peach, Blab, Renren, Sina Weibo, Renren, Line, and Momo. In some embodiments, the test results are shared by SMS, MMS or instant message. In some embodiments, the test results are shared by email.

In some embodiments, the mobile application optionally includes a home screen allowing a user to access additional features such as a blog and timeline of important information and events related to the test results, which is optionally shared. In various embodiments, suitable information and events include those pertaining to clinical trial outcomes, newly marketed therapeutics, nutrition, exercise, fetal development, health, etc. In this embodiment, the home screen further includes access to user preferences and settings.

In some instances, devices and systems disclosed herein are in communication with the mobile application. The mobile application may provide for obtaining a Patient ID and electronic health record (EHR), arranging device shipment (to and/or from a user), online ordering of test results. The mobile application may provide for tracking a device or a portion thereof (e.g., shipping/storage compartment), or information obtained with the device, from one point to another. Various points may be selected from shipping, home, sample processing laboratory, and physician's office.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Google® Play, Chrome WebStore, BlackBerry® App World, App Store for Palm devices, App Catalog for webOS, Windows® Marketplace for Mobile, Ovi Store for Nokia® devices, and Samsung® Apps.

Aspects Related to Devices, Systems, Kits and Methods

The following aspects are related to devices, systems, kits and methods disclosed herein. Devices, systems, kits and methods disclosed herein are generally designed to process and analyze cell-free nucleic acids in biological samples of female subjects. The following descriptions of cell-free nucleic acids, biological samples, and subjects may aid in understanding the utility of devices, systems, kits and methods disclosed herein.

Diseases and Conditions

Disclosed herein are devices, systems, kits and methods for detecting the presence, absence, or severity of a disease or condition in a subject. In some instances, the disease or condition is due to a genetic mutation. The genetic mutation may be inherited (e.g., the mutation was present in an ancestor or relative). The genetic mutation may be a spontaneous mutation (e.g., an error in DNA replication or repair). The genetic mutation may be due to exposure to an environmental factor (e.g., UV light, carcinogen). By way of non-limiting example, the genetic mutation may be selected from a frameshift mutation, an insertion mutation, a deletion mutation, a substitution mutation, a single nucleotide polymorphism, a copy number variation, and a chromosomal translocation.

In some instances, the disease or condition is due to an environmental factor (e.g., carcinogen, diet, stress, pathogen). In some instances, the environmental factor causes a genetic mutation. In other instances, the environmental factor does not cause a genetic mutation. In some instances, the environmental factor causes a change in one or more epigenetic modifications in a subject relative to a healthy individual. In some instances, the environmental factor causes a change in one or more epigenetic modifications in a subject relative to that of the subject at an earlier time point.

Devices, systems, kits and methods disclosed herein may be used to detect or monitor a disease or condition that affects one or more tissues, organs or cell types. The disease or condition may cause a release of nucleic acids from one or more tissues, organs or cell types. The disease or condition may increase a release of nucleic acids from one or more tissues, organs or cell types relative to a corresponding release occurring in a healthy individual. A tissue may be classified as epithelial, connective, muscle, or nervous tissue. Non-limiting examples of tissues are adipose, muscle, connective tissue, mammary tissue, and bone marrow. Non-limiting examples of organs are brain, thymus, thyroid, lung, heart, spleen, liver, kidney, pancreas, stomach, small intestine, large intestine, colon, prostate, ovary, uterus, and urinary bladder. Non-limiting examples of cell types are endothelial cells, vascular smooth muscle cells, cardiomyocytes, hepatocytes, pancreatic beta cells, adipocytes, neurons, endometrial cells, immune cells (T cells, B cells, dendritic cells, monocytes, macrophages, Kupffer cells, microglia).

Devices, systems, kits and methods disclosed herein may be used to detect or monitor general health. Devices, systems, kits and methods disclosed herein may be used to detect or monitor fitness. Devices, systems, kits and methods disclosed herein may be used to detect or monitor the health of an organ transplant recipient and/or the health of the transplanted organ.

The disease or condition may comprise an abnormal cell growth or proliferation. The disease or condition may comprise leukemia. Non-limiting types of leukemia include acute lymphoblastic leukemia (ALL), chronic lymphocytic leukemia (CLL), acute myelogenous leukemia (AML), chronic myelogenous leukemia (CML), and hairy cell leukemia (HCL). The disease or condition may comprise a lymphoma. The lymphoma may be a non-Hodgkin's lymphoma (e.g., B cell lymphoma, diffuse large B-cell lymphoma, T cell lymphoma, Waldenstrom macroglobulinemia) or a Hodgkin's lymphoma. The disease or condition may comprise a cancer. The cancer may be breast cancer. The cancer may be lung cancer. The cancer may be esophageal cancer. The cancer may be pancreatic cancer. The cancer may be ovarian cancer. The cancer may be uterine cancer. The cancer may be cervical cancer. The cancer may be testicular cancer. The cancer may be prostate cancer. The cancer may be bladder cancer. The cancer may be colon cancer. The cancer may be a sarcoma. The cancer may be an adenocarcinoma. The cancer may be isolated, that is it has not spread to other tissues besides the organ or tissue where the cancer originated. The cancer may be metastatic. The cancer may have spread to neighboring tissues. The cancer may have spread to cells, tissues or organs in physical contact with the organ or tissue where the cancer originated. The cancer may have spread to cells, tissues or organs not in physical contact with the organ or tissue where the cancer originated. The cancer may be in an early stage, such as Stage 0 (abnormal cell with the potential to become cancer) or Stage 1 (small and confined to one tissue). The cancer may be intermediate, such as Stage 2 or Stage 3, grown into tissues and lymph nodes in physical contact with the tissue of the original tumor. The cancer may be advanced, such as Stage 4 or Stage 5, wherein the cancer has metastasized to tissues that are distant (e.g., not adjacent or in physical contact) to the tissue of the original tumor. In some instances, the cancer is not advanced. In some instances, the cancer is not metastatic. In some instances, the cancer is metastatic.

The disease or condition may comprise an autoimmune disorder. Autoimmune and immune disorders include, but are not limited to, type 1 diabetes, rheumatoid arthritis, psoriasis, multiple sclerosis, lupus, inflammatory bowel disease, Addison's Disease, Graves Disease, Crohn's Disease and Celiac disease.

The disease or condition may comprise a metabolic disorder. Metabolic conditions and disease, include, but are not limited to obesity, a thyroid disorder, hypertension, type 1 diabetes, type 2 diabetes, non-alcoholic steatohepatitis, coronary artery disease, and atherosclerosis.

The disease or condition may comprise a cardiovascular condition. Non-limiting examples of cardiovascular conditions are atherosclerosis, myocardial infarction, pericarditis, myocarditis, ischemic stroke, hypertensive heart disease, rheumatic heart disease, cardiomyopathy, congenital heart disease, valvular heart disease, carditis, aortic aneurysms, peripheral artery disease, thromboembolic disease, and venous thrombosis.

The disease or condition may comprise a neurological disorder. The neurological disorder may comprise a neurodegenerative disease. Non-limiting examples of neurodegenerative and neurological disorders are Alzheimer's disease, Parkinson's disease, Huntington's disease, Spinocerebellar ataxia, amyotrophic lateral sclerosis (ALS), motor neuron disease, chronic pain, and spinal muscular atrophy. Devices, systems, kits and methods disclosed herein may be used to test for, detect, and/or monitor a psychiatric disorder in a subject and/or a response to a drug to treat the psychiatric disorder.

The disease or condition may comprise an infection. The disease or condition may be caused by an infection. The disease or condition may be exacerbated by an infection. The infection may be a viral infection. The infection may be a bacterial infection. The infection may be a fungal infection.

The disease or condition may be associated with aging. Disease and conditions associated with aging include, but are not limited to, cancer, osteoporosis, dementia, macular degeneration, metabolic conditions, and neurodegenerative disorders.

The disease or condition may be a blood disorder. Non-limiting examples of blood disorders are anemia, hemophilia, blood clotting and thrombophilia. For example, detecting thrombophilia may comprise detecting a polymorphism present in a gene selected from Factor V Leiden (FVL), prothrombin gene (PT G20210A), and methylenetetrahydrofolate reductase (MTHFR).

The disease or condition may be an allergy or intolerance to a food, liquid or drug. By way of non-limiting example, a subject can be allergic or intolerant to lactose, wheat, soy, dairy, caffeine, alcohol, nuts, shellfish, and eggs. A subject could also be allergic or intolerant to a drug, a supplement or a cosmetic. In some instances, methods comprise analyzing genetic markers that are predictive of skin type or skin health.

In some instances, the condition is associated with an allergy. In some instances, the subject is not diagnosed with a disease or condition, but is experiencing symptoms that indicate a disease or condition is present. In other instances, the subject is already diagnosed with a disease or condition, and the devices, systems, kits and methods disclosed herein are useful for monitoring the disease or condition, or an effect of a drug on the disease or condition.

Chromosomal Abnormalities

Disclosed herein are devices, systems, kits and methods for detecting chromosomal abnormalities. Those of skill in the field may also refer to chromosomal abnormalities as chromosomal aberrations. In some instances, the chromosomal abnormality is a chromosomal duplication. In some instances, the chromosomal abnormality is a chromosomal deletion. In some instances, the chromosomal abnormality is deletion of an arm of a chromosome. In some instances, the chromosomal abnormality is a partial deletion of an arm of a chromosome. In some instances, the chromosomal abnormality comprises at least one copy of a gene. In some instances, the chromosomal abnormality is due to a breakage of a chromosome. In some instances, the chromosomal abnormality is due to a translocation of a portion of a first chromosome to a portion of a second chromosome.

Many known chromosomal abnormalities results in chromosomal disorders. Thus, the devices, systems, kits and methods disclosed herein may be used for detecting chromosomal disorders. By way of non-limiting example, chromosomal disorders include Down's syndrome (trisomy 21), Edward's syndrome (trisomy 18), Patau syndrome (trisomy 13), Cri du chat syndrome (partial deletion of short arm of chromosome 5), Wolf-Hirschhorn syndrome (deletion of short arm of chromosome 4), Jacobsen syndrome (deletion of long arm of chromosome 11), diGeorge's syndrome (small deletion of chromosome 22), Klinefelter's syndrome (presence of additional X chromosome in males), and Turner syndrome (presence of only a single X chromosome in females).

Biological Samples

Disclosed herein are devices, systems, kits and methods for analyzing cell-free nucleic acids in a biological sample. Non-limiting examples of biological samples include samples of whole blood, plasma, serum, saliva, urine, sweat, tears, and vaginal fluid. In some instances, the biological sample comprises whole blood. In some instances, the biological sample is an environmental sample that contains biological matter. For instance, the biological sample may be a food sample or water sample that contains a virus, bacteria or a fragment/particle thereof.

Methods, systems and kits described herein generally detect and quantify cell-free nucleic acids. For this reason, biological samples described herein are generally biological fluids that are substantially acellular or can be modified to be acellular biological fluids. Samples from subjects, by way of non-limiting example, may be blood from which cells are removed, plasma, serum, urine, saliva, or vaginal fluid. For instance, the cell-free nucleic acid may be circulating in the bloodstream of the subject, and therefore the detection reagent may be used to detect or quantify the marker in a blood or serum sample from the subject. The terms "plasma" and "serum" are used interchangeably herein, unless otherwise noted. However, in some cases they are included in a single list of sample species to indicate that both are covered by the description or claim. In some instances, the biological fluid does not comprise amniotic fluid.

In some instances, devices, systems, kits and methods disclosed herein are capable of removing cells from a biological sample. The resulting sample may be referred to as a cell-depleted sample. The cell-depleted sample may have at least 95% fewer whole, intact cells than the biological sample. The cell-depleted sample may have at least 90% fewer whole, intact cells than the biological sample. The cell-depleted sample may have at least 80% fewer whole, intact cells than the biological sample. The cell-depleted sample may have at least about 75%, at least about 70%, at least about 60%, at least about 50%, at least about 40%, or at least about 25% fewer whole, intact cells than the biological sample. The cell-depleted sample may be completely free of any whole, intact cells.

Blood obtained from capillaries (e.g., blood vessels of extremities like fingers, toes) may be referred to herein as "capillary blood." Blood obtained from veins (e.g., arm, middle of hand) may be referred to herein as "venous blood." Common veins for venipuncture to obtain venous blood are the median cubital vein, cephalic vein, basilic vein, and dorsal metacarpal veins. In some instances, the biological sample comprises capillary blood. In some instances, the biological sample consists essentially of capillary blood. In some instances, the biological sample consists of capillary blood. In some embodiments, the biological sample does not comprise venous blood. In some instances, the biological sample comprises plasma. In some instances, the biological sample consists essentially of plasma. In some instances, the biological sample consists of plasma. In some instances, the biological sample comprises serum. In some instances, the biological sample consists essentially of serum. In some instances, the biological sample consists of serum. In some instances, the biological sample comprises urine. In some instances, the biological sample consists essentially of urine. In some instances, the biological sample consists of urine. In some instances, the biological sample comprises saliva. In some instances, the biological sample consists essentially of saliva. In some instances, the biological sample consists of saliva. In some instances, the biological fluid comprises vaginal fluid. In some instances, the biological fluid consists essentially of vaginal fluid. In some instances, the biological fluid consists of vaginal fluid. In some instances, the vaginal fluid is obtained by performing a vaginal swab of the pregnant subject. In some instances, the biological fluid comprises interstitial fluid. In some instances, the biological fluid consists essentially of interstitial fluid. In some instances, the biological fluid comprises synovial fluid. In some instances, the biological fluid consists essentially of synovial fluid. In some instances, the biological fluid comprises fluid from a liquid biopsy. In some instances, the biological fluid consists essentially of fluid from a liquid biopsy. An example of a liquid biopsy is obtaining blood from a cancer patient and testing for nucleic acids that have been released into the blood stream from a tumor or cancer cells. Nucleic acids may be released from tumor or cancer cells due to necrosis, apoptosis, autophagy, and cancer therapies that cause death/damage to cancer cells.

In some instances, the biological sample is whole blood. Generally, the devices, systems, kits, and methods disclosed herein are capable of analyzing cell-free nucleic acids from very small samples of whole blood. In some instances, the small sample of whole blood may be obtained with a finger prick, such as performed with a lancet or pin/needle. In some instances, the small sample of whole blood may be obtained without a phlebotomy.

In some instances, the devices, systems, kits, and methods disclosed herein require at least about 1 µL of blood to provide a test result with at least about 95% confidence or accuracy. In some instances, the devices, systems, kits, and methods disclosed herein require at least about 10 µL of blood to provide a test result with at least about 95% confidence or accuracy. In some instances, the devices, systems, kits, and methods disclosed herein require at least about 20 µL of blood to provide a test result with at least about 95% confidence or accuracy. In some instances, the devices, systems and kits disclosed herein require at least about 30 µL of blood to provide a test result with at least about 95% confidence or accuracy. In some instances, the devices, systems and kits disclosed herein require at least about 40 µL of blood to provide a test result with at least about 95% confidence or accuracy. In some instances, the devices, systems and kits disclosed herein require at least about 50 µL it of blood to provide a test result with at least about 95% confidence or accuracy. In some instances, the devices, systems and kits disclosed herein require at least about 60 µL of blood to provide a test result with at least about 95% confidence or accuracy. In some instances, the devices, systems and kits disclosed herein require at least about 70 µL of blood to provide a test result with at least about 95% confidence or accuracy.

In some instances, the devices, systems and kits disclosed herein require at least about 1 IA of blood to provide a test result with at least about 99% confidence or accuracy. In some instances, the devices, systems and kits disclosed herein require at least about 10 µL of blood to provide a test result with at least about 99% confidence or accuracy. In some instances, the devices, systems and kits disclosed herein require at least about 20 µL of blood to provide a test result with at least about 99% confidence or accuracy. In some instances, the devices, systems and kits disclosed herein require at least about 30 µL of blood to provide a test result with at least about 99% confidence or accuracy. In some instances, the devices, systems and kits disclosed herein require at least about 40 µL of blood to provide a test result with at least about 99% confidence or accuracy. In some instances, the devices, systems and kits disclosed herein require at least about 60 µL of blood to provide a test result with at least about 99% confidence or accuracy. In some instances, the devices, systems and kits disclosed herein require at least about 80 µL of blood to provide a test result with at least about 99% confidence or accuracy. In some instances, the devices, systems and kits disclosed herein require at least about 100 µl of blood to provide a test result with at least about 90% confidence or accuracy.

In some instances, the method comprise obtaining only about 1 µL to about 500 µL of blood to provide a test result with at least about 95% confidence or accuracy. In some instances, the method comprise obtaining only about 10 µL to about 200 µL of blood to provide a test result with at least about 95% confidence or accuracy. In some instances, the method comprise obtaining only about 15 µL to about 1504 of blood to provide a test result with at least about 95% confidence or accuracy. In some instances, the method comprise obtaining only about 20 µL to about 100 µL of blood to provide a test result with at least about 95% confidence or accuracy. In some instances, the devices, systems and kits disclosed herein require only about 20 µL to about 100 µL of blood to provide a test result with at least about 98% confidence or accuracy. In some instances, the devices, systems and kits disclosed herein require only about 20 µL to about 100 µL of blood to provide a test result with at least about 99% confidence or accuracy. In some instances, the devices, systems and kits disclosed herein require only about 20 µL to about 100 µL of blood to provide a test result with about 99.5% confidence or accuracy. In some instances, the devices, systems and kits disclosed herein require only about 20 µL to about 100 µL of blood to provide a test result with about 99.9% confidence or accuracy.

In some instances, the biological sample is plasma or serum. Plasma or serum makes up roughly 55% of whole blood. In some instances, the devices, systems, kits, and methods disclosed herein require at least about 1 µL of plasma or serum to provide a test result with at least about 95% confidence or accuracy. In some instances, the devices, systems, kits, and methods disclosed herein require at least about 10 µL of plasma or serum to provide a test result with at least about 95% confidence or accuracy. In some instances, the devices, systems and kits disclosed herein require at least about 20 µL of plasma or serum to provide a test result with at least about 95% confidence or accuracy. In some instances, the devices, systems and kits disclosed herein require at least about 30 µL of plasma or serum to provide a test result with at least about 95% confidence or accuracy. In some instances, the devices, systems and kits disclosed herein require at least about 40 µL of plasma or serum to provide a test result with at least about 95% confidence or accuracy. In some instances, the devices, systems and kits disclosed herein require at least about 50 µL of plasma or serum to provide a test result with at least about 95% confidence or accuracy. In some instances, the devices, systems and kits disclosed herein require at least about 10 µL of plasma or serum to provide a test result with at least about 99% confidence or accuracy. In some instances, the devices, systems and kits disclosed herein require at least about 20 µL of plasma or serum to provide a test result with at least about 99% confidence or accuracy. In some instances, the devices, systems and kits disclosed herein require at least about 30 µL of plasma or serum to provide a test result with at least about 99% confidence or accuracy. In some instances, the devices, systems and kits disclosed herein require at least about 40 µL of plasma or serum to provide a test result with at least about 99% confidence or accuracy. In some instances, the devices, systems and kits disclosed herein require at least about 50 µL of plasma or serum to provide a test result with at least about 99% confidence or accuracy. In some instances, the devices, systems and kits disclosed herein require only about 10 µL to about 50 µL of plasma or serum to provide a test result with at least about 95% confidence or accuracy. In some instances, the devices, systems and kits disclosed herein require only about 20 µL to about 604 of plasma or serum to provide a test result with at least about 95% confidence or accuracy. In some instances, the devices, systems and kits disclosed herein require only about 10 µL it to about 50 µL of plasma or serum to provide a test result with at least about 99% confidence or accuracy.

In some instances, the biological sample is saliva. In some instances, the devices, systems, kits, and methods disclosed herein require at least about 100 µL of saliva to provide a test result with at least about 95% confidence or accuracy. In some instances, the devices, systems, kits, and methods disclosed herein require at least about 200 µL of saliva to provide a test result with at least about 95% confidence or accuracy. In some instances, the devices, systems, kits, and methods disclosed herein require at least about 500 µL of saliva to provide a test result with at least about 95% confidence or accuracy. In some instances, the devices, systems, kits, and methods disclosed herein require at least about 1 ml of saliva to provide a test result with at least about 95% confidence or accuracy. In some instances, the devices, systems, kits, and methods disclosed herein require at least about 2 ml of saliva to provide a test result with at least about 95% confidence or accuracy. In some instances, the devices, systems, kits, and methods disclosed herein require at least about 3 ml of saliva to provide a test result with at least about 95% confidence or accuracy.

In some instances, the biological sample is vaginal fluid. In some instances, the devices, systems, kits, and methods disclosed herein require at least about 50 µL of vaginal fluid to provide a test result with at least about 95% confidence or accuracy. In some instances, the devices, systems, kits, and methods disclosed herein require at least about 100 µL of vaginal fluid to provide a test result with at least about 95% confidence or accuracy. In some instances, the devices, systems, kits, and methods disclosed herein require at least about 200 µL of vaginal fluid to provide a test result with at least about 95% confidence or accuracy. In some instances, the devices, systems, kits, and methods disclosed herein require at least about 500 µL of vaginal fluid to provide a test result with at least about 95% confidence or accuracy. In some instances, the devices, systems, kits, and methods disclosed herein require at least about 1 ml of vaginal fluid to provide a test result with at least about 95% confidence or accuracy. In some instances, the devices, systems, kits, and methods disclosed herein require at least about 2 ml of vaginal fluid to provide a test result with at least about 95% confidence or accuracy. In some instances, the devices, systems, kits, and methods disclosed herein require at least about 3 ml of vaginal fluid to provide a test result with at least about 95% confidence or accuracy.

In some instances, biological samples disclosed herein comprise cell-free nucleic acids wherein a fraction of the cell-free nucleic acids are from a foreign tissue or an abnormal tissue. The cell-free nucleic acids in the fraction may be referred to as "foreign cell-free nucleic acids" or "foreign cell-free nucleic acids." By way of non-limiting example, the foreign or abnormal tissue may comprise a tissue or organ that has been transplanted into the subject. The foreign or abnormal tissue may be referred to as donor tissue and the subject may be referred to as host tissue. Also by way of non-limiting example, an abnormal tissue may comprise a tumor. In some instances, the fraction is a fraction of all (total) cell-free nucleic acids in the biological sample, wherein the fraction comprises the foreign or abnormal cell-free nucleic acids. In some instances, the fraction consists essentially of the foreign or abnormal cell-free nucleic acids. In some instances, the foreign or abnormal cell-free nucleic acids comprise DNA. In some instances, the foreign or abnormal cell-free nucleic acids comprise RNA. In some instances, the foreign or abnormal cell-free nucleic acids consist essentially of DNA. In some instances, the foreign or abnormal cell-free nucleic acids consist essentially of RNA.

The fraction of cell-free nucleic acids that are from a foreign or abnormal tissue may be characterized as a percentage of the total cell-free nucleic acids in a sample. In some instances, the fraction of the cell-free nucleic acids that are from a foreign or abnormal tissue is less than 25%. In some instances, the fraction of the cell-free nucleic acids that are from a foreign or abnormal tissue is less than 20%. In some instances, the fraction is less than 15%. In some instances, the fraction is less than 10%. In some instances, the fraction is less than 8%. In some instances the fraction is less than 6%. In some instances, the fraction is less than 5%. In some instances, the fraction is less than 4%. In some instances, the fraction is less than 2%. In some instances, the fraction is at least 1%. In some instances, the fraction is about 1.5% to about 15%. In some instances, the fraction is about 2% to about 12%. In some instances, the fraction is about 4% to about 10%. In some instances, the fraction is about 4% to about 9%. In some instances, the fetal fraction is about 4% to about 8%. In some instances, the fetal fraction is about 1% to about 5%. In some instances, the fetal fraction is about 1% to about 4%.

In some instances, biological samples disclosed herein comprise cell-free nucleic acids wherein a fraction of the cell-free nucleic acids are from a fetus. This fraction may be referred to as a fetal fraction. In some instances, the fetal fraction is a fraction of all (total) nucleic acids in the biological sample, wherein the fraction consists of fetal nucleic acids. In some instances, the nucleic acids and/or fetal nucleic acids comprise DNA. In some instances, the nucleic acids and/or fetal nucleic acids comprise RNA. In some instances, the nucleic acids and/or fetal nucleic acids consist essentially of DNA. In some instances, the nucleic acids and/or fetal nucleic acids comprise DNA and RNA. In some instances, the fetal fraction is about 1.5% to about 15% of the total cell-free nucleic acids in the biological sample. In some instances, the fetal fraction is about 2% to about 12% of the total cell-free nucleic acids in the biological sample. In some instances, the fetal fraction is about 4% to about 10% of the total cell-free nucleic acids in the biological sample. In some instances, the fetal fraction is about 4% to about 9% of the total cell-free nucleic acids in the biological sample. In some instances, the fetal fraction is about 4% to about 8% of the total cell-free nucleic acids in the biological sample. In some instances, the fetal fraction is about 1% to about 5% of the total cell-free nucleic acids in the biological sample. In some instances, the fetal fraction is about 1% to about 4% of the total cell-free nucleic acids in the biological sample. In some instances, at least a portion of fetal nucleic acids are from the fetus. In some instances, at least a portion of the fetal nucleic acids are from the placenta. In some instances, at least a portion of fetal nucleic acids are from the fetus and at least a portion of the fetal nucleic acids are from the placenta. In some instances, the fetal nucleic acids are only from the fetus. In some instances, the fetal nucleic acids are only from the placenta. In some instances, the fetal nucleic acids are all nucleic acids from the fetus and the placenta. In some instances, the fetal nucleic acids are not from a maternal tissue or maternal fluid. In some instances, the maternal tissue is a maternal tissue other than the placenta. In some instances, the maternal fluid is a maternal fluid other than the amniotic fluid.

In some instances, methods disclosed herein comprise modifying the biological fluid to make the biological sample compatible with amplifying or sequencing. In some instances, methods disclosed herein may comprise adding a buffer, salt, protein, or nucleic acid to the biological sample. By way of non-limiting example, EDTA may be added to a blood sample to prevent coagulation. For simplicity, such a modified biological sample is still referred to as the 'biological sample.'

Cell-Free Nucleic Acids

In some instances, the compositions and methods of the instant disclosure are useful for evaluating a cell-free nucleic acid in a biological sample. The cell-free nucleic acid could be from an animal. The cell-free nucleic acid could be from a mammal. The cell-free nucleic acid could be from a human subject. The cell-free nucleic acid could be from a plant. The cell-free nucleic acid could be from a pathogen. The cell-free nucleic acid could be from a pathogen that is present in the biological sample, wherein the biological sample is from an animal. The cell-free nucleic acid could be from a pathogen that is present in the biological sample, wherein the biological sample is from a human subject. The pathogen may comprise bacteria or a component thereof. The pathogen may be a virus or a component thereof. The pathogen may be a fungus or a component thereof.

In some instances, the cell-free nucleic acid is DNA (cf-DNA). In some instances, the cell-free nucleic acid is genomic DNA. In some instances, the cell-free nucleic acid is RNA (cf-RNA). In some instances, the cell-free nucleic acid is a nucleic acid from a cell of a fetus, referred to herein as a cell-free fetal nucleic acid. In some instances, the cell-free fetal nucleic acid is cell-free fetal DNA (cff-DNA) or cell-free fetal RNA (cff-RNA). In some instances, the cf-DNA or cff-DNA is genomic DNA. In some instances, the cell-free nucleic acid is in the form of complementary DNA (cDNA), generated by reverse transcription of a cf-RNA or cff-RNA. In some instances, the cf-DNA comprises mitochondrial DNA. In some instances, the cf-RNA or cff-RNA is a messenger RNA (mRNA), a microRNA (miRNA), mitochondrial RNA, or a natural antisense RNA (NAS-RNA). In some instances, the cell-free nucleic acid is a mixture of maternal and fetal nucleic acid. A cell-free fetal nucleic acid that circulates in the maternal bloodstream can be referred to as a "circulating cell-free nucleic acid" or a "circulatory extracellular DNA." In some instances, the cell-free nucleic acid comprises epigenetic modifications. In some instances, the cell-free nucleic acid comprises a pattern of epigenetic modifications that corresponds to gender or other genetic information of interest. In some instances, the cell-free nucleic acid comprises methylated cytosines. In some instances, the cell-free nucleic acid comprises a cytosine methylation pattern that corresponds to gender or other genetic information of interest.

In some instances, methods, devices, systems and kits disclosed herein are configured to detect or quantify cellular nucleic acids, such as nucleic acids from disrupted cells or lysed cells. In some instances, cellular nucleic acids are from cells that are intentionally disrupted or lysed. In some instances, cellular nucleic acids are from cells that are unintentionally disrupted or lysed. Methods, devices, systems and kits disclosed herein may be configured to analyze intentionally disrupted or lysed cells, but not unintentionally disrupted or lysed cells. In some instances, less than about 0.1% of the total nucleic acids in the biological sample are cellular nucleic acids. In some instances, less than about 1% of the total nucleic acids in the biological sample are cellular nucleic acids. In some instances, less than about 5% of the total nucleic acids in the biological sample are cellular nucleic acids. In some instances, less than about 10% of the total nucleic acids in the biological sample are cellular nucleic acids. In some instances, less than about 20% of the total nucleic acids in the biological sample are cellular nucleic acids. In some instances, less than about 30% of the total nucleic acids in the biological sample are cellular nucleic acids. In some instances, less than about 40% of the total nucleic acids in the biological sample are cellular nucleic acids. In some instances, less than about 50% of the total nucleic acids in the biological sample are cellular nucleic acids. In some instances, less than about 60% of the total nucleic acids in the biological sample are cellular nucleic acids. In some instances, less than about 70% of the total nucleic acids in the biological sample are cellular nucleic acids. In some instances, less than about 80% of the total nucleic acids in the biological sample are cellular nucleic acids. In some instances, less than about 90% of the total nucleic acids in the biological sample are cellular nucleic acids. In some instances, devices, systems, kits and methods comprise an experimental control or use thereof. In some instances, the experimental control comprises a nucleic acid, a protein, a peptide, an antibody, an antigen binding antibody fragment, a binding moiety. In some instances, the experimental control comprises a signal for detecting the experimental control. Non-limiting examples of signals are fluorescent molecules, dye molecules, nanoparticles, and colorimetric indicators. In some instances, the experimental control comprises a cell-free nucleic acid. In some instances, the cell-free nucleic acid comprises a cell-free fetal nucleic acid. In some instances, the cell-free nucleic acid comprises a maternal cell-free nucleic acid. In some instances, the cell-free nucleic acid comprises a maternal cell-free nucleic acid (e.g., to assess the amount of cellular disruption/lysis that occurs during sample processing). In some instances, the cell-free nucleic acid comprises a sequence corresponding to an autosome. In some instances, the cell-free nucleic acid comprises a sequence corresponding to sex chromosome. In some instances, the cell-free nucleic acid comprises a sequence corresponding to a chromosome that is possibly aneuploidy (e.g., chromosome 13, 16, 18, 21, 22, X, Y). In some instances, the cell-free nucleic acid comprises a sequence corresponding to a chromosome that is very unlikely to be aneuploidy (e.g., chromosome 1-12, 14, 15, 17, 19, or 20).

In some instances, the biological sample comprises a maternal body fluid sample. In some instances, the maternal bodily fluid sample comprises blood, e.g., whole blood, a peripheral blood sample, or a blood fraction (plasma, serum). In some instances, the maternal body fluid sample comprises sweat, tears, sputum, urine, ear flow, lymph, saliva, cerebrospinal fluid, bone marrow suspension, vaginal fluid, transcervical lavage, brain fluid, ascites, or milk. In some instances, the maternal body fluid sample comprises secretions of the respiratory, intestinal and genitourinary tracts, amniotic fluid, or a leukophoresis sample. In some instances, the biological fluid sample is a maternal body fluid sample that is can be obtained easily by non-invasive procedures, e.g., blood, plasma, serum, sweat, tears, sputum, urine, ear flow, or saliva. In some instances, the sample is a combination of at least two body fluid samples. In some instances, the cell-free fetal nucleic acid originates from the maternal placenta, e.g., from apoptosed placental cells. In some instances, the biological sample is placental blood.

In some instances, a nucleic acid evaluated or analyzed by devices, systems, kits, and methods disclosed herein has a preferable length. In some instances, the nucleic acid is a cell-free fetal DNA fragment. In some instances, the cell-free fetal DNA fragment is from a Y chromosome. In some instances, the nucleic acid is about 15 bp to about 500 bp in length. In some instances, the nucleic acid is about 50 bp in length to about 200 bp in length. In some instances, the nucleic acid is at least about 15 bp in length. In some instances, the nucleic acid is at most about 500 bp in length. In instances, the nucleic acid is about 15 bp in length to about 50 bp in length, about 15 bp in length to about 75 bp in length, about 15 bp in length to about 100 bp in length, about 15 bp in length to about 150 bp in length, about 15 bp in length to about 200 bp in length, about 15 bp in length to about 250 bp in length, about 15 bp in length to about 300 bp in length, about 15 bp in length to about 350 bp in length, about 15 bp in length to about 400 bp in length, about 15 bp in length to about 450 bp in length, about 15 bp in length to about 500 bp in length, about 50 bp in length to about 75 bp in length, about 50 bp in length to about 100 bp in length, about 50 bp in length to about 150 bp in length, about 50 bp in length to about 200 bp in length, about 50 bp in length to about 250 bp in length, about 50 bp in length to about 300 bp in length, about 50 bp in length to about 350 bp in length, about 50 bp in length to about 400 bp in length, about 50 bp in length to about 450 bp in length, about 50 bp in length to about 500 bp in length, about 75 bp in length to about 100 bp in length, about 75 bp in length to about 150 bp in length, about 75 bp in length to about 200 bp in length, about 75 bp in length to about 250 bp in length, about 75 bp in length to about 300 bp in length, about 75 bp in length to about 350 bp in length, about 75 bp in length to about 400 bp in length, about 75 bp in length to about 450 bp in length, about 75 bp in length to about 500 bp in length, about 100 bp in length to about 150 bp in length, about 100 bp in length to about 200 bp in length, about 100 bp in length to about 250 bp in length, about 100 bp in length to about 300 bp in length, about 100 bp in length to about 350 bp in length, about 100 bp in length to about 400 bp in length, about 100 bp in length to about 450 bp in length, about 100 bp in length to about 500 bp in length, about 150 bp in length to about 200 bp in length, about 150 bp in length to about 250 bp in length, about 150 bp in length to about 300 bp in length, about 150 bp in length to about 350 bp in length, about 150 bp in length to about 400 bp in length, about 150 bp in length to about 450 bp in length, about 150 bp in length to about 500 bp in length, about 200 bp in length to about 250 bp in length, about 200 bp in length to about 300 bp in length, about 200 bp in length to about 350 bp in length, about 200 bp in length to about 400 bp in length, about 200 bp in length to about 450 bp in length, about 200 bp in length to about 500 bp in length, about 250 bp in length to about 300 bp in length, about 250 bp in length to about 350 bp in length, about 250 bp in length to about 400 bp in length, about 250 bp in length to about 450 bp in length, about 250 bp in length to about 500 bp in length, about 300 bp in length to about 350 bp in length, about 300 bp in length to about 400 bp in length, about 300 bp in length to about 450 bp in length, about 300 bp in length to about 500 bp in length, about 350 bp in length to about 400 bp in length, about 350 bp in length to about 450 bp in length, about 350 bp in length to about 500 bp in length, about 400 bp in length to about 450 bp in length, about 400 bp in length to about 500 bp in length, or about 450 bp in length to about 500 bp in length. In some instances, the nucleic acid is about 15 bp in length, about 50 bp in length, about 75 bp in length, about 100 bp in length, about 150 bp in length, about 200 bp in length, about 250 bp in length, about 300 bp in length, about 350 bp in length, about 400 bp in length, about 450 bp in length, or about 500 bp in length.

The sizes of the cell-free nucleic acids evaluated using the device, systems, kits and methods of the present disclosure can vary depending upon, e.g., the particular body fluid sample used. For example, cff-DNA sequences have been observed to be shorter than maternal cf-DNA sequences, and both cff-DNA and maternal cf-DNA to be shorter in urine than in plasma samples.

In some instances, the cff-DNA sequences evaluated in urine range from about 20 bp to about 300 bp in length. In some instances, the cff-DNA sequences evaluated in a urine sample are about 15 bp in length to about 300 bp in length. In some instances, the cff-DNA sequences evaluated in a urine sample are at least about 15 bp in length. In some instances, the cff-DNA sequences evaluated in a urine sample are at most about 300 bp in length. In some instances, the cff-DNA sequences evaluated in a urine sample are about 15 bp in length to about 20 bp in length, about 15 bp in length to about 30 bp in length, about 15 bp in length to about 60 bp in length, about 15 bp in length to about 90 bp in length, about 15 bp in length to about 120 bp in length, about 15 bp in length to about 150 bp in length, about 15 bp in length to about 180 bp in length, about 15 bp in length to about 210 bp in length, about 15 bp in length to about 240 bp in length, about 15 bp in length to about 270 bp in length, about 15 bp in length to about 300 bp in length, about 20 bp in length to about 30 bp in length, about 20 bp in length to about 60 bp in length, about 20 bp in length to about 90 bp in length, about 20 bp in length to about 120 bp in length, about 20 bp in length to about 150 bp in length, about 20 bp in length to about 180 bp in length, about 20 bp in length to about 210 bp in length, about 20 bp in length to about 240 bp in length, about 20 bp in length to about 270 bp in length, about 20 bp in length to about 300 bp in length, about 30 bp in length to about 60 bp in length, about 30 bp in length to about 90 bp in length, about 30 bp in length to about 120 bp in length, about 30 bp in length to about 150 bp in length, about 30 bp in length to about 180 bp in length, about 30 bp in length to about 210 bp in length, about 30 bp in length to about 240 bp in length, about 30 bp in length to about 270 bp in length, about 30 bp in length to about 300 bp in length, about 60 bp in length to about 90 bp in length, about 60 bp in length to about 120 bp in length, about 60 bp in length to about 150 bp in length, about 60 bp in length to about 180 bp in length, about 60 bp in length to about 210 bp in length, about 60 bp in length to about 240 bp in length, about 60 bp in length to about 270 bp in length, about 60 bp in length to about 300 bp in length, about 90 bp in length to about 120 bp in length, about 90 bp in length to about 150 bp in length, about 90 bp in length to about 180 bp in length, about 90 bp in length to about 210 bp in length, about 90 bp in length to about 240 bp in length, about 90 bp in length to about 270 bp in length, about 90 bp in length to about 300 bp in length, about 120 bp in length to about 150 bp in length, about 120 bp in length to about 180 bp in length, about 120 bp in length to about 210 bp in length, about 120 bp in length to about 240 bp in length, about 120 bp in length to about 270 bp in length, about 120 bp in length to about 300 bp in length, about 150 bp in length to about 180 bp in length, about 150 bp in length to about 210 bp in length, about 150 bp in length to about 240 bp in length, about 150 bp in length to about 270 bp in length, about 150 bp in length to about 300 bp in length, about 180 bp in length to about 210 bp in length, about 180 bp in length to about 240 bp in length, about 180 bp in length to about 270 bp in length, about 180 bp in length to about 300 bp in length, about 210 bp in length to about 240 bp in length, about 210 bp in length to about 270 bp in length, about 210 bp in length to about 300 bp in length, about 240 bp in length to about 270 bp in length, about 240 bp in length to about 300 bp in length, or about 270 bp in length to about 300 bp in length. In some instances, the cff-DNA sequences evaluated in a urine sample are about 15 bp in length, about 20 bp in length, about 30 bp in length, about 60 bp in length, about 90 bp in length, about 120 bp in length, about 150 bp in length, about 180 bp in length, about 210 bp in length, about 240 bp in length, about 270 bp in length, or about 300 bp in length.

In some instances, the cff-DNA sequences evaluated in a plasma or serum sample are at least about 20 bp in length. In some instances, the cff-DNA sequences evaluated in a plasma or serum sample are at least about 40 bp in length. In some instances, the cff-DNA sequences evaluated in a plasma or serum sample are at least about 80 bp in length. In some instances, the cff-DNA sequences evaluated in a plasm or serum sample are at most about 500 bp in length. In some instances, the cff-DNA sequences evaluated in plasma or serum range from about 100 bp to about 500 bp in length. In some instances, the cff-DNA sequences evaluated in a plasma or serum sample are about 50 bp in length to about 500 bp in length. In some instances, the cff-DNA sequences evaluated in a plasma or serum sample are about 80 bp in length to about 100 bp in length, about 80 bp in length to about 125 bp in length, about 80 bp in length to about 150 bp in length, about 80 bp in length to about 175 bp in length, about 80 bp in length to about 200 bp in length, about 80 bp in length to about 250 bp in length, about 80 bp in length to about 300 bp in length, about 80 bp in length to about 350 bp in length, about 80 bp in length to about 400 bp in length, about 80 bp in length to about 450 bp in length, about 80 bp in length to about 500 bp in length, about 100 bp in length to about 125 bp in length, about 100 bp in length to about 150 bp in length, about 100 bp in length to about 175 bp in length, about 100 bp in length to about 200 bp in length, about 100 bp in length to about 250 bp in length, about 100 bp in length to about 300 bp in length, about 100 bp in length to about 350 bp in length, about 100 bp in length to about 400 bp in length, about 100 bp in length to about 450 bp in length, about 100 bp in length to about 500 bp in length, about 125 bp in length to about 150 bp in length, about 125 bp in length to about 175 bp in length, about 125 bp in length to about 200 bp in length, about 125 bp in length to about 250 bp in length, about 125 bp in length to about 300 bp in length, about 125 bp in length to about 350 bp in length, about 125 bp in length to about 400 bp in length, about 125 bp in length to about 450 bp in length, about 125 bp in length to about 500 bp in length, about 150 bp in length to about 175 bp in length, about 150 bp in length to about 200 bp in length, about 150 bp in length to about 250 bp in length, about 150 bp in length to about 300 bp in length, about 150 bp in length to about 350 bp in length, about 150 bp in length to about 400 bp in length, about 150 bp in length to about 450 bp in length, about 150 bp in length to about 500 bp in length, about 175 bp in length to about 200 bp in length, about 175 bp in length to about 250 bp in length, about 175 bp in length to about 300 bp in length, about 175 bp in length to about 350 bp in length, about 175 bp in length to about 400 bp in length, about 175 bp in length to about 450 bp in length, about 175 bp in length to about 500 bp in length, about 200 bp in length to about 250 bp in length, about 200 bp in length to about 300 bp in length, about 200 bp in length to about 350 bp in length, about 200 bp in length to about 400 bp in length, about 200 bp in length to about 450 bp in length, about 200 bp in length to about 500 bp in length, about 250 bp in length to about 300 bp in length, about 250 bp in length to about 350 bp in length, about 250 bp in length to about 400 bp in length, about 250 bp in length to about 450 bp in length, about 250 bp in length to about 500 bp in length, about 300 bp in length to about 350 bp in length, about 300 bp in length to about 400 bp in length, about 300 bp in length to about 450 bp in length, about 300 bp in length to about 500 bp in length, about 350 bp in length to about 400 bp in length, about 350 bp in length to about 450 bp in length, about 350 bp in length to about 500 bp in length, about 400 bp in length to about 450 bp in length, about 400 bp in length to about 500 bp in length, or about 450 bp in length to about 500 bp in length. In some instances, the cff-DNA sequences evaluated in a plasma or serum sample are about 80 bp in length, about 100 bp in length, about 125 bp in length, about 150 bp in length, about 175 bp in length, about 200 bp in length, about 250 bp in length, about 300 bp in length, about 350 bp in length, about 400 bp in length, about 450 bp in length, or about 500 bp in length.

Subjects

Disclosed herein are devices, systems, kits and methods for analyzing a biological component in a sample from a subject. The subject may be human. The subject may be non-human. The subject may be non-mammalian (e.g., bird, reptile, insect). In some instances, the subject is a mammal. In some instances, the mammal is female. In some instances, the subject is a human subject. In some instances, the mammal is a primate (e.g., human, great ape, lesser ape, monkey). In some instances, the mammal is canine (e.g., dog, fox, wolf). In some instances, the mammal is feline (e.g., domestic cat, big cat). In some instances, the mammal is equine (e.g., horse). In some instances, the mammal is bovine (e.g., cow, buffalo, bison). In some instances, the mammal is a sheep. In some instances, the mammal is a goat). In some instances, the mammal is a pig. In some instances, the mammal is a rodent (e.g., mouse, rat, rabbit, guinea pig).

In some instances, a subject described herein is affected by a disease or a condition. Devices, systems, kits and methods disclosed herein may be used to test for the disease or condition, detect the disease or condition, and/or monitor the disease or condition. Devices, systems, kits and methods disclosed herein may be used to test for the presence of inherited traits, monitor fitness, and detect family ties.

Devices, systems, kits and methods disclosed herein may be used to test for, detect, and/or monitor cancer in a subject. Non-limiting examples of cancers include breast cancer, prostate cancer, skin cancer, lung cancer, colorectal cancer/colon cancer, bladder cancer, pancreatic cancer, lymphoma, and leukemia.

Devices, systems, kits and methods disclosed herein may be used to test for, detect, and/or monitor an immune disorder or autoimmune disorder in a subject. Autoimmune and immune disorders include, but are not limited to, type 1 diabetes, rheumatoid arthritis, psoriasis, multiple sclerosis, lupus, inflammatory bowel disease, Addison's Disease, Graves Disease, Crohn's Disease and Celiac disease.

Devices, systems, kits and methods disclosed herein may be used to test for, detect, and/or monitor a disease or condition that is associated with aging of a subject. Disease and conditions associated with aging include, but are not limited to, cancer, osteoporosis, dementia, macular degeneration, metabolic conditions, and neurodegenerative disorders.

Devices, systems, kits and methods disclosed herein may be used to test for, detect, and/or monitor a blood disorder. Non-limiting examples of blood disorders are anemia, hemophilia, blood clotting and thrombophilia. For example, detecting thrombophilia may comprise detecting a polymorphism present in a gene selected from Factor V Leiden (FVL), prothrombin gene (PT G20210A), and methylenetetrahydrofolate reductase (MTHFR).

Devices, systems, kits and methods disclosed herein may be used to test for, detect, and/or monitor a neurological disorder or a neurodegenerative disorder in a subject. Non-limiting examples of neurodegenerative and neurological disorders are Alzheimer's disease, Parkinson's disease, Huntington's disease, Spinocerebellar ataxia, amyotrophic lateral sclerosis (ALS), motor neuron disease, chronic pain, and spinal muscular atrophy. Devices, systems, kits and methods disclosed herein may be used to test for, detect, and/or monitor a psychiatric disorder in a subject and/or a response to a drug to treat the psychiatric disorder.

Devices, systems, kits and methods disclosed herein may be used to test for, detect, and/or monitor a metabolic condition or disease. Metabolic conditions and disease, include, but are not limited to obesity, a thyroid disorder, hypertension, type 1 diabetes, type 2 diabetes, non-alcoholic steatohepatitis, coronary artery disease, and atherosclerosis.

Devices, systems, kits and methods disclosed herein may be used to test for, detect, and/or monitor an allergy or intolerance to a food, liquid or drug. By way of non-limiting example, a subject can be allergic or intolerant to lactose, wheat, soy, dairy, caffeine, alcohol, nuts, shellfish, and eggs. A subject could also be allergic or intolerant to a drug, a supplement or a cosmetic. In some instances, methods comprise analyzing genetic markers that are predictive of skin type or skin health.

In some instances, the condition is associated with an allergy. In some instances, the subject is not diagnosed with a disease or condition, but is experiencing symptoms that indicate a disease or condition is present. In other instances, the subject is already diagnosed with a disease or condition, and the devices, systems, kits and methods disclosed herein are useful for monitoring the disease or condition, or an effect of a drug on the disease or condition.

Disclosed herein are devices, systems, kits and methods for analyzing cell-free nucleic acids from a fetus in a maternal biological sample from a pregnant subject. Generally, the pregnant subject is a human pregnant subject. However, one of skill in the art would understand that the instant disclosure could be applied to other mammals, perhaps for breeding purposes on farms or in zoos. In some instances, the pregnant subject is euploid. In some instances, the pregnant subject comprises an aneuploidy. In some instances, the pregnant subject has a copy variation of a gene or portion thereof. In some instances, the pregnant subject has a genetic insertion mutation. In some instances, the pregnant subject has a genetic deletion mutation. In some instances, the pregnant subject has a genetic missense mutation. In some instances, the pregnant subject has a single nucleotide polymorphism. In some instances, the pregnant subject has a single nucleotide polymorphism. In some instances, the pregnant subject has translocation mutation resulting in a fusion gene. By way of non-limiting example, the BCR-ABL gene is a fusion gene that can be found on chromosome 22 of many leukemia patients. The altered chromosome 22 is referred to as the Philadelphia chromosome.

In some instances, the pregnant subject is about 2 weeks pregnant to about 42 weeks pregnant. In some instances, the pregnant subject is about 3 weeks pregnant to about 42 weeks pregnant. In some instances, the pregnant subject is about 4 weeks pregnant to about 42 weeks pregnant. In some instances, the pregnant subject is about 5 weeks pregnant to about 42 weeks pregnant. In some instances, the pregnant subject is about 6 weeks pregnant to about 42 weeks pregnant. In some instances, the pregnant subject is about 7 weeks pregnant to about 42 weeks pregnant. In some instances, the pregnant subject is about 8 weeks pregnant to about 42 weeks pregnant.

In some instances, the pregnant subject is at fewer than about 6 weeks, about 7 weeks, about 8 weeks, about 9 weeks, about 10 weeks, about 12 weeks, about 16 weeks, about 20 weeks, about 21 weeks, about 22 weeks, about 24 weeks, about 26 weeks, or about 28 weeks of gestation. In some instances, the pregnant subject is as few as 5 weeks pregnant. In some instances, the human subject is a pregnant human female who has reached at least about 5 weeks, at least about 6 weeks, at least about 7 weeks, or at least about 8 weeks of gestation. In some instances, the human subject is a pregnant human female who has reached at least about 5 to about 8 weeks of gestation. In some instances, the human subject is a pregnant human female who has reached at least about 5 to about 8, at least about 5 to about 12, at least about 5 to about 16, at least about 5 to about 20, at least about 6 to about 21, at least about 6 to about 22, at least about 6 to about 24, at least about 6 to about 26, at least about 6 to about 28, at least about 6 to about 9, at least about 6 to about 12, at least about 6 to about 16, at least about 6 to about 20, at least about 6 to about 21, at least about 6 to about 22, at least about 6 to about 24, at least about 6 to about 26, or at least about 6 to about 28 weeks of gestation. In some instances, the human subject is a pregnant human female who has reached at least about 7 to about 8, at least about 7 to about 12, at least about 7 to about 16, at least about 7 to about 20, at least about 7 to about 21, at least about 7 to about 22, at least about 7 to about 24, at least about 7 to about 26, at least about 7 to about 28, at least about 8 to about 9, at least about 8 to about 12, at least about 6 to about 16, at least about 8 to about 20, at least about 8 to about 21, at least about 6 to about 22, at least about 8 to about 24, at least about 8 to about 26, or at least about 8 to about 28 weeks of gestation. In some instances, gestation times are detected by measuring the gestation time from the first day of the last menstrual period.

In some instances, the biological sample is a maternal body fluid sample obtained from a pregnant subject, a subject suspected of being pregnant, or a subject that has given birth recently, e.g., within the past day. In some instances, the subject is a mammal. In some instances, the mammal is female. In some instances, the mammal is a primate (e.g., human, great ape, lesser ape, monkey), canine (e.g., dog, fox, wolf), feline (e.g., domestic cat, big cat), equine (e.g., horse), bovine (e.g., cow, buffalo, bison), ovine (e.g., sheep), caprine (e.g., goat) porcine (e.g., pig), a rhinoceros, or a rodent (e.g., mouse, rat, rabbit, guinea pig). In some instances, the subject is a pregnant human female in her first, second, or third trimester of pregnancy. In some instances, the human subject is a pregnant human female at fewer than about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, or about 40 weeks gestation.

Numbered Embodiments

The disclosure is further understood through review of the numbered embodiments recited herein. 1. A method comprising: obtaining capillary blood from a subject, wherein the capillary blood comprises cell-free nucleic acids; sequencing at least a portion of the cell-free nucleic acids to produce sequencing reads; measuring at least a portion of sequencing reads corresponding to at least one target sequence of interest; and detecting a normal representation, an overrepresentation or an underrepresentation of the at least one target sequence. 2. A method comprising: obtaining capillary blood from a subject, wherein the capillary blood comprises cell-free nucleic acids; optionally amplifying the cell-free nucleic acids; tagging at least a portion of the cell-free nucleic acids to produce a library of tagged cell-free nucleic acids; optionally amplifying the tagged cell-free nucleic acids; sequencing at least a portion of the tagged cell-free nucleic acids; and detecting a normal representation, an overrepresentation or an underrepresentation of at least one target sequence in the at least a portion of the tagged cell-free nucleic acids. 3. The method of embodiment 1 or 2, comprising producing a library having an efficiency of at least 0.5. 4. The method of any previous embodiment, comprising amplifying the cell-free nucleic acids or tagged cell-free nucleic acids in the presence of a crowding agent. 5. The method of any previous embodiment, comprising repairing ends of the cell-free nucleic acids. 6. A method comprising obtaining a biological sample from a subject, wherein the biological sample comprises target cell-free nucleic acids and non-target cell-free nucleic acids that together make up total cell-free nucleic acids, and wherein the target cell-free nucleic acids are less than 5% of the total cell-free nucleic acids; sequencing at least a portion of the target cell-free nucleic acids to produce sequencing reads; measuring at least a portion of sequencing reads corresponding to at least one target sequence of interest; and detecting a normal representation, an overrepresentation or an underrepresentation of the at least one target sequence. 7. The method of embodiment 6, wherein the biological sample comprises capillary blood. 8. The method of embodiment 6, wherein the biological sample consists essentially of capillary blood. 9. The method of embodiment 6, wherein obtaining the biological sample comprises obtaining capillary blood. 10. The method of embodiment 6, wherein obtaining the biological sample comprises obtaining capillary blood. 11. The method of embodiment 6, wherein obtaining the biological sample consists essentially of obtaining capillary blood. 12. The method of embodiment 6, wherein obtaining the biological sample does not comprise obtaining venous blood. 13. The method of embodiment 6, wherein obtaining the biological sample does not comprise performing a phlebotomy. 14. The method of any previous embodiment, wherein obtaining the biological sample comprises obtaining not more than 1 milliliter of blood. 15. The method of any previous embodiment, wherein obtaining the biological sample comprises obtaining not more than 100 microliters of blood. 16. The method of any previous embodiment, wherein obtaining the biological sample comprises obtaining not more than 40 microliters of blood. 17. The method of any previous embodiment, wherein the target cell-free nucleic acids are cell-free nucleic acids from a tumor. 18. The method of any previous embodiment, wherein the target cell-free nucleic acids are cell-free nucleic acids from a fetus. 19. The method of any previous embodiment, wherein the target cell-free nucleic acids are cell-free nucleic acids from a transplanted tissue or organ. 20. The method of any previous embodiment, wherein the method comprises detecting the normal representation, overrepresentation or underrepresentation of the at least one target sequence with at least 98% accuracy. 21. The method of any previous embodiment, wherein the method does not comprise whole genome amplification. 22. A method comprising: obtaining a biological sample from a subject, wherein the biological sample contains up to about $10^9$ cell-free nucleic acid molecules;

sequencing at least a portion of the cell-free nucleic acid molecules to produce sequencing reads; measuring at least a portion of sequencing reads corresponding to at least one chromosomal region; and detecting a normal representation, an overrepresentation or an underrepresentation of the at least one chromosomal region. 23. The method of any previous embodiment, wherein the biological sample is a biological fluid having a volume of less than about 500 µl. 24. The method of any previous embodiment, wherein the biological sample is a biological fluid having a volume of about 1 µl to about 100 µl. 25. The method of any previous embodiment, wherein the biological sample is a biological fluid having a volume of about 5 µL to about 80 µl. 26. The method of any previous embodiment, wherein the biological sample has a volume of about 5 µL to about 60 µl. 27. The method of any previous embodiment, comprising amplifying the cell-free nucleic acid molecules before sequencing. 28. The method of any previous embodiment, comprising tagging the cell-free nucleic acid molecules before sequencing and after amplifying. 29. The method of any previous embodiment, comprising tagging the cell-free nucleic acid molecules before sequencing. 30. The method of any previous embodiment, comprising amplifying the cell-free nucleic acid molecules after tagging the cell-free nucleic acid molecules. 31. The method of any previous embodiment, comprising amplifying the cell-free nucleic acid molecules before tagging the cell-free nucleic acid molecules. 32. The method of any previous embodiment, wherein amplifying comprises contacting the cell-free nucleic acid molecules with random oligonucleotide primers. 33. The method of any previous embodiment, wherein the amplifying comprises isothermal amplification. 34. The method of any previous embodiment, comprising detecting an overrepresentation of sequencing reads corresponding to at least one target chromosome. 35. The method of any previous embodiment, comprising detecting an underrepresentation of sequencing reads corresponding to at least one target chromosome. 36. The method of any previous embodiment, comprising comparing the number of sequencing reads corresponding to the at least one target chromosome to a reference number of sequencing reads corresponding to the at least one target chromosome. 37. The method of any previous embodiment, comprising measuring at least 1000 sequencing reads corresponding to the at least one chromosomal region. 38. The method of any previous embodiment, comprising measuring at least 1000 sequencing reads corresponding to at least one non-target chromosomal region. 39. The method of any previous embodiment, wherein the biological sample is biological fluid. 40. The method of any previous embodiment, wherein the biological sample comprises blood, plasma, serum, urine, interstitial fluid, vaginal cells, vaginal fluid, buccal cells, or saliva. 41. The method of any previous embodiment, wherein the biological sample is serum or plasma. 42. The method of embodiment 41, further comprising separating the plasma or serum from a blood sample. 43. The method of embodiment 41, wherein separating comprises filtering the blood sample to remove cells, cell fragments, microvesicles, or a combination thereof, from the blood sample to produce the plasma sample. 44. The method of any previous embodiment, wherein the biological sample is a blood sample having a volume of about 5 µl to about 1 ml. 45. The method of any previous embodiment, wherein the biological sample is a blood sample having a volume of about 5 µl to about 150 µl. 46. The method of embodiment 44 or 45, wherein obtaining the blood sample comprises pricking a finger. 47. The method of embodiment 46, further comprising milking or squeezing blood from the pricked finger. 48. The method of embodiment 46, wherein the method does not comprising milking or squeezing blood from the pricked finger. 49. The method of any previous embodiment, wherein obtaining the blood sample does not comprise a phlebotomy. 50. The method of any previous embodiment, wherein the biological sample contains about $10^4$ to about $10^9$ cell-free nucleic acid molecules. 51. The method of any previous embodiment, wherein the biological sample contains about $10^4$ to about $10^8$ cell-free nucleic acid molecules. 52. The method of any previous embodiment, wherein the biological sample contains about $10^4$ to about $10^7$ cell-free nucleic acid molecules. 53. The method of any previous embodiment, wherein the biological sample contains less than 300 pg of cell-free nucleic acid molecules. 54. The method of any previous embodiment, wherein the biological sample contains less than 3 ng of cell-free nucleic acid molecules. 55. The method of any previous embodiment, comprising detecting the normal representation, overrepresentation or underrepresentation with greater than 98% accuracy. 56. The method of any previous embodiment, comprising detecting the normal representation, overrepresentation or underrepresentation with greater than 99% accuracy. 57. The method of any previous embodiment, wherein the subject is a pregnant subject and the cell-free nucleic acid molecules comprise cell-free fetal nucleic acid molecules. 58. The method of any previous embodiment, comprising comparing the number of sequencing reads corresponding to the at least one chromosomal region to a reference number of sequencing reads corresponding to the at least one chromosomal region. 59. The method embodiment 58, wherein the reference number is based on at least one sample from at least one euploid pregnant subject with a euploid fetus. 60. The method embodiment 58, wherein the reference number is based on at least one sample from at least one euploid pregnant subject with an aneuploid fetus. 61. The method embodiment 60, wherein the at least one sample is the same sample type and same sample volume as the biological sample. 62. The method of embodiment 57, wherein the biological sample comprises about $10^6$ to about $10^{12}$ total cell-free nucleic acid molecules, wherein the total cell-free nucleic acid molecules consist essentially of the cell-free fetal nucleic acid molecules and maternal cell-free nucleic acid molecules. 63. The method of any previous embodiment, comprising detecting that there is a fetal aneuploidy of the at least one chromosomal region when a ratio of sequencing reads corresponding to the at least one chromosomal region to sequencing reads corresponding to at least one non-target chromosomal region is different from a respective ratio in a control biological sample from a control pregnant euploid subject with a euploid fetus. 64. The method of any previous embodiment, comprising detecting, that there is not a fetal aneuploidy of the at least one chromosomal region when a ratio of sequencing reads corresponding to the at least one chromosomal region to sequencing reads corresponding to at least one non-target chromosomal region is the same as a respective ratio in a control biological sample from a control pregnant euploid subject with a euploid fetus. 65. The method of embodiment 63 or 64, wherein the at least one chromosomal region is located on at least one of chromosome 13, chromosome 16, chromosome 18, chromosome 21, chromosome 22, chromosome X, or chromosome Y. 66. The method of embodiment 64 or 65, wherein the at least one non-target chromosomal region is at least one of a chromosome other than chromosome 13, chromosome 16, chromosome 18, chromosome 21, chromosome 22, chromosome X, or chromosome Y. 67. The method of any one of embodiments 57-66, wherein the pregnant subject is as few as 5 weeks pregnant. 68. The method of embodiment 57, wherein the pregnant subject is euploid. 69. The method of embodiment 57, the biological sample contains about $10^4$ to about $10^9$ cell-free fetal nucleic acids. 70. The method of embodiment 57, wherein the biological sample contains about $10^4$ to about $10^8$ cell-free fetal nucleic acids. 71. The method of embodiment 57, comprising sequencing at least 2000 cell-free fetal nucleic acids. 72. The method of embodiment 58, comprising measuring at least 1000 of the sequencing reads corresponding to the at least chromosomal region. 73. The method of embodiment 58, wherein representation of the at least one chromosomal region is relative to control representation in at least one control pregnant subject carrying a control fetus. 74. The method of embodiment 73, wherein the at least one control pregnant subject and control fetus does not have an aneuploidy. 74. The method of embodiment 73, wherein the at least one control pregnant subject and control fetus does not have a genetic abnormality. 75. The method of embodiment 73, wherein the at least one control pregnant subject and control fetus has an aneuploidy corresponding to the chromosomal region. 76. The method of embodiment 73, wherein the at least one control pregnant subject and control fetus has a genetic abnormality corresponding to the target chromosomal region. 77. The method of any preceding embodiment, wherein the cell-free nucleic acids comprise nucleic acids from a tumor in a tissue. 78. The method of embodiment 77, comprising comparing the number of sequencing reads corresponding to the at least one chromosomal region to a reference number of sequencing reads corresponding to the at least one chromosomal region. 79. The method of embodiment 78, wherein the reference number is based on at least one sample from a subject without the tumor in the tissue. 80. The method of embodiment 78, wherein the reference number is based on at least one sample from a subject with the tumor in the tissue. 81. The method of any preceding embodiment, wherein the cell-free nucleic acids comprise nucleic acids from an organ or a tissue that has been transplanted into the subject. 82. The method of any preceding embodiment, wherein the cell-free nucleic acids are specific to the organ or the tissue. 83. The method of any preceding embodiment, wherein sequencing comprises whole genome sequencing. 84. The method of any preceding embodiment, wherein sequencing comprises random massively parallel sequencing. 85. The method of any preceding embodiment, wherein sequencing comprises targeted sequencing. 86. The method of any preceding embodiment, wherein sequencing comprises nanopore sequencing. 87. A method comprising: obtaining a biological sample from a subject, wherein the biological sample contains up to about $10^9$ cell-free nucleic acid molecules; analyzing epigenetic modifications on at least one chromosomal region of at least a portion of the cell-free nucleic acid molecules; and detecting a normal representation, an overrepresentation or an underrepresentation of the at least one chromosomal region. 88. A method comprising: obtaining capillary blood from a subject; analyzing epigenetic modifications on at least one chromosomal region of at least a portion of the cell-free nucleic acid molecules; and detecting a normal representation, an overrepresentation or an underrepresentation of the at least one chromosomal region. 89. The method of embodiment 88, comprising obtaining not more than 200 µl of capillary blood. 90. The method of embodiment 88, comprising obtaining not more than 100 µl of capillary blood. 91. A method comprising: obtaining a biological sample from a pregnant subject, wherein the biological sample contains up to about $10^9$ cell-free fetal nucleic acid molecules; tagging at least a portion of the cell-free fetal nucleic acid molecules to produce tagged cell-free fetal nucleic acid molecules; measuring the number of tagged cell-free fetal nucleic acid molecules; and detecting a normal representation, an overrepresentation or an underrepresentation of the at least one chromosomal region. 92. The method of embodiment 91, comprising tagging each cell-free fetal nucleic acid molecule in the biological sample. 93. The method of embodiment 91, wherein tagging at least a portion of the cell-free fetal nucleic acid molecules comprises tagging cell-free fetal nucleic acid molecules from a target chromosomal region. 94. The method of embodiment 91, wherein the method does not comprise sequencing. 95. The method of embodiment 91, comprising obtaining a plurality of biological sample from at least one pregnant subject, wherein the biological samples each contain up to about $10^9$ cell-free fetal nucleic acid molecules; and indexing the cell-free fetal nucleic acid molecules from each biological sample with a different index, thereby providing a sample identifier to the cell-free fetal nucleic acid molecules. 96. The method of embodiment 91, comprising tagging the cell-free fetal nucleic acid molecules from a target chromosomal region. 97. A system comprising: a sample collector configured to collect a fluid sample of a subject; a sample processor that is configured to isolate a sample component from the fluid sample; a nucleic acid detector that is configured to detect nucleic acids in the fluid sample or the sample component; and a nucleic acid information output. 98. The system of embodiment 97, wherein the sample collector comprises a transdermal puncture device. 99. The system of embodiment 97, wherein the transdermal puncture device comprises at least one of a needle, a lancet, a microneedle, a vacuum, and a microneedle array. 100. The system of embodiment 97, wherein the sample component is selected from a cell, a carbohydrate, a phospholipid, a protein, a nucleic acid, and a microvesicle. 101. The system of embodiment 100 or 101, wherein the sample component is a blood cell. 102. The system of embodiment 97, wherein the sample component does not comprise a cell-free nucleic acid. 103. The system of embodiment 97, wherein the sample component comprises a cell-free nucleic acid. 104. The system of embodiment 97, wherein the sample component is plasma or serum. 105. The system of embodiment 104, wherein the sample purifier is configured to isolate plasma from less than 1 milliliter of blood. 106. The system of embodiment 105, wherein the sample purifier is configured to isolate plasma from less than 250 µl of blood. 107. The system of embodiment 105, wherein the sample purifier is configured to isolate plasma from less than 150 µl of blood. 108. The system of embodiment 105, wherein the sample purifier is configured to isolate plasma from less than 100 µl of blood. 109. The system of embodiment 97, wherein the nucleic acid detector comprises a nucleic acid sequencer. 110. The system of embodiment 97, wherein the system is configured to label nucleic acids of interest in the fluid sample, and the nucleic acid detector comprises a counting system that counts the labels to detect a representation of the nucleic acids of interest in the sample. 111. The system of embodiment 110, comprising the labels, wherein the labels comprise an oligonucleotide that hybridizes to the nucleic acids of interest. 112. The system of embodiment 111, wherein the oligonucleotide is specific to a chromosomal region of interest. 113. The system of embodiment 112, wherein the chromosomal region of interest is located on a chromosome selected from chromosome 13, chromosome 16, chromosome 18, chromosome 21, chromosome 22, chromosome X, and chromosome Y. 114. The system of embodiment 112, wherein the chromosomal region of interest comprises, or is capable of comprising, a sequence that is indicative of a disease or condition. 115. The system of embodiment 112, wherein the chromosomal region of interest comprises, or is capable of comprising, at least one epigenetic modification that is indicative of a disease or condition. 116. The system of embodiment 114 or 115, wherein the condition is a genetic abnormality. 117. The system of embodiment 114 or 115, wherein the disease is cancer. 118. The system of embodiment 114 or 115, wherein the condition is a transplanted tissue or organ. 119. The system of embodiment 97, comprising at least one nucleic acid amplification reagent selected from a primer, a polymerase, and a combination thereof. 120. The system of embodiment 119, wherein the at least one nucleic acid amplification reagent comprises at least one isothermal amplification reagent. 121. The system of embodiment 119, wherein the at least one isothermal amplification reagent comprises a recombinase polymerase, a single-strand DNA-binding protein, a strand-displacing polymerase, or a combination thereof. 122. The system of any preceding embodiment, comprising at least one nucleic acid amplification reagent and at least one crowding agent. 123. The system of embodiment 97, comprising at least a first label for producing a library of cell-free nucleic acids from the fluid sample, and at least one amplification reagent. 124. The system of embodiment 123, wherein the system is configured to amplify the cell-free nucleic acids with the at least one amplification reagent to produce at least one amplicon and contacting the at least one amplicon with at least the first label to produce the library. 125. The system of embodiment 124, wherein the system is configured to contact the at least one amplicon with a second label, wherein the second label is detectable. 126. The system of embodiment 97, wherein the system is configured to produce the library and amplify at least one member of the library with the at least one amplification reagent. 127. The system of embodiment 97, wherein the nucleic acid sequence output is selected from a wireless communication device, a wired communication device, a cable port, and an electronic display. 128. The system of embodiment 97, wherein all components of the system are present in a single location. 129. The system of embodiment 97, wherein all components of the system are housed in a single device. 130. The system of embodiment 97, wherein the sample collector is located at a first location and at least one of the sample purifier and nucleic acid detector are second location. 131. The system of embodiment 97, wherein the sample collector and at least one of the sample purifier and nucleic acid detector are at the same location. 132. The system of embodiment 97, wherein the sample purifier comprises a filter. 133. The system of embodiment 97, wherein the sample purifier comprises a wicking material or capillary device for pushing or pulling the biological fluid through the filter. 134. The system of embodiment 147, wherein the filter has a pore size of about 0.05 microns to about 2 microns. 135. The system of embodiment 97, wherein the sample purifier comprises a binding moiety that binds a nucleic acid, protein, cell surface marker, or microvesicle surface marker in the biological fluid sample. 136. The system of embodiment 135, wherein the binding moiety comprises an antibody, antigen binding antibody fragment, a ligand, a receptor, a peptide, a small molecule, or a combination thereof. 137. The system of embodiment 135, wherein the binding moiety is capable of binding an extracellular vesicle, wherein the extracellular vesicle is released from a fetal cell or a placental cell of the female subject. 138. The system of embodiment 135, wherein the binding moiety is attached to a solid support, wherein the solid support can be separated from the rest of the biological sample or the biological sample can be separated from the solid support, after the binding moiety has made contact with the biological sample. 139. The system of embodiment 97, comprising a transport or storage compartment for transporting or storing at least a portion of the fluid sample. 140. The system of embodiment 139, wherein the transport or storage compartment comprises an absorption pad, a fluid container, a sample preservative, or a combination thereof. 141. The system of embodiment 139, wherein the transport or storage compartment contains a reagent or material that stabilizes a cell of the fluid sample for transport or storage. 142. The system of embodiment 97, comprising at least one of a container, pouch, wire and cable, for heating or cooling the device of a component thereof. 143. The system of embodiment 97, comprising at least one buffer for at least one of repairing, purifying, amplifying, and sequencing cell-free nucleic acids. 145. Use of a system according to embodiment 97 for detecting the presence of a tumor in the subject. 146. Use of a system according to embodiment 97 for detecting an aneuploidy of a fetus in the subject. 147. Use of a system according to embodiment 97 for detecting the status of a transplanted organ in the subject.

EXAMPLES

The following examples are given for the purpose of illustrating various embodiments of the devices, systems and kits disclosed herein and are not meant to limit the present devices, systems and kits in any fashion. The present examples, along with the methods described herein are presently representative of preferred embodiments, are exemplary, and are not intended as limitations on the scope of the invention. Changes therein and other uses which are encompassed within the spirit of the devices, systems and kits disclosed herein as defined by the scope of the claims will occur to those skilled in the art.

Example 1: Trisomy Detection in Ultra-Low (~20 µl) Amounts of Maternal Blood

Trisomy detection relies on the accurate representation of genetic material originating on a chromosome compared to genetic material originating from other chromosomes. This ratio is compared to the distribution of ratios in the euploid population. A trisomy is called when the ratio of ((chr21/chr.all)-MEDIAN(chr21))/MAD(chr21) is statistically sufficiently different from that distribution.

While 10% fetal fraction is the median of a typical population at 9 weeks gestational age and above, not all samples will have fetal fraction levels as high as 10% and some might have even higher levels. A typical cutoff for fetal fraction is 4%. A model that takes the distribution of fetal fraction in a typical population into account and requires the more common cutoff values for specificity (99.9%) and sensitivity (99%) can help to illustrate the input requirements for this method. With around 5 million marker counts (sequence reads), this sensitivity can be accomplished. However, if one analyzes one marker per chromosome, this would require 30,000 cell equivalents, which is not feasible.

Methods and systems disclosed herein are based on the fact that each genome equivalent is essentially divided into 20 million cfDNA fragments through the process of apoptosis (3 billion base pairs per genome divided by 150 base pairs average size of cfDNA). The implication is that if every single molecule of cfDNA can be transferred from blood to sequencer, the equivalent of a quarter of a euploid genome is sufficient for analysis.

However, in reality every step in the process is impaired by various amounts of DNA loss. Therefore much higher amounts are being sampled and moved through the library generation and sequencing process. While DNA loss occurs at every step of the process, the highest loss typically appears at the step of library preparation. Traditional methods show losses of 80% to 90% of material. Often this loss is compensated by a subsequent amplification step (Universal PCR), to bring the concentration of DNA up to the necessary level required for next generation sequencing. While amplification is a good method to increase the overall nucleic acid material available for sequencing, under specific conditions the amplification cannot compensate for a loss of information that occurred during the prior steps. To understand the loss of information a simple thought experiment can help. Assume one starts with 1000 genome equivalents, which represents $20*10^9$ cfDNA fragments. If one assumes an enormous loss and only two fragments are available for amplification. One fragment from the reference region and one from the target region. Two fragments alone are not sufficient to load sequencing equipment, but via amplification (PCR) each fragment can easily be copied billions of times. Now after amplification enough material is available to start the sequencing process but the information in the sample had been reduced to the information held in those two copies. And in this case the information is insufficient for classification of euploid and trisomic samples, because both sample type will show an indistinguishable 50% fraction.

Figure 6:
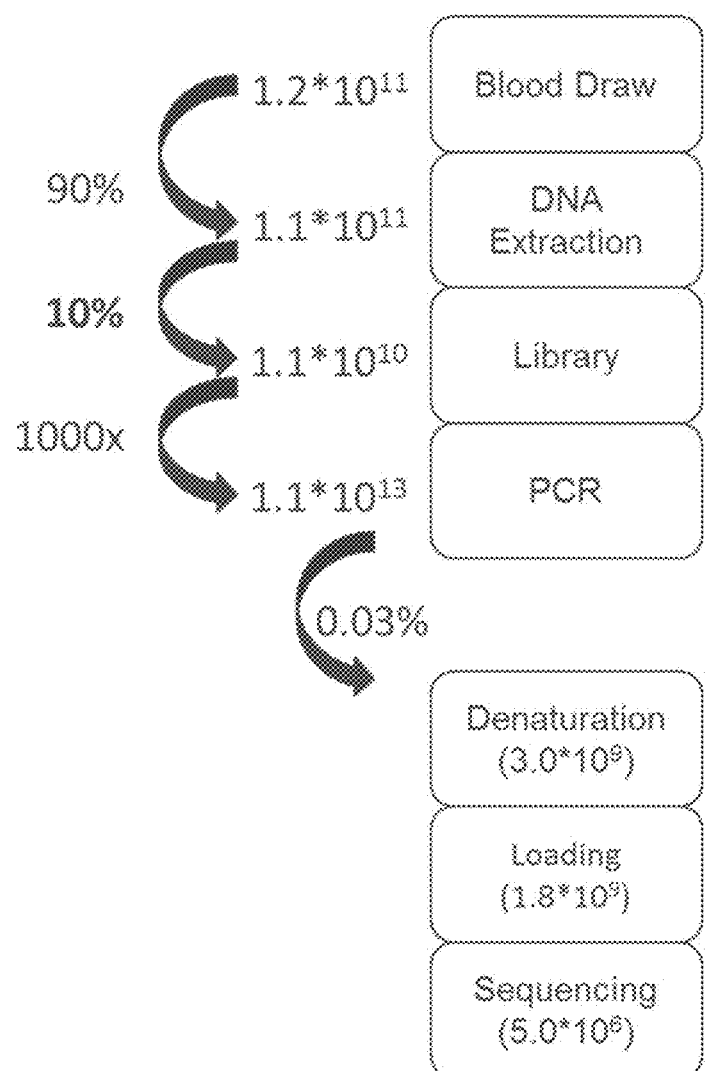
FIG. 6 shows typical amounts of cfDNA fragments expected in different process steps of low-coverage whole genome sequencing using 8-10 ml of venous blood as a starting amount.

Specifications for a typical next generation sequencer require that 5 µl of a 4 nM solution is diluted in 995 µl NaOH to make a 20 pM solution of which 600 µl are loaded on the sequencer. Consequently, a total of $1.2*10^{10}$ DNA fragments is needed, to create 20 million sequencing counts. As demonstrated above, 20 million counts are sufficient for 4 samples and therefore each sample has to contribute $~3*10^9$ DNA fragments. (Because each genome equivalent contributes 20 million DNA fragments a total of 150 genome equivalents would be needed when no loss and no amplification occurs.) This is outlined in FIG. 6.

Typical NIPT protocols start with a high amount of cfDNA (6000 genome equivalents), which allows for a high amount of loss during the library preparation. The material is then amplified and highly diluted to be suitable for sequencing. The problem with typical NIPT protocols is that high amount of loss during library preparation that are subsequently highly diluted lead to an inaccurate representation of the genetic material originating on a chromosome.

For example, a typical sample contains 1500 genome equivalents of cfDNA in ml of blood plasma. A regular blood draw of 8 to 10 ml of blood yields around 4 ml of plasma, resulting in 6000 available genome equivalents of cfDNA. Assuming typical numbers for DNA extraction efficiency (90%) and library preparation efficiency (10%) about 540 genome equivalents moved into amplification (typically 8 to 10 cycles, here for the example 1000 fold amplification). After amplification a total of 540000 genome equivalents or $1.08*10^{13}$ DNA fragments are available for sequencing. More than 1000 fold dilution is performed to adjust the amplified library to the required 4 nM. See Table 1.

TABLE 1

Standard 8-10 ml blood draw

| 4 ml plasma @1500 GE/ml | cfDNA Genome Equivalents | cfDNA fragments | efficiency |
|---|---|---|---|
| Blood Draw | 6000 | 1.20E+11 | |
| DNA Extraction | 5400 | 1.08E+11 | 0.9 |
| Library Prep | 540 | 1.08E+10 | 0.1 |
| Amplification | 540000 | 1.08E+13 | 1000 |
| Normalization and Multiplexing | 150 | 3.00E+09 | 0.0003 |
| Denaturation | 90 | 1.80E+09 | 0.6 |
| Sequencing | 0.25 | 5.00E+06 | 0.003 |

Figure 7:
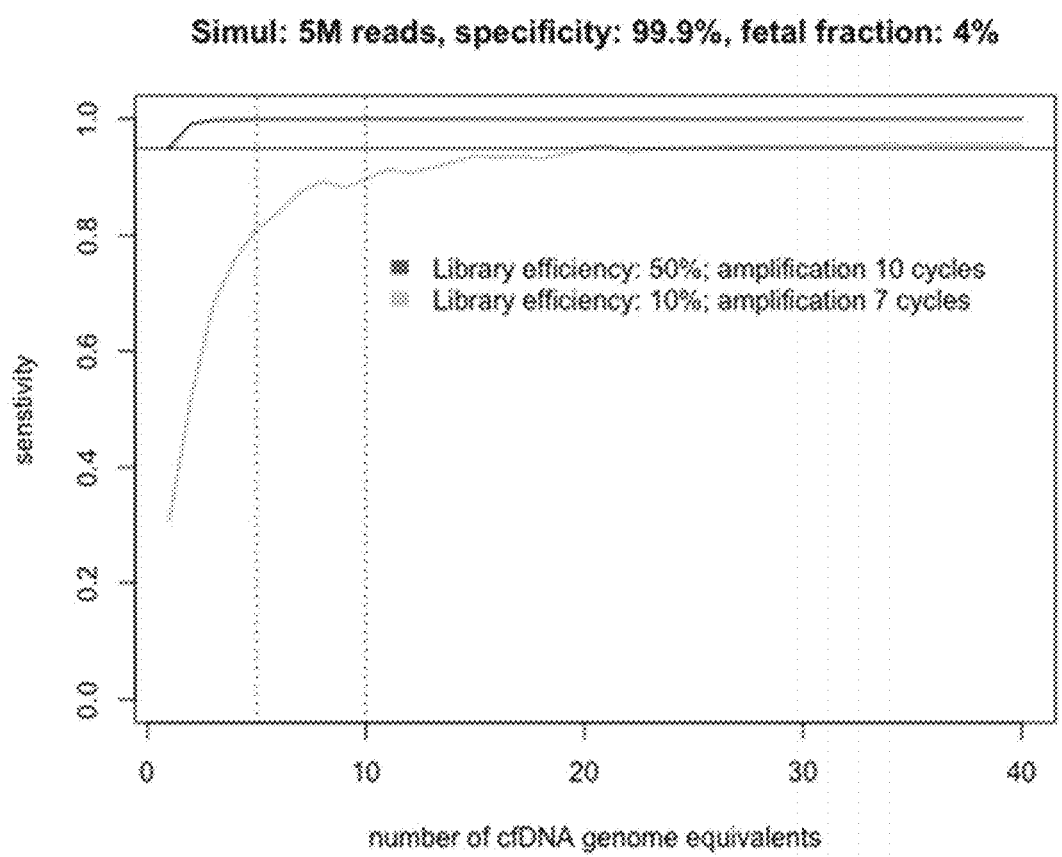
FIG. 7 shows the importance of increasing sequencing library efficiency to significantly improve sensitivity for applications using ultra-low cfDNA input amounts.

This data might mistakenly imply that because of the vast excess of DNA fragments created in the process, one could simply be scaled down the reactions to accommodate a blood volume of less than 100 However, because of the aforementioned loss in information this is not possible. See Table 2. Performing a simulation at lower limit of fetal fraction (4%) that takes into account the losses during DNA Extraction (efficiency 90%) and library preparation (efficiency 10%) as well as the PCR amplification (~10 cycles) shows that sensitivity decreases below 25 (inflection point at 10) copies of input DNA material. Sensitivity at 10 copies is reduced to 89% and at 5 copies to 81%, both values would not be acceptable in a market that requires ~95% theoretical sensitivity for samples at 4% fetal fraction. See FIG. 7.

TABLE 2

Scale down Standard protocol to 20 µl blood draw

| 4 ml plasma @1500 GE/ml | cfDNA Genome Equivalents | cfDNA fragments | efficiency |
|---|---|---|---|
| Blood Draw | 10 | 2.00E+08 | |
| DNA Extraction | 9 | 1.80E+08 | 0.9 |
| Library Prep | 1.8 | 3.60E+07 | 0.1 |
| Amplification | 1800 | 3.60E+10 | 1000 |
| Normalization and Multiplexing | 150 | 3.00E+09 | 0.0833 |
| Denaturation | 90 | 1.80E+09 | 0.6 |
| Sequencing | 0.25 | 5.00E+06 | 0.003 |

In contrast, the present disclosure provides methods, systems, and devices that increase the library preparation efficiency, preventing a high amount of loss during library preparation and obviating the need for overamplification and high dilutions. Thus, the present disclosure solves the problems associated with typical NIPT protocols, by maintaining an accurate representation of genetic material originating on the chromosome. Increasing library efficiency and decreasing amplification according the present embodiments (e.g., with crowding agents, end-repair), results in more genetic information that is preserved and sensitivities above 95% even at copy numbers (genome equivalents) below 5. See Table 3 and FIG. 7.

TABLE 3

Protocol with increased library efficiency and low amplification

| 20 ul plasma @1500 GE/ml | cfDNA Genome Equivalents | cfDNA fragments | efficiency |
|---|---|---|---|
| Blood Draw | 10 | 2.00E+08 | |
| DNA Extraction | 9 | 1.80E+08 | 0.9 |
| Library Prep | 4.5 | 9.00E+07 | 0.5 |
| Amplification | 450 | 9.00E+09 | 100 |
| Normalization and Multiplexing | 150 | 3.00E+09 | 0.33 |
| Denaturation | 90 | 1.80E+09 | 0.6 |
| Sequencing | 0.25 | 5.00E+06 | 0.003 |

Example 2. Viability of Low Coverage Whole Genome Sequencing-by-Synthesis Using Ultra-Low Input Amounts of ccfDNA (1-20 Genome Equivalents)

Male whole blood (10 ml) was collected via venous puncture into a Streck cell-free DNA BCT and processed to plasma by double-spin centrifugation as follows:
Spin 1-1330 rpm for 20 minutes, no brake
Spin 2-3300 rpm for 10 minutes Plasma was stored at 4° C. or −80° C. until use. Circulating cell-free DNA was extracted from the plasma using the 4 ml protocol for the Qiagen Circulating Nucleic Acid Extraction Kit per manufacturer's protocol with elution in 55 µl of EB. Genome equivalents for each sample were determined using a SRY/RNase P Taqman biplex qPCR assay (Life Technologies) on a Quantstudio 6 real-time instrument. DNA libraries were prepared using the NEBNext Ultra II DNA Library Prep Kit with the NEBNext Multiplex Oligos for Illumina (Index Set Primers 1) (New England Biolabs). Template ccfDNA for library preparation was titrated 1:5 from 96 GEs down to 1 GE per library. Libraries were generated using reduced volumes to account for the stoichiometry of the lower template amounts. The volumes used depended on the input amount of template. Library preparation consisted of:
1. End-repair, 5'-phosphorylation and A-tailing with incubation at 20° C. for 30 minutes followed by 65° C. for 30 minutes.
2. Adaptor ligation with incubation at 20° C. for 15 minutes followed by cleavage of the ligated adaptor loop with incubation at 37° C. for 15 minutes. Adaptors were diluted 1:25 to a 0.6 µM working concentration. The cleaved, adaptor-ligated library was then subjected to bead-based purification using SPRISelect beads. The volume of beads was increased to 116 µl to further enhance binding of highly-fragmented, low concentration ccfDNA following adaptor ligation.
3. Library amplification/indexing with initial denaturation at 98° C. for 1 minute followed by 13 cycles of 98° C. denaturation for 10 seconds and annealing/extension at 65° C. for 75 seconds with final extension at 65° C. for 5 minutes. Amplified library was then purified using SPRISelect beads (45 µl).

All libraries were sized and characterized using Agilent Bioanalyzer 2100 with a High-Sensitivity DNA Chip (Agilent Technologies). Concentrations were determined using Qubit v3.0 (Life Technologies) for library dilutions prior to sequencing. Each library was normalized to a concentration of 2 nM and pooled for denaturation and dilution prior to sequencing. Sequencing-by-synthesis was conducted using an Illumina NextSeq 550 at a loading concentration of 1.5 pM. Seventy-five cycle paired-end sequencing (2×75) was conducted for each index/sample. In general, each sample generated approximately 4 million passed-filter reads in each direction. All sequencing data (fasta.gz files) was aligned against the human reference genome build hg38 using Bowtie with alignment parameters "-k 1-n 0". For further analysis, the human genome was divided into consecutive 50,000 basepair regions, also called 50 kb bins, and the fraction of the base "G" and "C" was calculated for each bin with an accuracy up to 3 decimals. For each bin the aligned sequence reads that start in a bin were counted. For further analysis the data was reduced by filtering out bins not on chromosomes 1 to 22 (e.g. chromosomes X and Y were excluded). After this filtering, a Loess regression between GC content and read count per bin was performed and the median bin count was calculated. The Loess regression provided an expected bin count for each GC content value, also called the expected value. This expected value was divided by the median bin count to get a correction factor. The measured bin count was then divided by the correction factor resulting in a GC corrected bin count and the median of the GC corrected bin count was calculated. All 50 kb bins were divided by the median GC corrected bin count to yield GC normalized bin counts and for each bin a median and median absolute deviation (MAD) was calculated. Bins with a low MAD and a median around the expected value of 1 were selected (bins with MAD>=0.25 or Median <0.7 or Median >1.3 were filtered out).

Figure 8A:
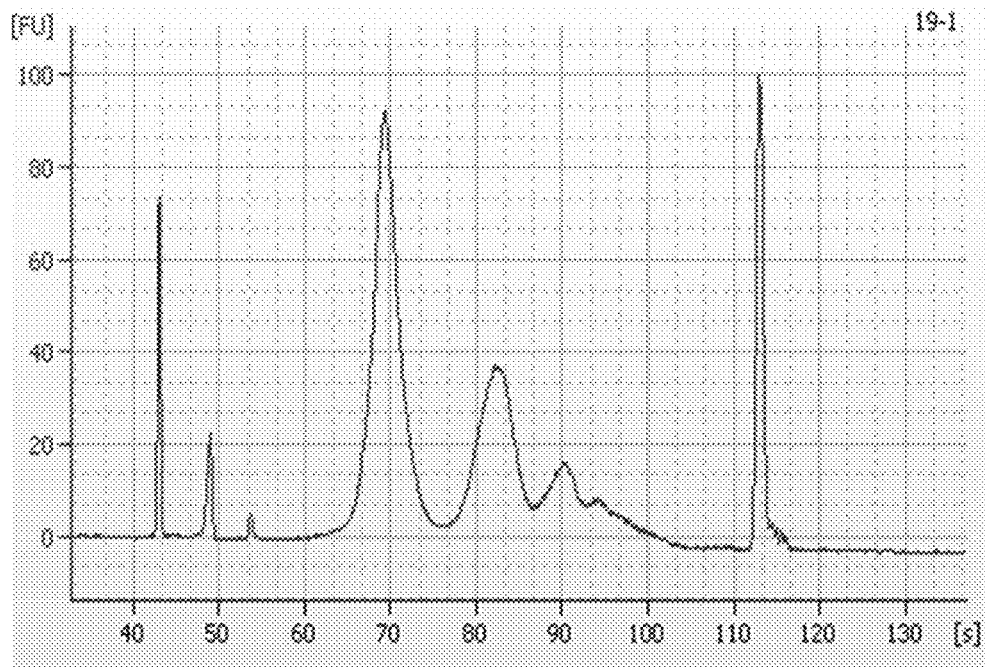
FIG. 8A-C shows electropherograms of sequencing libraries generated from decreasing amounts of cell-free (cfDNA) input. The input amount of cell-free DNA varied from 20 genome equivalents (20 GE) in FIG. 8A down to 1 genome equivalent (1 GE) in FIG. 8C. While the overall yield in library decreases, the amount adaptor dimers do not increase significantly and there is still sufficient amount and quality of library available for successful sequence analysis.
Figure 8B:
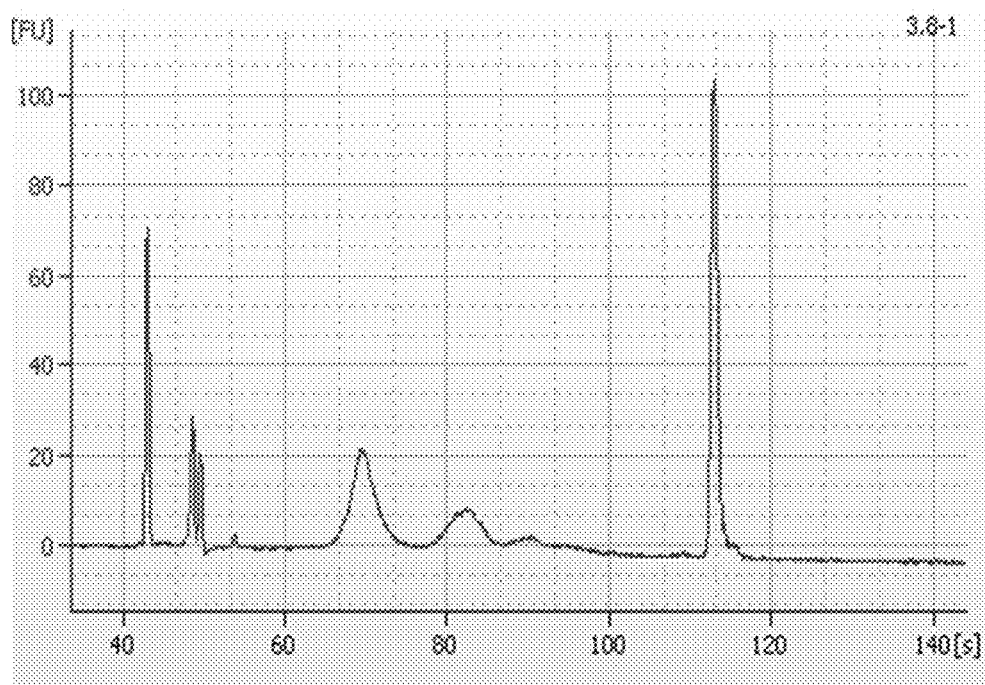
Figure 8C:
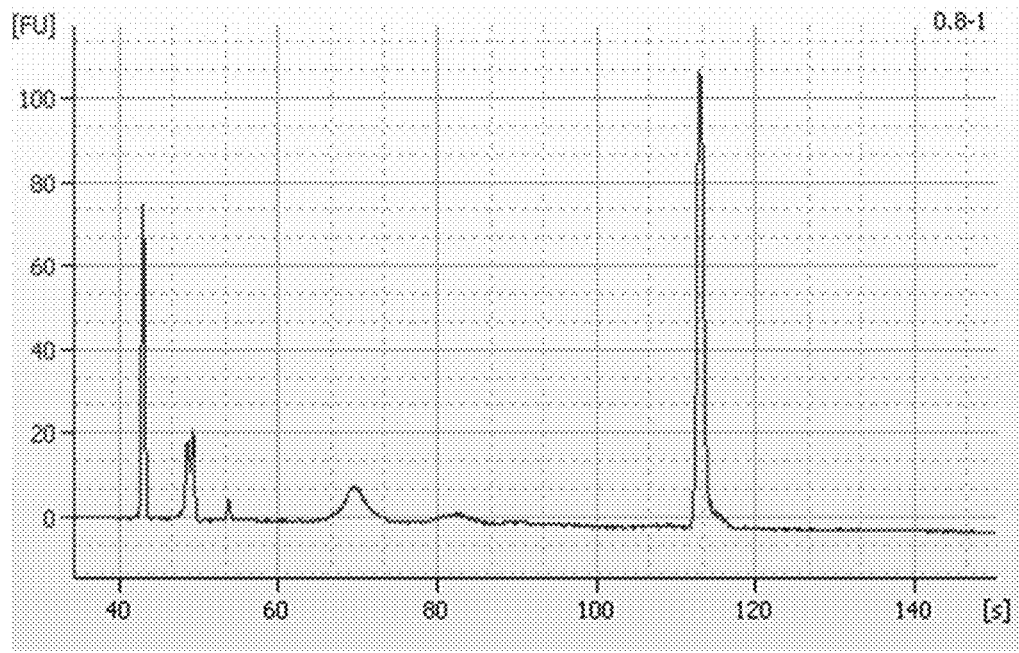

Electropherograms of libraries were generated from decreasing amounts of ccfDNA input and showed total library product decreases with input but adaptor dimer amounts do not increase significantly. See FIG. 8A-8C. The y-axis shows relative fluorescence units (intensity) and the x-axis shows time in seconds. The primary peak at 70 seconds is the desired 300 bp library product. From FIG. 8A to FIG. 8B to FIG. 8C, input genome equivalents are titrated 1:5 from 20 GEs. Input down to 1 GE generated sufficient library for viable sequencing-by-synthesis with acceptable sequencing metrics compared to other euploid samples with much higher template input.

Example 3. Detection of Low Fraction Y-Chromosome (2.5% or Greater) Using Low Coverage Whole Genome Sequencing-by-Synthesis with Ultra-Low Input Amounts of ccfDNA (10 Genome Equivalents) Isolated from Capillary Blood Female or male whole blood was collected by finger-tip capillary bed puncture using a contact-activated lancet (BD Microtainer) and blood collection into a SAFE-T FILL capillary collection device (KABE Labortechnik, GMBH). Capillary blood was processed to plasma by double-spin centrifugation as follows:

Spin 1-1330 rpm for 20 minutes
Spin 2-3300 rpm for 10 minutes
Plasma was stored at 4° C. until use. Male plasma was spiked into female plasma at varying percentages ranging from 2.5%-20% by volume. Circulating cell-free DNA was then extracted from the plasma using a modified protocol for 10 ul of plasma with the MagMax Cell-Free DNA Isolation Kit (Life Technologies). Isolation consisted of the following steps:
1. Incubation of plasma with Proteinase K (volume dependent on starting input) at 60° C. for 20 minutes.
2. Lysis/binding of plasma to DynaBeads MyOne Silane paramagnetic beads (2.5-5 ul) with binding for 10 minutes at room temperature.
3. Washing of the bead/ccfDNA complex (volume dependent on starting input).
4. Rinse bead/ccfDNA complex with 80% ethanol (volume dependent on starting input).
5. Elution of ccfDNA from beads (volume dependent on starting input) with incubation at room temperature for 2 minutes.

Genome equivalents for each sample were estimated to be 1 GE/μl of plasma based on previous extractions at volumes ranging from 10 μl-4000 μl and published data. All of the eluted ccfDNA was used as input for library generation. DNA libraires were prepared using the NEBNext Ultra II DNA Library Prep Kit with the NEBNext Multiplex Oligos for Illumina (Index Set Primers 1) (New England Biolabs). Libraries were generated using reduced volumes to account for the stoichiometry of the lower template amounts. The volumes used depended on the input amount of template. Library preparation consisted of:
1. End-repair, 5-phophphorylation and A-tailing with incubation at 20° C. for 30 minutes followed by 65° C. for 30 minutes.
2. Adaptor ligation with incubation at 20° C. for 15 minutes followed by cleavage of the ligated adaptor loop with incubation at 37° C. for 15 minutes. Adaptors were diluted 1:25 to a 0.6 μM working concentration. The cleaved, adaptor-ligated library was then subjected to bead-based purification using SPRISelect beads. The volume of beads was increased to 116 μl to further enhance binding of highly-fragmented, low concentration ccfDNA following adaptor ligation.
3. Library amplification/indexing with initial denaturation at 98° C. for 1 minute followed by 13 cycles of 98° C. denaturation for 10 seconds and annealing/extension at 65° C. for 75 seconds wth final extension at 65° C. for 5 minutes. Amplified library was then purified using SPRISelect beads (45 ul).

Figure 10:
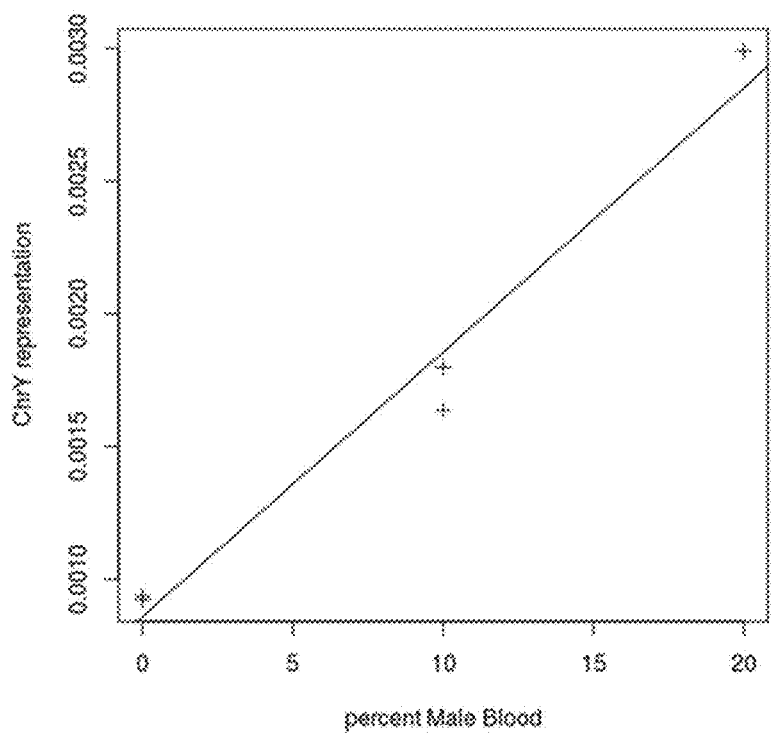
FIG. 10 shows detection of low fraction Y-chromosome (2.5% or greater) using low coverage Whole Genome Sequencing-by-Synthesis with ultra-low input amounts of cfDNA isolated from capillary blood/plasma mixtures of female and male DNA.
Figure 11:
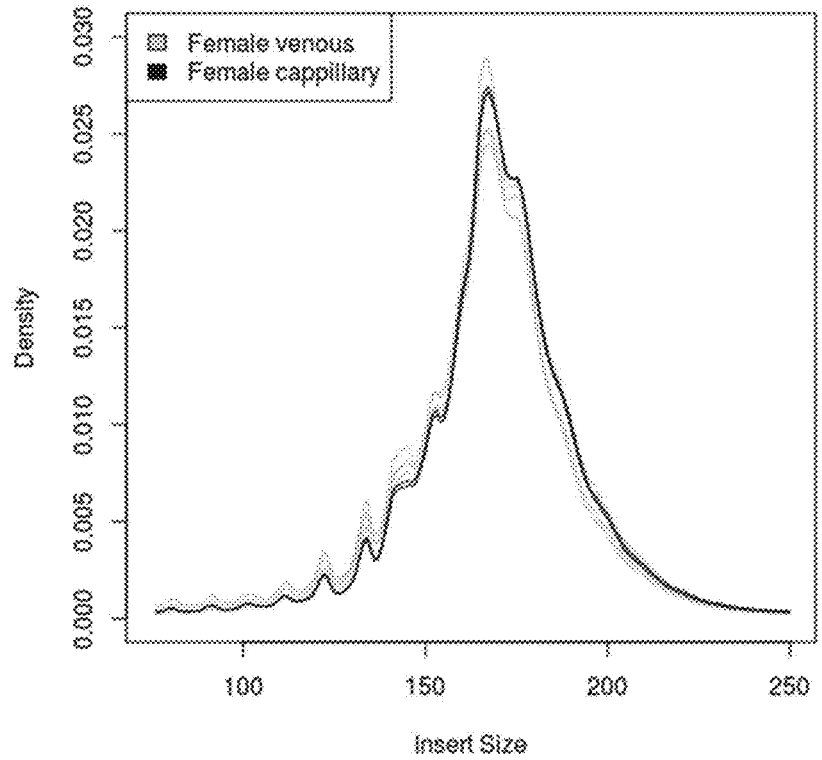
FIG. 11 shows a cfDNA fragment size distribution comparison between cfDNA from capillary blood and venous blood based on paired end sequencing data.

All libraries were sized and characterized using Agilent Bioanalyzer 2100 with a High-Sensitivity DNA Chip (Agilent Technologies). Concentrations were determined using Qubit v3.0 (Life Technologies) for library dilutions prior to sequencing. Each library was normalized to a concentration of 2 nM and pooled for denaturation and dilution prior to sequencing. Sequencing-by-synthesis was conducted using an Illumina NextSeq 550 at a loading concentration of 1.5 pM. Seventy-five cycle paired-end sequencing (2×75) was conducted for each index/sample. In general, each sample generated approximately 4 million passed-filter. All sequencing data (fasta.gz files) was aligned against the human reference genome build hg38 using Bowtie with alignment parameters "-k 1-n 0". For further analysis, the human genome was divided into consecutive 50,000 basepair regions, also called 50 kb bins, and the fraction of the base "G" and "C" was calculated for each bin with an accuracy up to 3 decimals. For each bin the aligned sequence reads that start in a bin were calculated. For further analysis the data was reduced by filtering out bins not on chromosomes 1 to 22 (e.g. chromosomes X and Y were excluded). After this filtering, a Loess regression between GC content and read count per bin was performed and the median bin count was calculated. The Loess regression provided an expected bin count for each GC content value, also called the expected value. This expected value was divided by the median bin count to get a correction factor. The measured bin count was then divided by the correction factor resulting in a GC corrected bin count and the median of the GC corrected bin count was calculated. All 50 kb bins were divided by the median GC corrected bin count to yield GC normalized bin counts and for each bin a median and median absolute deviation (MAD) was calculated. Bins with a low MAD and a median around the expected value of 1 were selected (bins with MAD>=0.25 or Median <0.7 or Median >1.3 were filtered out). Specifically for the calculation of Y chromosome representation, LOESS regression was performed for bins originating on chromosome Y. See FIG. 10 and FIG. 11. FIG. 10 shows detection of low fraction Y-chromosome (2.5% or greater) using low coverage Whole Genome Sequencing-by-Synthesis with ultra-low input amounts of cfDNA isolated from capillary blood/plasma mixtures of female and male DNA. With the ultra-low amounts of cfDNA in mixtures of female/male plasma derived from capillary blood collected by a finger prick, we still a corresponding increase of chromosome Y representation with increasing amounts of male capillary blood derived plasma. FIG. 11 shows a cfDNA fragment size distribution comparison between cfDNA from capillary blood and venous blood based on paired end sequencing data. Size profiles of cfDNA from ultra-low amounts of plasma derived from venous blood and capillary blood look similar. A percentage representation of sequence reads originating from chromosome Y was calculated by summing up all GC normalized values for bins originating on chromosome Y and dividing by the sum of all GC normalized values, excluding those originating from chromosome 21 and 19.

Example 4. Detection of Low Fraction Y-Chromosome (2.5% or Greater) Using Low Coverage Whole Genome Sequencing-by-Synthesis with Ultra-Low Input Amounts of ccfDNA (10 Genome Equivalents)

Female or male whole blood (10 ml) was collected by venous puncture into a Streck cell-free DNA BCT and processed to plasma by double-spin centrifugation as follows:
Spin 1-1330 rpm for 20 minutes, no brake
Spin 2-3300 rpm for 10 minutes
Plasma was stored at 4° C. until use. Male plasma was spiked into female plasma at varying percentages ranging from 2.5%-20% by volume. Circulating cell-free DNA was then extracted from the plasma using a modified protocol for 10 μl or 20 μl of plasma with the MagMax Cell-Free DNA Isolation Kit (Life Technologies). Isolation consisted of the following steps:
6. Incubation of plasma with Proteinase K (volume dependent on starting input) at 60° C. for 20 minutes.
7. Lysis/binding of plasma to DynaBeads MyOne Silane paramagnetic beads (2.5-5 μl) with binding for 10 minutes at room temperature.
8. Washing of the bead/ccfDNA complex (volume dependent on starting input). 9. Rinse bead/ccfDNA complex with 80% ethanol (volume dependent on starting input).
10. Elution of ccfDNA from beads (volume dependent on starting input) with incubation at room temperature for 2 minutes.
Genome equivalents for each sample were estimated to be 1 GE/ul of plasma based on previous extractions at volumes ranging from 10 ul-4000 ul and published data. All of the eluted ccfDNA was used as input for library generation. DNA libraries were prepared using the NEBNext Ultra II DNA Library Prep Kit with the NEBNext Multiplex Oligos for Illumina (Index Set Primers 1) (New England Biolabs). Libraries were generated using reduced volumes to account for the stoichiometry of the lower template amounts. The volumes used depended on the input amount of template. Library preparation consisted of:
4. End-repair, 5-phophphorylation and A-tailing with incubation at 20° C. for 30 minutes followed by 65° C. for 30 minutes.
5. Adaptor ligation with incubation at 20° C. for 15 minutes followed by cleavage of the ligated adaptor loop with incubation at 37° C. for 15 minutes. Adaptors were diluted 1:25 to a 0.6 uM working concentration. The cleaved, adaptor-ligated library was then subjected to bead-based purification using SPRISelect beads. The volume of beads was increased to 116 ul to further enhance binding of highly-fragmented, low concentration ccfDNA following adaptor ligation.
6. Library amplification/indexing with initial denaturation at 98° C. for 1 minute followed by 13 cycles of 98° C. denaturation for 10 seconds and annealing/extension at 65° C. for 75 seconds with final extension at 65° C. for 5 minutes. Amplified library was then purified using SPRISelect beads (45 ul).

All libraries were sized and characterized using Agilent Bioanalyzer 2100 with a High-Sensitivity DNA Chip (Agilent Technologies). Concentrations were determined using Qubit v3.0 (Life Technologies) for library dilutions prior to sequencing. Each library was normalized to a concentration of 2 nM and pooled for denaturation and dilution prior to sequencing. Sequencing-by-synthesis was conducted using an Illumina NextSeq 550 at a loading concentration of 1.5 pM. Seventy-five cycle paired-end sequencing (2×75) was conducted for each index/sample. In general, each sample generated approximately 4 million passed-filter. All sequencing data (fasta.gz files) was aligned against the human reference genome build hg38 using Bowtie with alignment parameters "-k 1-n 0". For further analysis, the human genome was divided into consecutive 50,000 base-pair regions, also called 50 kb bins, and the fraction of the base "G" and "C" was calculated for each bin with an accuracy up to 3 decimals. For each bin aligned sequence reads that start in a bin were counted. For further analysis the data was reduced by filtering out bins not on chromosomes 1 to 22 (e.g. chromosomes X and Y were excluded). After this filtering, a Loess regression between GC content and read count per bin was performed and the median bin count was calculated. The Loess regression provided an expected bin count for each GC content value, also called the expected value. This expected value was divided by the median bin count to get a correction factor. The measured bin count was then divided by the correction factor resulting in a GC corrected bin count and the median of the GC corrected bin count was calculated. All 50 kb bins were divided by the median GC corrected bin count to yield GC normalized bin counts and for each bin a median and median absolute deviation (MAD) was calculated. Bins with a low MAD and a median around the expected value of 1 were selected (bins with MAD>=0.25 or Median <0.7 or Median >1.3 were filtered out).

Figure 9:
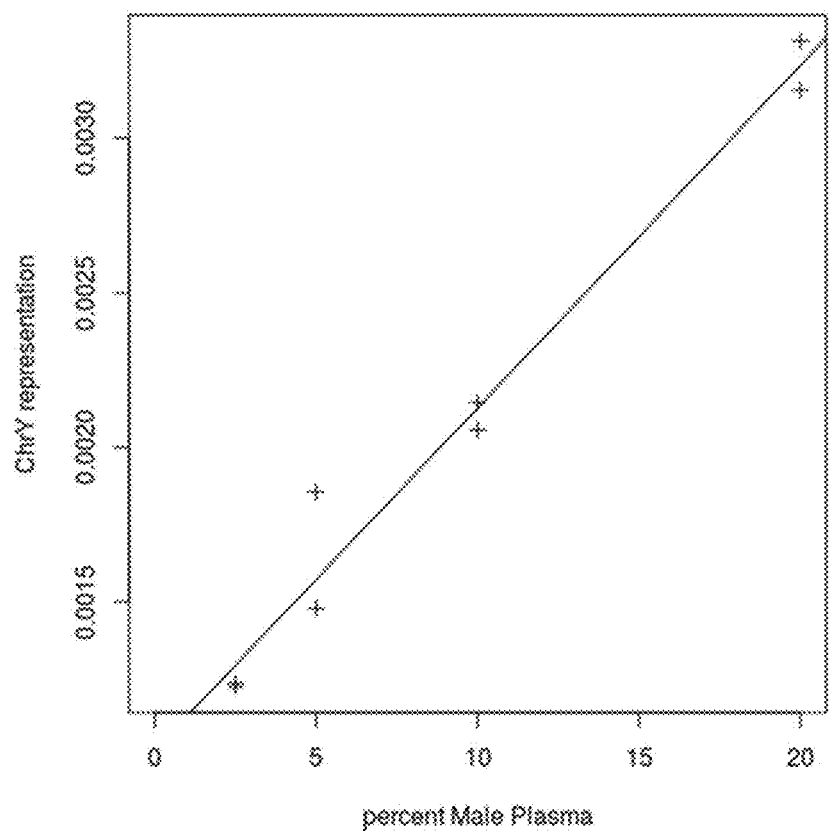
FIG. 9 shows detection of low fraction Y-chromosome (2.5% or greater) using low coverage Whole Genome Sequencing-by-Synthesis with ultra-low amounts of cfDNA (10 genome equivalents) isolated from venous blood.

Specifically for the calculation of Y chromosome representation, a LOESS regression was also performed for bins originating on chromosome Y. A percentage representation of sequence reads originating from chromosome Y was calculated by summing up all GC normalized values for bins originating on chromosome Y and dividing by the sum of all GC normalized values, excluding those originating from chromosome 21 and 19. See FIG. 9. FIG. 9 shows detection of low fraction Y-chromosome (2.5% or greater) using low coverage Whole Genome Sequencing-by-Synthesis with ultra-low amounts of cfDNA (10 genome equivalents) isolated from venous blood. Male plasma was mixed into female plasma at fixed amounts to create female/male plasma mixtures. cfDNA was extracted from the plasma mixtures and sequenced. The representation of chromosome Y was determined to show that with increasing amount of male plasma mixed into female plasma a corresponding increase in chromosome Y representation can still be detected precisely from ultra-low input amounts of cfDNA.

Example 5. Detection of Fetal Chromosomal Aneuploidy using low coverage Whole Genome Sequencing-by-Synthesis with Ultra-Low Input Amounts of ccfDNA (10 Genome Equivalents)

Whole blood (10 ml) was collected via venous puncture into a Streck cell-free DNA BCT and processed to plasma by double-spin centrifugation. Plasma was processed fresh, stored at 4° C. or −80° C. until use. Circulating cell-free DNA was then extracted from the plasma using a modified protocol for 1.2 ml of plasma with paramagnetic beads. Isolation consisted of the following steps:
1. Incubation of plasma with Proteinase K, glycogen and Lysis Buffer and beads at room temperature for 20 minutes for lysis/binding.
2. Washing of the bead/ccfDNA complex.
3. Elution of ccfDNA from beads (441) with incubation at 55° C. temperature for 10 minutes.

Extracted DNA was quantified for upstream applications. All samples were normalized to 33 pg (10GEs) total input per library. DNA libraries were prepared using the NEBNext Ultra II DNA Library Prep Kit with the NEBNext Multiplex Oligos for Illumina (Index Set Primers 1) (New England Biolabs). Libraries were generated using reduced volumes to account for the stoichiometry of the lower template amounts. The volumes used depended on the input amount of template. Library preparation consisted of:
1. End-repair, 5-phophphorylation and A-tailing with incubation at 20° C. for 30 minutes followed by 65° C. for 30 minutes.
2. Adaptor ligation with incubation at 20° C. for 15 minutes followed by cleavage of the ligated adaptor loop with incubation at 37° C. for 15 minutes. Adaptors were diluted 1:25 to a 0.6 uM working concentration. The cleaved, adaptor-ligated library was then subjected to bead-based purification using SPRISelect beads. The volume of beads was increased to 116 ul to further enhance binding of highly-fragmented, low concentration ccfDNA following adaptor ligation.
3. Library amplification/indexing with initial denaturation at 98° C. for 1 minute followed by 13 cycles of 98° C. denaturation for 10 seconds and annealing/extension at 65° C. for 75 seconds with final extension at 65° C. for 5 minutes. Amplified library was then purified using SPRISelect beads (45 ul).

All libraries were sized and characterized using Agilent Bioanalyzer 2100 with a High-Sensitivity DNA Chip (Agilent Technologies). Concentrations were determined using Qubit v3.0 (Life Technologies) for library dilutions prior to sequencing. Each library was normalized to a concentration of 2 nM and pooled for denaturation and dilution prior to sequencing. Sequencing-by-synthesis was conducted using an Illumina NextSeq 550 at a loading concentration of 1.5 pM. Seventy-five cycle paired-end sequencing (2×75) was conducted for each index/sample. In general, each sample generated approximately 4 million passed-filter. All sequencing data (fasta.gz files) was aligned against the human reference genome build hg38 using Bowtie with alignment parameters "-k 1-n 0". For further analysis, the human genome was divided into consecutive 50,000 base-pair regions, also called 50 kb bins, and the fraction of the base "G" and "C" was calculated for each bin with an accuracy up to 3 decimals. For each bin the aligned sequence reads that start in a bin were counted. For further analysis the data was reduced by filtering out bins not on chromosomes 1 to 22 (e.g. chromosomes X and Y were excluded). After this filtering, a Loess regression between GC contend and read count per bin was performed and the median bin count was calculated. The Loess regression provided an expected bin count for each GC content value, also called the expected value. This expected value was divided by the median bin count to get a correction factor. The measured bin count was then divided by the correction factor resulting in a GC corrected bin count and the median of the GC corrected bin count was calculated. All 50 kb bins were divided by the median GC corrected bin count to yield GC normalized bin counts and for each bin a median and median absolute deviation (MAD) was calculated. Bins with a low MAD and a median around the expected value of 1 were selected (bins with MAD>=0.25 or Median <0.7 or Median >1.3 were filtered out).

Figure 12:
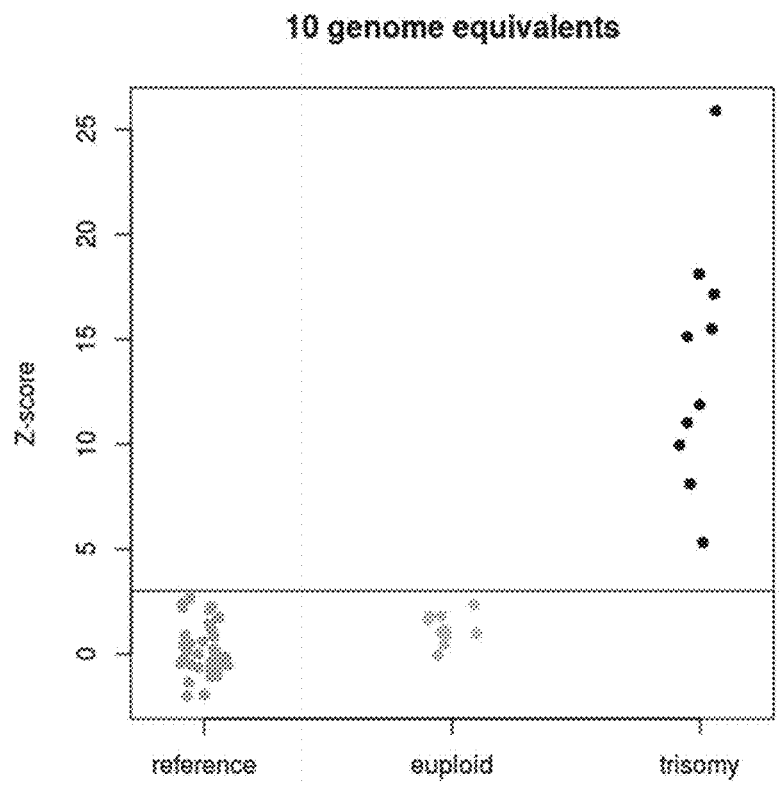
FIG. 12 shows the detection of fetal chromosomal aneuploidy using low coverage Whole Genome Sequencing-by-Synthesis with ultra-low input amounts of cfDNA derived from blood/plasma of pregnant women. Ultra-low input amounts of cfDNA from non-trisomic reference samples were used to determine the median and median absolute deviation of the chromosome 21 representation. Test samples were ultra-low amounts of cfDNA (10 GE) from pregnant women carrying either a normal fetus (no trisomy) or a fetus with a chromosome 21 trisomy.

From the reduced and normalized data, all sequence bins originating on chromosome 21 were identified. The percentage representation of sequence reads originating from chromosome 21 was calculated by summing up all GC normalized values for bins originating on chromosome 21 and dividing the sum by the sum of all GC normalized values excluding GC normalized values of bins originating from chromosome 21 and 19 (as well as other chromosomes already excluded in earlier steps, e.g. X and Y, chromosomes other than 1-22). The median and MAD of the chromosomes 21 representation were then calculated from a set of known euploid samples (reference samples). For each sample the median chromosome 21 representation was subtracted from the sample specific chromosome 21 representation resulting in a sample specific difference. This sample specific difference was divided by the chromosome 21 representation MAD, providing a value referred to as the Z-score. Test samples were then classify based on their Z-score, where samples with a Z-score of 3 and higher were classified as trisomic and samples with a Z-score of less than 3 were classified as euploid. See FIG. 12. The reference sample set used consisted of 36 sequencing results overall. 20 were obtained from one male individual. Libraries were generated with various amounts of ultra-low input amounts of circulating cell-free DNA (cfDNA): 2 sequencing libraries were generated from 1 Genomes Equivalent (GE) of cfDNA input amount (~3.5 pg of cfDNA); 2 sequencing libraries were generated from 4 GE of cfDNA (~14 pg of cfDNA); 4 sequencing libraries were generated from 10 GE of cfDNA (~35 pg of cfDNA); 2 sequencing libraries at 19 GE of cfDNA; 3 sequencing libraries at 25 GE of cfDNA; 3 sequencing libraries at 50 GE of cfDNA; 1 sequencing library at 96 GE of cfDNA; 2 sequencing libraries at 100 GE of cfDNA; 1 sequencing library at 2000 GE of cfDNA.

Data was also analyzed to establish a reference sample independent method to determine the presence of a fetal trisomy from ultra-low input circulating cell-free DNA from blood of a pregnant woman. All sequencing data (fasta.gz files) was aligned against the human reference genome build hg38 using Bowtie with alignment parameters "-k 1-n 0". For further analysis, the human genome was divided into consecutive 50,000 basepair regions, also called 50 kb bins, and the fraction of the base "G" and "C" was calculated for each bin with an accuracy up to 3 decimals. For each bin the aligned sequence reads that start in a bin were counted.

For further analysis, data was reduced by filtering out bins not on chromosomes 1 to 22 (e.g. chromosomes X and Y were excluded). After this filtering, a Loess regression between GC contend and read count per bin was performed and the median bin count was calculated. The Loess regression provided an expected bin count for each GC content value, also called the expected value. This expected value was divided by the median bin count to get a correction factor. The measured bin count was then divided by the correction factor resulting in a GC corrected bin count and the median of the GC corrected bin count was calculated.

All 50 kb bins were divided by the median GC corrected bin count to yield GC normalized bin counts and for each bin a median and median absolute deviation (MAD) was calculated. Bins with a low MAD and a median around the expected value of 1 were selected (bins with MAD>=0.25 or Median <0.7 or Median >1.3 were filtered out).

To detect a potential chromosomal aberration (e.g., trisomy), for each test sample all bins that originate from one chromosome were selected and a correction factor was subtracted. Specific correction values used in this analysis were: Chr1 0.018246891, Chr2 0.020434185, Chr3 0.011982353, Chr4 0.001049686, Chr5 0.020581150, Chr6 0.009152075, Chr7 0.005677261, Chr8 0.022754399, Chr9 0.015059119, Chr10 0.021188753, Chr11 0.017143964, Chr12 0.007069202 Chr13 0.002157471, Chr14 0.010356892, Chr15 0.019037573, Chr16 0.009929239, Chr17 0.004990359, Chr18 0.023177486, Chr19- 0.063998368, Chr20 0.042335516, Chr21 0.00498782, Chr22 0.025008553.

Figure 13:
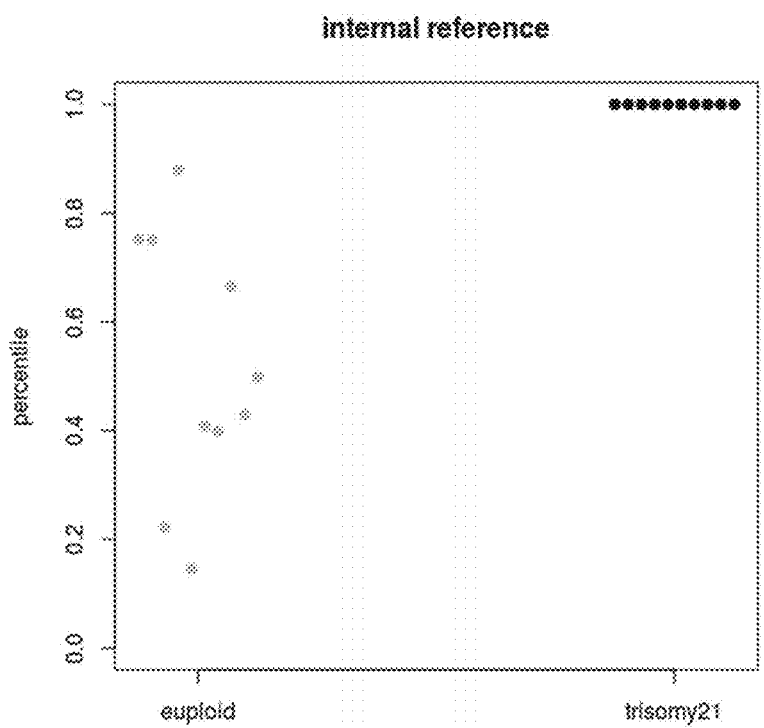
FIG. 13 shows the detection of fetal chromosomal aneuploidy using low coverage Whole Genome Sequencing-by-Synthesis with ultra-low input amounts of cfDNA derived from blood/plasma of pregnant women. Analysis was performed without a reference sample set using an sample internal method of determining trisomy 21 status. Test samples were ultra-low amounts of cfDNA (10 GE) from pregnant women carrying either a normal fetus (no trisomy) or a fetus with a chromosome 21 trisomy.

Then the number of bins originating from chromosome 21 in this filtered set (657 in this data set) was counted and then the same amount of bins (657) were selected randomly from all available bins such that they contain bins originating from various different chromosomes. Then a percentage representation was calculated for this set of randomly selected bins. All GC normalized values were summed up for this set of randomly selected bins and divided by the sum of all GC normalized values. The last steps were repeated ten-thousand times and each value was stored. Then a percentage representation of sequence reads originating from chromosome 21 was calculated by summing up all GC normalized values for bins originating from chromosome 21 and this number was divided by the sum of all GC normalized values. It was calculated how many times the percentage representation of the bins originating from chromosome 21 was higher than the chromosome representation from the ten-thousand repeats of randomly selected bins. See FIG. 13. The sum divided by 10,000 is a value between 0 and 1, referred to as "percentile" herein. Samples were classified based on their percentile value: a value of ten-thousand (percentile 1) classifies the sample as a trisomy, a value lower than ten-thousand (percentile below 1) classifies the sample as euploid.

Example 6. In-Home Non-Invasive Prenatal Testing

A pregnant woman with a history of miscarriages suspects she is pregnant again and that she is probably about 6 weeks into gestation. She would like to know as soon as possible if she is actually pregnant and if the fetus has any genetic abnormalities that may put it at risk. She purchases a Non-Invasive Prenatal Testing device disclosed herein and takes it home. With the emotional support of her closest family members and friends present, she initiates the test by pressing her finger against a microneedle array in a well of the device. A nanopore sequencer in the device sequences a sufficient amount of nucleic acids in her blood sample (less than $10^9$ fetal nucleic acids) to reveal desired genetic information in less than about one hour. A USB port or wireless technology relays the sequence information to an app on her phone or a website on her computer. The app or website employs software to obtain genetic information from the sequencing reads, revealing a panel of results for the woman to review. Alternatively, the device itself has software to read the sequences and produce a panel in a window of the device. The panel confirms the woman is pregnant and includes information about whether the fetus has a known chromosomal aberration (e.g., trisomy of chromosome 13, 16, 18, 21, 22, and/or X/Y) or other genetic abnormality. The panel also confirms she is pregnant and that she is expecting a boy.

Example 7: Non-Invasive Prenatal Testing with Microvolumes of Maternal Sample

Performing a simulation at lower limit of fetal fraction (4%) that takes into account the losses of standard methods during DNA Extraction (efficiency 90%) and library preparation (efficiency 10%) as well as the PCR amplification (~10 cycles) shows that accuracy decreases below 25 (inflection point at 10) copies of input DNA material. Accuracy at 10 copies is reduced to 89% and at 5 copies to 81%, both values would not be acceptable in a market that requires ~95% theoretical accuracy for samples at 4% fetal fraction. See FIG. 7 light grey line.

When increasing the library efficiency (to 50%, versus 10%) and decreasing the amplification, more information is preserved and sensitivities above 95% can be achieved even at copy numbers (genome equivalents) below 5. See FIG. 7, dark grey line.

TABLE 4

Workflow for obtaining fetal genetic information from 20 µl plasma

| 20 µl plasma @1500 genome equiv. per ml | cfDNA Genome Equivalents (fetal + maternal) | Total cfDNA fragments | Efficiency |
| --- | --- | --- | --- |
| Blood Draw | 10 | 2.00E+08 | |
| DNA Extraction | 9 | 1.80E+08 | 0.9 |
| Library Prep | 4.5 | 9.00E+07 | 0.5 |
| Amplification | 450 | 9.00E+09 | 100 |
| Normalization and Multiplexing | 150 | 3.00E+09 | 0.33 |
| Denaturation | 90 | 1.80E+09 | 0.6 |
| Sequencing | 0.25 | 5.00E+06 | 0.003 |

Example 8: Analysis of Fetal Chromosomal Abnormality by Whole Genome Sequencing of Cell-Free DNA from Pregnant Women 180 pg of cell-free DNA was obtained from a biological fluid of a pregnant woman, an amount that is equivalent to the amount of cell-free DNA in about 100 µl of blood. The cell-free DNA was purified with a DNA repair kit and contained in a buffered solution to preserve its integrity.

In order to prepare the cell-free DNA for sequencing, ends of the cell-free DNA fragments were repaired with a DNA fragment end repair kit. Next, the repaired ends were ligated to adapters to produce adapter ligated DNA.

The adapter ligated DNA was purified by incubating the adapter ligated DNA with beads that can bind DNA. Using a magnet to trap the beads, the beads with the DNA were washed several times with an ethanol solution, before the adapter ligated DNA was eluted from the beads.

Cycled amplification of the adapter ligated DNA was performed with an initial denaturation step at 98° C. for 30 seconds, followed by 10 cycles of 98° C. for 10 seconds and 65° C. for 75 seconds, followed by a final extension at 65° C. for 5 minutes. Optionally, the adapter ligated DNA can be amplified with the use of an index primer, which can be useful in a case of running multiple samples on the same sequencer run. These were different from unique barcodes/tags introduced prior to library amplification. Similar to the adapter ligated DNA, the amplified DNA was purified with a bead and magnet system. The resulting purified amplified DNA was subjected to sequencing.

Sequencing was performed with a high throughput sequencing machine that generates millions of sequencing reads with read lengths of 30 to 500 base pairs. The indices allowed for obtaining sequencing reads from multiple sample simultaneously. Approximately 4 million reads were obtained per sample per sequencing run.

For each sample the following steps were performed:

Sequence alignment to detect the genomic origin of all sequence reads.

Subsets of the genome were put into non-overlapping bins of 50 kb length. GC content was calculated for each bin based on a reference genome. The number of sequence reads located in each of the bin regions was counted. A linear model for the relationship between GC-content and count of the bins was calculated according to y=ax+b (y: expected counts, a: slope, x: GC content, b: intercept). The count per bin was adjusted based on the linear model to reduce GC bias. For each bin the difference between the median count of all bins was calculated and the expected count value was subtracted from the linear fit. This difference was added to the observed count value for each respective bin. The percentage of sequence reads that originated from a chromosome of interest was calculated. In this example, the chromosome of interest was chromosome 21.

A set of reference samples was used to calculate the percentage of sequence reads that originate from chromosome 21 (referred to as ref.p21). The median value (referred to as refined) was calculated, along with the median absolute deviation (MAD) (referred to as ref.mad) for the set of ref.p21 samples.

Figure 3:
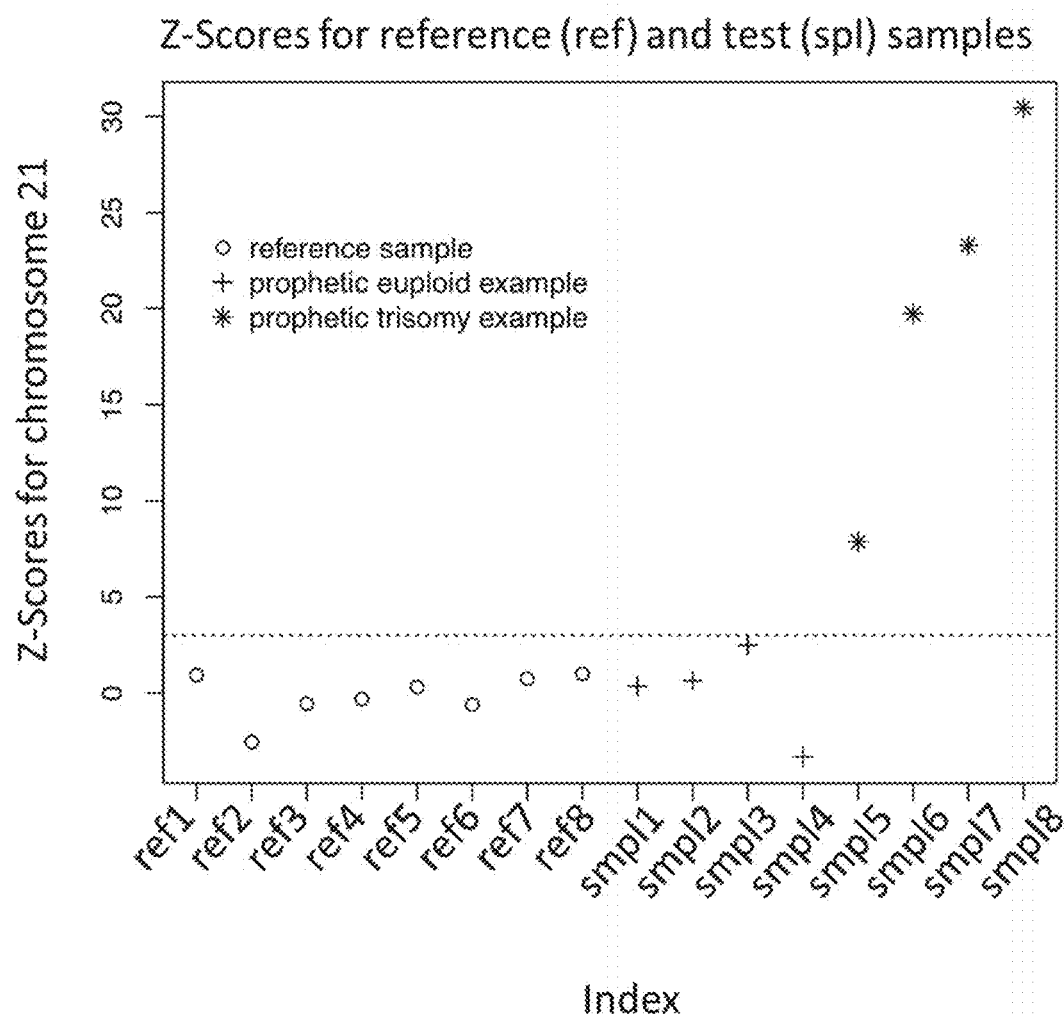
FIG. 3 shows results of trisomy detection from ultra-low sample amounts generated by low coverage whole genome sequencing-by-synthesis. Depicted are the Z scores for the representation of chromosome 21 from reference and test samples. The dotted line represents a Z score of 3. A test sample showing a Z score equal or higher than 3 means that the sample contains a higher representation of chromosome 21 and is considered trisomic for chromosome 21. If the sample came from a pregnant women, the extra amount of chromosome 21 detected is contributed by the fetus and therefore it is concluded the fetus is trisomic for chromosome 21.
Figure 4A:
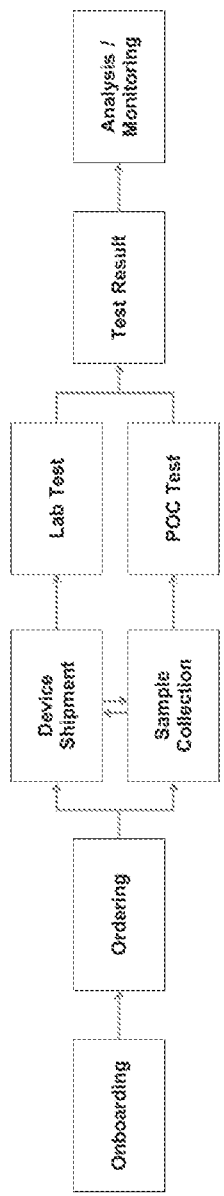
FIG. 4A shows a process overview for devices that are connected to remote systems and individuals.
Figure 4B:
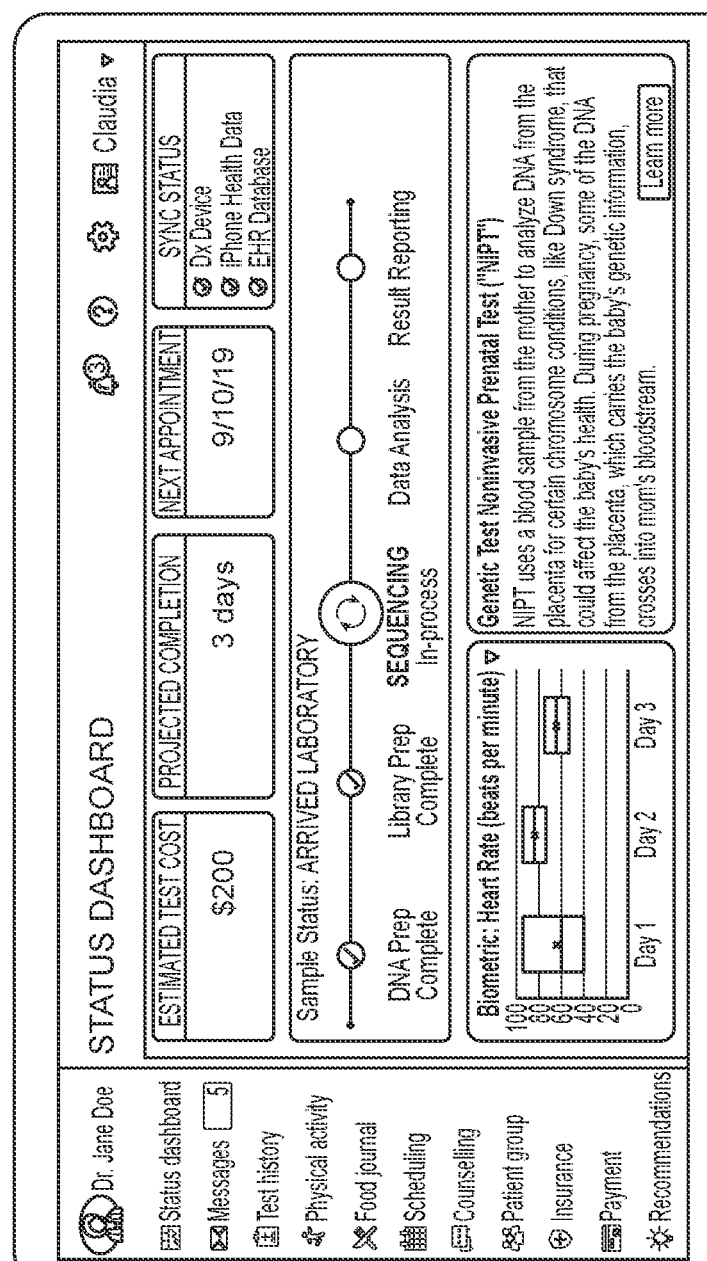
FIG. 4B shows an exemplary interface for devices that are connected to remote systems and individuals.

Similar values were measured in at least one test sample (same protocol as described above). The percentage of sequence reads that originate from chromosome 21, (referred to as test.p21) were calculated. For each sample the Z-score was calculated by calculating a difference between the test sample percentage of sequence reads that originate from chromosome 21 and the median of the reference (test.p21-ref.med) and dividing this difference by the median absolute deviation of the reference set ([test.p21-ref.med]/mad.ref). See FIG. 3 for results.

If it was found that the Z-score value was above a predetermined cut-off (typically the cutoff is equal to 3), the sample could be interpreted to have an overrepresentation of genomic material originating from chromosome 21. This overrepresentation was indicative for a fetal trisomy 21. Conversely, if the Z-score was below a predetermined cutoff, the sample could be interpreted to have a normal or underrepresentation of genomic material. This analysis could be applied to other chromosomes or chromosomal regions.

Example 9. Detecting Genetic Abnormalities by Sequencing Cell-Free Fetal Nucleic Acids in Maternal Plasma A blood sample is collected from a pregnant subject. The pregnant subject may be as little as 5 weeks into gestation. In some cases, she is as little as 7 weeks into gestation. In some instances, the pregnant subject collects the blood herself by pricking her finger on a device at home. The pregnant subject sends her sample, either in the device or in a container to a laboratory that has sample processing and sequencing equipment. Alternatively, the device performs sample processing (e.g., purification, target enrichment) and/or sequencing, and thus, the pregnant subject does not need to send her sample to a laboratory. The finger prick obtains about 100 µl of blood, of which about 50 µl of plasma or serum is obtained. The 50 µl of plasma contains about $1.5 \times 10^8$ of cell-free fetal nucleic acids, because the percentage of cell-free fetal nucleic acids in the total cell-free nucleic acids of the plasma sample at the time of sampling is on average 10%. In some instances, the fetal fraction is only 4%, and the 100 µl blood sample contains about $6 \times 10^7$ of cell-free fetal nucleic acids. Because the percentage of cell-free fetal nucleic acids in the total cell-free nucleic acids of the plasma sample can be as low as 1%, the minimum volume of blood that should be obtained from the subject to ensure reliable information at any stage of pregnancy is about 2 µl.

Example 10. Detecting Genetic Abnormalities by Sequencing Cell-Free Fetal Nucleic Acids in Maternal Urine A urine sample is collected from a pregnant subject. The pregnant subject may be as little as 5 weeks into gestation. In some cases, she is as little as 7 weeks into gestation. In some instances, the pregnant subject collects the urine herself at home. The pregnant subject sends her sample, either in the device or in a container to a laboratory that has sample processing and sequencing equipment. Alternatively, the pregnant subject puts the urine sample in a home device that performs sample processing (e.g., purification, target enrichment) and/or sequencing, and thus, the pregnant subject does not need to send her sample to a laboratory. In some cases, the urine sample has a volume of about 100 µl. The 100 µl of urine contains about $8 \times 10^{10}$ cell-free fetal nucleic acids, because the percentage of cell-free fetal nucleic acids in the total cell-free nucleic acids of the urine sample at the time of sampling is 4%, and the typical concentration of cell-free nucleic acids in urine is $8 \times 10^{11}$ fragments per ml. In some instances, the fetal fraction is 4%, and the urine sample contains about $3.2 \times 10^9$ cell-free fetal nucleic acids. Because the percentage of cell-free fetal nucleic acids in the total cell-free nucleic acids of the urine sample can be as low as 1%, the minimum volume of urine that should be obtained from the subject to ensure reliable information at any stage of pregnancy is about 2 µl.

Example 11. Detecting Genetic Abnormalities by Counting Cell-Free Fetal Nucleic Acids in Maternal Plasma in a Laboratory from a Home-Collected Sample A blood sample is collected from a pregnant subject. The pregnant subject may be as little as 5 weeks into gestation.

In some cases, she is as little as 7 weeks into gestation. In some instances, the pregnant subject collects capillary blood herself, for example, by pricking her finger, on a device at home. In some instances, the device separates the blood into plasma. The pregnant subject sends her blood (or plasma sample) in the device or a container to a laboratory that has reagents and equipment for sample processing, nucleic acid library preparation and sequencing. In some instances, library preparation involves tagging cell-free fetal nucleic acids with a label or signal that is counted or quantified. In some instances, the label or signal is connected to an oligonucleotide that hybridizes to specific cell-free fetal nucleic acids.

The amount of the specific cell-free fetal nucleic acids is translated into a quantity through the signal or label, and is detected by the pregnant subject, the device or a technician performing the analysis. The finger prick obtains about 100 µl of blood, of which about 50 µl of plasma or serum is obtained. The 50 µl of plasma contains about $1.5 \times 10^{\wedge}8$ cell-free fetal nucleic acids, because the percentage of cell-free fetal nucleic acids in the total cell-free nucleic acids of the plasma sample at the time of sampling is about 10%. In some instances, the fetal fraction is about 4%, and the 100 µl blood sample contains about $6 \times 10^{\wedge}7$ cell-free fetal nucleic acids. Because the percentage of cell-free fetal nucleic acids in the total cell-free nucleic acids of the plasma sample can be as low as 1%, the minimum volume of blood that should be obtained from the subject to ensure reliable information at any stage of pregnancy is about 2 µl.

Results of analysis in the lab are sent to the pregnant subject electronically.

Example 12. Detecting Genetic Abnormalities by Counting Cell-Free Fetal Nucleic Acids in Maternal Plasma in a Laboratory from a Home-Processed Sample A blood sample is collected from a pregnant subject. The pregnant subject may be as little as 5 weeks into gestation. In some cases, she is as little as 7 weeks into gestation. In some instances, the pregnant subject collects the blood herself by pricking her finger on a device at home. The device performs sample processing (e.g., purification, target enrichment) and library preparation. Thus, the pregnant subject only need send her processed and prepared sample to a sequencing facility or facility capable of sequencing nucleic acids.

The amount of the specific cell-free fetal nucleic acids is translated into a quantity through the signal or label, and is detected by the pregnant subject, the device or a technician performing the analysis. The finger prick obtains about 100 µl of blood, of which about 50 µl of plasma or serum is obtained. The 50 µl of plasma contains about $1.5 \times 10^{\wedge}8$ cell-free fetal nucleic acids, because the percentage of cell-free fetal nucleic acids in the total cell-free nucleic acids of the plasma sample at the time of sampling is about 10%. In some instances, the fetal fraction is about 4%, and the 100 µl blood sample contains about $6 \times 10^{\wedge}7$ cell-free fetal nucleic acids. Because the percentage of cell-free fetal nucleic acids in the total cell-free nucleic acids of the plasma sample can be as low as 1%, the minimum volume of blood that should be obtained from the subject to ensure reliable information at any stage of pregnancy is about 2 µl.

Results of analysis in the lab are sent to the pregnant subject electronically.

Example 13. Detecting a Fetal Trisomy

Reads from each chromosome are roughly represented according to the length of the chromosome. Most reads are obtained from chromosome 1, while the fewest reads from an autosome will originate from chromosome 21. A common method for detecting a trisomic sample is to measure the percentage of reads originating from a chromosome in a population of euploid samples. Next a mean and a standard deviation for this set of chromosome percentage values are calculated. A cutoff value is determined by adding three standard deviations to the mean. If a new sample has a chromosome percentage value above the cutoff value, an overrepresentation of that chromosome can be assumed, which is often consistent with a trisomy of the chromosome.

For a pregnant subject with a euploid fetus, the average value for the percentage of reads obtained from chromosome 21 is 1.27% with a standard deviation of 0.01 percent. Therefore the cutoff to indicate a trisomy is 1.30%. This theoretical example shows a trisomy sample with a fetal fraction of 10% and a chromosome 21 percentage of 1.34. The sample is above the cutoff and would be correctly classified as a trisomy sample. Exemplary averages of chromosome percentages for all chromosomes in a euploid subject's sample with a euploid fetus, as well as percentages for all chromosomes in a euploid subject's sample with an aneuploid fetus is shown in Table 5.

TABLE 5

Average of chromosome percentages for chromosomes

| Chromo-some | Average of chromosome percentages for a euploid sample | Standard deviation of chromosome percentages | Cutoff for chromosome percentage to enable trisomy detection based on mean plus three standard deviations method | Example of trisomy 21 sample percentages |
|---|---|---|---|---|
| 1 | 8.38 | 0.02 | 8.46 | 8.39 |
| 2 | 8.51 | 0.02 | 8.59 | 8.48 |
| 3 | 6.92 | 0.02 | 7.01 | 6.93 |
| 4 | 6.27 | 0.03 | 6.39 | 6.22 |
| 5 | 6.18 | 0.03 | 6.31 | 6.18 |
| 6 | 5.88 | 0.02 | 5.96 | 5.87 |
| 7 | 5.55 | 0.01 | 5.61 | 5.54 |
| 8 | 5.13 | 0.02 | 5.20 | 5.13 |
| 9 | 4.10 | 0.01 | 4.15 | 4.08 |
| 10 | 4.96 | 0.01 | 5.00 | 4.97 |
| 11 | 4.87 | 0.01 | 4.91 | 4.85 |
| 12 | 4.76 | 0.03 | 4.86 | 4.75 |
| 13 | 3.23 | 0.02 | 3.32 | 3.21 |
| 14 | 3.21 | 0.02 | 3.28 | 3.20 |
| 15 | 3.02 | 0.02 | 3.09 | 3.06 |
| 16 | 3.07 | 0.02 | 3.15 | 3.07 |
| 17 | 3.07 | 0.02 | 3.17 | 3.04 |
| 18 | 2.69 | 0.01 | 2.72 | 2.68 |
| 19 | 2.27 | 0.03 | 2.40 | 2.28 |
| 20 | 2.44 | 0.03 | 2.55 | 2.44 |
| 21 | 1.27 | 0.01 | 1.30 | 1.34 |
| 22 | 1.46 | 0.02 | 1.54 | 1.45 |
| X | 2.50 | 0.02 | * | 2.47 |
| Y | 0.25 | 0.01 | * | 0.24 |

* a similar cutoff is not available for sex chromosomes, because this exemplary method is only applicable to autosomes.

Example 14: Device for Analysis of Fetal Cell-Free Nucleic Acids from Maternal Blood A device for separating plasma from whole blood for the purpose of analyzing cell-free nucleic acids comprises 6 layers. From bottom to top these are:

(1) Lower Adhesive Sheet (2) Lower Separation Disc: 16 mm diameter disc of adhesive sheet material (polymer material that is inert to DNA or Plasma) with glue on the side facing the Lower Adhesive Sheet (3) Polyethersulfone (PES) membrane, various sizes, typically between 6 and 16 mm, preferred design features 10 mm PES membrane. The membrane serves as wicking material which attracts the plasma from the filter through capillary force.

(4) Filter Disc (e.g., Pall Vivid™ Membrane), 16 mm diameter, rough side facing up, shiny side facing the PES membrane.

(5) Upper Separation Disc: same material as Lower Separation Disc, size 12 or 14 mm diameter, containing a 4 mm hole in the center. When using adhesive sheet material, now the glue side is facing up to meet the Upper Adhesive Sheet. The Upper Separation Disc is smaller than the Filter Disc in diameter. This allows the glue from the Upper Adhesive Sheet to interact with the edges of the Filter Disc and thereby sealing it at the edges.

(6) Upper Adhesive Sheet, a 6 mm hole is punched in the location where the center of the device will be located.

All layers are lined up at their center and then laminated using a standard office lamination machine.

The device is configured to perform the test described in Example 6.

Application of blood and filtration to the device occurs as follows:

100 µl of whole blood is applied to the center of the device through a hole in an Upper Adhesive Sheet and a hole in an Upper Separation Disc. The blood distributes centripetally throughout a Filter Disc by capillary forces. Plasma is also wicked through the Filter Disc into a PES membrane by capillary forces. After about two minutes, the maximum amount of plasma has been transferred into the PES membrane. The device or portion thereof with the PES membrane is shipped to a laboratory for DNA testing.

The PES membrane containing cell-free nucleic acids is recovered as follows:

The PES membrane is removed from the device. For example, the device is cut out around the edges of the PES membrane. The membrane separates easily from the Filter and the Lower Disc.

DNA is eluted from the membrane as follows:

The PES membrane containing the plasma is transferred into an Eppendorf tube (0.5 ml) and 100 µl of elution buffer are added (elution buffer can be H$_2$O, EB buffer (QGEN), PBS, TE or others suitable for subsequent molecular analysis). After elution of the DNA from the membrane, the buffer, containing the eluted cfDNA, is subjected to genetic analysis which involves nucleic acid amplification, tagging, sequencing, or a combination thereof.

While preferred embodiments of the devices, systems and kits disclosed herein have been shown and described herein, it will be obvious to those skilled in the art that such embodiments are provided by way of example only. Numerous variations, changes, and substitutions will now occur to those skilled in the art without departing from the devices, systems and kits disclosed herein. It should be understood that various alternatives to the embodiments of the devices, systems and kits disclosed herein may be employed in practicing the invention. It is intended that the following claims define the scope of the devices, systems and kits and that methods and structures within the scope of these claims and their equivalents be covered thereby.

What is claimed is:

1. A method comprising:
   (a) obtaining or providing capillary blood comprising cell-free nucleic acids obtained from a subject;
   (b) extracting the cell-free nucleic acids from the capillary blood;
   (c) preparing a nucleic acid library from the cell-free nucleic acids with an efficiency of at least about 0.5, wherein the nucleic acid library obtains the efficiency of at least about 0.5 by using one or more crowding agents;
   (d) detecting at least one target nucleic acid sequence present in the nucleic acid library; and
   (e) identifying one or more genetic or chromosomal abnormalities based on the detecting of (d).

2. The method of claim 1, wherein the detecting of (d) comprises sequencing the at least one target nucleic acid sequence.

3. The method of claim 1, wherein the subject is pregnant with a fetus.

4. The method of claim 3, wherein the cell-free nucleic acids comprise fetal cell-free nucleic acids.

5. The method of claim 4, wherein the one or more genetic or chromosomal abnormalities comprises a fetal aneuploidy or a fetal chromosomal abnormality.

6. The method of claim 1, wherein the subject has, is suspected of having, or is at risk of developing cancer.

7. The method of claim 1, wherein the capillary blood is obtained from the subject by use of a transdermal puncture device.

8. The method of claim 1, further comprising separating plasma or serum from the capillary blood or a portion thereof, and the extracting of (b) comprises extracting the cell-free nucleic acids from the plasma or serum.

9. The method of claim 1, wherein the extracting of (b) comprises binding the cell-free nucleic acids to a solid support.

10. The method of claim 9, wherein the solid support is selected from the group consisting of: a bead, a nanoparticle, a magnetic particle, a chip, a microchip, a fibrous strip, a polymer strip, a membrane, a matrix, a column, a plate, and any combination thereof.

11. The method of claim 9, further comprising, eluting the cell-free nucleic acids from the solid support.

12. The method of claim 1, further comprising, purifying the cell-free nucleic acids.

13. The method of claim 8, wherein the separating comprises centrifuging the capillary blood, filtering the capillary blood, or both.

14. The method of claim 1, wherein the detecting of (d) comprises detecting an overrepresentation, an underrepresentation, or a normal representation of the at least one target nucleic acid sequence in the cell-free nucleic acids.

15. The method of claim 1, wherein a total volume of the capillary blood is from about 5 µL to about 1 mL.

16. The method of claim 1, further comprising enriching for the cell-free nucleic acids thereby generating enriched cell-free nucleic acids.

17. The method of claim 16, wherein the enriching comprises removing a first amount of blood from the capillary blood.

18. The method of claim 16, wherein the enriching comprises enriching for the at least one target sequence present in the cell-free nucleic acids.

19. The method of claim 16, wherein the enriching comprises enriching for fetal cell-free nucleic acids.

20. The method of claim 16, wherein the enriching comprises removing white blood cells, cellular nucleic acids, or both, from the capillary blood.

21. The method of claim 1, wherein the one or more crowding agents is selected from the group consisting of: polyethylene glycol, dextran, and polysaccharide.

* * * * *